United States Patent
Berrebi-Bertrand et al.

(10) Patent No.: US 9,255,101 B2
(45) Date of Patent: Feb. 9, 2016

(54) 6,11-DIHYDRO-5H-BENZO[D]IMIDAZO[1,2-A]AZEPINES DERIVATIVES AS HISTAMINE H4 RECEPTOR LIGANDS

(71) Applicant: BIOPROJECT, Paris (FR)

(72) Inventors: Isabelle Berrebi-Bertrand, Pace (FR); Xavier Billot, Rennes (FR); Thierry Calmels, Melesse (FR); Marc Capet, Melesse (FR); Stéphane Krief, Rennes (FR); Olivier Labeeuw, Fougeres (FR); Jeanne-Marie Lecomte, Paris (FR); Nicolas Levoin, L'Hermitage (FR); Xavier Ligneau, Saint Gregoire (FR); Philippe Robert, Pace (FR); Jean-Charles Schwartz, Paris (FR)

(73) Assignee: BIOPROJET, Paris (FR)

( * ) Notice: Subject to any disclaimer, the term of this patent is extended or adjusted under 35 U.S.C. 154(b) by 31 days.

(21) Appl. No.: 13/910,475

(22) Filed: Jun. 5, 2013

(65) Prior Publication Data

US 2013/0324506 A1 Dec. 5, 2013

(30) Foreign Application Priority Data

Jun. 5, 2012 (EP) .................................... 12305633

(51) Int. Cl.
| | |
|---|---|
| *A61K 31/55* | (2006.01) |
| *C07D 487/04* | (2006.01) |
| *C07D 233/64* | (2006.01) |
| *A61K 45/06* | (2006.01) |
| *A61K 31/335* | (2006.01) |
| *A61K 31/4545* | (2006.01) |
| *A61K 31/495* | (2006.01) |

(52) U.S. Cl.
CPC ............ *C07D 487/04* (2013.01); *A61K 31/335* (2013.01); *A61K 31/4545* (2013.01); *A61K 31/495* (2013.01); *A61K 31/55* (2013.01); *A61K 45/06* (2013.01); *C07D 233/64* (2013.01)

(58) Field of Classification Search
CPC .............................. A61K 31/55; C07D 487/04
USPC ...................... 514/214.02; 540/579
See application file for complete search history.

(56) References Cited

U.S. PATENT DOCUMENTS 7,576,092 B2   8/2009   Chavez et al.
8,030,321 B2   10/2011  Chavez et al.

OTHER PUBLICATIONS

European Search Report for EP 12 30 5633 dated Jul. 18, 2012.
Database Chemcats [Online] Chemical Abstracts Service, Columbus, Ohio, US; (Apr. 2, 2012), XP002680266, retrieved from STN, Database accession No. 0112186645 * the whole document * & "Uorsy Library", Ukrorgsyntez Ltd., Kiev, Ukrraine.
Lazewska D et al:"Histamine H3 and H4 receptor affinity of branched 3-(1H-imidazol-4-yl)propyl N-alkylcarbamates", Technical Fields Bioorganic & Medicinal Chemistry Letters, vol. 19, No. 23, Searched (IPC) (Dec. 1, 2009), pp. 6682-6685.
Cowden, et al., "The Histamine $H_4$ Receptor Mediates Inflammation and Pruritus in Th2-Dependent Dermal Inflammation", 2010, pp. 1023-1033, vol. 130, Journal of Investigative Dermatology.
Cowden, et al., "The histamine $H_4$ receptor mediates inflammation and Th17 responses in preclinical models of arthritis", 2014, pp. 600-608, vol. 73, Ann Rheum Dis.
Cowden, et al., Histamine H4 receptor antagonism diminishes existing airway inflammation and dysfunction via modulation of Th2 cytokines, 2010, pp. 1-12, vol. 11, No. 86, Respiratory Research.
Coruzzi, et al., "Antiinflammatory and antinociceptive effects of the selective histamine H4-receptor antagonists JNJ7777120 and VUF6002 in a rat model of carrageenan-induced acute inflammation", 2007, pp. 240-244, vol. 563, European Journal of Pharmacology.
Buckland, et al., "Histamine induces cytoskeletal changes in human eosinophils via the $H_4$ receptor", 2003, pp. 1117-1127, vol. 140, British Journal of Pharmacology.
Cowden, et al., "Antagonism of the histamine $H_4$ receptor reduces LPS-Induced TNF production in vivo", 2013, pp. 599-607, vol. 62, Inflamm. Res.
Gantner, et al., "Histamine $H_4$ and $H_2$ Receptors Control Histamine-Induced Interleukin-16 Release from Human CD8+ T Cells", 2002, pp. 300-307, vol. 303, No. 1, The Journal of Pharmacology and Experimental Therapeutics.
Dunford, et al., "The Histamine $H_4$ Receptor Mediates Allergic Airway Inflammation by Regulating the Activation of CD4+T Cells", 2006, pp. 7062-7070, vol. 176, J. Immunol.
Hsieh, et al., "$H_4$ receptor antagonism exhibits anti-nociceptive effects in inflammatory and neuropathic pain models in rats", 2010, pp. 41-50, vol. 95, Pharmacology, Biochemistry and Behavior.
Kollmeier, et al., "The Histamine $H_4$ Receptor Antagonist, JNJ 39758979, Is Effective in Reducing Histamine-Induced Pruritus in a Randomized Clinical Study in Healthy Subjects", 2014, pp. 181-187, vol. 350, J Pharmacol Exp Ther.
Hofstra, et al., "Histamine $H_4$ Receptor Mediates Chemotaxis and Calcium Mobilization of Mast Cells", 2003, pp. 1212-1221, vol. 305, No. 3, The Journal of Pharmacology and Experimental Therapeutics.
Dunford, et al., "Histamine $H_4$ receptor antagonists are superior to traditional antihistamines in the attenuation of experimental pruritus", Jan. 2007, pp. 176-183, vol. 119, No. 1, J Allergy Clin Immunol.
Suwa, et al., "Histamine H4 receptor antagonist reduces dermal inflammation and pruritus in a hapten-induced experimental model", 2011, pp. 383,388, vol. 66, European Journal of Pharmacology.
1 C '' Takahashi, et al., "Effect of histamine H4 receptor antagonist on allergic rhinitis in mice", 2009, pp. 34-38, vol. 9, International Immunopharmacolgy.

(Continued)

*Primary Examiner* — Brenda Coleman
(74) *Attorney, Agent, or Firm* — B. Aaron Schulman, Esq.; Stites & Harbison, PLLC.

(57) ABSTRACT

The present patent application concerns new ligands of the H4-receptor, their process of preparation and their therapeutic use.

13 Claims, No Drawings

(56) References Cited

OTHER PUBLICATIONS

Somma, et al., "A selective antagonist of histamine H4 receptors prevents antigen-induced airway inflammation and bronchoconstriction in guinea pigs; involvement of lipocortin-1", 2013, pp. 200-213, vol. 170, British Journal of Pharmacology.

Ohsawa, et al., "The antagonism of histamine H1 and H4 receptors ameliorates chronic allergic dermatitis via anti-pruritic and anti-inflammatory effects in NC/Nga mice", 2012, pp. 1014-1022, vol. 67, Allergy.

Neumann, et al., "The therapeutic potential of histamine receptor ligands in inflammatory bowel disease", 2014, pp. 12-17, vol. 91, Biochemical Pharmacology.

Rosa, et al., "Prevention of Bleomycin-Induced Lung Inflammation and Fibrosis in Mice by Naproxen and JNJ7777120 Treatment", 2014, pp. 308-316, vol. 351, J Pharmacol Exp Ther.

Ohki, et al., "Expression of Histamine $H_4$ Receptor in Synovial Cells from Rheumatoid Arthritic Patients", 2007, pp. 2217-2220, vol. 30, No. 11, Biol. Pharm. Bull.

Thurmond, et al., "A Potent and Selective Histamine $H_4$ Receptor Antagonist with Anti-Inflammatory Properties", 2004, pp. 404-413, vol. 309, No. 1, The Journal of Pharmacology and Experimental Therapeutics.

Varga, et al., "Inhibitory effects of histamine $H_4$ receptor antagonists on experimental colitis in the rat", 2005, pp. 130-138, vol. 522, European Journal of Pharmacology.

Yu, et al., "Copy number variations of the human histamine $H_4$ receptor gene are associated with systemic lupus erythematosus", 2010, pp. 935940, vol. 163, British Journal of Dermatology.

Thurmond, et al., "The role of histamine $H_1$ and $H_4$ receptors in allergic inflammation: the search for new antihistamines", Jan. 2008, pp. 41-53, vol. 7, Nature Reviews/Drug Discovery.

Murata, et al., "Phase 2a, randomized, double-blind, placebo-controlled, multicenter, parallel-group study of a H4R-antagonist (JNJ-39758979) in Japanese adults with moderate atopic dermatitis" 2015, pp. 129-139, vol. 42, Journal of Dermatology.

Ling, et al., "Histamine H4 receptor mediates eosinophil chemotaxis with cell shape change and adhesion molecule upregulation" 2004, pp. 161-171, vol. 142, British Journal of Pharmacology.

Shiraishi, et al., "Sequential Engagement of EceRI on Mast Cells in Basophil Histamine $H_4$ Receptor and FceRI in Allertic Rhinitis", 2013, pp. 539-548, vol. 190, J Immunol.

Martinel Lamas, et al., "Protection of Radiation-Induced Damage to the Hematopoietic System, Small Intestine and Salivary Glands in Rats by JNJ7777120 Compound, a Histamine Ligand", Jul. 2013, pp. 1-13, vol. 8, No. 7, Plos One.

Nakano, et al., "Role of histamine H4 receptor in allergic conjunctivitis in mice", 2009, pp. 71-75, vol. 608, European Journal of Pharmacology.

6,11-DIHYDRO-5H-BENZO[D]IMIDAZO[1,2-A]AZEPINES DERIVATIVES AS HISTAMINE H4 RECEPTOR LIGANDS

The present patent application concerns new 6,11-dihydro-5H-benzo[d]imidazo[1,2-a]azepines ligands of the H4-receptor, their process of preparation and their therapeutic use.

Until recently, the pro-inflammatory actions of histamine were thought to be essentially mediated by the H1 receptor and H1 receptor antagonists have found large therapeutic applications in allergic manifestations like the anaphylactic shock, allergic rhinitis, dermatitis, pruritus, etc.

However these drugs essentially prevent the occurrence of major symptoms of these manifestations without modifying clearly the progressive development of the inflammatory process leading to chronic diseases like asthma in which, however, histamine release from mast-cells might represent an important trigger (reviewed in Galli et al, Nature, 2008, 454, 445).

The recent discovery of the histamine H4 receptor (H4R) has modified this landscape (reviewed in Thurmond et al, Nature Rev. Drug Disc., 2008, 7, 41). The H4R belongs to the superfamily of G-protein coupled heptahelical receptors and is expressed on the plasma membranes of a variety of immunocompetent/inflammatory cells, e.g. eosinophils, basophils, mast-cells or dendritic cells. The H4R has a chimiotactic role, controlling the afflux of e.g. mast-cells or eosinophils to inflammatory sites that is elicited by histamine release and, thereby plays a major role in the development of chronic inflammatory disorders. It also controls the activity of eosinophils and some classes of lymphocytes. Blockade of the H4R by antagonists or inverse agonists should therefore constitute a novel therapeutic approach in diseases like asthma, emphysema, allergic rhinitis, nasal congestion, bronchitis, chronic obstructive pulmonary disease, dermatitis, arthritis, psoriasis, colitis, etc. in which they could be used alone or in association with already used other classes of anti-inflammatory medications, namely H1R antagonists. In addition the utilisation of H4R antagonists/inverse agonists is also of potential interest in a variety of autoimmune diseases e.g. type I diabetes, Crohn's disease, multiple sclerosis, lupus, etc. . . . The itch-preventing effect of some H4R antagonists in a rodent model (Bell et al, Br J Pharmacol, 2004, 142, 374) also suggests the use of these agents in pruritus, a manifestation only imperfectly controlled by available medications, namely H1R antagonists.

H4R antagonists/inverse agonists have not yet reached clinical uses and there is therefore a need for compounds displaying high potency and safety. In the present application a novel chemical class of H4R ligands is disclosed.

The instant invention thus relates to novel 6,11-dihydro-5H-benzo[d]imidazo[1,2-a]azepines derivatives as H4 receptor ligands, to their preparation and to their application in therapeutics.

The present invention concerns new compounds of formula (I):

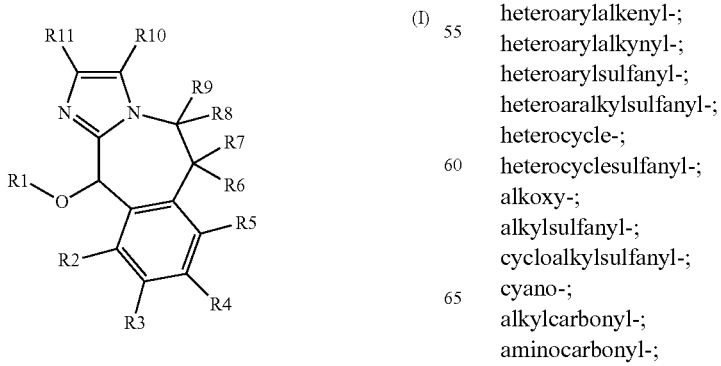

wherein
R1 is chosen from:
an alkyl optionally substituted by an amino, alkylamino, dialkylamino group or a monocyclic or bicyclic heterocycle possessing a nitrogen atom; and
a monocyclic or bicyclic heterocycle possessing a nitrogen atom, said heterocycle being optionally substituted by an alkyl group;
R2, R3, R4 and R5 identical or different are independently chosen from:
hydrogen-;
halogen-;
alkyl-;
alkenyl-;
optionally substituted aryl-;
aralkyl-;
alkylamino-;
dialkylamino-;
alkoxy-;
aralkoxy-;
alkylsulfanyl-;
R6, R7, R8 and R9 identical or different are independently chosen from:
hydrogen-;
alkyl-;
R10 and R11 identical or different are independently chosen from the following list L1:
hydrogen-;
halogen-;
alkyl-;
cycloalkyl-;
cyloalkylalkyl-;
cycloalkylalkenyl;
alkenyl-;
cycloalkenyl-;
alkynyl-;
aryl-;
aralkyl-;
aralkenyl-;
aralkynyl-;
aralkoxyalkyl-;
aryloxyalkyl-;
aralkoxyalkenyl-;
aryloxyalkenyl-;
arylcarbonyl-;
arylsulfanyl-;
aralkylsulfanyl-;
heteroaryl-;
heteroarylalkyl-;
heteroarylalkenyl-;
heteroarylalkynyl-;
heteroarylsulfanyl-;
heteroaralkylsulfanyl-;
heterocycle-;
heterocyclesulfanyl-;
alkoxy-;
alkylsulfanyl-;
cycloalkylsulfanyl-;
cyano-;
alkylcarbonyl-;
aminocarbonyl-;

alkylaminocarbonyl-;
dialkylaminocarbonyl-;
arylaminocarbonyl-;
aralkylaminocarbonyl-;
N-alkyl-arylaminocarbonyl-;
N-alkyl-aralkylaminocarbonyl-;
alkoxycarbonyl-;
alkoxycarbonylalkyl-;
alkoxycarbonylalkenyl-;
alkoxycarbonylalkynyl-;
alkoxycarbonylheterocycle-;
alkoxycarbonylheterocyclesulfanyl-;
the aryl and heteroaryl groups being optionally substituted with one or more:
halogen-;
hydroxyl-;
nitro-;
alkyl-;
(per)halogenoalkyl-;
alkenyl-;
alkynyl-;
cycloalkyl-;
cycloalkenyl-;
alkylcarbonyl-;
(per)halogenoalkylcarbonyl-;
cycloalkylalkyl-;
alkoxy-;
(per)halogenoalkoxy-;
alkoxyalkyl-;
alkenyloxy-;
akynyloxy-;
hydroxyalkyl-;
amino-;
alkylamino-;
dialkylamino-;
aminoalkyl-;
alkylaminoalkyl-;
dialkylaminoalkyl-;
aminoalkoxy-;
alkylaminoalkoxy-;
dialkylaminoalkoxy-;
alkylsulfonyl-;
alkylsulfanyl-;
alkylsulfonylalkyl-;
alkylsulfanylalkyl-;
alkylsulfonylalkenyl-;
alkylsulfanylalkenyl-;
alkylsulfonylalkynyl-;
alkylsulfanylalkynyl-;
hydroxyalkylsufanyl-;
aminoalkylsulfanyl-;
cycloalkylsulfonylamino-;
alkoxycarbonylaminoalkylsulfanyl-;
alkylcarbonylaminoalkylsulfanyl-;
guanidinoalkylsulfanyl-;
sulfamoyl-;
alkylsulfamoyl-;
dialkylsulfamoyl-;
cyano-;
cyanoalkyl-;
aryl-;
arylcarbonyl-;
aralkyl-;
aralkenyl-;
aralkynyl-;
arylsulfanyl-;
aralkylsulfanyl-;
heteroaryl-;
heteroarycarbonyl-;
heteroaralkyl-;
heteroaralkenyl-;
heteroaralkynyl-;
heteroarylsulfanyl-;
heteroaralkylsulfanyl-;
alkoxycarbonyl-;
alkoxycarbonylamino-;
(per)halogenoalkoxycarbonylamino-;
alkoxyalkylcarbonylaminoalkyl-;
cycloalkylalkoxy-;
cycloalkylalkoxycarbonylamino-;
N-alkyl-alkoxycarbonylamino-;
N-alkyl-aminocarbonyloxyalkyl-;
alkoxycarbonylhydrazinyl-;
alkylcarbonylamino-;
hydroxyalkylaminocarbonyl-;
alkoxyalkylcarbonylamino-;
N-alkyl-alkylcarbonylamino-;
2-oxopyrrolidin-1-yl-;
2-oxopiperidin-1-yl-;
2-oxoperhydroazepin-1-yl-;
2-oxo-1,3-oxazolidin-3-yl-;
4-aralkyl-2-oxo-1,3-oxazolidin-3-yl-;
2-oxoimidazolidin-1-yl-;
3-alkyl-2-oxoimidazolidin-1-yl-;
2-oxopyrrolidin-1-ylalkyl-;
2-oxopiperidin-1-ylalkyl-;
2-oxoperhydroazepin-1-ylalkyl-;
2-oxo-1,3-oxazolidin-3-ylalkyl-;
4-aralkyl-2-oxo-1,3-oxazolidin-3-ylalkyl-;
5,5-dialkyl-2,4-dioxo-1,3-oxazolidin-3-ylalkyl-;
2-oxoimidazolidin-1-ylalkyl-;
3-alkyl-2-oxoimidazolidin-1-ylalkyl-;
hydroxyheterocyclylcarbonyl-;
hydroxycycloalkylaminocarbonyl-;
hydroxyheterocyclylaminocarbonyl-;
alcoxycarbonylheterocyclyl-;
oxoheterocyclylcarbonyl-;
alkoxycarbonylalkyl-;
alkoxycarbonylalkenyl-;
alkoxycarbonylalkynyl-;
alkoxycarbonylalkylsulfanyl-;
alkoxycarbonylaminoalkyl-;
N-alkyl-alkoxycarbonylaminoalkyl-;
alkylcarbonylaminoalkyl-;
N-alkyl-acylaminoalkyl-;
ureido-;
alkylureido-;
cycloalkylureido-;
adamantylureido-;
thioureido-;
alkylthioureido-;
cycloalkylthioureido-;
oxo-;
the alkyl, alkenyl, alkynyl chains of L1 being optionally substituted with one or more:
halogen-;
hydroxyl-;
alkoxycarbonylamino-;
as well as its enantiomers, diastereomers, mixtures thereof and pharmaceutically acceptable salts, tautomers, hydrates and solvates.

Unless specified otherwise, the terms used hereabove or hereafter have the meaning ascribed to them below:

"halogen" refers to fluorine, chlorine, bromine or iodine atom.

"alkyl" represents an aliphatic-hydrocarbon group which may be straight or branched having 1 to 8 carbon atoms in the chain unless specified otherwise. Preferred alkyl groups have 1 to 6 carbon atoms in the chain. Branched means that one or more alkyl groups such as methyl, ethyl or propyl are attached to a linear alkyl chain. Exemplary alkyl groups include methyl, ethyl, n-propyl, i-propyl, n-butyl, t-butyl, 2,2-dimethylbutyl, n-pentyl, n-hexyl, octyl.

"alkenyl" refers to an aliphatic hydrocarbon group containing a carbon-carbon double bond and which may be straight or branched having 2 to 8 carbon atoms in the chain unless specified otherwise. Preferred alkenyl groups have 2 to 6 carbon atoms in the chain. Exemplary alkenyl groups include ethenyl, n-propenyl, i-propenyl, n-butenyl, i-butenyl, 2,2-dimethylbut-1-enyl, n-pentenyl, heptenyl, octenyl.

"alkynyl" refers to an aliphatic hydrocarbon group containing a carbon-carbon triple bond and which may be straight or branched having 2 to 8 carbon atoms in the chain unless specified otherwise. Preferred alkynyl groups have 2 to 6 carbon atoms in the chain. Exemplary alkynyl groups include ethynyl, propynyl, n-butynyl, 2-butynyl, 3-methyl-1-butynyl, n-pentynyl, heptynyl, octynyl.

"cycloalkyl" refers to a saturated non-aromatic monocyclic hydrocarbon ring system of 3 to 10 carbon atoms. Preferred ring sizes of rings of the ring system include 3 to 8 ring atoms. Exemplary monocyclic cycloalkyl include cyclopropyl, cyclopentyl, cyclohexyl, and the like.

"cycloalkenyl" refers to a cycloalkyl as herein described containing a carbon-carbon double bond. Exemplary cycloalkenyl include cyclopentenyl, cyclohexenyl, cycloheptenyl, and the like.

"aryl" refers to an aromatic monocyclic or multicyclic hydrocarbon ring system of 6 to 14 carbon atoms, preferably of 6 to 10 carbon atoms. Exemplary aryl groups include phenyl, naphthyl, benzyl, phenanthryl, biphenyl.

"heterocycle" or "heterocyclyl" refer to a saturated or partially unsaturated non aromatic stable 3 to 14, preferably 5 to 10-membered mono, bi or multicyclic rings which can optionally be bridged and wherein at least one member of the ring is a hetero atom. Typically, heteroatoms include, but are not limited to, oxygen, nitrogen, sulfur, selenium, and phosphorus atoms. Preferable heteroatoms are oxygen, nitrogen and sulfur. Suitable heterocycles are also disclosed in the *Handbook of Chemistry and Physics,* 76th Edition, CRC Press, Inc., 1995-1996, pages 2-25 to 2-26, the disclosure of which is hereby incorporated by reference. Preferred heterocyclyl include, but are not limited to tetrahydropyridyl, tetraydrofuranyl, dioxolanyl, tetrahydropyranyl, dioxanyl, pyrrolidinyl, piperidyl, morpholinyl, imidazolidinyl, pyranyl, dihydropyranyl, thiopyranyl, dihydrothiopyranyl, 8-aza-bicyclo[3.2.1]oct-3-yl, azetidin-3-ylmethyl, piperidin-4-yl, pyrrolidin-3-yl, quinoclidin-3-yl, benzodioxole. Preferred heterocycles are chosen from piperidyl, tetrahydropyridyl, dihydropyranyl, dihydrothiopyranyl, 8-aza-bicyclo[3.2.1]oct-3-yl, azetidin-3-ylmethyl, piperidin-4-yl, pyrrolidin-3-yl, quinoclidin-3-yl, benzodioxole.

"heteroaryl" refers to a 5 to 14, preferably 5 to 10 membered aromatic mono-, bi- or multicyclic ring wherein at least one member of the ring is a hetero atom. Examples include pyrrolyl, pyridyl, piperidinyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazoyl, tetrazolyl, isoquinolyl, benzothienyl, isobenzofuryl, pyrazolyl, carbazolyl, benzimidazolyl, oxazolyl.

"aralkyl" refers to an arylalkyl group, the "aryl" and "alkyl" groups being as herein described.

"heteroaralkyl" refers to an heteroaryl group, the "heteroaryl" and "alkyl" groups being as herein described.

"aralkoxy" refers to an arylalkoxy group, the "aryl" and "alkoxy" groups being as herein described.

"aralkenyl" refers to an arylalkenyl group, the "aryl" and "alkenyl" groups being as herein described.

"aralkynyl" refers to an arylalkynyl group, the "aryl" and "alkynyl" groups being as herein described.

"sulfanyl" refers to a radical —S—. Ths radical can be linked for example to an alkyl, cycloalkyl, aryl, aralkyl, heteroaryl or an heteroaralkyl group as herein described.

"ureido" refers to a radical NH—CO—NH$_2$. This radical can be linked for example to an alkyl or cycloalkyl group as herein described.

"thioureido" refers to radical —NH—S—NH$_2$. This radical can be linked for example to an alkyl or cycloalkyl group as herein described.

"guanidino" refers to a radical:

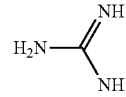

"sulfamoyl" refers to a radical NH$_2$—SO$_2$—;

A first group of compounds according to the invention may be defined by compounds of formula (I) wherein:

R1 is chosen from:

an alkyl optionally substituted by an amino, alkylamino, dialkylamino group or a monocyclic or bicyclic heterocycle possessing a nitrogen atom; and a monocyclic or bicyclic heterocycle possessing a nitrogen atom, said heterocycle being optionally substituted by an alkyl group;

R2, R3, R4 and R5 identical or different are independently chosen from:

hydrogen-;
halogen-;
alkyl-;
alkenyl-;
optionally substituted aryl-;
aralkyl-;
alkylamino-;
alkoxy-;
aralkoxy-;
alkylsulfanyl-;

R6, R7, R8 and R9 identical or different are independently chosen from:

hydrogen-;
alkyl-;

R10 and R11 identical or different are independently chosen from the following list L2:

hydrogen-;
halogen-;
alkyl-;

cycloalkyl-;
cyloalkylalkyl-;
cycloalkylalkenyl;
alkenyl-;
cycloalkenyl-;
alkynyl-;
aryl-;
aralkyl-;
aralkenyl-;
aralkynyl-;
aryloxyalkyl-;
aralkoxyalkenyl-;
aryloxyalkenyl-;
arylcarbonyl-;
arylsulfanyl-;
aralkylsulfanyl-;
heteroaryl-;
heteroarylalkyl-;
heteroarylalkenyl-;
heteroarylalkynyl-;
heteroarylsulfanyl-;
heteroaralkylsulfanyl-;
heterocycle-;
heterocyclesulfanyl-;
alkoxy-;
alkylsulfanyl-;
cycloalkylsulfanyl-;
cyano-;
alkylcarbonyl-;
aminocarbonyl-;
alkylaminocarbonyl-;
arylaminocarbonyl-;
aralkylaminocarbonyl-;
N-alkyl-arylaminocarbonyl-;
N-alkyl-aralkylaminocarbonyl-;
alkoxycarbonyl-;
alkoxycarbonylalkyl-;
alkoxycarbonylalkenyl-;
alkoxycarbonylalkynyl-;
alkoxycarbonylheterocycle-;
alkoxycarbonylheterocyclesulfanyl-;
the aryl and heteroaryl groups being optionally substituted with one or more:
halogen-;
hydroxyl-;
nitro-;
alkyl-;
(per)halogenoalkyl-;
cycloalkenyl-;
alkylcarbonyl-;
(per)halogenoalkylcarbonyl-;
cycloalkylalkyl-;
alkoxy-;
(per)halogenoalkoxy-;
alkoxyalkyl-;
alkenyloxy-;
hydroxyalkyl-;
amino-;
alkylamino-;
dialkylamino-;
aminoalkyl-;
dialkylaminoalkyl-;
dialkylaminoalkoxy-;
alkylsulfonyl-;
alkylsulfanyl-;
alkylsulfonylalkyl-;
alkylsulfanylalkyl-;
alkylsulfonylalkenyl-;
alkylsulfanylalkenyl-;
alkylsulfanylalkynyl-;
hydroxyalkylsufanyl-;
aminoalkylsulfanyl-;
cycloalkylsulfonylamino-;
alkoxycarbonylaminoalkylsulfanyl-;
alkylcarbonylaminoalkylsulfanyl-;
guanidinoalkylsulfanyl-;
sulfamoyl-;
alkylsulfamoyl-;
dialkylsulfamoyl-;
cyano-;
aralkylsulfanyl-;
heteroaryl-;
heteroaralkylsulfanyl-;
alkoxycarbonyl-;
alkoxycarbonylamino-;
(per)halogenoalkoxycarbonylamino-;
alkoxyalkylcarbonylaminoalkyl-;
cycloalkylalkoxy-;
cycloalkylalkoxycarbonylamino-;
N-alkyl-alkoxycarbonylamino-;
N-alkyl-aminocarbonyloxyalkyl-;
alkoxycarbonylhydrazinyl-;
alkylcarbonylamino-;
hydroxyalkylaminocarbonyl-;
N-alkyl-alkylcarbonylamino-;
2-oxopyrrolidin-1-yl-;
2-oxopiperidin-1-yl-;
2-oxoperhydroazepin-1-yl-;
2-oxo-1,3-oxazolidin-3-yl-;
4-aralkyl-2-oxo-1,3-oxazolidin-3-yl-;
3-alkyl-2-oxoimidazolidin-1-yl-;
2-oxopyrrolidin-1-ylalkyl-;
2-oxopiperidin-1-ylalkyl-;
2-oxoperhydroazepin-1-ylalkyl-;
2-oxo-1,3-oxazolidin-3-ylalkyl-;
5,5-dialkyl-2,4-dioxo-1,3-oxazolidin-3-ylalkyl-;
2-oxoimidazolidin-1-ylalkyl-;
3-alkyl-2-oxoimidazolidin-1-ylalkyl-;
hydroxyheterocyclylcarbonyl-;
hydroxycycloalkylaminocarbonyl-;
hydroxyheterocyclylaminocarbonyl-;
alcoxycarbonylheterocyclyl-;
oxoheterocyclylcarbonyl-;
alkoxycarbonylalkenyl-;
alkoxycarbonylalkylsulfanyl-;
alkoxycarbonylaminoalkyl-;
N-alkyl-alkoxycarbonylaminoalkyl-;
alkylcarbonylaminoalkyl-;
N-alkyl-acylaminoalkyl-;
alkylureido-;
cycloalkylureido-;
adamantylureido-;
alkylthioureido-;
cycloalkylthioureido-;
oxo-;
the alkyl, alkenyl, alkynyl chains of L2 being optionally substituted with one or more:
halogen-;
hydroxyl-;
alkoxycarbonylamino-;
as well as its enantiomers, diastereomers, mixtures thereof and pharmaceutically acceptable salts, tautomers, hydrates and solvates.

Another group of compounds according to the invention may be defined by compounds of formula (I) wherein:
R1 is a monocyclic or bicyclic heterocycle possessing a nitrogen atom, said heterocycle being optionally substituted by an alkyl group;
R2, R3, R4, R5, R6, R7, R8 and R9 are hydrogen;
R10 represents:
hydrogen-;
halogen-;
alkyl-;
cyano-;
R11 is chosen from the following list L3:
halogen-;
alkyl-;
cycloalkyl-;
cycloalkylalkenyl;
a cyloalkylalkyl-;
alkenyl-;
cycloalkenyl-;
alkynyl-;
aryl-;
a aralkyl-;
aralkenyl-;
aralkylsulfanyl-;
aryloxyalkenyl-;
heteroaryl-;
a heteroarylalkenyl-;
a heteroarylsulfanyl-;
a cycloalkylsulfanyl-;
the aryl and heteroaryl groups being optionally substituted with one or more:
halogen-;
alkyl-;
(per)halogenoalkyl-;
cycloalkyl-;
cycloalkenyl-;
alkylcarbonyl-;
(per)halogenoalkylcarbonyl-;
alkenyloxy-;
alkoxy-;
(per)halogenoalkoxy-;
alkoxyalkyl-;
alkylsulfanyl-;
alkylsulfonylalkyl-;
alkylsulfonylalkenyl-;
hydroxyalkylsufanyl-;
aminoalkylsulfanyl-;
alkoxycarbonylaminoalkylsulfanyl-;
alkylcarbonylaminoalkylsulfanyl-;
alkoxycarbonylalkylsulfanyl-;
guanidinoalkylsulfanyl-;
cyano-;
aralkylsulfanyl-;
heteroaralkylsulfanyl-;
alkoxycarbonyl-;
alkoxycarbonylamino-;
(per)halogenoalkoxycarbonylamino-;
cycloalkylalkoxycarbonylamino-;
alkoxycarbonylhydrazinyl-;
N-alkyl-alkoxycarbonylamino-;
N-alkyl-alkoxycarbonylaminoalkyl-;
3-alkyl-2-oxoimidazolidin-1-yl-;
4-aralkyl-2-oxo-1,3-oxazolidin-3-yl-;
alcoxycarbonylheterocyclyl-;
alkoxycarbonylalkyl-;
alkoxycarbonylaminoalkyl-;
alkylureido-;
cycloalkylureido-;
adamantylureido-;
alkylthioureido-;
the alkyl, alkenyl, alkynyl chains of L3 being optionally substituted with one or more:
halogen-;
hydroxyl-;
alkoxycarbonylamino-;
as well as its enantiomers, diastereomers, mixtures thereof and pharmaceutically acceptable salts, tautomers, hydrates and solvates.

A further group of compounds according to the invention may be defined by compounds of formula (I) wherein:
R1 is chosen from:
8-Me-8-aza-bicyclo[3.2.1]oct-yl-;
Dimethylaminoethyl-;
Dimethylaminopropyl-;
N-Me-azetidin-3-ylmethyl-;
N-Me-piperidin-4-yl-;
N-Me-pyrrolidin-3-yl-;
Piperidinoethyl-;
Quinuclidin-3-yl-;
R1 being preferably N-Me-piperidin-4-yl;
R2, R3, R4 and R5, R6, R7, R8 and R9 each represent hydrogen;
R10 represents:
hydrogen-;
halogen-;
alkyl-;
cyano-;
R11 is chosen from the following list L4:
halogen-;
alkyl-;
cycloalkyl-;
cyloalkylalkyl-;
cycloalkylalkenyl;
alkenyl-;
cycloalkenyl-;
alkynyl-;
aryl-;
aralkyl-;
aralkenyl-;
aralkylsulfanyl-;
aryloxyalkenyl-;
heteroaryl-;
heteroarylalkenyl-;
heteroarylsulfanyl-;
cycloalkylsulfanyl-;
the aryl and heteroaryl groups being optionally substituted with one or more:
halogen-;
alkyl-;
(per)halogenoalkyl-;
cycloalkyl-;
cycloalkenyl-;
alkylcarbonyl-;
(per)halogenoalkylcarbonyl-;
alkenyloxy-;
alkoxy-;
(per)halogenoalkoxy-;
alkoxyalkyl-;
alkylsulfanyl-;
alkylsulfonylalkyl-;
alkylsulfonylalkenyl-;
hydroxyalkylsufanyl-;
aminoalkylsulfanyl-;
alkoxycarbonylaminoalkylsulfanyl-;

alkylcarbonylaminoalkylsulfanyl-;
alkoxycarbonylalkylsulfanyl-;
guanidinoalkylsulfanyl-;
cyano-;
aralkylsulfanyl-;
heteroaralkylsulfanyl-;
alkoxycarbonyl-;
alkoxycarbonylamino-;
(per)halogenoalkoxycarbonylamino-;
cycloalkylalkoxycarbonylamino-;
alkoxycarbonylhydrazinyl-;
N-alkyl-alkoxycarbonylamino-;
N-alkyl-alkoxycarbonylaminoalkyl-;
3-alkyl-2-oxoimidazolidin-1-yl-;
4-aralkyl-2-oxo-1,3-oxazolidin-3-yl-;
alcoxycarbonylheterocyclyl-;
alkoxycarbonylalkyl-;
alkoxycarbonylaminoalkyl-;
alkylureido-;
cycloalkylureido-;
adamantylureido-;
alkylthioureido-;
the alkyl, alkenyl, alkynyl chains of L4 being optionally substituted with one or more:
    halogen-;
    hydroxyl-;
    alkoxycarbonylamino-;
as well as its enantiomers, diastereomers, mixtures thereof and pharmaceutically acceptable salts, tautomers, hydrates and solvates.

In one preferred embodiment, the present invention provides a compound selected from the group consisting of:
4-(1-Methyl-piperidin-4-yloxy)-2-trifluoromethyl-9,10-dihydro-4H-3,10a-diaza-benzo[f]azulene
4-(1-Methyl-piperidin-4-yloxy)-1-trifluoromethyl-9,10-dihydro-4H-3,10a-diaza-benzo[f]azulene
2-Iodo-4-(1-methyl-piperidin-4-yloxy)-9,10-dihydro-4H-3,10a-diaza-benzo[f]azulene
1-Iodo-4-(1-methyl-piperidin-4-yloxy)-9,10-dihydro-4H-3,10a-diaza-benzo[f]azulene
4-(1-Methyl-piperidin-4-yloxy)-2-phenyl-9,10-dihydro-4H-3,10a-diaza-benzo[f]azulene
4-(1-Methyl-piperidin-4-yloxy)-2-p-tolyl-9,10-dihydro-4H-3,10a-diaza-benzo[f]azulene
4-(1-Methyl-piperidin-4-yloxy)-2-m-tolyl-9,10-dihydro-4H-3,10a-diaza-benzo[f]azulene
2-Iodo-4-(1-methyl-azetidin-3-ylmethoxy)-9,10-dihydro-4H-3,10a-diaza-benzo[f]azulene
4-(1-Methyl-piperidin-4-yloxy)-2-o-tolyl-9,10-dihydro-4H-3,10a-diaza-benzo[f]azulene
4-(1-Methyl-piperidin-4-yloxy)-2-vinyl-9,10-dihydro-4H-3,10a-diaza-benzo[f]azulene
2-(4-tert-Butyl-phenyl)-4-(1-methyl-piperidin-4-yloxy)-9,10-dihydro-4H-3,10a-diaza-benzo[f]azulene
1-{4-[4-(1-Methyl-piperidin-4-yloxy)-9,10-dihydro-4H-3,10a-diaza-benzo[f]azulen-2-yl]-phenyl}-ethanone
4-(1-Methyl-piperidin-4-yloxy)-2-thiophen-3-yl-9,10-dihydro-4H-3,10a-diaza-benzo[f]azulene
2-Ethyl-4-(1-methyl-piperidin-4-yloxy)-9,10-dihydro-4H-3,10a-diaza-benzo[f]azulene
2-(4-Methoxy-phenyl)-4-(1-methyl-piperidin-4-yloxy)-9,10-dihydro-4H-3,10a-diaza-benzo[f]azulene
4-(1-Methyl-piperidin-4-yloxy)-2-(4-trifluoromethoxy-phenyl)-9,10-dihydro-4H-3,10a-diaza-benzo[f]azulene
4-[4-(1-Methyl-piperidin-4-yloxy)-9,10-dihydro-4H-3,10a-diaza-benzo[f]azulen-2-yl]-phenylamine
2-(4-Methanesulfonyl-phenyl)-4-(1-methyl-piperidin-4-yloxy)-9,10-dihydro-4H-3,10a-diaza-benzo[f]azulene
{4-[4-(1-Methyl-piperidin-4-yloxy)-9,10-dihydro-4H-3,10a-diaza-benzo[f]azulen-2-yl]-phenyl}-methanol
2-(4-Methoxymethyl-phenyl)-4-(1-methyl-piperidin-4-yloxy)-9,10-dihydro-4H-3,10a-diaza-benzo[f]azulene
4-(1-Methyl-piperidin-4-yloxy)-2-(4-methylsulfanyl-phenyl)-9,10-dihydro-4H-3,10a-diaza-benzo[f]azulene
4-(1-Methyl-piperidin-4-yloxy)-2-(4-methylsulfanyl-phenyl)-9,10-dihydro-4H-3,10a-diaza-benzo[f]azulene
4-(1-Methyl-piperidin-4-yloxy)-2-(4-propyl-phenyl)-9,10-dihydro-4H-3,10a-diaza-benzo[f]azulene
4-(1-Methyl-piperidin-4-yloxy)-2-pyridin-2-yl-9,10-dihydro-4H-3,10a-diaza-benzo[f]azulene
2-Furan-2-yl-4-(1-methyl-piperidin-4-yloxy)-9,10-dihydro-4H-3,10a-diaza-benzo[f]azulene
4-(1-Methyl-piperidin-4-yloxy)-2-(4-trifluoromethyl-phenyl)-9,10-dihydro-4H-3,10a-diaza-benzo[f]azulene
2-(2-Chloro-phenyl)-4-(1-methyl-piperidin-4-yloxy)-9,10-dihydro-4H-3,10a-diaza-benzo[f]azulene
2-(2-Fluoro-phenyl)-4-(1-methyl-piperidin-4-yloxy)-9,10-dihydro-4H-3,10a-diaza-benzo[f]azulene
2-(4-Isobutyl-phenyl)-4-(1-methyl-piperidin-4-yloxy)-9,10-dihydro-4H-3,10a-diaza-benzo[f]azulene
N,N-Dimethyl-4-[4-(1-methyl-piperidin-4-yloxy)-9,10-dihydro-4H-3,10a-diaza-benzo[f]azulen-2-yl]-benzenesulfonamide
2-Allyl-4-(1-methyl-piperidin-4-yloxy)-9,10-dihydro-4H-3,10a-diaza-benzo[f]azulene
2,2,2-Trifluoro-1-{4-[4-(1-methyl-piperidin-4-yloxy)-9,10-dihydro-4H-3,10a-diaza-benzo[f]azulen-2-yl]-phenyl}-ethanone
2-(4-Isopropyl-phenyl)-4-(1-methyl-piperidin-4-yloxy)-9,10-dihydro-4H-3,10a-diaza-benzo[f]azulene
{4-[4-(1-Methyl-piperidin-4-yloxy)-9,10-dihydro-4H-3,10a-diaza-benzo[f]azulen-2-yl]-phenyl}-acetonitrile
4-(1-Methyl-piperidin-4-yloxy)-2-phenylethynyl-9,10-dihydro-4H-3,10a-diaza-benzo[f]azulene
Dimethyl-{4-[4-(1-methyl-piperidin-4-yloxy)-9,10-dihydro-4H-3,10a-diaza-benzo[f]azulen-2-yl]-phenyl}-amine
4-[4-(1-Methyl-piperidin-4-yloxy)-9,10-dihydro-4H-3,10a-diaza-benzo[f]azulen-2-yl]-benzoic acid tert-butyl ester
4-[4-(1-Methyl-piperidin-4-yloxy)-9,10-dihydro-4H-3,10a-diaza-benzo[f]azulen-2-yl]-benzonitrile
4-(1-Methyl-piperidin-4-yloxy)-2-phenethyl-9,10-dihydro-4H-3,10a-diaza-benzo[f]azulene
4-(1-Methyl-piperidin-4-yloxy)-2-(6-methyl-pyridin-3-yl)-9,10-dihydro-4H-3,10a-diaza-benzo[f]azulene
4-(1-Methyl-piperidin-4-yloxy)-2-oxazol-2-yl-9,10-dihydro-4H-3,10a-diaza-benzo[f]azulene
2-(4-Butyl-phenyl)-4-(1-methyl-piperidin-4-yloxy)-9,10-dihydro-4H-3,10a-diaza-benzo[f]azulene
2-(4-Butyl-phenyl)-4-(1-methyl-piperidin-4-yloxy)-9,10-dihydro-4H-3,10a-diaza-benzo[f]azulene
4-(1-Methyl-piperidin-4-yloxy)-2-(4-pentyl-phenyl)-9,10-dihydro-4H-3,10a-diaza-benzo[f]azulene
2-(4-Hexyl-phenyl)-4-(1-methyl-piperidin-4-yloxy)-9,10-dihydro-4H-3,10a-diaza-benzo[f]azulene
4-(1-Methyl-piperidin-4-yloxy)-2-pyridin-4-yl-9,10-dihydro-4H-3,10a-diaza-benzo[f]azulene
4-(1-Methyl-piperidin-4-yloxy)-2-pyridin-3-yl-9,10-dihydro-4H-3,10a-diaza-benzo[f]azulene
2-(4-Ethylsulfanyl-phenyl)-4-(1-methyl-piperidin-4-yloxy)-9,10-dihydro-4H-3,10a-diaza-benzo[f]azulene
4-(1-Methyl-piperidin-4-yloxy)-2-thiophen-2-yl-9,10-dihydro-4H-3,10a-diaza-benzo[f]azulene 4-(1-Methyl-piperidin-4-yloxy)-2-thiazol-5-yl-9,10-dihydro-4H-3,10a-diaza-benzo[f]azulene {4-[4-(1-Methyl-piperidin-4-yloxy)-9,10-dihydro-4H-3,10a-diaza-benzo[f]azulen-2-yl]-phenyl}-carbamic acid tert-butyl ester 2-Benzo[1,3]dioxol-5-yl-4-(1-methyl-piperidin-4-yloxy)-9,10-dihydro-4H-3,10a-diaza-benzo[f]azulene 2-(5-Methyl-furan-2-yl)-4-(1-methyl-piperidin-4-yloxy)-9,10-dihydro-4H-3,10a-diaza-benzo[f]azulene 2-(4-Chloro-phenyl)-4-(1-methyl-piperidin-4-yloxy)-9,10-dihydro-4H-3,10a-diaza-benzo[f]azulene 3-[4-(1-Methyl-piperidin-4-yloxy)-9,10-dihydro-4H-3,10a-diaza-benzo[f]azulen-2-yl]-acrylic acid tert-butyl ester 2-(2-Chloro-phenyl)-4-(1-methyl-piperidin-4-yloxy)-9,10-dihydro-4H-3,10a-diaza-benzo[f]azulene 4-(1-Methyl-piperidin-4-yloxy)-2-(2-methyl-4-trifluoromethyl-phenyl)-9,10-dihydro-4H-3,10a-diaza-benzo[f]azulene 2-(4-Fluoro-phenyl)-4-(1-methyl-piperidin-4-yloxy)-9,10-dihydro-4H-3,10a-diaza-benzo[f]azulene 2-(3,6-Dihydro-2H-thiopyran-4-yl)-4-(1-methyl-piperidin-4-yloxy)-9,10-dihydro-4H-3,10a-diaza-benzo[f]azulene 2,2-Dimethyl-N-{4-[4-(1-methyl-piperidin-4-yloxy)-9,10-dihydro-4H-3,10a-diaza-benzo[f]azulen-2-yl]-phenyl}-propionamide 2-(2-Cyclohexyl-vinyl)-4-(1-methyl-piperidin-4-yloxy)-9,10-dihydro-4H-3,10a-diaza-benzo[f]azulene 1-{4-[4-(1-Methyl-piperidin-4-yloxy)-9,10-dihydro-4H-3,10a-diaza-benzo[f]azulen-2-yl]-phenyl}-3-propyl-urea 2-(2,4-Dimethyl-phenyl)-4-(1-methyl-piperidin-4-yloxy)-9,10-dihydro-4H-3,10a-diaza-benzo[f]azulene 2-Cyclohex-1-enyl-4-(1-methyl-piperidin-4-yloxy)-9,10-dihydro-4H-3,10a-diaza-benzo[f]azulene 4-(1-Methyl-piperidin-4-yloxy)-2-pyridin-3-ylethynyl-9,10-dihydro-4H-3,10a-diaza-benzo[f]azulene 2-[4-(1,1-Difluoro-ethyl)-phenyl]-4-(1-methyl-piperidin-4-yloxy)-9,10-dihydro-4H-3,10a-diaza-benzo[f]azulene 2-Cyclopent-1-enyl-4-(1-methyl-piperidin-4-yloxy)-9,10-dihydro-4H-3,10a-diaza-benzo[f]azulene 4-(1-Methyl-piperidin-4-yloxy)-2-thiazol-2-yl-9,10-dihydro-4H-3,10a-diaza-benzo[f]azulene 2-Benzylsulfanyl-4-(1-methyl-piperidin-4-yloxy)-9,10-dihydro-4H-3,10a-diaza-benzo[f]azulene 2-(3-Fluoro-phenyl)-4-(1-methyl-piperidin-4-yloxy)-9,10-dihydro-4H-3,10a-diaza-benzo[f]azulene 2-(4-Difluoromethyl-phenyl)-4-(1-methyl-piperidin-4-yloxy)-9,10-dihydro-4H-3,10a-diaza-benzo[f]azulene 2-(2-Methyl-allyl)-4-(1-methyl-piperidin-4-yloxy)-9,10-dihydro-4H-3,10a-diaza-benzo[f]azulene 2-(2,4-Dichloro-phenyl)-4-(1-methyl-piperidin-4-yloxy)-9,10-dihydro-4H-3,10a-diaza-benzo[f]azulene {3-[4-(1-Methyl-piperidin-4-yloxy)-9,10-dihydro-4H-3,10a-diaza-benzo[f]azulen-2-yl]-prop-2-ynyl}-carbamic acid tert-butyl ester 4-(1-Methyl-piperidin-4-yloxy)-2-phenylsulfanyl-9,10-dihydro-4H-3,10a-diaza-benzo[f]azulene 4-[4-(1-Methyl-piperidin-4-yloxy)-9,10-dihydro-4H-3,10a-diaza-benzo[f]azulen-2-yl]3,6-dihydro-2H-pyridine-1-carboxylic acid tert-butyl ester 2-(2-Chloro-4-methyl-phenyl)-4-(1-methyl-piperidin-4-yloxy)-9,10-dihydro-4H-3,10a-diaza-benzo[f]azulene 4-(1-Methyl-piperidin-4-yloxy)-2-(3-phenyl-propenyl)-9,10-dihydro-4H-3,10a-diaza-benzo[f]azulene 2-(3-Chloro-phenyl)-4-(1-methyl-piperidin-4-yloxy)-9,10-dihydro-4H-3,10a-diaza-benzo[f]azulene 8-Chloro-2-iodo-4-(1-methyl-piperidin-4-yloxy)-9,10-dihydro-4H-3,10a-diaza-benzo[f]azulene 8-Bromo-2-iodo-4-(1-methyl-piperidin-4-yloxy)-9,10-dihydro-4H-3,10a-diaza-benzo[f]azulene 2-Cyclohept-1-enyl-4-(1-methyl-piperidin-4-yloxy)-9,10-dihydro-4H-3,10a-diaza-benzo[f]azulene 2-(4-Bromo-phenyl)-4-(1-methyl-piperidin-4-yloxy)-9,10-dihydro-4H-3,10a-diaza-benzo[f]azulene 2-(2-Fluoro-4-methyl-phenyl)-4-(1-methyl-piperidin-4-yloxy)-9,10-dihydro-4H-3,10a-diaza-benzo[f]azulene 4-(1-Methyl-piperidin-4-yloxy)-2-(1-methyl-1H-pyrrol-2-yl)-9,10-dihydro-4H-3,10a-diaza-benzo[f]azulene {2-[4-(1-Methyl-piperidin-4-yloxy)-9,10-dihydro-4H-3,10a-diaza-benzo[f]azulen-2-ylsulfanyl]-ethyl}-carbamic acid tert-butyl ester 2-(Furan-2-ylmethylsulfanyl)-4-(1-methyl-piperidin-4-yloxy)-9,10-dihydro-4H-3,10a-diaza-benzo[f]azulene 2-Cyclopentylsulfanyl-4-(1-methyl-piperidin-4-yloxy)-9,10-dihydro-4H-3,10a-diaza-benzo[f]azulene 4-(1-Methyl-piperidin-4-yloxy)-2-(3-phenyl-propyl)-9,10-dihydro-4H-3,10a-diaza-benzo[f]azulene 4-(1-Methyl-piperidin-4-yloxy)-2-(thiophen-2-ylmethylsulfanyl)-9,10-dihydro-4H-3,10a-diaza-benzo[f]azulene 4-(1-Methyl-piperidin-4-yloxy)-2-(5-phenyl-pent-1-enyl)-9,10-dihydro-4H-3,10a-diaza-benzo[f]azulene 4-(1-Methyl-piperidin-4-yloxy)-2-(5-phenyl-pentyl)-9,10-dihydro-4H-3,10a-diaza-benzo[f]azulene 8-Chloro-4-(1-methyl-piperidin-4-yloxy)-2-phenyl-9,10-dihydro-4H-3,10a-diaza-benzo[f]azulene 4-(1-Methyl-piperidin-4-yloxy)-2,8-diphenyl-9,10-dihydro-4H-3,10a-diaza-benzo[f]azulene 2-(3,3-Dimethyl-but-1-enyl)-4-(1-methyl-piperidin-4-yloxy)-9,10-dihydro-4H-3,10a-diaza-benzo[f]azulene 2-(3,3-Dimethyl-butyl)-4-(1-methyl-piperidin-4-yloxy)-9,10-dihydro-4H-3,10a-diaza-benzo[f]azulene 2-(2-Cyclohexyl-ethyl)-4-(1-methyl-piperidin-4-yloxy)-9,10-dihydro-4H-3,10a-diaza-benzo[f]azulene 4-(1-Methyl-piperidin-4-yloxy)-2-(5-methyl-thiophen-2-yl)-9,10-dihydro-4H-3,10a-diaza-benzo[f]azulene Methyl-{4-[4-(1-methyl-piperidin-4-yloxy)-9,10-dihydro-4H-3,10a-diaza-benzo[f]azulen-2-yl]-phenyl}-carbamic acid tert-butyl ester 2-Cyclohexylsulfanyl-4-(1-methyl-piperidin-4-yloxy)-9,10-dihydro-4H-3,10a-diaza-benzo[f]azulene 2-(2-Cyclopropyl-vinyl)-4-(1-methyl-piperidin-4-yloxy)-9,10-dihydro-4H-3,10a-diaza-benzo[f]azulene Methyl-{4-[4-(1-methyl-piperidin-4-yloxy)-9,10-dihydro-4H-3,10a-diaza-benzo[f]azulen-2-yl]-phenyl}-amine 2,2,N-Trimethyl-N-{4-[4-(1-methyl-piperidin-4-yloxy)-9,10-dihydro-4H-3,10a-diaza-benzo[f]azulen-2-yl]-phenyl}-propionamide

[4-(1-Methyl-piperidin-4-yloxy)-9,10-dihydro-4H-3,10a-diaza-benzo[f]azulen-2-yl]-phenyl-methanone 1-Methyl-4-(1-methyl-piperidin-4-yloxy)-2-phenyl-9,10-dihydro-4H-3,10a-diaza-benzo[f]azulene 2-(3-Cyclopentyl-propenyl)-4-(1-methyl-piperidin-4-yloxy)-9,10-dihydro-4H-3,10a-diaza-benzo[f]azulene 2-(3-Cyclopentyl-propyl)-4-(1-methyl-piperidin-4-yloxy)-9,10-dihydro-4H-3,10a-diaza-benzo[f]azulene 2-(3,6-Dihydro-2H-pyran-4-yl)-4-(1-methyl-piperidin-4-yloxy)-9,10-dihydro-4H-3,10a-diaza-benzo[f]azulene 8-Fluoro-4-(1-methyl-piperidin-4-yloxy)-2-phenyl-9,10-dihydro-4H-3,10a-diaza-benzo[f]azulene N-(4-Hydroxy-cyclohexyl)-4-[4-(1-methyl-piperidin-4-yloxy)-9,10-dihydro-4H-3,10a-diaza-benzo[f]azulen-2-yl]-benzamide 2-Isobutyl-4-(1-methyl-piperidin-4-yloxy)-9,10-dihydro-4H-3,10a-diaza-benzo[f]azulene 2-Benzyl-4-(1-methyl-piperidin-4-yloxy)-9,10-dihydro-4H-3,10a-diaza-benzo[f]azulene
4-(1-Methyl-piperidin-4-yloxy)-2-(2-thiophen-2-yl-vinyl)-9,10-dihydro-4H-3,10a-diaza-benzo[f]azulene
4-(1-Methyl-piperidin-4-yloxy)-2-(2-thiophen-3-yl-vinyl)-9,10-dihydro-4H-3,10a-diaza-benzo[f]azulene
Dimethyl-{4-[4-(1-methyl-piperidin-4-yloxy)-9,10-dihydro-4H-3,10a-diaza-benzo[f]azulen-2-yl]-benzyl}-amine
4-[4-(1-Methyl-piperidin-4-yloxy)-9,10-dihydro-4H-3,10a-diaza-benzo[f]azulen-2-ylsulfanyl]-piperidine-1-carboxylic acid tert-butyl ester
{4-[4-(1-Methyl-piperidin-4-yloxy)-9,10-dihydro-4H-3,10a-diaza-benzo[f]azulen-2-yl]-benzyl}-carbamic acid tert-butyl ester
2-Methyl-4-(1-methyl-piperidin-4-yloxy)-9,10-dihydro-4H-3,10a-diaza-benzo[f]azulene-1-carboxylic acid ethyl ester
2-[1-(4-Chloro-phenyl)-1-methyl-ethyl]-4-(1-methyl-piperidin-4-yloxy)-9,10-dihydro-4H-3,10a-diaza-benzo[f]azulene
1-Methyl-4-(1-methyl-piperidin-4-yloxy)-9,10-dihydro-4H-3,10a-diaza-benzo[f]azulene-2-carboxylic acid ethyl ester
4-(1-Methyl-piperidin-4-yloxy)-2-phenethylsulfanyl-9,10-dihydro-4H-3,10a-diaza-benzo[f]azulene
1-Ethyl-4-(1-methyl-piperidin-4-yloxy)-2-phenyl-9,10-dihydro-4H-3,10a-diaza-benzo[f]azulene
4-(1-Methyl-piperidin-4-yloxy)-2-(3-phenoxy-propenyl)-9,10-dihydro-4H-3,10a-diaza-benzo[f]azulene
2-(4-Bromo-phenyl)-1-methyl-4-(1-methyl-piperidin-4-yloxy)-9,10-dihydro-4H-3,10a-diaza-benzo[f]azulene
2-Methyl-4-(1-methyl-piperidin-4-yloxy)-1-phenyl-9,10-dihydro-4H-3,10a-diaza-benzo[f]azulene
2-(3-Benzyloxy-propenyl)-4-(1-methyl-piperidin-4-yloxy)-9,10-dihydro-4H-3,10a-diaza-benzo[f]azulene
Methyl-{4-[1-methyl-4-(1-methyl-piperidin-4-yloxy)-9,10-dihydro-4H-3,10a-diaza-benzo[f]azulen-2-yl]-phenyl}-carbamic acid tert-butyl ester
4-(1-Methyl-piperidin-4-yloxy)-2-(2-thiophen-2-yl-ethyl)-9,10-dihydro-4H-3,10a-diaza-benzo[f]azulene
2-(4-Bromo-phenyl)-1-chloro-4-(1-methyl-piperidin-4-yloxy)-9,10-dihydro-4H-3,10a-diaza-benzo[f]azulene
2-(3-Benzyloxy-propyl)-4-(1-methyl-piperidin-4-yloxy)-9,10-dihydro-4H-3,10a-diaza-benzo[f]azulene
4-(1-Methyl-piperidin-4-yloxy)-2-(4-phenyl-butyl)-9,10-dihydro-4H-3,10a-diaza-benzo[f]azulene
{4-[1-Methyl-4-(1-methyl-piperidin-4-yloxy)-9,10-dihydro-4H-3,10a-diaza-benzo[f]azulen-2-yl]-phenyl}-carbamic acid tert-butyl ester
3-{4-[1-Methyl-4-(1-methyl-piperidin-4-yloxy)-9,10-dihydro-4H-3,10a-diaza-benzo[f]azulen-2-yl]-phenyl}-oxazolidin-2-one
1-Methyl-3-{4-[1-methyl-4-(1-methyl-piperidin-4-yloxy)-9,10-dihydro-4H-3,10a-diaza-benzo[f]azulen-2-yl]-phenyl}-imidazolidin-2-one
2-Iodo-1-methyl-4-(1-methyl-piperidin-4-yloxy)-9,10-dihydro-4H-3,10a-diaza-benzo[f]azulene
1-Chloro-4-(1-methyl-piperidin-4-yloxy)-2-phenyl-9,10-dihydro-4H-3,10a-diaza-benzo[f]azulene
1-Methyl-4-(1-methyl-piperidin-4-yloxy)-2-phenyl-9,10-dihydro-4H-3,10a-diaza-benzo[f]azulene
2,2-Dimethyl-N-{4-[4-(1-methyl-piperidin-4-yloxy)-9,10-dihydro-4H-3,10a-diaza-benzo[f]azulen-2-yl]-benzyl}-propionamide
2,2-Dimethyl-N-{4-[4-(1-methyl-piperidin-4-yloxy)-9,10-dihydro-4H-3,10a-diaza-benzo[f]azulen-2-yl]-benzyl}-propionamide
1-Chloro-4-(1-methyl-piperidin-4-yloxy)-2-(5-phenyl-pentyl)-9,10-dihydro-4H-3,10a-diaza-benzo[f]azulene
1-tert-Butyl-3-{4-[1-methyl-4-(1-methyl-piperidin-4-yloxy)-9,10-dihydro-4H-3,10a-diaza-benzo[f]azulen-2-yl]-phenyl}-imidazolidin-2-one
{4-[1-Chloro-4-(1-methyl-piperidin-4-yloxy)-9,10-dihydro-4H-3,10a-diaza-benzo[f]azulen-2-yl]-phenyl}-carbamic acid tert-butyl ester
2-(2-Fluoro-phenyl)-1-methyl-4-(1-methyl-piperidin-4-yloxy)-9,10-dihydro-4H-3,10a-diaza-benzo[f]azulene
2-(3-Fluoro-phenyl)-1-methyl-4-(1-methyl-piperidin-4-yloxy)-9,10-dihydro-4H-3,10a-diaza-benzo[f]azulene
1-Methyl-4-(1-methyl-piperidin-4-yloxy)-2-m-tolyl-9,10-dihydro-4H-3,10a-diaza-benzo[f]azulene
2-(3-Chloro-phenyl)-1-methyl-4-(1-methyl-piperidin-4-yloxy)-9,10-dihydro-4H-3,10a-diaza-benzo[f]azulene
2-(2-Chloro-phenyl)-1-methyl-4-(1-methyl-piperidin-4-yloxy)-9,10-dihydro-4H-3,10a-diaza-benzo[f]azulene
1-Methyl-4-(1-methyl-piperidin-4-yloxy)-2-o-tolyl-9,10-dihydro-4H-3,10a-diaza-benzo[f]azulene
1-Methyl-4-(1-methyl-piperidin-4-yloxy)-2-thiophen-3-yl-9,10-dihydro-4H-3,10a-diaza-benzo[f]azulene
2-(2-Methoxy-phenyl)-1-methyl-4-(1-methyl-piperidin-4-yloxy)-9,10-dihydro-4H-3,10a-diaza-benzo[f]azulene
2-(3-Methoxy-phenyl)-1-methyl-4-(1-methyl-piperidin-4-yloxy)-9,10-dihydro-4H-3,10a-diaza-benzo[f]azulene
3-{4-[1-Methyl-4-(1-methyl-piperidin-4-yloxy)-9,10-dihydro-4H-3,10a-diaza-benzo[f]azulen-2-yl]-phenyl}-acrylic acid tert-butyl ester
3-Methyl-3-{4-[1-methyl-4-(1-methyl-piperidin-4-yloxy)-9,10-dihydro-4H-3,10a-diaza-benzo[t]azulen-2-yl]-phenylsulfanyl}-butan-1-ol
1-Methyl-4-(1-methyl-piperidin-4-yloxy)-2-p-tolyl-9,10-dihydro-4H-3,10a-diaza-benzo[f]azulene
2-(4-Fluoro-phenyl)-1-methyl-4-(1-methyl-piperidin-4-yloxy)-9,10-dihydro-4H-3,10a-diaza-benzo[f]azulene
2-(4-Chloro-phenyl)-1-methyl-4-(1-methyl-piperidin-4-yloxy)-9,10-dihydro-4H-3,10a-diaza-benzo[f]azulene
2-(4-Methoxy-phenyl)-1-methyl-4-(1-methyl-piperidin-4-yloxy)-9,10-dihydro-4H-3,10a-diaza-benzo[f]azulene
2-(2-Chloro-4-methyl-phenyl)-1-methyl-4-(1-methyl-piperidin-4-yloxy)-9,10-dihydro-4H-3,10a-diaza-benzo[f]azulene
2-[4-(2-Methanesulfonyl-vinyl)-phenyl]-1-methyl-4-(1-methyl-piperidin-4-yloxy)-9,10-dihydro-4H-3,10a-diaza-benzo[f]azulene
2-[4-(2-Methanesulfonyl-ethyl)-phenyl]-1-methyl-4-(1-methyl-piperidin-4-yloxy)-9,10-dihydro-4H-3,10a-diaza-benzo[f]azulene
(2-{4-[1-Methyl-4-(1-methyl-piperidin-4-yloxy)-9,10-dihydro-4H-3,10a-diaza-benzo[f]azulen-2-yl]-phenylsulfanyl}-ethyl)-carbamic acid tert-butyl ester
2-{4-[1-Methyl-4-(1-methyl-piperidin-4-yloxy)-9,10-dihydro-4H-3,10a-diaza-benzo[f]azulen-2-yl]-phenylsulfanyl}-ethylamine
1-{4-[1-Methyl-4-(1-methyl-piperidin-4-yloxy)-9,10-dihydro-4H-3,10a-diaza-benzo[f]azulen-2-yl]-phenyl}-piperidin-2-one
N-(2-{4-[1-Methyl-4-(1-methyl-piperidin-4-yloxy)-9,10-dihydro-4H-3,10a-diaza-benzo[f]azulen-2-yl]-phenylsulfanyl}-ethyl)acetamide
2-(4-Benzylsulfanyl-phenyl)-1-methyl-4-(1-methyl-piperidin-4-yloxy)-9,10-dihydro-4H-3,10a-diaza-benzo[f]azulene
{4-[1-Methyl-4-(1-methyl-piperidin-4-yloxy)-9,10-dihydro-4H-3,10a-diaza-benzo[f]azulen-2-yl]-phenylsulfanyl}-acetic acid methyl ester 2-(4-tert-Butylsulfanyl-phenyl)-1-methyl-4-(1-methyl-piperidin-4-yloxy)-9,10-dihydro-4H-3,10a-diaza-benzo[f]azulene 2-[4-(Furan-2-ylmethylsulfanyl)-phenyl]-1-methyl-4-(1-methyl-piperidin-4-yloxy)-9,10-dihydro-4H-3,10a-diaza-benzo[f]azulene 4-{4-[1-Methyl-4-(1-methyl-piperidin-4-yloxy)-9,10-dihydro-4H-3,10a-diaza-benzo[f]azulen-2-yl]-phenyl}-3,6-dihydro-2H-pyridine-1-carboxylic acid tert-butyl ester 2-(4-Cyclopent-1-enyl-phenyl)-1-methyl-4-(1-methyl-piperidin-4-yloxy)-9,10-dihydro-4H-3,10a-diaza-benzo[f]azulene 2-(4-Cyclohex-1-enyl-phenyl)-1-methyl-4-(1-methyl-piperidin-4-yloxy)-9,10-dihydro-4H-3,10a-diaza-benzo[f]azulene 2-(4-Cyclohept-1-enyl-phenyl)-1-methyl-4-(1-methyl-piperidin-4-yloxy)-9,10-dihydro-4H-3,10a-diaza-benzo[f]azulene {4-[1-Methyl-4-(1-methyl-piperidin-4-yloxy)-9,10-dihydro-4H-3,10a-diaza-benzo[f]azulen-2-yl]-phenyl}-carbamic acid cyclopentyl ester 4-[1-Methyl-4-(1-methyl-piperidin-4-yloxy)-9,10-dihydro-4H-3,10a-diaza-benzo[f]azulen-2-yl]-phenylamine {4-[1-Methyl-4-(1-methyl-piperidin-4-yloxy)-9,10-dihydro-4H-3,10a-diaza-benzo[f]azulen-2-yl]-phenyl}-carbamic acid isobutyl ester {4-[1-Methyl-4-(1-methyl-piperidin-4-yloxy)-9,10-dihydro-4H-3,10a-diaza-benzo[f]azulen-2-yl]-phenyl}-carbamic acid 2,2,2-trichloro-1,1-dimethyl-ethyl ester 4-Benzyl-3-{4-[1-methyl-4-(1-methyl-piperidin-4-yloxy)-9,10-dihydro-4H-3,10a-diaza-benzo[f]azulen-2-yl]-phenyl}-oxazolidin-2-one 4-{4-[1-Methyl-4-(1-methyl-piperidin-4-yloxy)-9,10-dihydro-4H-3,10a-diaza-benzo[f]azulen-2-yl]-phenyl}-piperidine-1-carboxylic acid tert-butyl ester 1-Isopropyl-3-{4-[1-methyl-4-(1-methyl-piperidin-4-yloxy)-9,10-dihydro-4H-3,10a-diaza-benzo[f]azulen-2-yl]-phenyl}-imidazolidin-2-one {2-[4-(1-Methyl-piperidin-4-yloxy)-9,10-dihydro-4H-3,10a-diaza-benzo[f]azulen-2-yl]-phenyl}-methanol Dimethyl-(2-{4-[4-(1-methyl-piperidin-4-yloxy)-9,10-dihydro-4H-3,10a-diaza-benzo[f]azulen-2-yl]-phenoxy}-ethyl)-amine 3-{4-[4-(1-Methyl-piperidin-4-yloxy)-9,10-dihydro-4H-3,10a-diaza-benzo[f]azulen-2-yl]-benzyl}-oxazolidin-2-one Methyl-{4-[4-(1-methyl-piperidin-4-yloxy)-9,10-dihydro-4H-3,10a-diaza-benzo[f]azulen-2-yl]-benzyl}-carbamic acid tert-butyl ester 2-(4-Allyloxy-phenyl)-4-(1-methyl-piperidin-4-yloxy)-9,10-dihydro-4H-3,10a-diaza-benzo[f]azulene 1-{4-[4-(1-Methyl-piperidin-4-yloxy)-9,10-dihydro-4H-3,10a-diaza-benzo[f]azulen-2-yl]-benzyl}-pyrrolidin-2-one 1-{4-[4-(1-Methyl-piperidin-4-yloxy)-9,10-dihydro-4H-3,10a-diaza-benzo[f]azulen-2-yl]-benzyl}-piperidin-2-one 2-(4-Isopropylsulfanylmethyl-phenyl)-4-(1-methyl-piperidin-4-yloxy)-9,10-dihydro-4H-3,10a-diaza-benzo[f]azulene Cyclopropanesulfonic acid {4-[1-methyl-4-(1-methyl-piperidin-4-yloxy)-9,10-dihydro-4H-3,10a-diaza-benzo[f]azulen-2-yl]-phenyl}-amide 1-{4-[4-(1-Methyl-piperidin-4-yloxy)-9,10-dihydro-4H-3,10a-diaza-benzo[f]azulen-2-yl]-benzyl}-azepan-2-one 2-[4-(2-tert-Butylsulfanyl-ethyl)-phenyl]-4-(1-methyl-piperidin-4-yloxy)-9,10-dihydro-4H-3,10a-diaza-benzo[f]azulene 4-(1-Methyl-piperidin-4-yloxy)-2-(2-nitro-phenyl)-9,10-dihydro-4H-3,10a-diaza-benzo[f]azulene 1-tert-Butyl-3-{4-[4-(1-methyl-piperidin-4-yloxy)-9,10-dihydro-4H-3,10a-diaza-benzo[f]azulen-2-yl]-benzyl}-imidazolidin-2-one 2-{4-[4-(1-Methyl-piperidin-4-yloxy)-9,10-dihydro-4H-3,10a-diaza-benzo[f]azulen-2-yl]-phenyl}-ethanol 2-(4-Cyclopropylmethoxy-phenyl)-4-(1-methyl-piperidin-4-yloxy)-9,10-dihydro-4H-3,10a-diaza-benzo[f]azulene 3-{4-[1-Methyl-4-(1-methyl-piperidin-4-yloxy)-9,10-dihydro-4H-3,10a-diaza-benzo[f]azulen-2-yl]-phenylsulfanyl}-propane-1,2-diol 3-{4-[1-Methyl-4-(1-methyl-piperidin-4-yloxy)-9,10-dihydro-4H-3,10a-diaza-benzo[f]azulen-2-yl]-phenylsulfanyl}-propan-1-ol (2-{4-[4-(1-Methyl-piperidin-4-yloxy)-9,10-dihydro-4H-3,10a-diaza-benzo[f]azulen-2-yl]-phenyl}-ethyl)-carbamic acid tert-butyl ester Methyl-(2-{4-[4-(1-methyl-piperidin-4-yloxy)-9,10-dihydro-4H-3,10a-diaza-benzo[f]azulen-2-yl]-phenyl}-ethyl)-carbamic acid tert-butyl ester 5,5-Dimethyl-3-{4-[4-(1-methyl-piperidin-4-yloxy)-9,10-dihydro-4H-3,10a-diaza-benzo[f]azulen-2-yl]-benzyl}-oxazolidine-2,4-dione (2-{4-[4-(1-Methyl-piperidin-4-yloxy)-9,10-dihydro-4H-3,10a-diaza-benzo[f]azulen-2-yl]-benzylsulfanyl}-ethyl)-carbamic acid tert-butyl ester tert-Butyl-carbamic acid 2-{4-[4-(1-methyl-piperidin-4-yloxy)-9,10-dihydro-4H-3,10a-diaza-benzo[f]azulen-2-yl]-phenyl}-ethyl ester

[1-Methyl-4-(1-methyl-piperidin-4-yloxy)-9,10-dihydro-4H-3,10a-diaza-benzo[f]azulen-2-yl]-phenyl-methanol

[1-Methyl-4-(1-methyl-piperidin-4-yloxy)-9,10-dihydro-4H-3,10a-diaza-benzo[f]azulen-2-yl]-phenyl-methanone 1-Methyl-4-(1-methyl-piperidin-4-yloxy)-9,10-dihydro-4H-3,10a-diaza-benzo[f]azulene-2-carboxylic acid benzyl-methyl-amide 1-Methyl-4-(1-methyl-piperidin-4-yloxy)-9,10-dihydro-4H-3,10a-diaza-benzo[f]azulene-2-carboxylic acid methyl-phenyl-amide 1-Methyl-4-(1-methyl-piperidin-4-yloxy)-9,10-dihydro-4H-3,10a-diaza-benzo[f]azulene-2-carboxylic acid propylamide 1-Isopropyl-3-{4-[1-methyl-4-(1-methyl-piperidin-4-yloxy)-9,10-dihydro-4H-3,10a-diaza-benzo[f]azulen-2-yl]-phenyl}-thiourea 2-(1-Methyl-1-phenyl-ethyl)-4-(1-methyl-piperidin-4-yloxy)-9,10-dihydro-4H-3,10a-diaza-benzo[f]azulene 1-Cyclopropyl-3-{4-[1-methyl-4-(1-methyl-piperidin-4-yloxy)-9,10-dihydro-4H-3,10a-diaza-benzo[f]azulen-2-yl]-phenyl}-thiourea 1-tert-Butyl-3-{4-[1-methyl-4-(1-methyl-piperidin-4-yloxy)-9,10-dihydro-4H-3,10a-diaza-benzo[f]azulen-2-yl]-phenyl}-urea 2-Methyl-1-[1-methyl-4-(1-methyl-piperidin-4-yloxy)-9,10-dihydro-4H-3,10a-diaza-benzo[f]azulen-2-yl]-propan-1-ol N-(2-{4-[1-Methyl-4-(1-methyl-piperidin-4-yloxy)-9,10-dihydro-4H-3,10a-diaza-benzo[f]azulen-2-yl]-phenylsulfanyl}-ethyl)-guanidine N-(2-Hydroxy-ethyl)-4-[4-(1-methyl-piperidin-4-yloxy)-9,10-dihydro-4H-3,10a-diaza-benzo[f]azulen-2-yl]-benzamide 1-Adamantan-1-yl-3-{4-[1-methyl-4-(1-methyl-piperidin-4-yloxy)-9,10-dihydro-4H-3,10a-diaza-benzo[f]azulen-2-yl]-phenyl}-urea N-{4-[1-Methyl-4-(1-methyl-piperidin-4-yloxy)-9,10-dihydro-4H-3,10a-diaza-benzo[f]azulen-2-yl]-phenyl}-hydrazinecarboxylic acid tert-butyl ester
1-{4-[4-(1-Methyl-piperidin-4-yloxy)-9,10-dihydro-4H-3,10a-diaza-benzo[f]azulen-2-yl]-benzoyl}-piperidin-4-one
N-(4-Hydroxy-cyclohexyl)-4-[1-methyl-4-(1-methyl-piperidin-4-yloxy)-9,10-dihydro-4H-3,10a-diaza-benzo[f]azulen-2-yl]-benzamide
N-(2-Hydroxy-ethyl)-4-[1-methyl-4-(1-methyl-piperidin-4-yloxy)-9,10-dihydro-4H-3,10a-diaza-benzo[f]azulen-2-yl]-benzamide
1-{4-[1-Methyl-4-(1-methyl-piperidin-4-yloxy)-9,10-dihydro-4H-3,10a-diaza-benzo[f]azulen-2-yl]-benzoyl}-piperidin-4-one
1,2-Diiodo-4-(1-methyl-piperidin-4-yloxy)-9,10-dihydro-4H-3,10a-diaza-benzo[f]azulene
(4-Hydroxy-piperidin-1-yl)-{4-[1-methyl-4-(1-methyl-piperidin-4-yloxy)-9,10-dihydro-4H-3,10a-diaza-benzo[f]azulen-2-yl]-phenyl}-methanone
2-Iodo-4-(1-methyl-piperidin-4-yloxy)-9,10-dihydro-4H-3,10a-diaza-benzo[f]azulene-1-carbonitrile
1-Methyl-4-(1-methyl-piperidin-4-yloxy)-9,10-dihydro-4H-3,10a-diaza-benzo[f]azulene-2-carboxylic acid benzylamide
(2-{4-[1-Methyl-4-(1-methyl-piperidin-4-yloxy)-9,10-dihydro-4H-3,10a-diaza-benzo[f]azulen-2-yl]-phenyl}-ethyl)-carbamic acid tert-butyl ester
4-[1-Cyano-4-(1-methyl-piperidin-4-yloxy)-9,10-dihydro-4H-3,10a-diaza-benzo[f]azulen-2-yl]-benzoic acid tert-butyl ester
2-(3,3-Dimethyl-but-1-enyl)-1-methyl-4-(1-methyl-piperidin-4-yloxy)-9,10-dihydro-4H-3,10a-diaza-benzo[f]azulene
2-Cyclohex-1-enyl-1-methyl-4-(1-methyl-piperidin-4-yloxy)-9,10-dihydro-4H-3,10a-diaza-benzo[f]azulene
4-[1-Methyl-4-(1-methyl-piperidin-4-yloxy)-9,10-dihydro-4H-3,10a-diaza-benzo[f]azulen-2-yl]-but-3-yn-1-ol
2-(6-Chloro-hex-1-ynyl)-1-methyl-4-(1-methyl-piperidin-4-yloxy)-9,10-dihydro-4H-3,10a-diaza-benzo[f]azulene
2-(3,3-Dimethyl-butyl)-1-methyl-4-(1-methyl-piperidin-4-yloxy)-9,10-dihydro-4H-3,10a-diaza-benzo[f]azulene
9,9-Dimethyl-4-(1-methyl-piperidin-4-yloxy)-2-phenyl-9,10-dihydro-4H-3,10a-diaza-benzo[f]azulene
8-Bromo-4-(1-methyl-piperidin-4-yloxy)-2-phenyl-9,10-dihydro-4H-3,10a-diaza-benzo[f]azulene
1,9,9-Trimethyl-4-(1-methyl-piperidin-4-yloxy)-2-phenyl-9,10-dihydro-4H-3,10a-diaza-benzo[f]azulene
8-Benzyl-4-(1-methyl-piperidin-4-yloxy)-2-phenyl-9,10-dihydro-4H-3,10a-diaza-benzo[f]azulene
4-(1-Methyl-piperidin-4-yloxy)-8-methylsulfanyl-2-phenyl-9,10-dihydro-4H-3,10a-diaza-benzo[f]azulene
4-(1-Methyl-piperidin-4-yloxy)-2-phenyl-9,10-dihydro-4H-3,10a-diaza-benzo[f]azulene-1-carbonitrile
8-Methyl-4-(1-methyl-piperidin-4-yloxy)-2-phenyl-9,10-dihydro-4H-3,10a-diaza-benzo[f]azulene
8-But-3-enyl-4-(1-methyl-piperidin-4-yloxy)-2-phenyl-9,10-dihydro-4H-3,10a-diaza-benzo[f]azulene
4-(1-Methyl-piperidin-4-yloxy)-2-phenyl-1-propyl-9,10-dihydro-4H-3,10a-diaza-benzo[f]azulene
4-(1-Methyl-piperidin-4-yloxy)-2-phenyl-8-o-tolyl-9,10-dihydro-4H-3,10a-diaza-benzo[f]azulene
8-(4-Fluoro-phenyl)-4-(1-methyl-piperidin-4-yloxy)-2-phenyl-9,10-dihydro-4H-3,10a-diaza-benzo[f]azulene
8-(3-Methoxy-phenyl)-4-(1-methyl-piperidin-4-yloxy)-2-phenyl-9,10-dihydro-4H-3,10a-diaza-benzo[f]azulene
3-[4-(1-Methyl-piperidin-4-yloxy)-2-phenyl-9,10-dihydro-4H-3,10a-diaza-benzo[f]azulen-8-yl]-phenylamine
1-Isopropyl-4-(1-methyl-piperidin-4-yloxy)-2-phenyl-9,10-dihydro-4H-3,10a-diaza-benzo[f]azulene
Methyl-[4-(1-methyl-piperidin-4-yloxy)-2-phenyl-9,10-dihydro-4H-3,10a-diaza-benzo[f]azulen-8-yl]-amine
8-Methoxy-4-(1-methyl-piperidin-4-yloxy)-2-phenyl-9,10-dihydro-4H-3,10a-diaza-benzo[f]azulene
4-(1-Methyl-piperidin-4-yloxy)-1-phenyl-2-propyl-9,10-dihydro-4H-3,10a-diaza-benzo[f]azulene
1-Iodo-4-(1-methyl-piperidin-4-yloxy)-2-phenyl-9,10-dihydro-4H-3,10a-diaza-benzo[f]azulene
8-Benzyloxy-4-(1-methyl-piperidin-4-yloxy)-2-phenyl-9,10-dihydro-4H-3,10a-diaza-benzo[f]azulene
4-(1-Methyl-piperidin-4-yloxy)-8-phenethyl-2-phenyl-9,10-dihydro-4H-3,10a-diaza-benzo[f]azulene
1-Methyl-4-(1-methyl-piperidin-4-yloxy)-2-pyridin-4-yl-9,10-dihydro-4H-3,10a-diaza-benzo[f]azulene
1-Methyl-4-(1-methyl-piperidin-4-yloxy)-2-pyridin-2-yl-9,10-dihydro-4H-3,10a-diaza-benzo[f]azulene
4-(1-Methyl-piperidin-4-yloxy)-1,2-diphenyl-9,10-dihydro-4H-3,10a-diaza-benzo[f]azulene
2-Iodo-4-(1-methyl-piperidin-4-yloxy)-9,10-dihydro-4H-3,10a-diaza-benzo[f]azulene-1-carboxylic acid amide
4-(1-Methyl-piperidin-4-yloxy)-2-phenyl-9,10-dihydro-4H-3,10a-diaza-benzo[f]azulene-1-carboxylic acid amide
4-(1-Methyl-piperidin-4-yloxy)-2-phenyl-1-trifluoromethyl-9,10-dihydro-4H-3,10a-diaza-benzo[f]azulene
4-(1-Methyl-piperidin-4-yloxy)-2-phenyl-9,10-dihydro-4H-3,10a-diaza-benzo[f]azulene-1-carboxylic acid methyl ester
[4-(1-Methyl-piperidin-4-yloxy)-2-phenyl-9,10-dihydro-4H-3,10a-diaza-benzo[f]azulen-1-yl]-methanol
6-Iodo-1-methyl-4-(1-methyl-piperidin-4-yloxy)-2-phenyl-9,10-dihydro-4H-3,10a-diaza-benzo[f]azulene
2-(2-Methyl-allyl)-4-(1-methyl-piperidin-4-yloxy)-9,10-dihydro-4H-3,10a-diaza-benzo[f]azulene-1-carbonitrile
1-Methyl-2-(2-methyl-allyl)-4-(1-methyl-piperidin-4-yloxy)-9,10-dihydro-4H-3,10a-diaza-benzo[f]azulene
7-Bromo-4-(1-methyl-piperidin-4-yloxy)-2-phenyl-9,10-dihydro-4H-3,10a-diaza-benzo[f]azulene
4-(1-Methyl-piperidin-4-yloxy)-2-phenyl-9,10-dihydro-4H-3,10a-diaza-benzo[f]azulene-1-carbaldehyde
2-Benzyl-4-(1-methyl-piperidin-4-yloxy)-9,10-dihydro-4H-3,10a-diaza-benzo[f]azulene-1-carbonitrile
[2-(1,2-Diiodo-9,10-dihydro-4H-3,10a-diaza-benzo[f]azulen-4-yloxy)-ethyl]-dimethyl-amine
1,2-Diiodo-4-(2-piperidin-1-yl-ethoxy)-9,10-dihydro-4H-3,10a-diaza-benzo[f]azulene
2-(2-Methyl-allyl)-4-(1-methyl-piperidin-4-yloxy)-9,10-dihydro-4H-3,10a-diaza-benzo[f]azulene-1-carboxylic acid amide
1,2-Bis-(2-methyl-allyl)-4-(1-methyl-piperidin-4-yloxy)-9,10-dihydro-4H-3,10a-diaza-benzo[f]azulene
1,2-Diiodo-4-(1-methyl-pyrrolidin-3-yloxy)-9,10-dihydro-4H-3,10a-diaza-benzo[f]azulene
1,2-Diiodo-4-(8-methyl-8-aza-bicyclo[3.2.1]oct-3-yloxy)-9,10-dihydro-4H-3,10a-diaza-benzo[f]azulene
[3-(1,2-Diiodo-9,10-dihydro-4H-3,10a-diaza-benzo[f]azulen-4-yloxy)-propyl]-dimethyl-amine
4-(1-Aza-bicyclo[2.2.2]oct-3-yloxy)-1,2-diiodo-9,10-dihydro-4H-3,10a-diaza-benzo[f]azulene
2-(2-Chloro-phenyl)-4-(1-methyl-piperidin-4-yloxy)-9,10-dihydro-4H-3,10a-diaza-benzo[f]azulene-1-carbonitrile
2-(2-Chloro-phenyl)-4-(1-methyl-piperidin-4-yloxy)-9,10-dihydro-4H-3,10a-diaza-benzo[f]azulene-1-carboxylic acid amide as well as its enantiomers, diastereomers, mixtures thereof and pharmaceutically acceptable salts, tautomers, hydrates and solvates.

In another preferred embodiment, the present invention provides a compound selected from the group consisting of:
4-(1-Methyl-piperidin-4-yloxy)-2-trifluoromethyl-9,10-dihydro-4H-3,10a-diaza-benzo[f]azulene, oxalate
4-(1-Methyl-piperidin-4-yloxy)-1-trifluoromethyl-9,10-dihydro-4H-3,10a-diaza-benzo[f]azulene, oxalate
2-Iodo-4-(1-methyl-piperidin-4-yloxy)-9,10-dihydro-4H-3,10a-diaza-benzo[f]azulene
1-Iodo-4-(1-methyl-piperidin-4-yloxy)-9,10-dihydro-4H-3,10a-diaza-benzo[f]azulene
4-(1-Methyl-piperidin-4-yloxy)-2-phenyl-9,10-dihydro-4H-3,10a-diaza-benzo[f]azulene
4-(1-Methyl-piperidin-4-yloxy)-2-p-tolyl-9,10-dihydro-4H-3,10a-diaza-benzo[f]azulene
4-(1-Methyl-piperidin-4-yloxy)-2-m-tolyl-9,10-dihydro-4H-3,10a-diaza-benzo[f]azulene, oxalate
2-Iodo-4-(1-methyl-azetidin-3-ylmethoxy)-9,10-dihydro-4H-3,10a-diaza-benzo[f]azulene
4-(1-Methyl-piperidin-4-yloxy)-2-o-tolyl-9,10-dihydro-4H-3,10a-diaza-benzo[f]azulene, oxalate
4-(1-Methyl-piperidin-4-yloxy)-2-vinyl-9,10-dihydro-4H-3,10a-diaza-benzo[f]azulene, oxalate
2-(4-tert-Butyl-phenyl)-4-(1-methyl-piperidin-4-yloxy)-9,10-dihydro-4H-3,10a-diaza-benzo[f]azulene, oxalate
1-{4-[4-(1-Methyl-piperidin-4-yloxy)-9,10-dihydro-4H-3,10a-diaza-benzo[f]azulen-2-yl]-phenyl}-ethanone, oxalate
4-(1-Methyl-piperidin-4-yloxy)-2-thiophen-3-yl-9,10-dihydro-4H-3,10a-diaza-benzo[f]azulene, oxalate
2-Ethyl-4-(1-methyl-piperidin-4-yloxy)-9,10-dihydro-4H-3,10a-diaza-benzo[f]azulene, oxalate
2-(4-Methoxy-phenyl)-4-(1-methyl-piperidin-4-yloxy)-9,10-dihydro-4H-3,10a-diaza-benzo[f]azulene, oxalate
4-(1-Methyl-piperidin-4-yloxy)-2-(4-trifluoromethoxy-phenyl)-9,10-dihydro-4H-3,10a-diaza-benzo[f]azulene, oxalate
4-[4-(1-Methyl-piperidin-4-yloxy)-9,10-dihydro-4H-3,10a-diaza-benzo[f]azulen-2-yl]-phenylamine
2-(4-Methanesulfonyl-phenyl)-4-(1-methyl-piperidin-4-yloxy)-9,10-dihydro-4H-3,10a-diaza-benzo[f]azulene
{4-[4-(1-Methyl-piperidin-4-yloxy)-9,10-dihydro-4H-3,10a-diaza-benzo[f]azulen-2-yl]-phenyl}-methanol
2-(4-Methoxymethyl-phenyl)-4-(1-methyl-piperidin-4-yloxy)-9,10-dihydro-4H-3,10a-diaza-benzo[f]azulene, oxalate
4-(1-Methyl-piperidin-4-yloxy)-2-(4-methylsulfanyl-phenyl)-9,10-dihydro-4H-3,10a-diaza-benzo[f]azulene
4-(1-Methyl-piperidin-4-yloxy)-2-(4-methylsulfanyl-phenyl)-9,10-dihydro-4H-3,10a-diaza-benzo[f]azulene
4-(1-Methyl-piperidin-4-yloxy)-2-(4-propyl-phenyl)-9,10-dihydro-4H-3,10a-diaza-benzo[f]azulene
4-(1-Methyl-piperidin-4-yloxy)-2-pyridin-2-yl-9,10-dihydro-4H-3,10a-diaza-benzo[f]azulene, oxalate
2-Furan-2-yl-4-(1-methyl-piperidin-4-yloxy)-9,10-dihydro-4H-3,10a-diaza-benzo[f]azulene, oxalate
4-(1-Methyl-piperidin-4-yloxy)-2-(4-trifluoromethyl-phenyl)-9,10-dihydro-4H-3,10a-diaza-benzo[f]azulene
2-(2-Chloro-phenyl)-4-(1-methyl-piperidin-4-yloxy)-9,10-dihydro-4H-3,10a-diaza-benzo[f]azulene, oxalate
2-(2-Fluoro-phenyl)-4-(1-methyl-piperidin-4-yloxy)-9,10-dihydro-4H-3,10a-diaza-benzo[f]azulene
2-(4-Isobutyl-phenyl)-4-(1-methyl-piperidin-4-yloxy)-9,10-dihydro-4H-3,10a-diaza-benzo[f]azulene
N,N-Dimethyl-4-[4-(1-methyl-piperidin-4-yloxy)-9,10-dihydro-4H-3,10a-diaza-benzo[f]azulen-2-yl]-benzenesulfonamide
2-Allyl-4-(1-methyl-piperidin-4-yloxy)-9,10-dihydro-4H-3,10a-diaza-benzo[f]azulene, oxalate
2,2,2-Trifluoro-1-{4-[4-(1-methyl-piperidin-4-yloxy)-9,10-dihydro-4H-3,10a-diaza-benzo[f]azulen-2-yl]-phenyl}ethanone, oxalate
2-(4-Isopropyl-phenyl)-4-(1-methyl-piperidin-4-yloxy)-9,10-dihydro-4H-3,10a-diaza-benzo[f]azulene, oxalate
{4-[4-(1-Methyl-piperidin-4-yloxy)-9,10-dihydro-4H-3,10a-diaza-benzo[f]azulen-2-yl]-phenyl}-acetonitrile, oxalate
4-(1-Methyl-piperidin-4-yloxy)-2-phenylethynyl-9,10-dihydro-4H-3,10a-diaza-benzo[f]azulene, oxalate
Dimethyl-{4-[4-(1-methyl-piperidin-4-yloxy)-9,10-dihydro-4H-3,10a-diaza-benzo[f]azulen-2-yl]-phenyl}-amine, oxalate
4-[4-(1-Methyl-piperidin-4-yloxy)-9,10-dihydro-4H-3,10a-diaza-benzo[f]azulen-2-yl]-benzoic acid tert-butyl ester
4-[4-(1-Methyl-piperidin-4-yloxy)-9,10-dihydro-4H-3,10a-diaza-benzo[f]azulen-2-yl]-benzonitrile
4-(1-Methyl-piperidin-4-yloxy)-2-phenethyl-9,10-dihydro-4H-3,10a-diaza-benzo[f]azulene, oxalate
4-(1-Methyl-piperidin-4-yloxy)-2-(6-methyl-pyridin-3-yl)-9,10-dihydro-4H-3,10a-diaza-benzo[f]azulene, oxalate
4-(1-Methyl-piperidin-4-yloxy)-2-oxazol-2-yl-9,10-dihydro-4H-3,10a-diaza-benzo[f]azulene, oxalate
2-(4-Butyl-phenyl)-4-(1-methyl-piperidin-4-yloxy)-9,10-dihydro-4H-3,10a-diaza-benzo[f]azulene
2-(4-Butyl-phenyl)-4-(1-methyl-piperidin-4-yloxy)-9,10-dihydro-4H-3,10a-diaza-benzo[f]azulene, oxalate
4-(1-Methyl-piperidin-4-yloxy)-2-(4-pentyl-phenyl)-9,10-dihydro-4H-3,10a-diaza-benzo[f]azulene
2-(4-Hexyl-phenyl)-4-(1-methyl-piperidin-4-yloxy)-9,10-dihydro-4H-3,10a-diaza-benzo[f]azulene
4-(1-Methyl-piperidin-4-yloxy)-2-pyridin-4-yl-9,10-dihydro-4H-3,10a-diaza-benzo[f]azulene, oxalate
4-(1-Methyl-piperidin-4-yloxy)-2-pyridin-3-yl-9,10-dihydro-4H-3,10a-diaza-benzo[f]azulene, oxalate
2-(4-Ethylsulfanyl-phenyl)-4-(1-methyl-piperidin-4-yloxy)-9,10-dihydro-4H-3,10a-diaza-benzo[f]azulene, oxalate
4-(1-Methyl-piperidin-4-yloxy)-2-thiophen-2-yl-9,10-dihydro-4H-3,10a-diaza-benzo[f]azulene, oxalate
4-(1-Methyl-piperidin-4-yloxy)-2-thiazol-5-yl-9,10-dihydro-4H-3,10a-diaza-benzo[f]azulene, oxalate
{4-[4-(1-Methyl-piperidin-4-yloxy)-9,10-dihydro-4H-3,10a-diaza-benzo[f]azulen-2-yl]-phenyl}-carbamic acid tert-butyl ester
2-Benzo[1,3]dioxol-5-yl-4-(1-methyl-piperidin-4-yloxy)-9,10-dihydro-4H-3,10a-diaza-benzo[f]azulene
2-(5-Methyl-furan-2-yl)-4-(1-methyl-piperidin-4-yloxy)-9,10-dihydro-4H-3,10a-diaza-benzo[f]azulene, oxalate
2-(4-Chloro-phenyl)-4-(1-methyl-piperidin-4-yloxy)-9,10-dihydro-4H-3,10a-diaza-benzo[f]azulene, oxalate
3-[4-(1-Methyl-piperidin-4-yloxy)-9,10-dihydro-4H-3,10a-diaza-benzo[f]azulen-2-yl]-acrylic acid tert-butyl ester, oxalate
2-(2-Chloro-phenyl)-4-(1-methyl-piperidin-4-yloxy)-9,10-dihydro-4H-3,10a-diaza-benzo[f]azulene, oxalate
4-(1-Methyl-piperidin-4-yloxy)-2-(2-methyl-4-trifluoromethyl-phenyl)-9,10-dihydro-4H-3,10a-diaza-benzo[f]azulene
2-(4-Fluoro-phenyl)-4-(1-methyl-piperidin-4-yloxy)-9,10-dihydro-4H-3,10a-diaza-benzo[f]azulene
2-(3,6-Dihydro-2H-thiopyran-4-yl)-4-(1-methyl-piperidin-4-yloxy)-9,10-dihydro-4H-3,10a-diaza-benzo[f]azulene 2,2-Dimethyl-N-{4-[4-(1-methyl-piperidin-4-yloxy)-9,10-dihydro-4H-3,10a-diaza-benzo[f]azulen-2-yl]-phenyl}-propionamide
2-(2-Cyclohexyl-vinyl)-4-(1-methyl-piperidin-4-yloxy)-9,10-dihydro-4H-3,10a-diaza-benzo[f]azulene
1-{4-[4-(1-Methyl-piperidin-4-yloxy)-9,10-dihydro-4H-3,10a-diaza-benzo[f]azulen-2-yl]-phenyl}-3-propyl-urea
2-(2,4-Dimethyl-phenyl)-4-(1-methyl-piperidin-4-yloxy)-9,10-dihydro-4H-3,10a-diaza-benzo[f]azulene
2-Cyclohex-1-enyl-4-(1-methyl-piperidin-4-yloxy)-9,10-dihydro-4H-3,10a-diaza-benzo[f]azulene, oxalate
4-(1-Methyl-piperidin-4-yloxy)-2-pyridin-3-ylethynyl-9,10-dihydro-4H-3,10a-diaza-benzo[f]azulene, oxalate
2-[4-(1,1-Difluoro-ethyl)-phenyl]-4-(1-methyl-piperidin-4-yloxy)-9,10-dihydro-4H-3,10a-diaza-benzo[f]azulene, oxalate
2-Cyclopent-1-enyl-4-(1-methyl-piperidin-4-yloxy)-9,10-dihydro-4H-3,10a-diaza-benzo[f]azulene
4-(1-Methyl-piperidin-4-yloxy)-2-thiazol-2-yl-9,10-dihydro-4H-3,10a-diaza-benzo[f]azulene, oxalate
2-Benzylsulfanyl-4-(1-methyl-piperidin-4-yloxy)-9,10-dihydro-4H-3,10a-diaza-benzo[f]azulene, oxalate
2-(3-Fluoro-phenyl)-4-(1-methyl-piperidin-4-yloxy)-9,10-dihydro-4H-3,10a-diaza-benzo[f]azulene, oxalate
2-(4-Difluoromethyl-phenyl)-4-(1-methyl-piperidin-4-yloxy)-9,10-dihydro-4H-3,10a-diaza-benzo[f]azulene, oxalate
2-(2-Methyl-allyl)-4-(1-methyl-piperidin-4-yloxy)-9,10-dihydro-4H-3,10a-diaza-benzo[f]azulene, oxalate
2-(2,4-Dichloro-phenyl)-4-(1-methyl-piperidin-4-yloxy)-9,10-dihydro-4H-3,10a-diaza-benzo[f]azulene, oxalate
{3-[4-(1-Methyl-piperidin-4-yloxy)-9,10-dihydro-4H-3,10a-diaza-benzo[f]azulen-2-yl]-prop-2-ynyl}-carbamic acid tert-butyl ester
4-(1-Methyl-piperidin-4-yloxy)-2-phenylsulfanyl-9,10-dihydro-4H-3,10a-diaza-benzo[f]azulene, oxalate
4-[4-(1-Methyl-piperidin-4-yloxy)-9,10-dihydro-4H-3,10a-diaza-benzo[f]azulen-2-yl]3,6-dihydro-2H-pyridine-1-carboxylic acid tert-butyl ester, oxalate
2-(2-Chloro-4-methyl-phenyl)-4-(1-methyl-piperidin-4-yloxy)-9,10-dihydro-4H-3,10a-diaza-benzo[f]azulene, oxalate
4-(1-Methyl-piperidin-4-yloxy)-2-(3-phenyl-propenyl)-9,10-dihydro-4H-3,10a-diaza-benzo[f]azulene, oxalate
2-(3-Chloro-phenyl)-4-(1-methyl-piperidin-4-yloxy)-9,10-dihydro-4H-3,10a-diaza-benzo[f]azulene, oxalate
8-Chloro-2-iodo-4-(1-methyl-piperidin-4-yloxy)-9,10-dihydro-4H-3,10a-diaza-benzo[f]azulene
8-Bromo-2-iodo-4-(1-methyl-piperidin-4-yloxy)-9,10-dihydro-4H-3,10a-diaza-benzo[f]azulene
2-Cyclohept-1-enyl-4-(1-methyl-piperidin-4-yloxy)-9,10-dihydro-4H-3,10a-diaza-benzo[f]azulene
2-(4-Bromo-phenyl)-4-(1-methyl-piperidin-4-yloxy)-9,10-dihydro-4H-3,10a-diaza-benzo[f]azulene
2-(2-Fluoro-4-methyl-phenyl)-4-(1-methyl-piperidin-4-yloxy)-9,10-dihydro-4H-3,10a-diaza-benzo[f]azulene
4-(1-Methyl-piperidin-4-yloxy)-2-(1-methyl-1H-pyrrol-2-yl)-9,10-dihydro-4H-3,10a-diaza-benzo[f]azulene
{2-[4-(1-Methyl-piperidin-4-yloxy)-9,10-dihydro-4H-3,10a-diaza-benzo[f]azulen-2-ylsulfanyl]-ethyl}-carbamic acid tert-butyl ester, oxalate
2-(Furan-2-ylmethylsulfanyl)-4-(1-methyl-piperidin-4-yloxy)-9,10-dihydro-4H-3,10a-diaza-benzo[f]azulene, oxalate
2-Cyclopentylsulfanyl-4-(1-methyl-piperidin-4-yloxy)-9,10-dihydro-4H-3,10a-diaza-benzo[f]azulene, oxalate
4-(1-Methyl-piperidin-4-yloxy)-2-(3-phenyl-propyl)-9,10-dihydro-4H-3,10a-diaza-benzo[f]azulene, oxalate
4-(1-Methyl-piperidin-4-yloxy)-2-(thiophen-2-ylmethylsulfanyl)-9,10-dihydro-4H-3,10a-diaza-benzo[f]azulene, oxalate
4-(1-Methyl-piperidin-4-yloxy)-2-(5-phenyl-pent-1-enyl)-9,10-dihydro-4H-3,10a-diaza-benzo[f]azulene
4-(1-Methyl-piperidin-4-yloxy)-2-(5-phenyl-pentyl)-9,10-dihydro-4H-3,10a-diaza-benzo[f]azulene, oxalate
8-Chloro-4-(1-methyl-piperidin-4-yloxy)-2-phenyl-9,10-dihydro-4H-3,10a-diaza-benzo[f]azulene
4-(1-Methyl-piperidin-4-yloxy)-2,8-diphenyl-9,10-dihydro-4H-3,10a-diaza-benzo[f]azulene
2-(3,3-Dimethyl-but-1-enyl)-4-(1-methyl-piperidin-4-yloxy)-9,10-dihydro-4H-3,10a-diaza-benzo[f]azulene
2-(3,3-Dimethyl-butyl)-4-(1-methyl-piperidin-4-yloxy)-9,10-dihydro-4H-3,10a-diaza-benzo[f]azulene
2-(2-Cyclohexyl-ethyl)-4-(1-methyl-piperidin-4-yloxy)-9,10-dihydro-4H-3,10a-diaza-benzo[f]azulene, oxalate
4-(1-Methyl-piperidin-4-yloxy)-2-(5-methyl-thiophen-2-yl)-9,10-dihydro-4H-3,10a-diaza-benzo[f]azulene, oxalate
Methyl-{4-[4-(1-methyl-piperidin-4-yloxy)-9,10-dihydro-4H-3,10a-diaza-benzo[f]azulen-2-yl]-phenyl}-carbamic acid tert-butyl ester, oxalate
2-Cyclohexylsulfanyl-4-(1-methyl-piperidin-4-yloxy)-9,10-dihydro-4H-3,10a-diaza-benzo[f]azulene, oxalate
2-(2-Cyclopropyl-vinyl)-4-(1-methyl-piperidin-4-yloxy)-9,10-dihydro-4H-3,10a-diaza-benzo[f]azulene, oxalate
Methyl-{4-[4-(1-methyl-piperidin-4-yloxy)-9,10-dihydro-4H-3,10a-diaza-benzo[f]azulen-2-yl]-phenyl}-amine, oxalate
2,2,N-Trimethyl-N-{4-[4-(1-methyl-piperidin-4-yloxy)-9,10-dihydro-4H-3,10a-diaza-benzo[f]azulen-2-yl]-phenyl}-propionamide, oxalate
[4-(1-Methyl-piperidin-4-yloxy)-9,10-dihydro-4H-3,10a-diaza-benzo[f]azulen-2-yl]-phenyl-methanone, oxalate
1-Methyl-4-(1-methyl-piperidin-4-yloxy)-2-phenyl-9,10-dihydro-4H-3,10a-diaza-benzo[f]azulene
2-(3-Cyclopentyl-propenyl)-4-(1-methyl-piperidin-4-yloxy)-9,10-dihydro-4H-3,10a-diaza-benzo[f]azulene
2-(3-Cyclopentyl-propyl)-4-(1-methyl-piperidin-4-yloxy)-9,10-dihydro-4H-3,10a-diaza-benzo[f]azulene
2-(3,6-Dihydro-2H-pyran-4-yl)-4-(1-methyl-piperidin-4-yloxy)-9,10-dihydro-4H-3,10a-diaza-benzo[f]azulene
8-Fluoro-4-(1-methyl-piperidin-4-yloxy)-2-phenyl-9,10-dihydro-4H-3,10a-diaza-benzo[f]azulene
N-(4-Hydroxy-cyclohexyl)-4-[4-(1-methyl-piperidin-4-yloxy)-9,10-dihydro-4H-3,10a-diaza-benzo[f]azulen-2-yl]-benzamide
2-Isobutyl-4-(1-methyl-piperidin-4-yloxy)-9,10-dihydro-4H-3,10a-diaza-benzo[f]azulene, oxalate
2-Benzyl-4-(1-methyl-piperidin-4-yloxy)-9,10-dihydro-4H-3,10a-diaza-benzo[f]azulene, oxalate
4-(1-Methyl-piperidin-4-yloxy)-2-(2-thiophen-2-yl-vinyl)-9,10-dihydro-4H-3,10a-diaza-benzo[f]azulene
4-(1-Methyl-piperidin-4-yloxy)-2-(2-thiophen-3-yl-vinyl)-9,10-dihydro-4H-3,10a-diaza-benzo[f]azulene
Dimethyl-{4-[4-(1-methyl-piperidin-4-yloxy)-9,10-dihydro-4H-3,10a-diaza-benzo[f]azulen-2-yl]-benzyl}-amine
4-[4-(1-Methyl-piperidin-4-yloxy)-9,10-dihydro-4H-3,10a-diaza-benzo[f]azulen-2-ylsulfanyl]-piperidine-1-carboxylic acid tert-butyl ester
{4-[4-(1-Methyl-piperidin-4-yloxy)-9,10-dihydro-4H-3,10a-diaza-benzo[f]azulen-2-yl]-benzyl}-carbamic acid tert-butyl ester 2-Methyl-4-(1-methyl-piperidin-4-yloxy)-9,10-dihydro-4H-3,10a-diaza-benzo[f]azulene-1-carboxylic acid ethyl ester
2-[1-(4-Chloro-phenyl)-1-methyl-ethyl]-4-(1-methyl-piperidin-4-yloxy)-9,10-dihydro-4H-3,10a-diaza-benzo[f]azulene, oxalate
1-Methyl-4-(1-methyl-piperidin-4-yloxy)-9,10-dihydro-4H-3,10a-diaza-benzo[f]azulene-2-carboxylic acid ethyl ester
4-(1-Methyl-piperidin-4-yloxy)-2-phenethylsulfanyl-9,10-dihydro-4H-3,10a-diaza-benzo[f]azulene, oxalate
1-Ethyl-4-(1-methyl-piperidin-4-yloxy)-2-phenyl-9,10-dihydro-4H-3,10a-diaza-benzo[f]azulene, oxalate
4-(1-Methyl-piperidin-4-yloxy)-2-(3-phenoxy-propenyl)-9,10-dihydro-4H-3,10a-diaza-benzo[f]azulene, oxalate
2-(4-Bromo-phenyl)-1-methyl-4-(1-methyl-piperidin-4-yloxy)-9,10-dihydro-4H-3,10a-diaza-benzo[f]azulene
2-Methyl-4-(1-methyl-piperidin-4-yloxy)-1-phenyl-9,10-dihydro-4H-3,10a-diaza-benzo[f]azulene, oxalate
2-(3-Benzyloxy-propenyl)-4-(1-methyl-piperidin-4-yloxy)-9,10-dihydro-4H-3,10a-diaza-benzo[f]azulene, oxalate
Methyl-{4-[1-methyl-4-(1-methyl-piperidin-4-yloxy)-9,10-dihydro-4H-3,10a-diaza-benzo[f]azulen-2-yl]-phenyl}-carbamic acid tert-butyl ester, oxalate
4-(1-Methyl-piperidin-4-yloxy)-2-(2-thiophen-2-yl-ethyl)-9,10-dihydro-4H-3,10a-diaza-benzo[f]azulene, oxalate
2-(4-Bromo-phenyl)-1-chloro-4-(1-methyl-piperidin-4-yloxy)-9,10-dihydro-4H-3,10a-diaza-benzo[f]azulene
2-(3-Benzyloxy-propyl)-4-(1-methyl-piperidin-4-yloxy)-9,10-dihydro-4H-3,10a-diaza-benzo[f]azulene, oxalate
4-(1-Methyl-piperidin-4-yloxy)-2-(4-phenyl-butyl)-9,10-dihydro-4H-3,10a-diaza-benzo[f]azulene, oxalate
{4-[1-Methyl-4-(1-methyl-piperidin-4-yloxy)-9,10-dihydro-4H-3,10a-diaza-benzo[t]azulen-2-yl]-phenyl}-carbamic acid tert-butyl ester
3-{4-[1-Methyl-4-(1-methyl-piperidin-4-yloxy)-9,10-dihydro-4H-3,10a-diaza-benzo[t]azulen-2-yl]-phenyl}-oxazolidin-2-one
1-Methyl-3-{4-[1-methyl-4-(1-methyl-piperidin-4-yloxy)-9,10-dihydro-4H-3,10a-diaza-benzo[f]azulen-2-yl]-phenyl}-imidazolidin-2-one
2-Iodo-1-methyl-4-(1-methyl-piperidin-4-yloxy)-9,10-dihydro-4H-3,10a-diaza-benzo[f]azulene
1-Chloro-4-(1-methyl-piperidin-4-yloxy)-2-phenyl-9,10-dihydro-4H-3,10a-diaza-benzo[f]azulene
1-Methyl-4-(1-methyl-piperidin-4-yloxy)-2-phenyl-9,10-dihydro-4H-3,10a-diaza-benzo[f]azulene
2,2-Dimethyl-N-{4-[4-(1-methyl-piperidin-4-yloxy)-9,10-dihydro-4H-3,10a-diaza-benzo[t]azulen-2-yl]-benzyl}-propionamide
2,2-Dimethyl-N-{4-[4-(1-methyl-piperidin-4-yloxy)-9,10-dihydro-4H-3,10a-diaza-benzo[t]azulen-2-yl]-benzyl}-propionamide
1-Chloro-4-(1-methyl-piperidin-4-yloxy)-2-(5-phenyl-pentyl)-9,10-dihydro-4H-3,10a-diaza-benzo[f]azulene, oxalate
1-tert-Butyl-3-{4-[1-methyl-4-(1-methyl-piperidin-4-yloxy)-9,10-dihydro-4H-3,10a-diaza-benzo[f]azulen-2-yl]-phenyl}-imidazolidin-2-one
{4-[1-Chloro-4-(1-methyl-piperidin-4-yloxy)-9,10-dihydro-4H-3,10a-diaza-benzo[t]azulen-2-yl]-phenyl}-carbamic acid tert-butyl ester
2-(2-Fluoro-phenyl)-1-methyl-4-(1-methyl-piperidin-4-yloxy)-9,10-dihydro-4H-3,10a-diaza-benzo[f]azulene
2-(3-Fluoro-phenyl)-1-methyl-4-(1-methyl-piperidin-4-yloxy)-9,10-dihydro-4H-3,10a-diaza-benzo[f]azulene
1-Methyl-4-(1-methyl-piperidin-4-yloxy)-2-m-tolyl-9,10-dihydro-4H-3,10a-diaza-benzo[f]azulene
2-(3-Chloro-phenyl)-1-methyl-4-(1-methyl-piperidin-4-yloxy)-9,10-dihydro-4H-3,10a-diaza-benzo[f]azulene
2-(2-Chloro-phenyl)-1-methyl-4-(1-methyl-piperidin-4-yloxy)-9,10-dihydro-4H-3,10a-diaza-benzo[f]azulene
1-Methyl-4-(1-methyl-piperidin-4-yloxy)-2-o-tolyl-9,10-dihydro-4H-3,10a-diaza-benzo[f]azulene
1-Methyl-4-(1-methyl-piperidin-4-yloxy)-2-thiophen-3-yl-9,10-dihydro-4H-3,10a-diaza-benzo[f]azulene
2-(2-Methoxy-phenyl)-1-methyl-4-(1-methyl-piperidin-4-yloxy)-9,10-dihydro-4H-3,10a-diaza-benzo[f]azulene
2-(3-Methoxy-phenyl)-1-methyl-4-(1-methyl-piperidin-4-yloxy)-9,10-dihydro-4H-3,10a-diaza-benzo[f]azulene
3-{4-[1-Methyl-4-(1-methyl-piperidin-4-yloxy)-9,10-dihydro-4H-3,10a-diaza-benzo[f]azulen-2-yl]-phenyl}-acrylic acid tert-butyl ester
3-Methyl-3-{4-[1-methyl-4-(1-methyl-piperidin-4-yloxy)-9,10-dihydro-4H-3,10a-diaza-benzo[t]azulen-2-yl]-phenylsulfanyl}-butan-1-ol, oxalate
1-Methyl-4-(1-methyl-piperidin-4-yloxy)-2-p-tolyl-9,10-dihydro-4H-3,10a-diaza-benzo[f]azulene
2-(4-Fluoro-phenyl)-1-methyl-4-(1-methyl-piperidin-4-yloxy)-9,10-dihydro-4H-3,10a-diaza-benzo[f]azulene
2-(4-Chloro-phenyl)-1-methyl-4-(1-methyl-piperidin-4-yloxy)-9,10-dihydro-4H-3,10a-diaza-benzo[f]azulene
2-(4-Methoxy-phenyl)-1-methyl-4-(1-methyl-piperidin-4-yloxy)-9,10-dihydro-4H-3,10a-diaza-benzo[f]azulene
2-(2-Chloro-4-methyl-phenyl)-1-methyl-4-(1-methyl-piperidin-4-yloxy)-9,10-dihydro-4H-3,10a-diaza-benzo[f]azulene, oxalate
2-[4-(2-Methanesulfonyl-vinyl)-phenyl]-1-methyl-4-(1-methyl-piperidin-4-yloxy)-9,10-dihydro-4H-3,10a-diaza-benzo[f]azulene
2-[4-(2-Methanesulfonyl-ethyl)-phenyl]-1-methyl-4-(1-methyl-piperidin-4-yloxy)-9,10-dihydro-4H-3,10a-diaza-benzo[f]azulene
(2-{4-[1-Methyl-4-(1-methyl-piperidin-4-yloxy)-9,10-dihydro-4H-3,10a-diaza-benzo[f]azulen-2-yl]-phenylsulfanyl}-ethyl)-carbamic acid tert-butyl ester, oxalate
2-{4-[1-Methyl-4-(1-methyl-piperidin-4-yloxy)-9,10-dihydro-4H-3,10a-diaza-benzo[f]azulen-2-yl]-phenylsulfanyl}-ethylamine, oxalate
1-{4-[1-Methyl-4-(1-methyl-piperidin-4-yloxy)-9,10-dihydro-4H-3,10a-diaza-benzo[f]azulen-2-yl]-phenyl}-piperidin-2-one, oxalate
N-(2-{4-[1-Methyl-4-(1-methyl-piperidin-4-yloxy)-9,10-dihydro-4H-3,10a-diaza-benzo[f]azulen-2-yl]-phenylsulfanyl}-ethyl)-acetamide, oxalate
2-(4-Benzylsulfanyl-phenyl)-1-methyl-4-(1-methyl-piperidin-4-yloxy)-9,10-dihydro-4H-3,10a-diaza-benzo[f]azulene, oxalate
{4-[1-Methyl-4-(1-methyl-piperidin-4-yloxy)-9,10-dihydro-4H-3,10a-diaza-benzo[f]azulen-2-yl]-phenylsulfanyl}-acetic acid methyl ester, oxalate
2-(4-tert-Butylsulfanyl-phenyl)-1-methyl-4-(1-methyl-piperidin-4-yloxy)-9,10-dihydro-4H-3,10a-diaza-benzo[f]azulene, oxalate
2-[4-(Furan-2-ylmethylsulfanyl)-phenyl]-1-methyl-4-(1-methyl-piperidin-4-yloxy)-9,10-dihydro-4H-3,10a-diaza-benzo[f]azulene, oxalate
4-{4-[1-Methyl-4-(1-methyl-piperidin-4-yloxy)-9,10-dihydro-4H-3,10a-diaza-benzo[f]azulen-2-yl]-phenyl}-3,6-dihydro-2H-pyridine-1-carboxylic acid tert-butyl ester
2-(4-Cyclopent-1-enyl-phenyl)-1-methyl-4-(1-methyl-piperidin-4-yloxy)-9,10-dihydro-4H-3,10a-diaza-benzo[f]azulene 2-(4-Cyclohex-1-enyl-phenyl)-1-methyl-4-(1-methyl-piperidin-4-yloxy)-9,10-dihydro-4H-3,10a-diaza-benzo[f]azulene
2-(4-Cyclohept-1-enyl-phenyl)-1-methyl-4-(1-methyl-piperidin-4-yloxy)-9,10-dihydro-4H-3,10a-diaza-benzo[f]azulene
{4-[1-Methyl-4-(1-methyl-piperidin-4-yloxy)-9,10-dihydro-4H-3,10a-diaza-benzo[f]azulen-2-yl]-phenyl}-carbamic acid cyclopentyl ester
4-[1-Methyl-4-(1-methyl-piperidin-4-yloxy)-9,10-dihydro-4H-3,10a-diaza-benzo[f]azulen-2-yl]-phenylamine
{4-[1-Methyl-4-(1-methyl-piperidin-4-yloxy)-9,10-dihydro-4H-3,10a-diaza-benzo[f]azulen-2-yl]-phenyl}-carbamic acid isobutyl ester
{4-[1-Methyl-4-(1-methyl-piperidin-4-yloxy)-9,10-dihydro-4H-3,10a-diaza-benzo[f]azulen-2-yl]-phenyl}-carbamic acid 2,2,2-trichloro-1,1-dimethyl-ethyl ester
4-Benzyl-3-{4-[1-methyl-4-(1-methyl-piperidin-4-yloxy)-9,10-dihydro-4H-3,10a-diaza-benzo[f]azulen-2-yl]-phenyl}-oxazolidin-2-one
4-{4-[1-Methyl-4-(1-methyl-piperidin-4-yloxy)-9,10-dihydro-4H-3,10a-diaza-benzo[f]azulen-2-yl]-phenyl}-piperidine-1-carboxylic acid tert-butyl ester
1-Isopropyl-3-{4-[1-methyl-4-(1-methyl-piperidin-4-yloxy)-9,10-dihydro-4H-3,10a-diaza-benzo[f]azulen-2-yl]-phenyl}-imidazolidin-2-one
{2-[4-(1-Methyl-piperidin-4-yloxy)-9,10-dihydro-4H-3,10a-diaza-benzo[f]azulen-2-yl]-phenyl}-methanol, oxalate
Dimethyl-(2-{4-[4-(1-methyl-piperidin-4-yloxy)-9,10-dihydro-4H-3,10a-diaza-benzo[f]azulen-2-yl]-phenoxy}-ethyl)-amine, dioxalate
3-{4-[4-(1-Methyl-piperidin-4-yloxy)-9,10-dihydro-4H-3,10a-diaza-benzo[f]azulen-2-yl]-benzyl}-oxazolidin-2-one
Methyl-{4-[4-(1-methyl-piperidin-4-yloxy)-9,10-dihydro-4H-3,10a-diaza-benzo[f]azulen-2-yl]-benzyl}-carbamic acid tert-butyl ester
2-(4-Allyloxy-phenyl)-4-(1-methyl-piperidin-4-yloxy)-9,10-dihydro-4H-3,10a-diaza-benzo[f]azulene
1-{4-[4-(1-Methyl-piperidin-4-yloxy)-9,10-dihydro-4H-3,10a-diaza-benzo[f]azulen-2-yl]-benzyl}-pyrrolidin-2-one
1-{4-[4-(1-Methyl-piperidin-4-yloxy)-9,10-dihydro-4H-3,10a-diaza-benzo[f]azulen-2-yl]-benzyl}-piperidin-2-one
2-(4-Isopropylsulfanylmethyl-phenyl)-4-(1-methyl-piperidin-4-yloxy)-9,10-dihydro-4H-3,10a-diaza-benzo[f]azulene
Cyclopropanesulfonic acid {4-[1-methyl-4-(1-methyl-piperidin-4-yloxy)-9,10-dihydro-4H-3,10a-diaza-benzo[f]azulen-2-yl]-phenyl}-amide
1-{4-[4-(1-Methyl-piperidin-4-yloxy)-9,10-dihydro-4H-3,10a-diaza-benzo[f]azulen-2-yl]-benzyl}-azepan-2-one
2-[4-(2-tert-Butylsulfanyl-ethyl)-phenyl]-4-(1-methyl-piperidin-4-yloxy)-9,10-dihydro-4H-3,10a-diaza-benzo[f]azulene
4-(1-Methyl-piperidin-4-yloxy)-2-(2-nitro-phenyl)-9,10-dihydro-4H-3,10a-diaza-benzo[f]azulene
1-tert-Butyl-3-{4-[4-(1-methyl-piperidin-4-yloxy)-9,10-dihydro-4H-3,10a-diaza-benzo[f]azulen-2-yl]-benzyl}-imidazolidin-2-one
2-{4-[4-(1-Methyl-piperidin-4-yloxy)-9,10-dihydro-4H-3,10a-diaza-benzo[f]azulen-2-yl]-phenyl}-ethanol
2-(4-Cyclopropylmethoxy-phenyl)-4-(1-methyl-piperidin-4-yloxy)-9,10-dihydro-4H-3,10a-diaza-benzo[f]azulene
3-{4-[1-Methyl-4-(1-methyl-piperidin-4-yloxy)-9,10-dihydro-4H-3,10a-diaza-benzo[f]azulen-2-yl]-phenylsulfanyl}-propane-1,2-diol
3-{4-[1-Methyl-4-(1-methyl-piperidin-4-yloxy)-9,10-dihydro-4H-3,10a-diaza-benzo[f]azulen-2-yl]-phenylsulfanyl}-propan-1-ol
(2-{4-[4-(1-Methyl-piperidin-4-yloxy)-9,10-dihydro-4H-3,10a-diaza-benzo[f]azulen-2-yl]-phenyl}-ethyl)-carbamic acid tert-butyl ester
Methyl-(2-{4-[4-(1-methyl-piperidin-4-yloxy)-9,10-dihydro-4H-3,10a-diaza-benzo[f]azulen-2-yl]-phenyl}ethyl)-carbamic acid tert-butyl ester
5,5-Dimethyl-3-{4-[4-(1-methyl-piperidin-4-yloxy)-9,10-dihydro-4H-3,10a-diaza-benzo[f]azulen-2-yl]-benzyl}-oxazolidine-2,4-dione
(2-{4-[4-(1-Methyl-piperidin-4-yloxy)-9,10-dihydro-4H-3,10a-diaza-benzo[f]azulen-2-yl]-benzylsulfanyl}-ethyl)-carbamic acid tert-butyl ester
tert-Butyl-carbamic acid 2-{4-[4-(1-methyl-piperidin-4-yloxy)-9,10-dihydro-4H-3,10a-diaza-benzo[f]azulen-2-yl]-phenyl}-ethyl ester
[1-Methyl-4-(1-methyl-piperidin-4-yloxy)-9,10-dihydro-4H-3,10a-diaza-benzo[f]azulen-2-yl]-phenyl-methanol, formate
[1-Methyl-4-(1-methyl-piperidin-4-yloxy)-9,10-dihydro-4H-3,10a-diaza-benzo[f]azulen-2-yl]-phenyl-methanone, formate
1-Methyl-4-(1-methyl-piperidin-4-yloxy)-9,10-dihydro-4H-3,10a-diaza-benzo[f]azulene-2-carboxylic acid benzyl-methyl-amide
1-Methyl-4-(1-methyl-piperidin-4-yloxy)-9,10-dihydro-4H-3,10a-diaza-benzo[f]azulene-2-carboxylic acid methyl-phenyl-amide
1-Methyl-4-(1-methyl-piperidin-4-yloxy)-9,10-dihydro-4H-3,10a-diaza-benzo[f]azulene-2-carboxylic acid propylamide
1-Isopropyl-3-{4-[1-methyl-4-(1-methyl-piperidin-4-yloxy)-9,10-dihydro-4H-3,10a-diaza-benzo[f]azulen-2-yl]-phenyl}-thiourea
2-(1-Methyl-1-phenyl-ethyl)-4-(1-methyl-piperidin-4-yloxy)-9,10-dihydro-4H-3,10a-diaza-benzo[f]azulene
1-Cyclopropyl-3-{4-[1-methyl-4-(1-methyl-piperidin-4-yloxy)-9,10-dihydro-4H-3,10a-diaza-benzo[f]azulen-2-yl]-phenyl}-thiourea
1-tert-Butyl-3-{4-[1-methyl-4-(1-methyl-piperidin-4-yloxy)-9,10-dihydro-4H-3,10a-diaza-benzo[f]azulen-2-yl]-phenyl}-urea
2-Methyl-1-[1-methyl-4-(1-methyl-piperidin-4-yloxy)-9,10-dihydro-4H-3,10a-diaza-benzo[f]azulen-2-yl]-propan-1-ol, oxalate
N-(2-{4-[1-Methyl-4-(1-methyl-piperidin-4-yloxy)-9,10-dihydro-4H-3,10a-diaza-benzo[f]azulen-2-yl]-phenylsulfanyl}-ethyl)-guanidine
N-(2-Hydroxy-ethyl)-4-[4-(1-methyl-piperidin-4-yloxy)-9,10-dihydro-4H-3,10a-diaza-benzo[f]azulen-2-yl]-benzamide
1-Adamantan-1-yl-3-{4-[1-methyl-4-(1-methyl-piperidin-4-yloxy)-9,10-dihydro-4H-3,10a-diaza-benzo[f]azulen-2-yl]-phenyl}-urea
N-{4-[1-Methyl-4-(1-methyl-piperidin-4-yloxy)-9,10-dihydro-4H-3,10a-diaza-benzo[f]azulen-2-yl]-phenyl}-hydrazinecarboxylic acid tert-butyl ester
1-{4-[4-(1-Methyl-piperidin-4-yloxy)-9,10-dihydro-4H-3,10a-diaza-benzo[f]azulen-2-yl]-benzoyl}-piperidin-4-one
N-(4-Hydroxy-cyclohexyl)-4-[1-methyl-4-(1-methyl-piperidin-4-yloxy)-9,10-dihydro-4H-3,10a-diaza-benzo[f]azulen-2-yl]-benzamide N-(2-Hydroxy-ethyl)-4-[1-methyl-4-(1-methyl-piperidin-4-yloxy)-9,10-dihydro-4H-3,10a-diaza-benzo[f]azulen-2-yl]-benzamide
1-{4-[1-Methyl-4-(1-methyl-piperidin-4-yloxy)-9,10-dihydro-4H-3,10a-diaza-benzo[f]azulen-2-yl]-benzoyl}-piperidin-4-one
1,2-Diiodo-4-(1-methyl-piperidin-4-yloxy)-9,10-dihydro-4H-3,10a-diaza-benzo[f]azulene
(4-Hydroxy-piperidin-1-yl)-{4-[1-methyl-4-(1-methyl-piperidin-4-yloxy)-9,10-dihydro-4H-3,10a-diaza-benzo[f]azulen-2-yl]-phenyl}-methanone
2-Iodo-4-(1-methyl-piperidin-4-yloxy)-9,10-dihydro-4H-3,10a-diaza-benzo[f]azulene-1-carbonitrile
1-Methyl-4-(1-methyl-piperidin-4-yloxy)-9,10-dihydro-4H-3,10a-diaza-benzo[f]azulene-2-carboxylic acid benzylamide
(2-{4-[1-Methyl-4-(1-methyl-piperidin-4-yloxy)-9,10-dihydro-4H-3,10a-diaza-benzo[f]azulen-2-yl]-phenyl}ethyl)-carbamic acid tert-butyl ester
4-[1-Cyano-4-(1-methyl-piperidin-4-yloxy)-9,10-dihydro-4H-3,10a-diaza-benzo[f]azulen-2-yl]-benzoic acid tert-butyl ester
2-(3,3-Dimethyl-but-1-enyl)-1-methyl-4-(1-methyl-piperidin-4-yloxy)-9,10-dihydro-4H-3,10a-diaza-benzo[f]azulene
2-Cyclohex-1-enyl-1-methyl-4-(1-methyl-piperidin-4-yloxy)-9,10-dihydro-4H-3,10a-diaza-benzo[f]azulene
4-[1-Methyl-4-(1-methyl-piperidin-4-yloxy)-9,10-dihydro-4H-3,10a-diaza-benzo[f]azulen-2-yl]-but-3-yn-1-ol
2-(6-Chloro-hex-1-ynyl)-1-methyl-4-(1-methyl-piperidin-4-yloxy)-9,10-dihydro-4H-3,10a-diaza-benzo[f]azulene
2-(3,3-Dimethyl-butyl)-1-methyl-4-(1-methyl-piperidin-4-yloxy)-9,10-dihydro-4H-3,10a-diaza-benzo[f]azulene
9,9-Dimethyl-4-(1-methyl-piperidin-4-yloxy)-2-phenyl-9,10-dihydro-4H-3,10a-diaza-benzo[f]azulene
8-Bromo-4-(1-methyl-piperidin-4-yloxy)-2-phenyl-9,10-dihydro-4H-3,10a-diaza-benzo[f]azulene
1,9,9-Trimethyl-4-(1-methyl-piperidin-4-yloxy)-2-phenyl-9,10-dihydro-4H-3,10a-diaza-benzo[f]azulene
8-Benzyl-4-(1-methyl-piperidin-4-yloxy)-2-phenyl-9,10-dihydro-4H-3,10a-diaza-benzo[f]azulene
4-(1-Methyl-piperidin-4-yloxy)-8-methylsulfanyl-2-phenyl-9,10-dihydro-4H-3,10a-diaza-benzo[f]azulene, oxalate
4-(1-Methyl-piperidin-4-yloxy)-2-phenyl-9,10-dihydro-4H-3,10a-diaza-benzo[f]azulene-1-carbonitrile
8-Methyl-4-(1-methyl-piperidin-4-yloxy)-2-phenyl-9,10-dihydro-4H-3,10a-diaza-benzo[f]azulene
8-But-3-enyl-4-(1-methyl-piperidin-4-yloxy)-2-phenyl-9,10-dihydro-4H-3,10a-diaza-benzo[f]azulene, oxalate
4-(1-Methyl-piperidin-4-yloxy)-2-phenyl-1-propyl-9,10-dihydro-4H-3,10a-diaza-benzo[f]azulene
4-(1-Methyl-piperidin-4-yloxy)-2-phenyl-8-o-tolyl-9,10-dihydro-4H-3,10a-diaza-benzo[f]azulene
8-(4-Fluoro-phenyl)-4-(1-methyl-piperidin-4-yloxy)-2-phenyl-9,10-dihydro-4H-3,10a-diaza-benzo[f]azulene
8-(3-Methoxy-phenyl)-4-(1-methyl-piperidin-4-yloxy)-2-phenyl-9,10-dihydro-4H-3,10a-diaza-benzo[f]azulene
3-[4-(1-Methyl-piperidin-4-yloxy)-2-phenyl-9,10-dihydro-4H-3,10a-diaza-benzo[f]azulen-8-yl]-phenylamine
1-Isopropyl-4-(1-methyl-piperidin-4-yloxy)-2-phenyl-9,10-dihydro-4H-3,10a-diaza-benzo[f]azulene, dioxalate
Methyl-[4-(1-methyl-piperidin-4-yloxy)-2-phenyl-9,10-dihydro-4H-3,10a-diaza-benzo[f]azulen-8-yl]-amine
8-Methoxy-4-(1-methyl-piperidin-4-yloxy)-2-phenyl-9,10-dihydro-4H-3,10a-diaza-benzo[f]azulene
4-(1-Methyl-piperidin-4-yloxy)-1-phenyl-2-propyl-9,10-dihydro-4H-3,10a-diaza-benzo[f]azulene
1-Iodo-4-(1-methyl-piperidin-4-yloxy)-2-phenyl-9,10-dihydro-4H-3,10a-diaza-benzo[f]azulene
8-Benzyloxy-4-(1-methyl-piperidin-4-yloxy)-2-phenyl-9,10-dihydro-4H-3,10a-diaza-benzo[f]azulene
4-(1-Methyl-piperidin-4-yloxy)-8-phenethyl-2-phenyl-9,10-dihydro-4H-3,10a-diaza-benzo[f]azulene
1-Methyl-4-(1-methyl-piperidin-4-yloxy)-2-pyridin-4-yl-9,10-dihydro-4H-3,10a-diaza-benzo[f]azulene
1-Methyl-4-(1-methyl-piperidin-4-yloxy)-2-pyridin-2-yl-9,10-dihydro-4H-3,10a-diaza-benzo[f]azulene
4-(1-Methyl-piperidin-4-yloxy)-1,2-diphenyl-9,10-dihydro-4H-3,10a-diaza-benzo[f]azulene
2-Iodo-4-(1-methyl-piperidin-4-yloxy)-9,10-dihydro-4H-3,10a-diaza-benzo[f]azulene-1-carboxylic acid amide
4-(1-Methyl-piperidin-4-yloxy)-2-phenyl-9,10-dihydro-4H-3,10a-diaza-benzo[f]azulene-1-carboxylic acid amide
4-(1-Methyl-piperidin-4-yloxy)-2-phenyl-1-trifluoromethyl-9,10-dihydro-4H-3,10a-diaza-benzo[f]azulene, oxalate
4-(1-Methyl-piperidin-4-yloxy)-2-phenyl-9,10-dihydro-4H-3,10a-diaza-benzo[f]azulene-1-carboxylic acid methyl ester
[4-(1-Methyl-piperidin-4-yloxy)-2-phenyl-9,10-dihydro-4H-3,10a-diaza-benzo[f]azulen-1-yl]-methanol
6-Iodo-1-methyl-4-(1-methyl-piperidin-4-yloxy)-2-phenyl-9,10-dihydro-4H-3,10a-diaza-benzo[f]azulene
2-(2-Methyl-allyl)-4-(1-methyl-piperidin-4-yloxy)-9,10-dihydro-4H-3,10a-diaza-benzo[f]azulene-1-carbonitrile
1-Methyl-2-(2-methyl-allyl)-4-(1-methyl-piperidin-4-yloxy)-9,10-dihydro-4H-3,10a-diaza-benzo[f]azulene
7-Bromo-4-(1-methyl-piperidin-4-yloxy)-2-phenyl-9,10-dihydro-4H-3,10a-diaza-benzo[f]azulene
4-(1-Methyl-piperidin-4-yloxy)-2-phenyl-9,10-dihydro-4H-3,10a-diaza-benzo[f]azulene-1-carbaldehyde
2-Benzyl-4-(1-methyl-piperidin-4-yloxy)-9,10-dihydro-4H-3,10a-diaza-benzo[f]azulene-1-carbonitrile
[2-(1,2-Diiodo-9,10-dihydro-4H-3,10a-diaza-benzo[f]azulen-4-yloxy)-ethyl]-dimethyl-amine
1,2-Diiodo-4-(2-piperidin-1-yl-ethoxy)-9,10-dihydro-4H-3,10a-diaza-benzo[f]azulene
2-(2-Methyl-allyl)-4-(1-methyl-piperidin-4-yloxy)-9,10-dihydro-4H-3,10a-diaza-benzo[f]azulene-1-carboxylic acid amide
1,2-Bis-(2-methyl-allyl)-4-(1-methyl-piperidin-4-yloxy)-9,10-dihydro-4H-3,10a-diaza-benzo[f]azulene, dioxalate
1,2-Diiodo-4-(1-methyl-pyrrolidin-3-yloxy)-9,10-dihydro-4H-3,10a-diaza-benzo[f]azulene
1,2-Diiodo-4-(8-methyl-8-aza-bicyclo[3.2.1]oct-3-yloxy)-9,10-dihydro-4H-3,10a-diaza-benzo[f]azulene
[3-(1,2-Diiodo-9,10-dihydro-4H-3,10a-diaza-benzo[f]azulen-4-yloxy)-propyl]-dimethyl-amine
4-(1-Aza-bicyclo[2.2.2]oct-3-yloxy)-1,2-diiodo-9,10-dihydro-4H-3,10a-diaza-benzo[f]azulene, oxalate
2-(2-Chloro-phenyl)-4-(1-methyl-piperidin-4-yloxy)-9,10-dihydro-4H-3,10a-diaza-benzo[f]azulene-1-carbonitrile, oxalate
2-(2-Chloro-phenyl)-4-(1-methyl-piperidin-4-yloxy)-9,10-dihydro-4H-3,10a-diaza-benzo[f]azulene-1-carboxylic acid amide, oxalate as well as its enantiomers, diastereomers, mixtures thereof, tautomers, hydrates and solvates.

In another preferred embodiment, the present invention provides a compound selected from the group consisting of:
4-(1-Methyl-piperidin-4-yloxy)-2-p-tolyl-9,10-dihydro-4H-3,10a-diaza-benzo[f]azulene
1-{4-[4-(1-Methyl-piperidin-4-yloxy)-9,10-dihydro-4H-3,10a-diaza-benzo[f]azulen-2-yl]-phenyl}-ethanone 4-(1-Methyl-piperidin-4-yloxy)-2-(4-trifluoromethoxy-phenyl)-9,10-dihydro-4H-3,10a-diaza-benzo[f]azulene
4-(1-Methyl-piperidin-4-yloxy)-2-(4-methylsulfanyl-phenyl)-9,10-dihydro-4H-3,10a-diaza-benzo[f]azulene
4-(1-Methyl-piperidin-4-yloxy)-2-(4-methylsulfanyl-phenyl)-9,10-dihydro-4H-3,10a-diaza-benzo[f]azulene
4-(1-Methyl-piperidin-4-yloxy)-2-(4-propyl-phenyl)-9,10-dihydro-4H-3,10a-diaza-benzo[f]azulene
4-(1-Methyl-piperidin-4-yloxy)-2-(4-trifluoromethyl-phenyl)-9,10-dihydro-4H-3,10a-diaza-benzo[f]azulene
2-(2-Chloro-phenyl)-4-(1-methyl-piperidin-4-yloxy)-9,10-dihydro-4H-3,10a-diaza-benzo[f]azulene
2-(4-Isobutyl-phenyl)-4-(1-methyl-piperidin-4-yloxy)-9,10-dihydro-4H-3,10a-diaza-benzo[f]azulene
2,2,2-Trifluoro-1-{4-[4-(1-methyl-piperidin-4-yloxy)-9,10-dihydro-4H-3,10a-diaza-benzo[f]azulen-2-yl]-phenyl}-ethanone
4-[4-(1-Methyl-piperidin-4-yloxy)-9,10-dihydro-4H-3,10a-diaza-benzo[f]azulen-2-yl]-benzoic acid tert-butyl ester
4-[4-(1-Methyl-piperidin-4-yloxy)-9,10-dihydro-4H-3,10a-diaza-benzo[f]azulen-2-yl]-benzonitrile
4-(1-Methyl-piperidin-4-yloxy)-2-phenethyl-9,10-dihydro-4H-3,10a-diaza-benzo[f]azulene
2-(4-Butyl-phenyl)-4-(1-methyl-piperidin-4-yloxy)-9,10-dihydro-4H-3,10a-diaza-benzo[f]azulene
2-(4-Butyl-phenyl)-4-(1-methyl-piperidin-4-yloxy)-9,10-dihydro-4H-3,10a-diaza-benzo[f]azulene
4-(1-Methyl-piperidin-4-yloxy)-2-pyridin-3-yl-9,10-dihydro-4H-3,10a-diaza-benzo[f]azulene
4-(1-Methyl-piperidin-4-yloxy)-2-thiazol-5-yl-9,10-dihydro-4H-3,10a-diaza-benzo[f]azulene
{4-[4-(1-Methyl-piperidin-4-yloxy)-9,10-dihydro-4H-3,10a-diaza-benzo[f]azulen-2-yl]-phenyl}-carbamic acid tert-butyl ester
2-(5-Methyl-furan-2-yl)-4-(1-methyl-piperidin-4-yloxy)-9,10-dihydro-4H-3,10a-diaza-benzo[f]azulene
3-[4-(1-Methyl-piperidin-4-yloxy)-9,10-dihydro-4H-3,10a-diaza-benzo[f]azulen-2-yl]-acrylic acid tert-butyl ester
4-(1-Methyl-piperidin-4-yloxy)-2-(2-methyl-4-trifluoromethyl-phenyl)-9,10-dihydro-4H-3,10a-diaza-benzo[f]azulene
4-(1-Methyl-piperidin-4-yloxy)-2-pyridin-3-ylethynyl-9,10-dihydro-4H-3,10a-diaza-benzo[f]azulene
2-Benzylsulfanyl-4-(1-methyl-piperidin-4-yloxy)-9,10-dihydro-4H-3,10a-diaza-benzo[f]azulene
2-(3-Fluoro-phenyl)-4-(1-methyl-piperidin-4-yloxy)-9,10-dihydro-4H-3,10a-diaza-benzo[f]azulene
2-(2-Methyl-allyl)-4-(1-methyl-piperidin-4-yloxy)-9,10-dihydro-4H-3,10a-diaza-benzo[f]azulene
2-(2,4-Dichloro-phenyl)-4-(1-methyl-piperidin-4-yloxy)-9,10-dihydro-4H-3,10a-diaza-benzo[f]azulene
4-[4-(1-Methyl-piperidin-4-yloxy)-9,10-dihydro-4H-3,10a-diaza-benzo[f]azulen-2-yl]3,6-dihydro-2H-pyridine-1-carboxylic acid tert-butyl ester
2-(2-Chloro-4-methyl-phenyl)-4-(1-methyl-piperidin-4-yloxy)-9,10-dihydro-4H-3,10a-diaza-benzo[f]azulene
4-(1-Methyl-piperidin-4-yloxy)-2-(3-phenyl-propenyl)-9,10-dihydro-4H-3,10a-diaza-benzo[f]azulene
8-Bromo-2-iodo-4-(1-methyl-piperidin-4-yloxy)-9,10-dihydro-4H-3,10a-diaza-benzo[f]azulene
2-Cyclohept-1-enyl-4-(1-methyl-piperidin-4-yloxy)-9,10-dihydro-4H-3,10a-diaza-benzo[f]azulene
2-(4-Bromo-phenyl)-4-(1-methyl-piperidin-4-yloxy)-9,10-dihydro-4H-3,10a-diaza-benzo[f]azulene
2-(Furan-2-ylmethylsulfanyl)-4-(1-methyl-piperidin-4-yloxy)-9,10-dihydro-4H-3,10a-diaza-benzo[f]azulene
2-Cyclopentylsulfanyl-4-(1-methyl-piperidin-4-yloxy)-9,10-dihydro-4H-3,10a-diaza-benzo[f]azulene
4-(1-Methyl-piperidin-4-yloxy)-2-(thiophen-2-ylmethylsulfanyl)-9,10-dihydro-4H-3,10a-diaza-benzo[f]azulene
4-(1-Methyl-piperidin-4-yloxy)-2-(5-phenyl-pent-1-enyl)-9,10-dihydro-4H-3,10a-diaza-benzo[f]azulene
4-(1-Methyl-piperidin-4-yloxy)-2,8-diphenyl-9,10-dihydro-4H-3,10a-diaza-benzo[f]azulene
2-(3,3-Dimethyl-but-1-enyl)-4-(1-methyl-piperidin-4-yloxy)-9,10-dihydro-4H-3,10a-diaza-benzo[f]azulene
2-(3,3-Dimethyl-butyl)-4-(1-methyl-piperidin-4-yloxy)-9,10-dihydro-4H-3,10a-diaza-benzo[f]azulene
4-(1-Methyl-piperidin-4-yloxy)-2-(5-methyl-thiophen-2-yl)-9,10-dihydro-4H-3,10a-diaza-benzo[f]azulene
[4-(1-Methyl-piperidin-4-yloxy)-9,10-dihydro-4H-3,10a-diaza-benzo[f]azulen-2-yl]-phenyl-methanone
1-Methyl-4-(1-methyl-piperidin-4-yloxy)-2-phenyl-9,10-dihydro-4H-3,10a-diaza-benzo[f]azulene
2-(3-Cyclopentyl-propenyl)-4-(1-methyl-piperidin-4-yloxy)-9,10-dihydro-4H-3,10a-diaza-benzo[f]azulene
2-Benzyl-4-(1-methyl-piperidin-4-yloxy)-9,10-dihydro-4H-3,10a-diaza-benzo[f]azulene
4-(1-Methyl-piperidin-4-yloxy)-2-(2-thiophen-2-yl-vinyl)-9,10-dihydro-4H-3,10a-diaza-benzo[f]azulene
1-Methyl-4-(1-methyl-piperidin-4-yloxy)-9,10-dihydro-4H-3,10a-diaza-benzo[f]azulene-2-carboxylic acid ethyl ester
4-(1-Methyl-piperidin-4-yloxy)-2-phenethylsulfanyl-9,10-dihydro-4H-3,10a-diaza-benzo[f]azulene
1-Ethyl-4-(1-methyl-piperidin-4-yloxy)-2-phenyl-9,10-dihydro-4H-3,10a-diaza-benzo[f]azulene
4-(1-Methyl-piperidin-4-yloxy)-2-(3-phenoxy-propenyl)-9,10-dihydro-4H-3,10a-diaza-benzo[f]azulene
2-(3-Benzyloxy-propenyl)-4-(1-methyl-piperidin-4-yloxy)-9,10-dihydro-4H-3,10a-diaza-benzo[f]azulene
4-(1-Methyl-piperidin-4-yloxy)-2-(2-thiophen-2-yl-ethyl)-9,10-dihydro-4H-3,10a-diaza-benzo[f]azulene
2-(3-Benzyloxy-propyl)-4-(1-methyl-piperidin-4-yloxy)-9,10-dihydro-4H-3,10a-diaza-benzo[f]azulene
4-(1-Methyl-piperidin-4-yloxy)-2-(4-phenyl-butyl)-9,10-dihydro-4H-3,10a-diaza-benzo[f]azulene
2-Iodo-1-methyl-4-(1-methyl-piperidin-4-yloxy)-9,10-dihydro-4H-3,10a-diaza-benzo[f]azulene
1-Chloro-4-(1-methyl-piperidin-4-yloxy)-2-phenyl-9,10-dihydro-4H-3,10a-diaza-benzo[f]azulene
1-Chloro-4-(1-methyl-piperidin-4-yloxy)-2-(5-phenyl-pentyl)-9,10-dihydro-4H-3,10a-diaza-benzo[f]azulene
1-tert-Butyl-3-{4-[1-methyl-4-(1-methyl-piperidin-4-yloxy)-9,10-dihydro-4H-3,10a-diaza-benzo[f]azulen-2-yl]-phenyl}-imidazolidin-2-one
{4-[1-Chloro-4-(1-methyl-piperidin-4-yloxy)-9,10-dihydro-4H-3,10a-diaza-benzo[f]azulen-2-yl]-phenyl}-carbamic acid tert-butyl ester
2-(2-Fluoro-phenyl)-1-methyl-4-(1-methyl-piperidin-4-yloxy)-9,10-dihydro-4H-3,10a-diaza-benzo[f]azulene
2-(3-Fluoro-phenyl)-1-methyl-4-(1-methyl-piperidin-4-yloxy)-9,10-dihydro-4H-3,10a-diaza-benzo[f]azulene
1-Methyl-4-(1-methyl-piperidin-4-yloxy)-2-m-tolyl-9,10-dihydro-4H-3,10a-diaza-benzo[f]azulene
2-(3-Chloro-phenyl)-1-methyl-4-(1-methyl-piperidin-4-yloxy)-9,10-dihydro-4H-3,10a-diaza-benzo[f]azulene
2-(2-Chloro-phenyl)-1-methyl-4-(1-methyl-piperidin-4-yloxy)-9,10-dihydro-4H-3,10a-diaza-benzo[f]azulene
1-Methyl-4-(1-methyl-piperidin-4-yloxy)-2-o-tolyl-9,10-dihydro-4H-3,10a-diaza-benzo[f]azulene
1-Methyl-4-(1-methyl-piperidin-4-yloxy)-2-thiophen-3-yl-9,10-dihydro-4H-3,10a-diaza-benzo[f]azulene 2-(3-Methoxy-phenyl)-1-methyl-4-(1-methyl-piperidin-4-yloxy)-9,10-dihydro-4H-3,10a-diaza-benzo[f]azulene
3-{4-[1-Methyl-4-(1-methyl-piperidin-4-yloxy)-9,10-dihydro-4H-3,10a-diaza-benzo[f]azulen-2-yl]-phenyl}-acrylic acid tert-butyl ester
3-Methyl-3-{4-[1-methyl-4-(1-methyl-piperidin-4-yloxy)-9,10-dihydro-4H-3,10a-diaza-benzo[f]azulen-2-yl]-phenylsulfanyl}-butan-1-ol
1-Methyl-4-(1-methyl-piperidin-4-yloxy)-2-p-tolyl-9,10-dihydro-4H-3,10a-diaza-benzo[f]azulene
2-(4-Fluoro-phenyl)-1-methyl-4-(1-methyl-piperidin-4-yloxy)-9,10-dihydro-4H-3,10a-diaza-benzo[f]azulene
2-(4-Chloro-phenyl)-1-methyl-4-(1-methyl-piperidin-4-yloxy)-9,10-dihydro-4H-3,10a-diaza-benzo[f]azulene
2-(4-Methoxy-phenyl)-1-methyl-4-(1-methyl-piperidin-4-yloxy)-9,10-dihydro-4H-3,10a-diaza-benzo[f]azulene
2-(2-Chloro-4-methyl-phenyl)-1-methyl-4-(1-methyl-piperidin-4-yloxy)-9,10-dihydro-4H-3,10a-diaza-benzo[f]azulene
2-[4-(2-Methanesulfonyl-vinyl)-phenyl]-1-methyl-4-(1-methyl-piperidin-4-yloxy)-9,10-dihydro-4H-3,10a-diaza-benzo[f]azulene
2-[4-(2-Methanesulfonyl-ethyl)-phenyl]-1-methyl-4-(1-methyl-piperidin-4-yloxy)-9,10-dihydro-4H-3,10a-diaza-benzo[f]azulene
(2-{4-[1-Methyl-4-(1-methyl-piperidin-4-yloxy)-9,10-dihydro-4H-3,10a-diaza-benzo[f]azulen-2-yl]-phenylsulfanyl}-ethyl)-carbamic acid tert-butyl ester
2-{4-[1-Methyl-4-(1-methyl-piperidin-4-yloxy)-9,10-dihydro-4H-3,10a-diaza-benzo[f]azulen-2-yl]-phenylsulfanyl}-ethylamine
N-(2-{4-[1-Methyl-4-(1-methyl-piperidin-4-yloxy)-9,10-dihydro-4H-3,10a-diaza-benzo[f]azulen-2-yl]-phenylsulfanyl}-ethyl)acetamide
2-(4-Benzylsulfanyl-phenyl)-1-methyl-4-(1-methyl-piperidin-4-yloxy)-9,10-dihydro-4H-3,10a-diaza-benzo[f]azulene
{4-[1-Methyl-4-(1-methyl-piperidin-4-yloxy)-9,10-dihydro-4H-3,10a-diaza-benzo[f]azulen-2-yl]-phenylsulfanyl}-acetic acid methyl ester
2-(4-tert-Butylsulfanyl-phenyl)-1-methyl-4-(1-methyl-piperidin-4-yloxy)-9,10-dihydro-4H-3,10a-diaza-benzo[f]azulene
2-[4-(Furan-2-ylmethylsulfanyl)-phenyl]-1-methyl-4-(1-methyl-piperidin-4-yloxy)-9,10-dihydro-4H-3,10a-diaza-benzo[f]azulene
4-{4-[1-Methyl-4-(1-methyl-piperidin-4-yloxy)-9,10-dihydro-4H-3,10a-diaza-benzo[f]azulen-2-yl]-phenyl}-3,6-dihydro-2H-pyridine-1-carboxylic acid tert-butyl ester
2-(4-Cyclopent-1-enyl-phenyl)-1-methyl-4-(1-methyl-piperidin-4-yloxy)-9,10-dihydro-4H-3,10a-diaza-benzo[f]azulene
2-(4-Cyclohex-1-enyl-phenyl)-1-methyl-4-(1-methyl-piperidin-4-yloxy)-9,10-dihydro-4H-3,10a-diaza-benzo[f]azulene
2-(4-Cyclohept-1-enyl-phenyl)-1-methyl-4-(1-methyl-piperidin-4-yloxy)-9,10-dihydro-4H-3,10a-diaza-benzo[f]azulene
{4-[1-Methyl-4-(1-methyl-piperidin-4-yloxy)-9,10-dihydro-4H-3,10a-diaza-benzo[f]azulen-2-yl]-phenyl}-carbamic acid cyclopentyl ester
{4-[1-Methyl-4-(1-methyl-piperidin-4-yloxy)-9,10-dihydro-4H-3,10a-diaza-benzo[f]azulen-2-yl]-phenyl}-carbamic acid isobutyl ester
{4-[1-Methyl-4-(1-methyl-piperidin-4-yloxy)-9,10-dihydro-4H-3,10a-diaza-benzo[f]azulen-2-yl]-phenyl}-carbamic acid 2,2,2-trichloro-1,1-dimethyl-ethyl ester
4-Benzyl-3-{4-[1-methyl-4-(1-methyl-piperidin-4-yloxy)-9,10-dihydro-4H-3,10a-diaza-benzo[f]azulen-2-yl]-phenyl}-oxazolidin-2-one
4-{4-[1-Methyl-4-(1-methyl-piperidin-4-yloxy)-9,10-dihydro-4H-3,10a-diaza-benzo[f]azulen-2-yl]-phenyl}-piperidine-1-carboxylic acid tert-butyl ester
1-Isopropyl-3-{4-[1-methyl-4-(1-methyl-piperidin-4-yloxy)-9,10-dihydro-4H-3,10a-diaza-benzo[f]azulen-2-yl]-phenyl}-imidazolidin-2-one
2-(4-Allyloxy-phenyl)-4-(1-methyl-piperidin-4-yloxy)-9,10-dihydro-4H-3,10a-diaza-benzo[f]azulene
3-{4-[1-Methyl-4-(1-methyl-piperidin-4-yloxy)-9,10-dihydro-4H-3,10a-diaza-benzo[f]azulen-2-yl]-phenylsulfanyl}-propane-1,2-diol
3-{4-[1-Methyl-4-(1-methyl-piperidin-4-yloxy)-9,10-dihydro-4H-3,10a-diaza-benzo[f]azulen-2-yl]-phenylsulfanyl}-propan-1-ol
Methyl-(2-{4-[4-(1-methyl-piperidin-4-yloxy)-9,10-dihydro-4H-3,10a-diaza-benzo[f]azulen-2-yl]-phenyl}-ethyl)-carbamic acid tert-butyl ester
1-Isopropyl-3-{4-[1-methyl-4-(1-methyl-piperidin-4-yloxy)-9,10-dihydro-4H-3,10a-diaza-benzo[f]azulen-2-yl]-phenyl}-thiourea
1-tert-Butyl-3-{4-[1-methyl-4-(1-methyl-piperidin-4-yloxy)-9,10-dihydro-4H-3,10a-diaza-benzo[f]azulen-2-yl]-phenyl}-urea
N-(2-{4-[1-Methyl-4-(1-methyl-piperidin-4-yloxy)-9,10-dihydro-4H-3,10a-diaza-benzo[f]azulen-2-yl]-phenylsulfanyl}-ethyl)-guanidine
1-Adamantan-1-yl-3-{4-[1-methyl-4-(1-methyl-piperidin-4-yloxy)-9,10-dihydro-4H-3,10a-diaza-benzo[f]azulen-2-yl]-phenyl}-urea
N-{4-[1-Methyl-4-(1-methyl-piperidin-4-yloxy)-9,10-dihydro-4H-3,10a-diaza-benzo[f]azulen-2-yl]-phenyl}-hydrazinecarboxylic acid tert-butyl ester
1,2-Diiodo-4-(1-methyl-piperidin-4-yloxy)-9,10-dihydro-4H-3,10a-diaza-benzo[f]azulene
(2-{4-[1-Methyl-4-(1-methyl-piperidin-4-yloxy)-9,10-dihydro-4H-3,10a-diaza-benzo[f]azulen-2-yl]-phenyl}-ethyl)-carbamic acid tert-butyl ester
4-[1-Cyano-4-(1-methyl-piperidin-4-yloxy)-9,10-dihydro-4H-3,10a-diaza-benzo[f]azulen-2-yl]-benzoic acid tert-butyl ester
2-(3,3-Dimethyl-but-1-enyl)-1-methyl-4-(1-methyl-piperidin-4-yloxy)-9,10-dihydro-4H-3,10a-diaza-benzo[f]azulene
2-Cyclohex-1-enyl-1-methyl-4-(1-methyl-piperidin-4-yloxy)-9,10-dihydro-4H-3,10a-diaza-benzo[f]azulene
2-(6-Chloro-hex-1-ynyl)-1-methyl-4-(1-methyl-piperidin-4-yloxy)-9,10-dihydro-4H-3,10a-diaza-benzo[f]azulene
2-(3,3-Dimethyl-butyl)-1-methyl-4-(1-methyl-piperidin-4-yloxy)-9,10-dihydro-4H-3,10a-diaza-benzo[f]azulene
4-(1-Methyl-piperidin-4-yloxy)-2-phenyl-9,10-dihydro-4H-3,10a-diaza-benzo[f]azulene-1-carbonitrile
1-Iodo-4-(1-methyl-piperidin-4-yloxy)-2-phenyl-9,10-dihydro-4H-3,10a-diaza-benzo[f]azulene
4-(1-Methyl-piperidin-4-yloxy)-2-phenyl-1-trifluoromethyl-9,10-dihydro-4H-3,10a-diaza-benzo[f]azulene
2-(2-Chloro-phenyl)-4-(1-methyl-piperidin-4-yloxy)-9,10-dihydro-4H-3,10a-diaza-benzo[f]azulene-1-carboxylic acid amide as well as its enantiomers, diastereomers, mixtures thereof and pharmaceutically acceptable salts, tautomers, hydrates and solvates.

In still another preferred embodiment, the present invention provides a compound selected from the group consisting of:

4-(1-Methyl-piperidin-4-yloxy)-2-p-tolyl-9,10-dihydro-4H-3,10a-diaza-benzo[f]azulene
1-{4-[4-(1-Methyl-piperidin-4-yloxy)-9,10-dihydro-4H-3,10a-diaza-benzo[f]azulen-2-yl]-phenyl}-ethanone, oxalate
4-(1-Methyl-piperidin-4-yloxy)-2-(4-trifluoromethoxy-phenyl)-9,10-dihydro-4H-3,10a-diaza-benzo[f]azulene, oxalate
4-(1-Methyl-piperidin-4-yloxy)-2-(4-methylsulfanyl-phenyl)-9,10-dihydro-4H-3,10a-diaza-benzo[f]azulene
4-(1-Methyl-piperidin-4-yloxy)-2-(4-methylsulfanyl-phenyl)-9,10-dihydro-4H-3,10a-diaza-benzo[f]azulene
4-(1-Methyl-piperidin-4-yloxy)-2-(4-propyl-phenyl)-9,10-dihydro-4H-3,10a-diaza-benzo[f]azulene
4-(1-Methyl-piperidin-4-yloxy)-2-(4-trifluoromethyl-phenyl)-9,10-dihydro-4H-3,10a-diaza-benzo[f]azulene
2-(2-Chloro-phenyl)-4-(1-methyl-piperidin-4-yloxy)-9,10-dihydro-4H-3,10a-diaza-benzo[f]azulene, oxalate
2-(4-Isobutyl-phenyl)-4-(1-methyl-piperidin-4-yloxy)-9,10-dihydro-4H-3,10a-diaza-benzo[f]azulene
2,2,2-Trifluoro-1-{4-[4-(1-methyl-piperidin-4-yloxy)-9,10-dihydro-4H-3,10a-diaza-benzo[f]azulen-2-yl]-phenyl}ethanone, oxalate
4-[4-(1-Methyl-piperidin-4-yloxy)-9,10-dihydro-4H-3,10a-diaza-benzo[f]azulen-2-yl]-benzoic acid tert-butyl ester
4-[4-(1-Methyl-piperidin-4-yloxy)-9,10-dihydro-4H-3,10a-diaza-benzo[f]azulen-2-yl]-benzonitrile
4-(1-Methyl-piperidin-4-yloxy)-2-phenethyl-9,10-dihydro-4H-3,10a-diaza-benzo[f]azulene, oxalate
2-(4-Butyl-phenyl)-4-(1-methyl-piperidin-4-yloxy)-9,10-dihydro-4H-3,10a-diaza-benzo[f]azulene
2-(4-Butyl-phenyl)-4-(1-methyl-piperidin-4-yloxy)-9,10-dihydro-4H-3,10a-diaza-benzo[f]azulene, oxalate
4-(1-Methyl-piperidin-4-yloxy)-2-pyridin-3-yl-9,10-dihydro-4H-3,10a-diaza-benzo[f]azulene, oxalate
4-(1-Methyl-piperidin-4-yloxy)-2-thiazol-5-yl-9,10-dihydro-4H-3,10a-diaza-benzo[f]azulene, oxalate
{4-[4-(1-Methyl-piperidin-4-yloxy)-9,10-dihydro-4H-3,10a-diaza-benzo[f]azulen-2-yl]-phenyl}-carbamic acid tert-butyl ester
2-(5-Methyl-furan-2-yl)-4-(1-methyl-piperidin-4-yloxy)-9,10-dihydro-4H-3,10a-diaza-benzo[f]azulene, oxalate
3-[4-(1-Methyl-piperidin-4-yloxy)-9,10-dihydro-4H-3,10a-diaza-benzo[f]azulen-2-yl]-acrylic acid tert-butyl ester, oxalate
4-(1-Methyl-piperidin-4-yloxy)-2-pyridin-3-ylethynyl-9,10-dihydro-4H-3,10a-diaza-benzo[f]azulene, oxalate
2-Benzylsulfanyl-4-(1-methyl-piperidin-4-yloxy)-9,10-dihydro-4H-3,10a-diaza-benzo[f]azulene, oxalate
2-(3-Fluoro-phenyl)-4-(1-methyl-piperidin-4-yloxy)-9,10-dihydro-4H-3,10a-diaza-benzo[f]azulene, oxalate
2-(2-Methyl-allyl)-4-(1-methyl-piperidin-4-yloxy)-9,10-dihydro-4H-3,10a-diaza-benzo[f]azulene, oxalate
2-(2,4-Dichloro-phenyl)-4-(1-methyl-piperidin-4-yloxy)-9,10-dihydro-4H-3,10a-diaza-benzo[f]azulene, oxalate
4-[4-(1-Methyl-piperidin-4-yloxy)-9,10-dihydro-4H-3,10a-diaza-benzo[f]azulen-2-yl]3,6-dihydro-2H-pyridine-1-carboxylic acid tert-butyl ester, oxalate
2-(2-Chloro-4-methyl-phenyl)-4-(1-methyl-piperidin-4-yloxy)-9,10-dihydro-4H-3,10a-diaza-benzo[f]azulene, oxalate
4-(1-Methyl-piperidin-4-yloxy)-2-(3-phenyl-propenyl)-9,10-dihydro-4H-3,10a-diaza-benzo[f]azulene, oxalate
8-Bromo-2-iodo-4-(1-methyl-piperidin-4-yloxy)-9,10-dihydro-4H-3,10a-diaza-benzo[f]azulene
2-Cyclohept-1-enyl-4-(1-methyl-piperidin-4-yloxy)-9,10-dihydro-4H-3,10a-diaza-benzo[f]azulene
2-(4-Bromo-phenyl)-4-(1-methyl-piperidin-4-yloxy)-9,10-dihydro-4H-3,10a-diaza-benzo[f]azulene
2-(Furan-2-ylmethylsulfanyl)-4-(1-methyl-piperidin-4-yloxy)-9,10-dihydro-4H-3,10a-diaza-benzo[f]azulene, oxalate
2-Cyclopentylsulfanyl-4-(1-methyl-piperidin-4-yloxy)-9,10-dihydro-4H-3,10a-diaza-benzo[f]azulene, oxalate
4-(1-Methyl-piperidin-4-yloxy)-2-(thiophen-2-ylmethylsulfanyl)-9,10-dihydro-4H-3,10a-diaza-benzo[f]azulene, oxalate
4-(1-Methyl-piperidin-4-yloxy)-2-(5-phenyl-pent-1-enyl)-9,10-dihydro-4H-3,10a-diaza-benzo[f]azulene
4-(1-Methyl-piperidin-4-yloxy)-2,8-diphenyl-9,10-dihydro-4H-3,10a-diaza-benzo[f]azulene
2-(3,3-Dimethyl-but-1-enyl)-4-(1-methyl-piperidin-4-yloxy)-9,10-dihydro-4H-3,10a-diaza-benzo[f]azulene
2-(3,3-Dimethyl-butyl)-4-(1-methyl-piperidin-4-yloxy)-9,10-dihydro-4H-3,10a-diaza-benzo[f]azulene
4-(1-Methyl-piperidin-4-yloxy)-2-(5-methyl-thiophen-2-yl)-9,10-dihydro-4H-3,10a-diaza-benzo[f]azulene, oxalate
[4-(1-Methyl-piperidin-4-yloxy)-9,10-dihydro-4H-3,10a-diaza-benzo[f]azulen-2-yl]-phenyl-methanone, oxalate
1-Methyl-4-(1-methyl-piperidin-4-yloxy)-2-phenyl-9,10-dihydro-4H-3,10a-diaza-benzo[f]azulene
2-(3-Cyclopentyl-propenyl)-4-(1-methyl-piperidin-4-yloxy)-9,10-dihydro-4H-3,10a-diaza-benzo[f]azulene
2-Benzyl-4-(1-methyl-piperidin-4-yloxy)-9,10-dihydro-4H-3,10a-diaza-benzo[f]azulene, oxalate
4-(1-Methyl-piperidin-4-yloxy)-2-(2-thiophen-2-yl-vinyl)-9,10-dihydro-4H-3,10a-diaza-benzo[f]azulene
1-Methyl-4-(1-methyl-piperidin-4-yloxy)-9,10-dihydro-4H-3,10a-diaza-benzo[f]azulene-2-carboxylic acid ethyl ester
4-(1-Methyl-piperidin-4-yloxy)-2-phenethylsulfanyl-9,10-dihydro-4H-3,10a-diaza-benzo[f]azulene, oxalate
1-Ethyl-4-(1-methyl-piperidin-4-yloxy)-2-phenyl-9,10-dihydro-4H-3,10a-diaza-benzo[f]azulene, oxalate
4-(1-Methyl-piperidin-4-yloxy)-2-(3-phenoxy-propenyl)-9,10-dihydro-4H-3,10a-diaza-benzo[f]azulene, oxalate
2-(3-Benzyloxy-propenyl)-4-(1-methyl-piperidin-4-yloxy)-9,10-dihydro-4H-3,10a-diaza-benzo[f]azulene, oxalate
4-(1-Methyl-piperidin-4-yloxy)-2-(2-thiophen-2-yl-ethyl)-9,10-dihydro-4H-3,10a-diaza-benzo[f]azulene, oxalate
2-(3-Benzyloxy-propyl)-4-(1-methyl-piperidin-4-yloxy)-9,10-dihydro-4H-3,10a-diaza-benzo[f]azulene, oxalate
4-(1-Methyl-piperidin-4-yloxy)-2-(4-phenyl-butyl)-9,10-dihydro-4H-3,10a-diaza-benzo[f]azulene, oxalate
2-Iodo-1-methyl-4-(1-methyl-piperidin-4-yloxy)-9,10-dihydro-4H-3,10a-diaza-benzo[f]azulene
1-Chloro-4-(1-methyl-piperidin-4-yloxy)-2-phenyl-9,10-dihydro-4H-3,10a-diaza-benzo[f]azulene
1-Chloro-4-(1-methyl-piperidin-4-yloxy)-2-(5-phenyl-pentyl)-9,10-dihydro-4H-3,10a-diaza-benzo[f]azulene, oxalate
1-tert-Butyl-3-{4-[1-methyl-4-(1-methyl-piperidin-4-yloxy)-9,10-dihydro-4H-3,10a-diaza-benzo[f]azulen-2-yl]-phenyl}-imidazolidin-2-one
{4-[1-Chloro-4-(1-methyl-piperidin-4-yloxy)-9,10-dihydro-4H-3,10a-diaza-benzo[f]azulen-2-yl]-phenyl}-carbamic acid tert-butyl ester
2-(2-Fluoro-phenyl)-1-methyl-4-(1-methyl-piperidin-4-yloxy)-9,10-dihydro-4H-3,10a-diaza-benzo[f]azulene
2-(3-Fluoro-phenyl)-1-methyl-4-(1-methyl-piperidin-4-yloxy)-9,10-dihydro-4H-3,10a-diaza-benzo[f]azulene
1-Methyl-4-(1-methyl-piperidin-4-yloxy)-2-m-tolyl-9,10-dihydro-4H-3,10a-diaza-benzo[f]azulene 2-(3-Chloro-phenyl)-1-methyl-4-(1-methyl-piperidin-4-yloxy)-9,10-dihydro-4H-3,10a-diaza-benzo[f]azulene 2-(2-Chloro-phenyl)-1-methyl-4-(1-methyl-piperidin-4-yloxy)-9,10-dihydro-4H-3,10a-diaza-benzo[f]azulene 1-Methyl-4-(1-methyl-piperidin-4-yloxy)-2-o-tolyl-9,10-dihydro-4H-3,10a-diaza-benzo[f]azulene 1-Methyl-4-(1-methyl-piperidin-4-yloxy)-2-thiophen-3-yl-9,10-dihydro-4H-3,10a-diaza-benzo[f]azulene 2-(3-Methoxy-phenyl)-1-methyl-4-(1-methyl-piperidin-4-yloxy)-9,10-dihydro-4H-3,10a-diaza-benzo[f]azulene 3-{4-[1-Methyl-4-(1-methyl-piperidin-4-yloxy)-9,10-dihydro-4H-3,10a-diaza-benzo[f]azulen-2-yl]-phenyl}-acrylic acid tert-butyl ester 3-Methyl-3-{4-[1-methyl-4-(1-methyl-piperidin-4-yloxy)-9,10-dihydro-4H-3,10a-diaza-benzo[f]azulen-2-yl]-phenylsulfanyl}-butan-1-ol, oxalate 1-Methyl-4-(1-methyl-piperidin-4-yloxy)-2-p-tolyl-9,10-dihydro-4H-3,10a-diaza-benzo[f]azulene 2-(4-Fluoro-phenyl)-1-methyl-4-(1-methyl-piperidin-4-yloxy)-9,10-dihydro-4H-3,10a-diaza-benzo[f]azulene 2-(4-Chloro-phenyl)-1-methyl-4-(1-methyl-piperidin-4-yloxy)-9,10-dihydro-4H-3,10a-diaza-benzo[f]azulene 2-(4-Methoxy-phenyl)-1-methyl-4-(1-methyl-piperidin-4-yloxy)-9,10-dihydro-4H-3,10a-diaza-benzo[f]azulene 2-(2-Chloro-4-methyl-phenyl)-1-methyl-4-(1-methyl-piperidin-4-yloxy)-9,10-dihydro-4H-3,10a-diaza-benzo[f]azulene, oxalate 2-[4-(2-Methanesulfonyl-vinyl)-phenyl]-1-methyl-4-(1-methyl-piperidin-4-yloxy)-9,10-dihydro-4H-3,10a-diaza-benzo[f]azulene 2-[4-(2-Methanesulfonyl-ethyl)-phenyl]-1-methyl-4-(1-methyl-piperidin-4-yloxy)-9,10-dihydro-4H-3,10a-diaza-benzo[f]azulene (2-{4-[1-Methyl-4-(1-methyl-piperidin-4-yloxy)-9,10-dihydro-4H-3,10a-diaza-benzo[f]azulen-2-yl]-phenylsulfanyl}-ethyl)-carbamic acid tert-butyl ester, oxalate 2-{4-[1-Methyl-4-(1-methyl-piperidin-4-yloxy)-9,10-dihydro-4H-3,10a-diaza-benzo[f]azulen-2-yl]-phenylsulfanyl}-ethylamine, oxalate N-(2-{4-[1-Methyl-4-(1-methyl-piperidin-4-yloxy)-9,10-dihydro-4H-3,10a-diaza-benzo[f]azulen-2-yl]-phenylsulfanyl}ethyl)-acetamide, oxalate 2-(4-Benzylsulfanyl-phenyl)-1-methyl-4-(1-methyl-piperidin-4-yloxy)-9,10-dihydro-4H-3,10a-diaza-benzo[f]azulene, oxalate {4-[1-Methyl-4-(1-methyl-piperidin-4-yloxy)-9,10-dihydro-4H-3,10a-diaza-benzo[f]azulen-2-yl]-phenylsulfanyl}-acetic acid methyl ester, oxalate 2-(4-tert-Butylsulfanyl-phenyl)-1-methyl-4-(1-methyl-piperidin-4-yloxy)-9,10-dihydro-4H-3,10a-diaza-benzo[f]azulene, oxalate 2-[4-(Furan-2-ylmethylsulfanyl)-phenyl]-1-methyl-4-(1-methyl-piperidin-4-yloxy)-9,10-dihydro-4H-3,10a-diaza-benzo[f]azulene, oxalate 4-{4-[1-Methyl-4-(1-methyl-piperidin-4-yloxy)-9,10-dihydro-4H-3,10a-diaza-benzo[f]azulen-2-yl]-phenyl}-3,6-dihydro-2H-pyridine-1-carboxylic acid tert-butyl ester 2-(4-Cyclopent-1-enyl-phenyl)-1-methyl-4-(1-methyl-piperidin-4-yloxy)-9,10-dihydro-4H-3,10a-diaza-benzo[f]azulene 2-(4-Cyclohex-1-enyl-phenyl)-1-methyl-4-(1-methyl-piperidin-4-yloxy)-9,10-dihydro-4H-3,10a-diaza-benzo[f]azulene 2-(4-Cyclohept-1-enyl-phenyl)-1-methyl-4-(1-methyl-piperidin-4-yloxy)-9,10-dihydro-4H-3,10a-diaza-benzo[f]azulene {4-[1-Methyl-4-(1-methyl-piperidin-4-yloxy)-9,10-dihydro-4H-3,10a-diaza-benzo[f]azulen-2-yl]-phenyl}-carbamic acid cyclopentyl ester {4-[1-Methyl-4-(1-methyl-piperidin-4-yloxy)-9,10-dihydro-4H-3,10a-diaza-benzo[f]azulen-2-yl]-phenyl}-carbamic acid isobutyl ester {4-[1-Methyl-4-(1-methyl-piperidin-4-yloxy)-9,10-dihydro-4H-3,10a-diaza-benzo[f]azulen-2-yl]-phenyl}-carbamic acid 2,2,2-trichloro-1,1-dimethyl-ethyl ester 4-Benzyl-3-{4-[1-methyl-4-(1-methyl-piperidin-4-yloxy)-9,10-dihydro-4H-3,10a-diaza-benzo[f]azulen-2-yl]-phenyl}-oxazolidin-2-one 4-{4-[1-Methyl-4-(1-methyl-piperidin-4-yloxy)-9,10-dihydro-4H-3,10a-diaza-benzo[f]azulen-2-yl]-phenyl}-piperidine-1-carboxylic acid tert-butyl ester 1-Isopropyl-3-{4-[1-methyl-4-(1-methyl-piperidin-4-yloxy)-9,10-dihydro-4H-3,10a-diaza-benzo[f]azulen-2-yl]-phenyl}-imidazolidin-2-one N-(2-{4-[1-Methyl-4-(1-methyl-piperidin-4-yloxy)-9,10-dihydro-4H-3,10a-diaza-benzo[f]azulen-2-yl]-phenylsulfanyl}-ethyl)-guanidine 1-Adamantan-1-yl-3-{4-[1-methyl-4-(1-methyl-piperidin-4-yloxy)-9,10-dihydro-4H-3,10a-diaza-benzo[f]azulen-2-yl]-phenyl}-urea N-{4-[1-Methyl-4-(1-methyl-piperidin-4-yloxy)-9,10-dihydro-4H-3,10a-diaza-benzo[f]azulen-2-yl]-phenyl}-hydrazinecarboxylic acid tert-butyl ester 1,2-Diiodo-4-(1-methyl-piperidin-4-yloxy)-9,10-dihydro-4H-3,10a-diaza-benzo[f]azulene (2-{4-[1-Methyl-4-(1-methyl-piperidin-4-yloxy)-9,10-dihydro-4H-3,10a-diaza-benzo[f]azulen-2-yl]-phenyl}-ethyl)-carbamic acid tert-butyl ester 4-[1-Cyano-4-(1-methyl-piperidin-4-yloxy)-9,10-dihydro-4H-3,10a-diaza-benzo[f]azulen-2-yl]-benzoic acid tert-butyl ester 2-(3,3-Dimethyl-but-1-enyl)-1-methyl-4-(1-methyl-piperidin-4-yloxy)-9,10-dihydro-4H-3,10a-diaza-benzo[f]azulene 2-Cyclohex-1-enyl-1-methyl-4-(1-methyl-piperidin-4-yloxy)-9,10-dihydro-4H-3,10a-diaza-benzo[f]azulene 2-(6-Chloro-hex-1-ynyl)-1-methyl-4-(1-methyl-piperidin-4-yloxy)-9,10-dihydro-4H-3,10a-diaza-benzo[f]azulene 2-(3,3-Dimethyl-butyl)-1-methyl-4-(1-methyl-piperidin-4-yloxy)-9,10-dihydro-4H-3,10a-diaza-benzo[f]azulene 4-(1-Methyl-piperidin-4-yloxy)-2-phenyl-9,10-dihydro-4H-3,10a-diaza-benzo[f]azulene-1-carbonitrile 1-Iodo-4-(1-methyl-piperidin-4-yloxy)-2-phenyl-9,10-dihydro-4H-3,10a-diaza-benzo[f]azulene 4-(1-Methyl-piperidin-4-yloxy)-2-phenyl-1-trifluoromethyl-9,10-dihydro-4H-3,10a-diaza-benzo[f]azulene, oxalate 2-(2-Chloro-phenyl)-4-(1-methyl-piperidin-4-yloxy)-9,10-dihydro-4H-3,10a-diaza-benzo[f]azulene-1-carboxylic acid amide, oxalate as well as its enantiomers, diastereomers, mixtures thereof and, tautomers, hydrates and solvates.

The compounds of formula (I) can comprise one or more asymmetric carbon atoms. They can therefore exist in the form of enantiomers or diastereoisomers. These enantiomers and diastereoisomers, as well as their mixtures, including racemic mixtures, form part of the invention.

The compounds of formula (I) can be provided in the form of a free base or in the form of addition salts with acids, which also form part of the invention.

These salts are advantageously prepared with pharmaceutically acceptable acids, but salts with other acids, useful for example for the purification or for the isolation of the compounds of formula (I), also form part of the invention.

As used herein, the term "patient" refers to a warm-blooded animal such as a mammal, preferably a human or a human child, which is afflicted with, or has the potential to be afflicted with one or more diseases and conditions described herein.

As used herein, a "therapeutically effective amount" refers to an amount of a compound of the present invention which is effective in reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment and chronic use.

As used herein, "pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propanoic, succinic, tartaric, citric, methanesulfonic, benzenesulfonic, glucuronic, glutamic, benzoic, salicylic, toluenesulfonic, oxalic, fumaric, maleic, and the like. Further addition salts include ammonium salts such as tromethamine, meglumine, epolamine, etc., metal salts such as sodium, potassium, calcium, zinc or magnesium. Hydrochloride and oxalate salts are preferred.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418, the disclosure of which is hereby incorporated by reference.

The compounds of the general formula (I) having geometrical and stereomers are also a part of the invention.

According to a further object, the present invention is also concerned with the process of preparation of the compounds of formula (I).

The compounds and process of the present invention may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art.

In particular, such methods can be found in R. C. Larock, *Comprehensive Organic Transformations*, VCH publishers, 1989.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups. Conventional protecting groups may be used in accordance with standard practice, for examples see T. W. Greene and P. G. M. Wuts in *Protective Groups in Organic Chemistry*, John Wiley and Sons, 1991; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, methylcyclohexane, toluene and xylene; amides, such as N,N-dimethylformamide; alcohols such as ethanol and methanol and ethers, such as diethyl ether, methyl tert-butyl ether, methyl cyclopentyl ether and tetrahydrofuran.

The reactions can take place over a wide range of temperatures. In general, we find it convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary, after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallization, reprecipitation or the various chromatography techniques, notably column chromatography, preparative HPLC or preparative thin layer chromatography.

The process of preparation of a compound of formula (I) of the invention is another object of the present invention.

Compounds of formula (I) can be prepared by condensing an alcohol of formula (II) in which R1 is as defined in general formula (I) with an alcohol of formula (III) in which R2, R3, R4, R5, R6, R7, R8, R9, R10 and R11 are as defined in general formula (I):

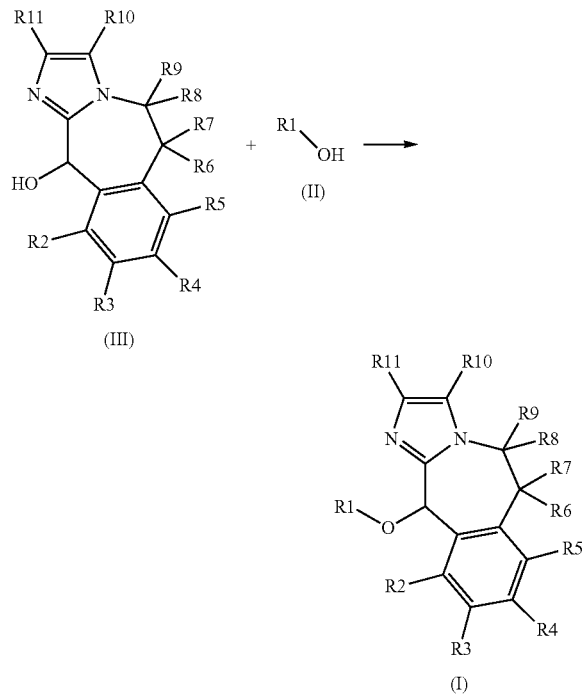

This reaction can be performed with an acidic catalyst (toluenesulfonic acid, methanesulfonic acid or trifluoromethanesulfonic acid neat or in 1,2-dichloroethane, dichloromethane, chloroforme, toluene, N-methyl-2-pyrrolidone or a mixture thereof) at a temperature comprised between room temperature and 140° C.

Alcohols of formula (III) can be prepared by cyclisation of an aldehyde of formula (IV) in which R2, R3, R4, R5, R6, R7, R8, R9, R10 and R11 are as defined in general formula (I):

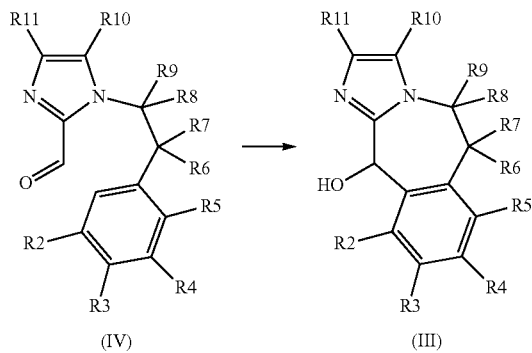

This reaction can be performed with an acidic catalyst (toluenesulfonic acid, methanesulfonic acid or trifluoromethanesulfonic acid neat or in 1,2-dichloroethane, dichloromethane, chloroforme, toluene, N-methyl-2-pyrrolidinone or a mixture thereof) at a temperature comprised between room temperature and 140° C.

Alternatively, compounds of formula (I) can be prepared by condensing an alcohol of formula (II) in which R1 is as defined in general formula (I) with an aldehyde of formula (IV) in which R2, R3, R4, R5, R6, R7, R8, R9, R10 and R11 are as defined in general formula (I):

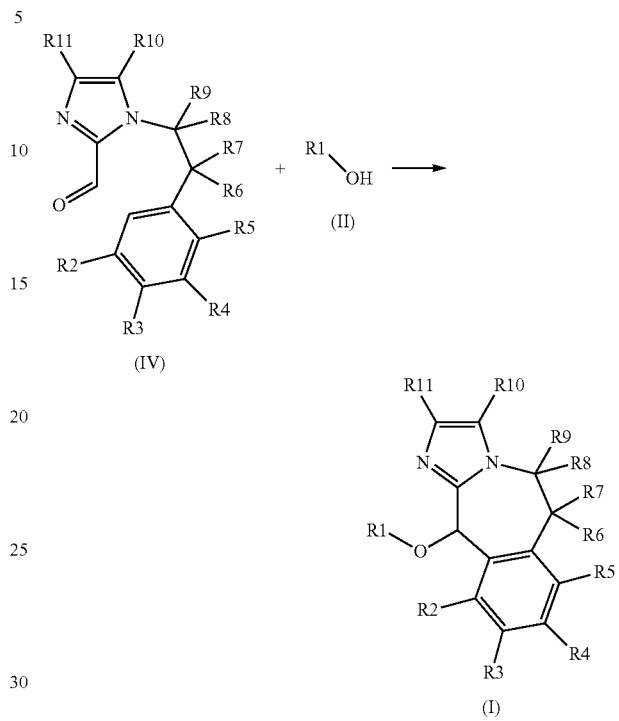

This reaction can be performed with an acidic catalyst (toluenesulfonic acid, methanesulfonic acid or trifluoromethanesulfonic acid neat or in 1,2-dichloroethane, dichloromethane, chloroforme, toluene, N-methyl-2-pyrrolidone or a mixture thereof) at a temperature comprised between room temperature and 140° C.

Aldehydes of formula (IV) in which R2, R3, R4, R5, R6, R7, R8, R9, R10 and R11 are as defined in general formula (I) can be prepared from an imidazole of formula (V) in which R2, R3, R4, R5, R6, R7, R8, R9, R10 and R11 are as defined in general formula (I):

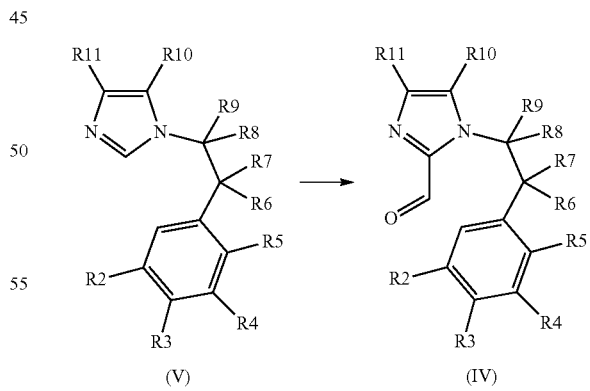

This reaction can be performed by metalation of the imidazole nucleus with a strong base (butyl lithium or lithium diisopropylamide) in an inert solvent (tetrahydrofurane) at a temperature comprised between −80° C. and 0° C., then condensing the anion with an electrophile (N,N-dimethylformamide, N-formylmorpholine) at a temperature comprised between −78° C. and room temperature.

Imidazoles of formula (V) can be prepared by alkylation of an imidazole of formula (VI) in which R10 and R11 are as defined in general formula (I) with an alkylating agent of formula (VII) in which R2, R3, R4, R5, R6, R7, R8 and R9 are as defined in general formula (I) and X represents a leaving group (halogen, alkylsulfonyloxy, polyfluoroalkylsulfonyloxy, optionally substituted arylsulfonyloxy):

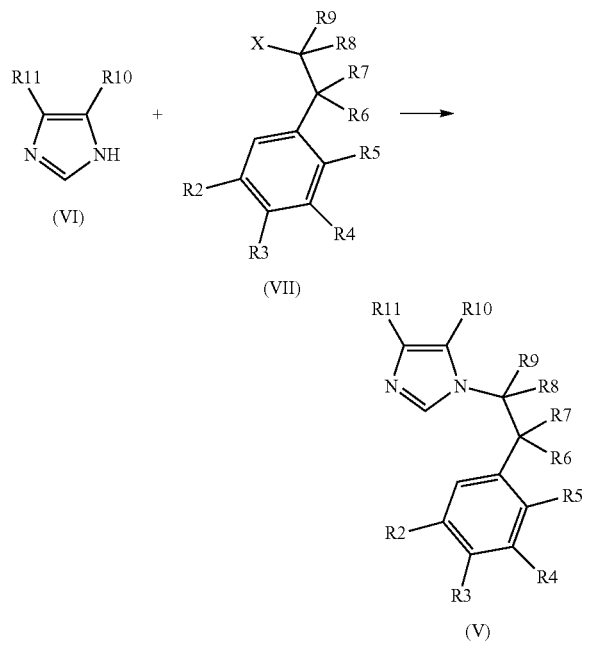

This reaction can be performed in the presence of a base (sodium hydride, sodium methylate, potassium carbonate or cesium carbonate), optionally in the presence of catalyst (tetrabutylammonium) in a solvent (methanol, N,N-dimethylformamide, N-methyl-2-pyrrolidinone or acetonitrile) at a temperature comprised between 60° C. and reflux temperature.

Alternatively, compounds of formula (I) can be prepared by transforming another compound of formula (I). Such transformations include, but are not limited to, the following:

Suzuki coupling of a boronic acid or an boronate ester with a compound of formula (I) in which R2, R3, R4, R5, R10 or R11 represent an halogen atom. This reaction can be performed in the presence of a transition metal catalyst (palladium acetate, [1,1'-bis(diphenylphosphino)ferrocene]dichloropalladium), a base (potassium carbonate, cesium fluoride) in a solvent (dioxane, tetrahydrofurane, water, toluene or a mixture thereof) at a temperature comprised between room temperature and reflux temperature.

Stille coupling of a stannane with a compound of formula (I) in which R2, R3, R4, R5, R10 or R11 represent an halogen atom. This reaction can be performed in the presence of a transition metal catalyst (tetrakis(triphenylphosphine)palladium) optionally in the presence of lithium chloride in a solvent (toluene of N,N-dimethylformamide) at a temperature comprised between room temperature and reflux temperature.

Sonogashira coupling of a compound bearing a terminal alkyne with a compound of formula (I) in which R2, R3, R4, R5, R10 or R11 represent an halogen atom. This reaction can be performed in the presence of transition metal catalysts (tetrakis(triphenylphosphine)palladium or bis(triphenylphosphine)dichloropalladium) and copper iodide, an inorganic base (triethylamine or diethylamine) in a solvent (toluene, N,N-dimethylformamide or acetonitrile) at a temperature comprised between room temperature and reflux temperature.

Heck coupling of a compound bearing an alkene with a compound of formula (I) in which R2, R3, R4, R5, R10 or R11 represent an halogen atom. This reaction can be performed in the presence of transition metal catalysts (palladium acetate or tetrakis(triphenylphosphine)palladium), a base (potassium carbonate or triethylamine) and optionally other catalysts (lithium chloride and tetrabutylammonium bromide), in an inert solvent (N,N-dimethylformamide) at a temperature comprised between room temperature and reflux temperature.

Coupling of a compound bearing a NHCO group such as a lactam, an amide or a urethane with a compound of formula (I) in which R2, R3, R4, R5, R10 or R11 represent a halogen atom. This reaction can be performed in the presence of transition metal catalysts (bis(dibenzilideneacetone)palladium), another ligand (xantphos), a base (cesium carbonate or sodium methoxide) in a solvent (toluene or dioxane) at a temperature comprised between room temperature and reflux temperature. This transformation can be performed by using a N-trialkylsilyl derivative and a fluoride source (tetrabutylammonium fluoride) instead of a compound bearing a NHCO group.

Transforming of a compound of formula (I) in which R2, R3, R4, R5, R10 or R11 represent an halogen atom into an amide with help of carbon monoxyde or a donnor of carbon monoxyde (molybdenum hexacarbonyl) and an amine in the presence of transition metal catalyst (trans-di-p-acetatobis[2-(di-o-tolyl-phosphino)-benzyl]dipalladium(II) and tri-tertbutylphosphonium tetrafluoroborate) in an inert solvent (tetrahydrofuran) at a temperature comprised between room temperature and reflux temperature.

Coupling of a thiol or a thiolate with a compound of formula (I) in which R2, R3, R4, R5, R10 or R11 represent an halogen atom. This reaction can be performed in the presence of transition metal catalysts (bis(dibenzilideneacetone)palladium), another ligand (xantphos), a base (diisopropylethylamine) in a solvent (dioxane) at a temperature comprised between room temperature and reflux temperature.

Coupling a compound of formula (I) in which R2, R3, R4, R5, R10 or R11 represent an halogen atom with an electrophile by first exchanging the halogen for a metal with a reagent such as butyl lithium or a grignard reagent in diethyl ether or tetrahydrofurane at a temperature comprised between −80° C. and 0° C., then reacting the organometallic species thus formed with an electrophile (aldehyde, tosylcyanide, an isocyanate, 3,3-dimethyl-1-trifluoromethyl-1,2-benzodioxole) optionally dissolved in an inert solvent (dichloromethane) at a temperature comprised between −80° C. and room temperature.

Coupling a compound of formula (I) in which R2, R3, R4, R5, R10 or R11 represent an halogen atom with an amine in the presence of a transition metal catalyst (palladium acetate, [1,1'-bis(diphenylphosphino)ferrocene]dichloropalladium or copper iodide) in the presence of a base (potassium carbonate, cesium carbonate, sodium tert-butylate) in a solvent (toluene or N,N-dimethylformamide) at a temperature comprised between 60° C. and reflux temperature.

Coupling a compound of formula (I) in which R2, R3, R4, R5, R10 or R11 represent an halogen atom with an alcohol in the presence of a transition metal catalyst (palladium acetate or copper iodide and optionally 3,4,7,8-tetramethylphenanthroline) in the presence of a base (potassium carbonate, cesium carbonate, potassium phosphate) in a solvent (toluene or N,N-dimethylformamide) at a temperature comprised between 60° C. and reflux temperature.

Converting a compound of formula (I) in which R10 represents hydrogen into a compound of formula (I) in which R10 represents chlorine by the action of a reagent such as N-chlorosuccinimide in an inert solvent (dichloromethane) at a temperature comprised between 0° C. and room temperature.

Reducing a compound of formula (I) in which R2, R3, R4, R5, R10 or R11 comprises a double or a triple bond with hydrogen or a hydrogen donor (ammonium formate or the eutectic mixture formic acid/triethylamine) in the presence of a transition metal catalyst (platinum oxide, palladium on charcoal or baryum sulfate) in an inert solvent (methanol, ethanol or ethyl acetate) at a temperature comprised between room temperature and 100° C.

Reducing a compound of formula (I) in which R2, R3, R4, R5, R10 or R11 comprises a nitro with hydrogen in the presence of a transition metal catalyst (nickel, palladium or platinum), or with stanous chloride or with iron in an inert solvent (methanol, ethanol) and optionally in the presence of an acid (acetic acid or hydrochloric acid).

Condensing a compound of formula (I) in which R2, R3, R4, R5, R10 or R11 comprises a primary or secondary amine with an acid chloride, an acid anhydride, an isocyanate, an isothiocyanate, a chloroformate or a sulfonyl chloride in the presence of a base (triethylamine, diisopropylethylamine or 4-dimethylaminopyridine) in an inert solvent (dichloromethane, acetonitrile) at a temperature comprised between 0° C. and the reflux temperature.

Condensing a compound of formula (I) in which R2, R3, R4, R5, R10 or R11 comprises a primary or secondary amine with a guanidyl transfer agent (N,N'-bis(tert-butoxycarbonyl)-1H-pyrazole-1-carboxamidine)) in the presence of a base (diisopropylethylamine) in an inert solvent (acetonitrile) at a temperature comprised between room temperature and reflux temperature and deprotecting with trifluoroacetic acid in dichloromethane at a temperature comprised between 0° C. and 40° C.

Condensing a compound of formula (I) in which R2, R3, R4, R5, R10 or R11 comprises an alcohol with an isocyanate optionally in the presence of a catalyst (cuprous chloride or an alcoholate) in an inert solvent (toluene or N,N-dimethylformamide) at a temperature comprised between room temperature and reflux temperature.

Oxidising a compound of formula (I) in which R2, R3, R4, R5, R10 or R11 comprises an alcohol into a compound of formula (I) in which R2, R3, R4, R5, R10 or R11 comprises a carbonyl with an oxidising agent (baryum manganate, manganese dioxide or a mixture themof) in an inert solvent (dioxane) at a temperature comprised between 60° C. and reflux temperature.

Reducing a compound of formula (I) in which R2, R3, R4, R5, R10 or R11 comprises a carbonyl or an ester into a compound of formula (I) in which R2, R3, R4, R5, R10 or R11 comprises an alcohol with a reducing agent (sodium borohydride) in a solvent (methanol, ethanol, water or a mixture thereof) or with borane dimethylsulfide complex in an inert solvent (tetrahydrofurane or dioxane) at a temperature comprised between 0° C. and reflux temperature.

Hydrolysing a compound of formula (I) in which R2, R3, R4, R5, R10 or R11 comprises a nitrile into a compound of formula (I) in which R2, R3, R4, R5, R10 or R11 comprises an amide with a mixture of sodium hydroxyde and hydrogen peroxyde in an inert solvent (methanol) at a temperature comprised between −20° C. and room temperature.

Hydrolysing a compound of formula (I) in which R2, R3, R4, R5, R10 or R11 comprises an amide into a compound of formula (I) in which R2, R3, R4, R5, R10 or R11 comprises a carboxylic acid with sodium hydroxyde at a temperature comprised between 80° C. and reflux temperature.

Converting a compound of formula (I) in which R2, R3, R4, R5, R10 or R11 comprises a carboxylic acid into a compound of formula (I) in which R2, R3, R4, R5, R10 or R11 comprises a carboxylic ester with diazomethane or trimethylsilyldiazomethane in an inert solvent (diethyl ether or dichloromethane) at a temperature comprised between 0° C. and reflux temperature.

The process of the invention may comprise the additional step of isolating the desired compound of formula (I).

According to a further object, the present invention is also concerned with the compound of formula (III) in which R2, R3, R4, R5, R6, R7, R8, R9, R10 and R11 are as defined in general formula (I) and with the compound of formula (IV) in which R2, R3, R4, R5, R6, R7, R8, R9, R10 and R11 are as defined in general formula (I).

According to a further object, the present invention is also concerned with the compound of formula (IV) as defined above, excluding 1-(2-phenylethyl)-1H-imidazole-2-carbaldehyde.

According to a still further object, the present invention is also concerned with pharmaceutical compositions comprising a compound of formula (I) as defined above with a pharmaceutically acceptable excipient.

The compounds of the invention are antagonists and/or inverse agonists of H4 R. The pharmaceutical compositions and compounds of the invention may thus be useful for use in the treatment and/or prevention of a disease associated with $H_4$ dysfunction, such as inflammatory disorders.

Said disease includes adult respiratory distress syndrome, acute respiratory distress syndrome, bronchitis, chronic bronchitis, chronic obstructive pulmonary disease, cystic fibrosis, asthma, emphysema, rhinitis, chronic sinusitis, allergy, allergy induced airway responses, allergic rhinitis, viral rhinitis, non-allergic rhinitis, perennial and seasonal rhinitis, conjunctivitis, nasal congestion, allergic congestion; disorders of the genito-urinary tract such as female and male sexual dysfunction, overactive bladder conditions, urinary incontinence, bladder overactivity, benign prostate hyperplasia and lower urinary tract symptoms; dermatological diseases such as dermatitis and psoriasis and treatment of itchy skin; diseases of the cardiovascular system including thromboembolic diseases, atherosclerosis, myocardial infarction, angina pectoris, myocardial ischaemia and arrhythmia, peripheral arterial occlusive diseases, pulmonary embolisms or deep venous thromboses, hypotension, pulmonary hypertension, malignant hypertension, cardiac insufficiency, heart or kidney failure, stroke and renal dysfunction; diseases of the gastrointestinal tract including inflammatory bowel disease, Crohn's disease, ulcerative colitis; autoimmune diseases including rheumatoid arthritis, multiple sclerosis; cancer; pain; lymphatic diseases.

According to a further object, the present invention also concerns a combination of a compound of the invention with one or more therapeutic agent(s) selected from:
Histamine $H_1$, $H_2$ or $H_3$ receptor antagonists;
Leukotriene antagonists;
5-Lipoxygenase (5-LO) inhibitors or 5-lipoxygenase activating protein (FLAP) antagonists;
$CX_1$- and $\alpha_2$-adrenoceptor agonist vasoconstrictor sympathomimetic agents for decongestant use;
Xanthines, such as theophylline and aminophylline;
Non-steroidal antiinflammatories, such as sodium cromoglycate and nedocromil sodium;
Ketotifen;
COX-1 inhibitors (NSAIDs) and COX-2 selective inhibitors;
Immunosuppressants; mucolytics or anti-tussive agents.

More particularly, the present invention also concerns combinations comprising a compound of formula (I) of the invention with a H1R antagonist, such as cetirizine, levocetirizine, desloratadine, bepotastine or doxepin.

According to a still further object, the present invention is also concerned with a compound of formula (I) for the above conditions to be administered to a patient in the need thereof.

According to a still further object, the present invention also concerns the methods of treatment comprising administering an effective amount of a compound of the invention for treating and/or preventing the above conditions or disorders.

The identification of those subjects who are in need of treatment of herein-described diseases and conditions is well within the ability and knowledge of one skilled in the art. A clinician skilled in the art can readily identify, by the use of clinical tests, physical examination and medical/family history, those subjects who are in need of such treatment.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of a compound of formula (I), which is required to achieve the desired biological effect, will vary depending upon a number of factors, including the dosage of the drug to be administered, the chemical characteristics (e.g. hydrophobicity) of the compounds employed, the potency of the compounds, the type of disease, the diseased state of the patient, and the route of administration.

In general terms, the compounds of this invention may be provided in an aqueous physiological buffer solution containing 0.1 to 10% w/v compound for parenteral administration. Typical dose ranges are from 1 µg/kg to 0.1 g/kg of body weight per day; a preferred dose range is from 0.01 mg/kg to 10 mg/kg of body weight per day. A preferred daily dose for adult humans includes 1, 5, 50, 100 and 200 mg, and an equivalent dose in a human child. The preferred dosage of drug to be administered is likely to depend on such variables as the type and extent of progression of the disease or disorder, the overall health status of the particular patient, the relative biological efficacy of the compound selected, and formulation of the compound excipient, and its route of administration.

The compounds of the present invention are capable of being administered in unit dose forms, wherein the term "unit dose" means a single dose which is capable of being administered to a patient, and which can be readily handled and packaged, remaining as a physically and chemically stable unit dose comprising either the active compound itself, or as a pharmaceutically acceptable composition, as described hereinafter. As such, typical daily dose ranges are from 0.01 to 10 mg/kg of body weight. By way of general guidance, unit doses for humans range from 0.1 mg to 1000 mg per day. Preferably, the unit dose range is from 1 to 500 mg administered one to four times a day, and even more preferably from 1 mg to 300 mg, once a day. Compounds provided herein can be formulated into pharmaceutical compositions by admixture with one or more pharmaceutically acceptable excipients. Such compositions may be prepared for use in oral administration, particularly in the form of tablets or capsules, in particular orodispersible (lyoc) tablets; or parenteral administration, particularly in the form of liquid solutions, suspensions or emulsions; or intranasally, particularly in the form of powders, nasal drops, or aerosols; or dermally, for example, topically or via transdermal patches or ocular administration, or intravaginal or intra-uterine administration, particularly in the form of pessaries or by rectal administration.

The compositions may conveniently be administered in unit dosage form and may be prepared by any of the methods well known in the pharmaceutical art, for example, as described in Remington: *The Science and Practice of Pharmacy*, $20^{th}$ ed.; Gennaro, A. R., Ed.; Lippincott Williams & Wilkins: Philadelphia, Pa., 2000. Pharmaceutically compatible binding agents and/or adjuvant materials can be included as part of the composition. Oral compositions will generally include an inert diluent carrier or an edible carrier.

The tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal.

Preferred formulations include pharmaceutical compositions in which a compound of the present invention is formulated for oral or parenteral administration, or more preferably those in which a compound of the present invention is formulated as a tablet. Preferred tablets contain lactose, cornstarch, magnesium silicate, croscarmellose sodium, povidone, magnesium stearate, or talc in any combination. It is also an aspect of the present disclosure that a compound of the present invention may be incorporated into a food product or a liquid.

Liquid preparations for administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, acrylate copolymers, vegetable oils such as olive oil, and organic esters such as ethyl oleate. Aqueous carriers include mixtures of alcohols and water, hydrogels, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

Alternative administrations include also solutions, ointments or other formulations acceptable for ocular administration.

Other features of the invention will become apparent in the course of the following description of exemplary embodiments that are given for illustration of the invention and not intended to be limiting thereof.

Acronyms

ACN: acetonitrile

DMF: N,N-dimethylformamide dppf: 1,1-bis(diphenylphosphino)ferrocene dba: dibenzilideneacetone Xantphos: 4,5-bis(diphenylphosphino)-9,9-dimethylxanthene RuPhos: 2-dicyclohexylphosphino-2',6'-diisopropoxybiphenyl LDA: lithium diisopropylamide THF: tetrahydrofuran TLC: thin layer chromatography KF: potassium fluoride NMP: methylpyrrolidone PPh3: triphenylphosphine mp: melting point

EXAMPLES

Melting points are determined on Buchi capillary melting point apparatus.

Proton NMR spectra are recorded on a Bruker 250 MHz NMR instrument. The chemicals shifts δ are expressed in ppm. The following abbreviations are used to denote signal patterns: s=singlet, sl=large singlet, d=doublet, t=triplet, q=quadruplet, m=multiplet. The coupling contents are expressed in Hz. $^1$H NMR experiments performed in $CDCl_3$ unless specified The spectra recorded are consistent with the proposed structures.

HPLC-MS analyses are performed on a Waters AutoPurification HPLC/MS System equipped with a 3100 Mass Spectrometer and a 2998 Photodiode Array (PDA) Detector.

The MS spectra recorded are consistent with the proposed structures.

The LC retention times are obtained using the following elution conditions:

LC-MS Method A: Xterra MS C18 5 μm 2.1×10 mm guard column, Xterra MS C18 5 μm 3.0×100 mm column, eluents: water/0.1% formic acid (A) and acetonitrile/0.1% formic acid (B), linear gradient from 5% (B) to 95% (B) in 6 minutes.

LC-MS Method B: Xterra MS C18 5 μm 2.1×10 mm guard column, Xterra MS C18 5 μm 3.0×100 mm column, eluents: water/0.1% formic acid (A) and acetonitrile/0.1% formic acid (B), linear gradient from 5% (B) to 40% (B) in 6 minutes.

LC-MS Method C: Xterra MS C18 5 μm 2.1×10 mm guard column, Xterra MS C18 5 μm 3.0×100 mm column, eluents: water/0.1% trifluoroacetic acid (A) and acetonitrile/0.1% trifluoroacetic acid (B), linear gradient from 5% (B) to 95% (B) in 6 minutes.

LC-MS Method E: Sunfire C18 5 μm 4.6×20 mm guard column, Sunfire C18 5 μm 4.6×150 mm column, eluents: water/0.1% formic acid (A) and acetonitrile/0.1% formic acid (B), linear gradient from 5% (B) to 95% (B) in 10 minutes.

Example 1

1A 4-(methylpiperidin-4-yloxy)-2-trifluoromethyl-9,10-dihydro-4H-3,10a-diaza benzo[f]azulene (compound 1a) and 4-(1-methylpiperidin-4-yloxy)-1-trifluoromethyl-9,10-dihydro-4H-3,10a-diaza-benzo[f]azulene (compound 1b)

To a solution of 4-hydroxy-N-methylpiperidine (173 mg, 1.5 mmoles) in methanesulfonic acid (2.5 mL) is added a solution of the mixture of 1-phenethyl-4-trifluoromethyl-imidazole-2-carbaldehyde and 1-phenethyl-5-trifluoromethyl-imidazole-2-carbaldehyde (example 1B). The reaction mixture is stirred overnight at room temperature. Water is added and the mixture is basified to pH 9-10 with 12N NaOH. The aqueous phase is extracted three times with dichloromethane. The organic phase is dried over magnesium sulphate, filtered and the solvent is removed under reduced pressure. The residue is purified by silica gel chromatography using ($CH_2Cl_2$:MeOH:$NH_4OH$) as eluent with a gradient from (99:5:0.1) to (95:5:0.5) to give pure 4-(1-methylpiperidin-4-yloxy)-2-trifluoromethyl-9,10-dihydro-4H-3,10a-diaza-benzo[f]azulene (compound 1a) and pure 4-(1-methylpiperidin-4-yloxy)-1-trifluoromethyl-9,10-dihydro-4H-3,10a-diaza-benzo[f]azulene (compound 1b).

4-(1-methylpiperidin-4-yloxy)-2-trifluoromethyl-9,10-dihydro-4H-3,10a-diaza-benzo[f]azulene (compound 1a)

$^1$H NMR: 7.40-7.15 (m, 5H), 5.62 (s, 1H), 4.60-4.45 (m, 1H), 4.32-4.17 (m, 1H), 4.15-3.98 (m, 1H), 3.60-3.45 (m, 1H), 3.00-2.88 (m, 1H), 2.79-2.60 (m, 2H), 2.27 (s, 3H), 2.25-2.08 (m, 2H), 2.00-1.58 (m, 4H); $^{19}$F NMR: −63.85 (CF$_3$).

4-(1-methylpiperidin-4-yloxy)-1-trifluoromethyl-9,10-dihydro-4H-3,10a-diaza-benzo[f]azulene (compound 1b)

$^1$H NMR: 7.40-7.20 (m, 5H), 5.62 (s, 1H), 4.68-4.52 (m, 1H), 4.35-3.98 (m, 2H), 3.65-3.48 (m, 1H), 3.05-2.92 (m, 1H), 2.85-2.65 (m, 2H), 2.32 (s, 3H), 2.40-2.12 (m, 2H), 2.08-1.60 (m, 4H); $^{19}$F NMR: −61.36 (CF$_3$).

1B Mixture of 1-phenethyl-4-trifluoromethyl-imidazole-2-carbaldehyde and 1-phenethyl-5-trifluoromethyl-imidazole-2-carbaldehyde A solution of isomers (example 1C) (565 mg, 2.35 mmoles) in THF (13 mL) under argon is cooled to −78° C. and 2.5M nBuLi (1.03 mL, 2.55 mmoles) is added dropwise. After 30 minutes at −78° C., DMF (364 μL, 4.7 mmoles) is added dropwise. The reaction mixture is allowed to reach 0° C., then it is quenched by adding a half-saturated NaHCO$_3$ solution. The aqueous phase is extracted three times with AcOEt. The organic phase is washed with water, brine, dried over magnesium sulphate, filtered and the solvent is removed under reduced pressure. The residue is purified by silica gel chromatography using (heptane:AcOEt) as eluent with a gradient from (95:5) to (90:10) to give 1-phenethyl-4-trifluoromethyl-imidazole-2-carbaldehyde and 1-phenethyl-5-trifluoromethyl-imidazole-2-carbaldehyde as a (7/1) mixture.

$^1$H NMR: 9.87 (s, 1H N-3 isomer), 9.45 (s, 1H N-1 isomer), 7.64-7.06 (m, 6H), 4.70-4.55 (m, 2H), 3.15-3.00 (m, 2H); $^{19}$F NMR: −61.18 (CF$_3$ of N-3 isomer), −64.21 (CF$_3$ of N-1 isomer).

1C Mixture of 1-phenethyl-4-trifluoromethyl-imidazole and 1-phenethyl-5-trifluoromethyl-imidazole To a solution of 4-trifluoromethyl-1H-imidazole (680 mg, 5 mmoles) in DMF (10 mL) is added NaH 60% dispersion in mineral oil (220 mg, 5.5 mmoles). The reaction mixture is heated at 50° C. for 1 h, then 2-bromoethylbenzene (751 μL, 5.5 mmoles) and a catalytic quantity of tetrabutylammonium bromide are added to the mixture. The reaction mixture is then heated at 80° C. overnight. Half-saturated ammonium chloride solution is added, and the aqueous phase is extracted three times with Et$_2$O. The organic phase is washed with water, brine, dried over magnesium sulphate, filtered and the solvent is removed under reduced pressure. The residue is purified by silica gel chromatography using (heptane:AcOEt) as eluent with a gradient from (95:5) to (70:30) to give a mixture of 1-phenethyl-4-trifluoromethyl-imidazole and 1-phenethyl-5-trifluoromethyl-imidazole.

$^1$H NMR: 7.45-7.20 (m, 4H), 7.18-7.00 (m, 3H), 4.30-4.15 (m, 2H), 3.15-3.00 (m, 2H); $^{19}$F NMR: −59.8 (CF$_3$ of N-3 isomer), −63.87 (CF$_3$ of N-1 isomer)

Example 2

2A 2-iodo-4-(1-methylpiperidin-4-yloxy)-9,10-dihydro-4H-3,10a-diaza-benzo[f]azulene To a solution of 4-hydroxy-N-methylpiperidine (223 mg, 2.02 mmoles) in methanesulfonic acid (3.4 mL) is added a solution of 4-Iodo-1-phenethyl-imidazole-2-carbaldehyde (example 2B) (220 mg, 0.675 mmoles) in chloroform (1 mL). The reaction mixture is stirred at room temperature overnight. Water is added to the reaction mixture, and the pH is adjusted to 9-10 by adding 12N NaOH dropwise. The aqueous phase is extracted three times with dichloromethane. The organic phase is dried over magnesium sulphate, filtered and the solvent is removed under reduced pressure. The residue is purified by silica gel chromatography using (CH$_2$Cl$_2$:MeOH:NH$_4$OH) as eluent with a gradient from (99:5:0.1) to (95:5:0.5) to give 2-iodo-4-(1-methylpiperidin-4-yloxy)-9,10-dihydro-4H-3,10a-diaza-benzo[f]azulene melting at 126° C.

2B 4-iodo-1-phenethyl-imidazole-2-carbaldehyde

A solution of 4-iodo-1-phenethyl-imidazole (example 2C) (563 mg, 1.89 mmoles) in THF (13 mL) under argon is cooled to −78° C. A 2.0M LDA solution (1.04 mL, 2.08 mmoles) is added dropwise. After 30 minutes at −78° C., DMF (161 μL, 2.08 mmoles) is added dropwise. The reaction mixture is allowed to reach 0° C., then it is quenched by adding a half-saturated NaHCO$_3$ solution. The aqueous phase is extracted three times with AcOEt. The organic phase is washed with water, brine, dried over magnesium sulphate, filtered and the solvent is removed under reduced pressure. The residue is purified by silica gel chromatography using (heptane:AcOEt) as eluent with a gradient from (95:5) to (70:30) to give 4-iodo-1-phenethyl-imidazole-2-carbaldehyde.

$^1$H NMR: 9.74 (s, 1H), 7.38-7.20 (m, 3H), 7.15-7.05 (m, 2H), 6.96 (s, 1H), 4.59 (t, J=8.5 Hz, 2H), 3.04 (t, J=8.5 Hz, 2H).

2C 4-iodo-1-phenethyl-imidazole and 5-iodo-1-phenethyl-imidazole

To a solution of 4-iomethyl-1H-imidazole (970 mg, 5 mmoles) in DMF (10 mL) is added NaH 60% dispersion in mineral oil (220 mg, 5.5 mmoles). The reaction mixture is heated at 50° C. for 1 h, then 2-bromoethylbenzene (781 μL, 5.5 mmoles) and a catalytic quantity of tetrabutylammonium bromide are added to the mixture. The reaction mixture is then heated at 80° C. for 5 hours. Half-saturated ammonium chloride solution is added, and the aqueous phase is extracted three times with Et$_2$O. The organic phase is washed with water, brine, dried over magnesium sulphate, filtered and the solvent is removed under reduced pressure. The residue is purified by silica gel chromatography using (heptane:AcOEt) as eluent with a gradient from (95:5) to (60:40) to give 4-iodo-1-phenethyl-imidazole and 5-iodo-1-phenethyl-imidazole.

4-iodo-1-phenethyl-imidazole $^1$H NMR: 7.38-7.15 (m, 4H), 7.10-6.96 (m, 2H), 6.93 (s, 1H), 4.14 (t, J=8.5 Hz, 2H), 3.04 (t, J=8.5 Hz, 2H).

5-iodo-1-phenethyl-imidazole $^1$H NMR: 7.41 (s, 1H), 7.36-7.18 (m, 3H), 7.15-7.00 (m, 3H), 4.15 (t, J=8.6 Hz, 2H), 3.04 (t, J=8.6 Hz, 2H).

Example 3

3A 1-iodo-4-(1-methylpiperidin-4-yloxy)-9,10-dihydro-4H-3,10a-diaza-benzo[f]azulene Compound 3A is obtained following the procedure already described in example 2A and 2B starting from compound 5-Iodo-1-phenethyl-imidazole (example 2C) to afford 1-iodo-4-(1-methylpiperidin-4-yloxy)-9,10-dihydro-4H-3,10a-diaza-benzo[f]azulene melting at 163° C.

Example 4

4A 4-(1-methylpiperidin-4-yloxy)-2-phenyl-9,10-dihydro-4H-3,10a-diaza-benzo[f]azulene To a solution of 4-hydroxy-N-methylpiperidine (275 mg, 2.39 mmoles) in methanesulfonic acid (2 mL) at 0° C. is added a solution of 1-phenethyl-4-phenyl-imidazole-2-carbaldehyde (example 4B) (250 mg, 0.904 mmoles) in chloroform (2 mL). The reaction mixture is stirred at room temperature overnight, then heated to reflux for 6 h. A saturated solution of $Na_2CO_3$ is added to reach pH 10. The aqueous phase is extracted three times with $CH_2Cl_2$. The organic phase is dried over magnesium sulphate, filtered and the solvent is removed under reduced pressure. The residue is purified by silica gel chromatography using ($CH_2Cl_2$:MeOH) (90:10) to give 4-(1-methylpiperidin-4-yloxy)-2-phenyl-9,10-dihydro-4H-3,10a-diaza-benzo[f]azulene melting at 113° C.

4B 1-phenethyl-4-phenyl-imidazole-2-carbaldehyde

Compound 4B is obtained following the procedure already described in example 2B starting from example 4C.

$^1$H NMR: 8.88 (s, 1H), 7.78-7.68 (m, 2H), 7.47-7.20 (m, 6H), 7.18-7.05 (m, 2H), 4.65 (t, J=8.6 Hz, 2H), 3.11 (t, J=8.6 Hz, 2H).

4C 1-phenethyl-4-phenyl-imidazole

To a solution of 4-phenyl-1H-imidazole (1 g, 8.75 mmoles) in DMF (8 mL) is added NaH 60% dispersion in mineral oil (455 mg, 11 mmoles). The reaction mixture is stirred at room temperature for 1 hour, then methanesulfonic acid phenethyl ester (example 4D) (1.84 g, 9.12 mmoles) is added. The reaction mixture is then heated at 60° C. for 2 hours. Water is added, and the aqueous phase is extracted three times with AcOEt. The organic phase is washed with water, brine, dried over magnesium sulphate, filtered and the solvent is removed under reduced pressure. The residue is purified by silica gel chromatography using ($CH_2Cl_2$:MeOH) (100:0) then (98:2) to give 1-phenethyl-4-phenyl-imidazole.

$^1$H NMR: 7.72 (s, 1H), 7.50-7.41 (m, 3H), 7.35-7.18 (m, 5H), 7.12 (s, 1H), 6.98-6.90 (m, 2H), 4.26 (t, J=8.8 Hz, 2H), 2.89 (t, J=8.8 Hz, 2H).

4D Methanesulfonic Acid Phenethyl Ester

To a solution of 2-phenylethanol (24.4 g, 0.2 mole) in $CH_2Cl_2$ (200 mL) is added $NEt_3$ (30.7 mL, 0.22 mole). The reaction mixture is cooled to 0° C. and methanesulfonyl chloride (16.3 mL, 0.21 mole) is added dropwise. The reaction mixture is allowed to reach room temperature and is stirred at room temperature overnight. Solvent is removed under reduced pressure. Water is added and the aqueous phase is extracted three times with $Et_2O$. The organic phase is washed with water, brine, dried over magnesium sulphate, filtered and the solvent is removed under reduced pressure to give methanesulfonic acid phenethyl ester.

$^1$H NMR: 7.40-7.20 (m, 5H), 4.46 (t, J=8.3 Hz, 2H), 3.06 (t, J=8.3 Hz, 2H), 2.84 (s, 3H).

Example 5

4-(1-methylpiperidin-4-yloxy)-2-p-tolyl-9,10-dihydro-4H-3,10a-diaza-benzo[f]azulene: General procedure for Suzuki coupling starting from 2-iodo-4-(1-methylpiperidin-4-yloxy)-9,10-dihydro-4H-3,10a-diaza-benzo[f]azulene (example 2)

5A 4-(1-methylpiperidin-4-yloxy)-2-p-tolyl-9,10-dihydro-4H-3,10a-diaza-benzo[f]azulene To a solution of 2-iodo-4-(1-methylpiperidin-4-yloxy)-9,10-dihydro-4H-3,10a-diaza-benzo[f]azulene (example 2) (50 mg, 0.12 mmole) in 1,4-dioxane (0.5 mL) are added water (0.1 mL), 4-methylbenzeneboronic acid (25 mg, 0.18 mmole), Pd(OAc)$_2$ (1.4 mg, 6 µmmole), 1,1-bis(diphenylphosphino)ferrocene (3.3 mg, 6 µmmole) and $K_2CO_3$ (50 mg, 0.36 mmole). The vial is evacuated and filled with argon. The reaction mixture is stirred at 100° C. for 3.5 hours. Water is added to the reaction mixture, and the pH is adjusted to 9-10 by adding saturated $Na_2CO_3$ solution. The aqueous phase is extracted three times with AcOEt. The organic phase is dried over magnesium sulphate, filtered and the solvent is removed under reduced pressure. The residue is pre-purified by silica gel chromatography using ($CH_2Cl_2$:MeOH:$NH_4OH$) as eluent with a gradient from (99:5:0.1) to (95:5:0.5). The residue is purified by preparative TLC eluting with ($CH_2Cl_2$:MeOH:$NH_4OH$) (9:9:0.1) to give 4-(1-methylpiperidin-4-yloxy)-2-p-tolyl-9,10-dihydro-4H-3,10a-diaza-benzo[f]azulene.

[M+H]$^+$=388.2; [M+Na]$^+$=410.2.

The following compounds are prepared using the same method and different kinds of boronic acids or boronic acid pinacol esters.

| example | product |
|---|---|
| 6 | 4-(1-methyl-piperidin-4-yloxy)-2-m-tolyl-9,10-dihydro-4H-3,10a-diaza-benzo[f]azulene<br>[M + H]$^+$ = 388.2 |
| 8 | 4-(1-methyl-piperidin-4-yloxy)-2-o-tolyl-9,10-dihydro-4H-3,10a-diaza-benzo[f]azulene<br>[M + H]$^+$ = 388.3; [M + Na]$^+$ = 410.2 |
| 10 | 2-(4-tert-butyl-phenyl)-4-(1-methylpiperidin-4-yloxy)-9,10-dihydro-4H-3,10a-diaza-benzo[f]azulene oxalate<br>$^1$H NMR (base): 7.72-7.62 (m, 2H), 7.38-7.18 (m, 4H), 7.04 (s, 1H), 6.98-6.85 (m, 2H), 5.68 (s, 1H), 4.59-4.47 (m, 1H), 4.35-4.18 (m, 1H), 4.12-3.98 (m, 1H), 3.84 (s, 3H), 3.62-3.45 (m, 1H), 2.98-2.85 (m, 1H), 2.75-2.61 (m, 2H), 2.24 (s, 3H), 2.18-1.85 (m, 4H), 1.83-1.55 (m, 2H). |

-continued

| example | product |
|---|---|
| 11 | 1-{4-[4-(1-methylpiperidin-4-yloxy)-9,10-dihydro-4H-3,10a-diaza-benzo[f]azulen-2-yl]-phenyl}ethanone |

[M + H]⁺ = 416.2; [M + Na]⁺ = 438.1

| | |
|---|---|
| 12 | 4-(1-methylpiperidin-4-yloxy)-2-thiophen-3-yl-9,10-dihydro-4H-3,10a-diaza-benzo[f]azulene |

[M + H]⁺ = 380.1; [M + Na]⁺ = 402.1

| | |
|---|---|
| 14 | 2-(4-methoxyphenyl)-4-(1-methylpiperidin-4-yloxy)-9,10-dihydro-4H-3,10a-diaza-benzo[f]azulene oxalate |

$^1$H NMR (base): 7.70-7.62 (m, 2H), 7.42-7.20 (m, 6H), 7.11 (s, 1H), 5.69 (s, 1H), 4.59-4.46 (m, 1H), 4.35-4.18 (m, 1H), 4.14-4.00 (m, 1H), 3.60-3.45 (m, 1H), 2.98-2.85 (m, 1H), 2.72-2.60 (m, 2H), 2.22 (s, 3H), 2.15-1.58 (m, 6H), 1.27 (s, 9H).

| | |
|---|---|
| 15 | 4-(1-methylpiperidin-4-yloxy)-2-(4-trifluoromethoxyphenyl)-9,10-dihydro-4H-3,10a-diaza-benzo[f]azulene oxalate |

[M + H]⁺ = 458.9; [M + Na]⁺ = 480.0

| | |
|---|---|
| 17 | 2-(4-methanesulfonylphenyl)-4-(1-methylpiperidin-4-yloxy)-9,10-dihydro-4H-3,10a-diaza-benzo[f]azulene | mp = 191° C.

| | |
|---|---|
| 18 | {4-[4-(1-methylpiperidin-4-yloxy)-9,10-dihydro-4H-3,10a-diaza-benzo[f]azulen-2-yl]-phenyl}-methanol |

[M + H]⁺ = 404.2

| | |
|---|---|
| 19 | 2-(4-methoxymethylphenyl)-4-(1-methylpiperidin-4-yloxy)-9,10-dihydro-4H-3,10a-diaza-benzo[f]azulene oxalate |

$^1$H NMR (base): 7.75-7.66 (m, 2H), 7.38-7.15 (m, 6H), 7.14 (s, 1H), 5.69 (s, 1H), 4.59-4.49 (m, 1H), 4.46 (s, 2H), 4.35-4.18 (m, 1H), 4.12-3.98 (m, 1H), 3.60-3.45 (m, 1H), 3.39 (s, 3H), 2.98-2.85 (m, 1H), 2.72-2.60 (m, 2H), 2.23 (s, 3H), 2.15-1.55 (m, 6H).

| | |
|---|---|
| 20 | 4-(1-methylpiperidin-4-yloxy)-2-(4-methylsulfanylphenyl)-9,10-dihydro-4H-3,10a-diaza-benzo[f]azulene |

[M + H]⁺ = 420.1; [M + Na]⁺ = 442.1; mp = 111° C.

| | |
|---|---|
| 21 | 2-(4-ethylphenyl)-4-(1-methylpiperidin-4-yloxy)-9,10-dihydro-4H-3,10a-diaza-benzo[f]azulene |

[M + H]⁺ = 402.3; [M + Na]⁺ = 424.2; mp = 65° C.

| | |
|---|---|
| 22 | 4-(1-methylpiperidin-4-yloxy)-2-(4-propylphenyl)-9,10-dihydro-4H-3,10a-diaza-benzo[f]azulene | mp = 75° C.

| | |
|---|---|
| 25 | 4-(1-methylpiperidin-4-yloxy)-2-(4-trifluoromethylphenyl)-9,10-dihydro-4H-3,10a-diaza-benzo[f]azulene |

$^1$H NMR: 7.83 (d, J = 9.8 Hz, 2H), 7.60 (d, J = 9.8 Hz, 2H), 7.40-7.20 (m, 5H), 5.69 (s, 1H), 4.62-4.49 (m, 1H), 4.37-4.20 (m, 1H), 4.17-4.00 (m, 1H), 3.60-3.45 (m, 1H), 3.39 (s, 3H), 3.00-2.87 (m, 1H), 2.75-2.60 (m, 2H), 2.23 (s, 3H), 2.18-1.98 (m, 2H), 1.95-1.55 (m, 4H).

| | |
|---|---|
| 26 | 2-(2-chlorophenyl)-4-(1-methylpiperidin-4-yloxy)-9,10-dihydro-4H-3,10a-diaza-benzo[f]azulene oxalate | mp = 69° C.

| | |
|---|---|
| 27 | 2-(2-fluorophenyl)-4-(1-methylpiperidin-4-yloxy)-9,10-dihydro-4H-3,10a-diaza-benzo[f]azulene | mp = 120° C.

| | |
|---|---|
| 28 | 2-(4-isobutylphenyl)-4-(1-methylpiperidin-4-yloxy)-9,10-dihydro-4H-3,10a-diaza-benzo[f]azulene |

$^1$H NMR (base): 7.77-7.68 (m, 2H), 7.35-7.18 (m, 4H), 7.16 (s, 1H), 7.13-7.05 (m, 2H), 5.69 (s, 1H), 4.58-4.45 (m, 1H), 4.33-4.17 (m, 1H), 4.11-3.98 (m, 1H), 3.63-3.45 (m, 1H), 3.00-2.85 (m, 1H), 2.75-2.60 (m, 2H), 2.47 (d, J = 8.6 Hz, 2H), 2.24 (s, 3H), 2.18-2.00 (m, 2H), 1.98-1.55 (m, 5H), 0.90 (d, J = 7.9 Hz, 6H).

| | |
|---|---|
| 29 | N,N-dimethyl-4-[4-(1-methylpiperidin-4-yloxy)-9,10-dihydro-4H-3,10a-diaza-benzo[f]azulen-2-yl]-benzenesulfonamide | mp = 103° C.

| | |
|---|---|
| 31 | 2,2,2-trifluoro-1-{4-[4-(1-methylpiperidin-4-yloxy)-9,10-dihydro-4H-3,10a-diaza-benzo[f]azulen-2-yl]-phenyl}-ethanone oxalate |

$^1$H NMR (base): 8.07 (d, J = 9.4 Hz, 2H), 7.88 (d, J = 9.4 Hz, 2H), 7.40-7.20 (m, 5H), 5.69 (s, 1H), 4.65-4.52 (m, 1H), 4.36-4.20 (m, 1H), 4.17-4.02 (m, 1H), 3.60-3.45 (m, 1H), 3.03-2.90 (m, 1H), 2.75-2.60 (m, 2H), 2.22 (s, 3H), 2.19-2.00 (m, 2H), 1.98-1.55 (m, 4H).

| | |
|---|---|
| 32 | 2-(4-isopropylphenyl)-4-(1-methyl-piperidin-4-yloxy)-9,10-dihydro-4H-3,10a-diaza-benzo[f]azulene oxalate |

$^1$H NMR (base): 7.68-7.58 (m, 2H), 7.38-7.15 (m, 6H), 7.10 (s, 1H), 5.69 (s, 1H), 4.58-4.47 (m, 1H), 4.35-4.15 (m, 1H), 4.10-3.95 (m, 1H), 3.58-3.45 (m, 1H), 2.98-2.83 (m, 2H), 2.72-2.58 (m, 2H), 2.22 (s, 3H), 2.15-1.83 (m, 3H), 1.80-1.55 (m, 4H), 1.26 (d, J = 8.3 Hz, 6H).

| | |
|---|---|
| 33 | {4-[4-(1-methylpiperidin-4-yloxy)-9,10-dihydro-4H-3,10a-diaza-benzo[f]azulen-2-yl]-phenyl}-acetonitrile oxalate |

$^1$H NMR (base): 7.78-7.70 (m, 2H), 7.38-7.19 (m, 6H), 7.16 (s, 1H), 5.69 (s, 1H), 4.58-4.47 (m, 1H), 4.35-4.15 (m, 1H), 4.10-3.95 (m, 1H), 3.75 (s, 2H), 3.58-3.45 (m, 1H), 2.99-2.86 (m, 1H), 2.72-2.58 (m, 2H), 2.22 (s, 3H), 2.15-1.98 (m, 2H), 1.95-1.55 (m, 4H).

| | |
|---|---|
| 35 | dimethyl-{4-[4-(1-methylpiperidin-4-yloxy)-9,10-dihydro-4H-3,10a-diaza-benzo[f]azulen-2-yl]-phenyl}-amine oxalate |

[M + H]⁺ = 417.2

| | |
|---|---|
| 36 | 4-[4-(1-methylpiperidin-4-yloxy)-9,10-dihydro-4H-3,10a-diaza-benzo[f]azulen-2-yl]-benzoic acid tert-butyl ester | mp = 85° C.

| example | product |
|---|---|
| 37 | 4-[4-(1-methylpiperidin-4-yloxy)-9,10-dihydro-4H-3,10a-diaza-benzo[f]azulen-2-yl]-benzonitrile |
| | mp = 92° C. |
| 39 | 4-(1-methylpiperidin-4-yloxy)-2-(6-methylpyridin-3-yl)-9,10-dihydro-4H-3,10a-diaza-benzo[f]azulene oxalate |
| | [M + H]$^+$ = 389.2 |
| 41 | 2-(4-butylphenyl)-4-(1-methylpiperidin-4-yloxy)-9,10-dihydro-4H-3,10a-diaza-benzo[f]azulene |
| | mp = 128° C. |
| 42 | 4-(1-methylpiperidin-4-yloxy)-2-(4-pentylphenyl)-9,10-dihydro-4H-3,10a-diaza-benzo[f]azulene |

$^1$H NMR: 7.68-7.59 (m, 2H), 7.38-7.12 (m, 6H), 7.10 (s, 1H), 5.68 (s, 1H), 4.58-4.46 (m, 1H), 4.32-4.18 (m, 1H), 4.12-3.98 (m, 1H), 3.65-3.50 (m, 1H), 2.99-2.86 (m, 1H), 2.78-2.65 (m, 2H), 2.60 (t, J = 9.2 Hz), 2.28 (s, 3H), 2.22-2.10 (m, 2H), 2.08-1.55 (m, 4H), 1.40-1.22 (m, 4H), 0.89 (t, J = 8.0 Hz).

| | |
|---|---|
| 43 | 2-(4-hexylphenyl)-4-(1-methylpiperidin-4-yloxy)-9,10-dihydro-4H-3,10a-diaza-benzo[f]azulene |

$^1$H NMR: 7.68-7.60 (m, 2H), 7.38-7.23 (m, 4H), 7.20-7.12 (m, 2H), 7.10 (s, 1H), 5.67 (s, 1H), 4.57-4.45 (m, 1H), 4.30-4.15 (m, 1H), 4.12-4.00 (m, 1H), 3.72-3.60 (m, 1H), 2.99-2.89 (m, 1H), 2.87-2.72 (m, 2H), 2.58 (t, J = 9.2 Hz), 2.18 (s, 3H), 2.15-1.70 (m, 6H), 1.58-1.25 (m, 8H), 0.88 (t, J = 8.0 Hz).

| | |
|---|---|
| 46 | 2-(4-ethylsulfanylphenyl)-4-(1-methylpiperidin-4-yloxy)-9,10-dihydro-4H-3,10a-diaza-benzo[f]azulene oxalate |
| | [M + H]$^+$ = 434.3; [M + Na]$^+$ = 456.2 |
| 49 | {4-[4-(1-methylpiperidin-4-yloxy)-9,10-dihydro-4H-3,10a-diaza-benzo[f]azulen-2-yl]-phenyl}-carbamic acid tert-butyl ester |
| | mp = 125° C. |
| 50 | 2-benzo[1,3]dioxol-5-yl-4-(1-methylpiperidin-4-yloxy)-9,10-dihydro-4H-3,10a-diaza-benzo[f]azulene |
| | mp = 145° C. |
| 52 | 2-(4-chloro-phenyl)-4-(1-methylpiperidin-4-yloxy)-9,10-dihydro-4H-3,10a-diaza-benzo[f]azulene oxalate |
| | [M + H]$^+$ = 408.1; [M + Na]$^+$ = 430.0 |
| 55 | 4-(1-methylpiperidin-4-yloxy)-2-(2-methyl-4-trifluoromethyl-phenyl)-9,10-dihydro-4H-3,10a-diaza-benzo[f]azulene |
| | mp = 115° C. |
| 56 | 2-(4-fluorophenyl)-4-(1-methylpiperidin-4-yloxy)-9,10-dihydro-4H-3,10a-diaza-benzo[f]azulene |
| | mp = 126° C. |
| 57 | 2-(3,6-dihydro-2H-thiopyran-4-yl)-4-(1-methylpiperidin-4-yloxy)-9,10-dihydro-4H-3,10a-diaza-benzo[f]azulene |
| | mp = 120° C. |
| 59 | 2-(2-cyclohexyl-vinyl)-4-(1-methylpiperidin-4-yloxy)-9,10-dihydro-4H-3,10a-diaza-benzo[f]azulene |
| | mp = 68° C. |
| 61 | 2-(2,4-dimethylphenyl)-4-(1-methylpiperidin-4-yloxy)-9,10-dihydro-4H-3,10a-diaza-benzo[f]azulene |
| | mp = 127° C. |
| 62 | 2-cyclohex-1-enyl-4-(1-methylpiperidin-4-yloxy)-9,10-dihydro-4H-3,10a-diaza-benzo[f]azulene oxalate |
| | [M + H]$^+$ = 378.2; [M + Na]$^+$ = 400.2 |
| 64 | 2-[4-(1,1-difluoroethyl)-phenyl]-4-(1-methylpiperidin-4-yloxy)-9,10-dihydro-4H-3,10a-diaza-benzo[f]azulene oxalate |
| | [M + H]$^+$ = 438.3 |
| 65 | 2-cyclopent-1-enyl-4-(1-methylpiperidin-4-yloxy)-9,10-dihydro-4H-3,10a-diaza-benzo[f]azulene |
| | mp = 60° C. |
| 68 | 2-(3-fluorophenyl)-4-(1-methylpiperidin-4-yloxy)-9,10-dihydro-4H-3,10a-diaza-benzo[f]azulene oxalate |
| | [M + H]$^+$ = 392.2 |
| 69 | 2-(4-difluoromethylphenyl)-4-(1-methylpiperidin-4-yloxy)-9,10-dihydro-4H-3,10a-diaza-benzo[f]azulene |
| | [M + H]$^+$ = 424.2 |
| 71 | 2-(2,4-dichlorophenyl)-4-(1-methylpiperidin-4-yloxy)-9,10-dihydro-4H-3,10a-diaza-benzo[f]azulene oxalate |

$^1$H NMR (base): 8.07 (d, J = 10.2 Hz, 1H), 7.56 (s, 1H), 7.42-7.18 (m, 6H), 5.67 (s, 1H), 4.61-4.49 (m, 1H), 4.35-4.20 (m, 1H), 4.15-4.02 (m, 1H), 3.58-3.45 (m, 1H), 3.00-2.88 (m, 1H), 2.73-2.58 (m, 2H), 2.24 (s, 3H), 2.20-2.00 (m, 2H), 1.98-1.55 (m, 4H).

| | |
|---|---|
| 74 | 4-[4-(1-methylpiperidin-4-yloxy)-9,10-dihydro-4H-3,10a-diaza-benzo[f]azulen-2-yl]-3,6-dihydro-2H-pyridine-1-carboxylic acid tert-butyl ester oxalate |
| | [M + H]$^+$ = 479.2; [M + Na]$^+$ = 501.2 |
| 75 | 2-(2-chloro-4-methylphenyl)-4-(1-methylpiperidin-4-yloxy)-9,10-dihydro-4H-3,10a-diaza-benzo[f]azulene oxalate |
| | [M + H]$^+$ = 422.4 and 424.0 $^{35}$Cl/$^{37}$Cl |
| 76 | 4-(1-methylpiperidin-4-yloxy)-2-(3-phenylpropenyl)-9,10-dihydro-4H-3,10a-diaza-benzo[f]azulene oxalate |
| | [M + H]$^+$ = 414.3; [M + Na]$^+$ = 436.2 |

| example | product |
|---|---|
| 77 | 2-(3-chlorophenyl)-4-(1-methylpiperidin-4-yloxy)-9,10-dihydro-4H-3,10a-diaza-benzo[f]azulene oxalate<br>$[M + H]^+ = 408.3; [M + Na]^+ = 430.1$ |
| 80 | 2-cyclohept-1-enyl-4-(1-methylpiperidin-4-yloxy)-9,10-dihydro-4H-3,10a-diaza-benzo[f]azulene<br>mp = 65° C. |
| 82 | 2-(2-fluoro-4-methylphenyl)-4-(1-methylpiperidin-4-yloxy)-9,10-dihydro-4H-3,10a-diaza-benzo[f]azulene<br>mp = 78° C. |
| 89 | 4-(1-methylpiperidin-4-yloxy)-2-(5-phenylpent-1-enyl)-9,10-dihydro-4H-3,10a-diaza-benzo[f]azulene |

$^1$H NMR: 7.35-7.12 (m, 9H), 6.73 (s, 1H), 6.30-6.18 (m, 2H), 5.60 (s, 1H), 4.50-4.38 (m, 1H), 4.29-4.11 (m, 1H), 4.03-3.89 (m, 1H), 3.59-3.45 (m, 1H), 2.95-2.82 (m, 1H), 2.75-2.60 (m, 4H), 2.26 (s, 3H), 2.25-2.05 (m, 4H), 2.00-1.55 (m, 6.H).

| | |
|---|---|
| 93 | 2-(3,3-dimethylbut-1-enyl)-4-(1-methylpiperidin-4-yloxy)-9,10-dihydro-4H-3,10a-diaza-benzo[f]azulene<br>mp = 70° C. |
| 97 | methyl-{4-[4-(1-methylpiperidin-4-yloxy)-9,10-dihydro-4H-3,10a-diaza-benzo[f]azulen-2-yl]-phenyl}-carbamic acid tert-butyl ester oxalate<br>$[M + H]^+ = 503.03$ |
| 99 | 2-(2-cyclopropylvinyl)-4-(1-methylpiperidin-4-yloxy)-9,10-dihydro-4H-3,10a-diaza-benzo[f]azulene oxalate |

$^1$H NMR (base): 7.33-7.18 (m, 4H), 6.69 (s, 1H), 6.30 (d, J = 18.8 Hz, 1H), 5.81 (dd, J = 10.7 Hz, J = 18.7 Hz, 1H), 5.58 (s, 1H), 4.50-4.39 (m, 1H), 4.30-4.13 (m, 1H), 4.03-3.88 (m, 1H), 3.57-3.42 (m, 1H), 2.95-2.81 (m, 1H), 2.74-2.59 (m, 2H), 2.23 (s, 3H), 2.18-2.00 (m, 2H), 1.98-1.40 (m, 5H), 0.81-0.70 (m, 2H), 0.55-0.45 (m, 2H).

| | |
|---|---|
| 104 | 2-(3-cyclopentylpropenyl)-4-(1-methylpiperidin-4-yloxy)-9,10-dihydro-4H-3,10a-diaza-benzo[f]azulene<br>mp = 110° C. |
| 106 | 2-(3,6-dihydro-2H-pyran-4-yl)-4-(1-methyldpiperidin-4-yloxy)-9,10-dihydro-4H-3,10a-diaza-benzo[f]azulene<br>mp = 70° C. |
| 108 | N-(4-hydroxycyclohexyl)-4-[4-(1-methylpiperidin-4-yloxy)-9,10-dihydro-4H-3,10a-diaza-benzo[f]azulen-2-yl]-benzamide<br>$[M + H]^+ = 515.43$ |
| 111 | 4-(1-methylpiperidin-4-yloxy)-2-(2-thiophen-2-ylvinyl)-9,10-dihydro-4H-3,10a-diaza-benzo[f]azulene<br>mp = 168° C. |
| 112 | 4-(1-methylpiperidin-4-yloxy)-2-(2-thiophen-3-ylvinyl)-9,10-dihydro-4H-3,10a-diaza-benzo[f]azulene<br>mp = 151° C. |
| 113 | dimethyl-{4-[4-(1-methylpiperidin-4-yloxy)-9,10-dihydro-4H-3,10a-diaza-benzo[f]azulen-2-yl-benzyl}-amine |

$^1$H NMR: 7.76 (d, J = 9.8 Hz, 2H), 7.52 (d, J = 9.8 Hz, 2H), 7.40-7.22 (m, 4H), 7.20 (s, 1H), 5.62 (s, 1H), 4.55-4.45 (m, 1H), 4.28-4.05 (m, 2H), 3.96 (s, 2H), 3.94-3.85 (m, 1H), 3.22-2.95 (m, 3H), 2.68 (s, 3H), 2.63 (s, 6H), 2.50-2.20 (m, 2H), 2.18-1.70 (m, 4H).

| | |
|---|---|
| 115 | {4-[4-(1-methylpiperidin-4-yloxy)-9,10-dihydro-4H-3,10a-diaza-benzo[f]azulen-2-yl]-benzyl}-carbamic acid tert-butyl ester<br>mp = 95° C. |
| 121 | 4-(1-methylpiperidin-4-yloxy)-2-(3-phenoxypropenyl)-9,10-dihydro-4H-3,10a-diaza-benzo[f]azulene<br>mp = 75° C. |
| 124 | 2-(3-benzyloxypropenyl)-4-(1-methylpiperidin-4-yloxy)-9,10-dihydro-4H-3,10a-diaza-benzo[f]azulene oxalate |

$^1$H NMR (base): 7.40-7.18 (m, 9H), 6.82 (s, 1H), 6.55-6.30 (m, 2H), 5.60 (s, 1H), 4.55 (s, 2H), 4.51-4.40 (m, 1H), 4.32-4.13 (m, 3H), 4.06-3.90 (m, 1H), 3.55-3.40 (m, 1H), 2.95-2.80 (m, 1H), 2.72-2.58 (m, 2H), 2.22 (s, 3H), 2.15-2.00 (m, 2H), 1.98-1.55 (m, 4H).

| | |
|---|---|
| 179 | {2-[4-(1-methylpiperidin-4-yloxy)-9,10-dihydro-4H-3,10a-diaza-benzo[f]azulen-2-yl]-phenyl}-methanol oxalate |

$^1$H NMR (base): 7.48-7.20 (m, 8H), 7.13 (s, 1H), 5.63 (s, 1H), 4.58 (s, 2H), 4.60-4.48 (m, 1H), 4.37-4.20 (m, 1H), 4.17-4.05 (m, 1H), 3.61-3.56 (m, 1H), 3.03-2.90 (m, 1H), 2.75-2.60 (m, 2H), 2.22 (s, 3H), 2.18-1.80 (m, 4H and OH), 1.78-1.55 (m, 2H).

-continued

| example | product |
|---|---|
| 180 | dimethyl-(2-{4-[4-(1-methylpiperidin-4-yloxy)-9,10-dihydro-4H-3,10a-diaza-benzo[f]azulen-2-yl]-phenoxy}-ethyl)-amine<br>mp = 95° C. |
| 181 | 3-{4-[4-(1-methylpiperidin-4-yloxy)-9,10-dihydro-4H-3,10a-diaza-benzo[f]azulen-2-yl]-benzyl}-oxazolidin-2-one<br>mp = 65° C. |
| 182 | methyl-{4-[4-(1-methylpiperidin-4-yloxy)-9,10-dihydro-4H-3,10a-diaza-benzo[f]azulen-2-yl]benzyl}-carbamic acid tert-butyl ester<br>mp = 80° C. |
| 183 | 2-(4-allyloxyphenyl)-4-(1-methylpiperidin-4-yloxy)-9,10-dihydro-4H-3,10a-diaza-benzo[f]azulene<br>mp = 80° C. |
| 184 | 1-{4-[4-(1-methylpiperidin-4-yloxy)-9,10-dihydro-4H-3,10a-diaza-benzo[f]azulen-2-yl]benzyl}-pyrrolidin-2-one<br>mp = 80° C. |
| 185 | 1-{4-[4-(1-methylpiperidin-4-yloxy)-9,10-dihydro-4H-3,10a-diaza-benzo[f]azulen-2-yl]benzyl}-piperidin-2-one<br>mp = 95° C. |
| 186 | 2-(4-isopropylsulfanylmethylphenyl)-4-(1-methylpiperidin-4-yloxy)-9,10-dihydro-4H-3,10a-diaza-benzo[f]azulene<br>mp = 80° C. |
| 188 | 1-{4-[4-(1-methylpiperidin-4-yloxy)-9,10-dihydro-4H-3,10a-diaza-benzo[f]azulen-2-yl]benzyl}-azepan-2-one<br>mp = 95° C. |
| 189 | 2-[4-(2-tert-butylsulfanylethyl)-phenyl]-4-(1-methylpiperidin-4-yloxy)-9,10-dihydro-4H-3,10a-diaza-benzo[f]azulene<br>mp = 80° C. |
| 190 | 4-(1-methylpiperidin-4-yloxy)-2-(2-nitrophenyl)-9,10-dihydro-4H-3,10a-diaza-benzo[f]azulene<br>mp = 170° C. |
| 191 | 1-tertbutyl-3-{4-[4-(1-methylpiperidin-4-yloxy)-9,10-dihydro-4H-3,10a-diaza-benzo[f]azulen-2-yl]benzyl}-imidazolidin-2-one<br>$[M + H]^+ = 528.46$ |
| 192 | 2-{4-[4-(1-methylpiperidin-4-yloxy)-9,10-dihydro-4H-3,10a-diaza-benzo[f]azulen-2-yl]-phenyl}-ethanol<br>$^1$H NMR: 7.72-7.62 (m, 2H), 7.38-7.18 (m, 6H), 7.12 (s, 1H), 5.69 (s, 1H), 4.60-4.47 (m, 1H), 4.37-4.20 (m, 1H), 4.14-4.00 (m, 1H), 3.87 (t, J = 7.8 Hz, 2H), 3.59-3.45 (m, 1H), 3.00-2.82 (m, 3H), 2.73-2.59 (m, 2H), 2.21 (s, 3H), 2.15-1.85 (m, 3H), 1.85-1.55 (m, 4H). |
| 193 | 2-(4-cyclopropylmethoxyphenyl)-4-(1-methylpiperidin-4-yloxy)-9,10-dihydro-4H-3,10a-diaza-benzo[f]azulene<br>mp = 142° C. |
| 196 | 2-{4-[4-(1-methylpiperidin-4-yloxy)-9,10-dihydro-4H-3,10a-diaza-benzo[f]azulen-2-yl]-phenyl}-ethyl)-carbamic acid tert-butyl ester<br>$[M + H]^+ = 517.46$ |
| 197 | methyl-(2-{4-[4-(1-methylpiperidin-4-yloxy)-9,10-dihydro-4H-3,10a-diaza-benzo[f]azulen-2-yl]-phenyl}-ethyl)-carbamic acid tert-butyl ester<br>$[M + H]^+ = 531.47$ |
| 198 | 5,5-dimethyl-3-{4-[4-(1-methylpiperidin-4-yloxy)-9,10-dihydro-4H-3,10a-diaza-benzo[f]azulen-2-yl]benzyl}-oxazolidine-2,4-dione<br>$[M + H]^+ = 515.39$ |
| 199 | (2-{4-[4-(1-methylpiperidin-4-yloxy)-9,10-dihydro-4H-3,10a-diaza-benzo[f]azulen-2-yl]benzylsulfanyl}-ethyl)-carbamic acid tert-butyl ester<br>mp = 80° C. |
| 212 | N-(2-hydroxyethyl)-4-[4-(1-methylpiperidin-4-yloxy)-9,10-dihydro-4H-3,10a-diaza-benzo[f]azulen-2-yl]benzamide<br>$[M + H]^+ = 461.36$ |
| 215 | 1-{4-[4-(1-methylpiperidin-4-yloxy)-9,10-dihydro-4H-3,10a-diaza-benzo[f]azulen-2-yl]-benzoyl}-piperidin-4-one<br>$[M + H]^+ = 499.35$ |

Example 7

2-Iodo-4-(1-methylazetidin-3-ylmethoxy)-9,10-dihydro-4H-3,10a-diaza-benzo[f]azulene Compound 7A is obtained following the procedure already described in example 2A starting from compound 4-iodo-1-phenethyl-imidazole-2-carbaldehyde (example 2B) and (1-methylazetidin-3-yl)-methanol to give 2-iodo-4-(1-methylazetidin-3-ylmethoxy)-9,10-dihydro-4H-3,10a-diaza-benzo[f]azulene melting at 100° C.

Example 9

4-(1-methylpiperidin-4-yloxy)-2-vinyl-9,10-dihydro-4H-3,10a-diaza-benzo[f]azulene oxalate To a solution of compound 2-iodo-4-(1-methylpiperidin-4-yloxy)-9,10-dihydro-4H-3,10a-diaza-benzo[f]azulene (example 2A) (50 mg, 0.12 mmoles) in 1,4-dioxane (500 μL) in a screw-capped vial under argon are added potassium vinyltrifluoroborate (21 mg, 0.156 mmole), Pd(OAc)$_2$ (1.35 mg, 6 μmole), RuPhos (3 mg, 6 μmole), K$_2$CO$_3$ (50 mg, 0.36 mmole) and water (400 μL). The reaction mixture is heated to 120° C. for overnight. As the reaction is not complete, potassium vinyltrifluoroborate (21 mg, 0.156 mmole), Pd(OAc)$_2$ (1.35 mg, 6 μmole), RuPhos (3 mg, 6 μmole) are added and the reaction mixture is heated to 120° C. for 3 hours. Water is added, pH adjusted to 9-10 with saturated $Na_2CO_3$ solution. The aqueous phase is extracted three times with $CH_2Cl_2$. The organic phase is dried over magnesium sulphate, filtered and the solvent is removed under reduced pressure. The residue is pre-purified by silica gel chromatography using ($CH_2Cl_2$: MeOH:$NH_4OH$) as eluent with a gradient from (99:1:0.1) to (95:5:0.5) and the residue is submitted to a preparative thin-layer chromatography eluting with ($CH_2Cl_2$:MeOH: $NH_4OH$) (9:1:1) to afford 4-(1-methylpiperidin-4-yloxy)-2-vinyl-9,10-dihydro-4H-3,10a-diaza-benzo[f]azulene.

$^1$H NMR: 7.35-7.18 (m, 4H), 6.84 (s, 1H), 6.56 (dd, J=21 Hz, J=13.2 Hz, 1H), 5.75 (d, J=13.2 Hz, 1H), 5.61 (s, 1H), 5.11 (d, J=13.2 Hz, 1H), 4.52-4.41 (m, 1H), 4.30-4.15 (m, 1H), 4.06-3.92 (m, 1H), 3.59-3.42 (m, 1H), 2.96-2.85 (m, 1H), 2.76-2.60 (m, 2H), 2.25 (s, 3H), 2.20-2.00 (m, 2H), 1.99-1.60 (m, 4H).

4-(1-methylpiperidin-4-yloxy)-2-vinyl-9,10-dihydro-4H-3,10a-diaza-benzo[f]azulene is dissolved in acetone (1.7 mL) and oxalic acid (1 equivalent) is added. Acetone is removed under reduced pressure to afford 4-(1-methylpiperidin-4-yloxy)-2-vinyl-9,10-dihydro-4H-3,10a-diaza-benzo[f]azulene oxalate.

Example 16

4-[4-(1-methylpiperidin-4-yloxy)-9,10-dihydro-4H-3,10a-diaza-benzo[f]azulen-2-yl]-phenylamine To a solution of {4-[4-(1-methylpiperidin-4-yloxy)-9,10-dihydro-4H-3,10a-diaza-benzo[f]azulen-2-yl]-phenyl}-carbamic acid tert-butyl ester (example 49A) (45 mg, 0.092 mmole) in $CH_2Cl_2$ (0.3 mL) is added trifluoroacetic acid (90 μL). The reaction mixture is stirred at room temperature for 1 hour. Water is added and pH adjusted to 9-10 with 1N NaOH. The aqueous phase is extracted three times with $CH_2Cl_2$. The organic phase is dried over magnesium sulphate, filtered and the solvent is removed under reduced pressure. The residue is purified by silica gel chromatography using ($CH_2Cl_2$:MeOH: $NH_4OH$) as eluent with a gradient from (98:2:0.2) to (95:5: 0.5) to give 4-[4-(1-methylpiperidin-4-yloxy)-9,10-dihydro-4H-3,10a-diaza-benzo[f]azulen-2-yl]-phenylamine melting at 197° C.

The following compounds are prepared using the same method.

| example | product |
|---|---|
| 100 | methyl-{4-[4-(1-methylpiperidin-4-yloxy)-9,10-dihydro-4H-3,10a-diaza-benzo[f]azulen-2-yl]-phenyl}-amine oxalate |
| | NMR $^1$H (base): 7.60-7.52 (m, 2H), 7.38-7.18 (m, 4H), 6.99 (s, 1H), 6.67-6.58 (m, 2H), 5.68 (s, 1H), 4.55-4.42 (m, 1H), 4.35-4.18 (m, 1H), 4.10-3.95 (m, 1H), 3.70 (sl, 1H), 3.60-3.42 (m, 1H), 2.98-2.82 (m, 1H), 2.86 (s, 3H), 2.75-2.58 (m, 2H), 2.23 (s, 3H), 2.15-2.00 (m, 2H), 1.99-1.55 (m, 4H). |
| 161 | 2-{4-[1-methyl-4-(1-methylpiperidin-4-yloxy)-9,10-dihydro-4H-3,10a-diaza-benzo[f]azulen-2-yl]-phenylsulfanyl}-ethylamine oxalate |
| | NMR $^1$H (base): 7.55-7.46 (m, 2H), 7.43-7.38 (m, 2H), 7.35-7.20 (m, 4H), 5.66 (s, 1H), 4.45-4.25 (m, 2H), 3.90-3.75 (m, 1H), 3.62-3.47 (m, 1H), 3.07-2.87 (m, 5H), 2.80-2.62 (m, 2H), 2.31 (s, 3H), 2.27 (s, 3H), 2.25-2.05 (m, 2H), 2.02-1.55 (m, 6H). |
| 173 | 4-[1-methyl-4-(1-methylpiperidin-4-yloxy)-9,10-dihydro-4H-3,10a-diaza-benzo[f]azulen-2-yl]-phenylamine |
| | mp = 105° C. |

Example 13

2-ethyl-4-(1-methylpiperidin-4-yloxy)-9,10-dihydro-4H-3,10a-diaza-benzo[f]azulene oxalate To a solution of 4-(1-methylpiperidin-4-yloxy)-2-vinyl-9, 10-dihydro-4H-3,10a-diaza-benzo[f]azulene oxalate (example 9A) (110 mg, 0.34 mmole) in MeOH (1.7 mL) is added Pd/C 10% (11 mg). The flask is evacuated and filled with hydrogen (balloon). The reaction mixture is stirred at room temperature overnight, then filtered on celite and cake washed with MeOH. Solvent is removed under reduced pressure. The residue is pre-purified by silica gel chromatography using ($CH_2Cl_2$:MeOH:$NH_4OH$) as eluent with a gradient from (98: 2:0.2) to (95:5:0.5) and the residue is submitted to a preparative thin-layer chromatography eluting with ($CH_2Cl_2$:MeOH: $NH_4OH$) (9:1:1) to afford 2-ethyl-4-(1-methylpiperidin-4-yloxy)-9,10-dihydro-4H-3,10a-diaza-benzo[f]azulene.

$[M+H]^+$=326.2; $[M+Na]^+$=348.2.

2-ethyl-4-(1-methyl piperidin-4-yloxy)-9,10-dihydro-4H-3,10a-diaza-benzo[f]azulene is dissolved in acetone (1.7 mL) and oxalic acid (1 equivalent) is added. Acetone is removed under reduced pressure to afford 2-ethyl-4-(1-methylpiperidin-4-yloxy)-9,10-dihydro-4H-3,10a-diaza-benzo[f]azulene oxalate.

Example 23

4-(1-methylpiperidin-4-yloxy)-2-pyridin-2-yl-9,10-dihydro-4H-3,10a-diaza-benzo[f]azulene To a solution of 2-iodo-4-(1-methylpiperidin-4-yloxy)-9, 10-dihydro-4H-3,10a-diaza-benzo[f]azulene (example 2A) (50 mg, 0.12 mmoles) in toluene (500 μL) in a screw-capped vial under argon are added 2-(tributylstannyl)pyridine (77 μL, 0.24 mmole), tetrakis(triphenylphosphine)palladium(0) (14 mg, 12 μmole). The reaction mixture is heated at 100° C. overnight. A solution of 10% KF in water is added, and the aqueous phase is extracted three times with $CH_2Cl_2$. The organic phase is washed with a solution of 10% KF in water, brine, dried over magnesium sulphate, filtered and the solvent is removed under reduced pressure. The residue is pre-purified by silica gel chromatography using ($CH_2Cl_2$:MeOH: $NH_4OH$) as eluent with a gradient from (99:1:0.1) to (95:5: 0.5) and the residue is submitted to a preparative thin-layer chromatography eluting with ($CH_2Cl_2$:MeOH:$NH_4OH$) (9:1: 1) to afford 4-(1-methylpiperidin-4-yloxy)-2-pyridin-2-yl-9, 10-dihydro-4H-3,10a-diaza-benzo[f]azulene.

$^1$H NMR: 8.52 (d, J=5.4 Hz, 1H), 7.92 (d, J=9.6 Hz, 1H), 7.69 (dd, J=5.4 Hz, J=9.6 Hz, 1H), 7.55 (s, 1H), 7.38-7.18 (m, 4H), 7.15-7.05 (m, 1H), 5.69 (s, 1H), 4.65-4.50 (m, 1H), 4.32-4.00 (m, 2H), 3.68-3.45 (m, 1H), 3.02-2.87 (m, 1H), 2.75-2.60 (m, 2H), 2.25 (s, 3H), 2.23-2.05 (m, 2H), 2.00-1.55 (m, 4H).

The following compounds are prepared using the same method and different kind of tributylstannyl reagents.

| example | product |
|---|---|
| 24 | 2-furan-2-yl-4-(1-methylpiperidin-4-yloxy)-9,10-dihydro-4H-3,10a-diaza-benzo[f]azulene |

$^1$H NMR: 7.36 (s, 1H), 7.34-7.18 (m, 4H), 7.08 (s, 1H), 6.62-6.57 (m, 1H), 6.45-6.38 (m, 1H), 5.66 (s, 1H), 4.58-4.45 (m, 1H), 4.35-4.18 (m, 1H), 4.10-3.96 (m, 1H), 3.58-3.45 (m, 1H), 2.98-2.85 (m, 1H), 2.71-2.58 (m, 2H), 2.21 (s, 3H), 2.15-1.55 (m, 6H)

| | |
|---|---|
| 30 | 2-allyl-4-(1-methylpiperidin-4-yloxy)-9,10-dihydro-4H-3,10a-diaza-benzo[f]azulene oxalate |

$^1$H NMR (base): 7.30-7.17 (m, 4H), 6.59 (s, 1H), 6.05-5.87 (m, 1H), 5.57 (s, 1H), 5.17-5.00 (m, 2H), 4.47-4.35 (m, 1H), 4.32-4.18 (m, 1H), 4.03-3.88 (m, 1H), 3.52-3.38 (m, 1H), 3.31 (d, J = 8 Hz, 2H), 2.92-2.79 (m, 1H), 2.73-2.58 (m, 2H), 2.22 (s, 3H), 2.18-1.98 (m, 2H), 1.95-1.55 (m, 4H).

| | |
|---|---|
| 40 | 4-(1-methylpiperidin-4-yloxy)-2-oxazol-2-yl-9,10-dihydro-4H-3,10a-diaza-benzo[f]azulene oxalate |

$^1$H NMR (base): 7.64 (s, 1H), 7.49 (s, 1H), 7.34-7.18 (m, 4H), 7.16 (s, 1H), 5.70 (s, 1H), 4.62-4.50 (m, 1H), 4.35-4.20 (m, 1H), 4.14-4.01 (m, 1H), 3.60-3.47 (m, 1H), 2.99-2.87 (m, 1H), 2.70-2.56 (m, 2H), 2.21 (s, 3H), 2.15-1.98 (m, 2H), 1.97-1.55 (m, 4H).

| | |
|---|---|
| 44 | 4-(1-methylpiperidin-4-yloxy)-2-pyridin-4-yl-9,10-dihydro-4H-3,10a-diaza-benzo[f]azulene oxalate |

$[M + H]^+ = 375.2; [M + Na]^+ = 397.2$

| | |
|---|---|
| 45 | 4-(1-methylpiperidin-4-yloxy)-2-pyridin-3-yl-9,10-dihydro-4H-3,10a-diaza-benzo[f]azulene oxalate |

$[M + H]^+ = 375.2; [M + Na]^+ = 397.2$

| | |
|---|---|
| 47 | 4-(1-methylpiperidin-4-yloxy)-2-thiophen-2-yl-9,10-dihydro-4H-3,10a-diaza-benzo[f]azulene oxalate |

$[M + H]^+ = 380.2; [M + Na]^+ = 402.2$

| | |
|---|---|
| 48 | 4-(1-methylpiperidin-4-yloxy)-2-thiazol-5-yl-9,10-dihydro-4H-3,10a-diaza-benzo[f]azulene oxalate |

$[M + H]^+ = 381.2$

| | |
|---|---|
| 51 | 2-(5-methylfuran-2-yl)-4-(1-methylpiperidin-4-yloxy)-9,10-dihydro-4H-3,10a-diaza-benzo[f]azulene oxalate |

$^1$H NMR (base): 7.35-7.18 (m, 4H), 7.03 (s, 1H), 6.44 (d, J = 3.8 Hz, 1H), 6.05-5.98 (m, 1H), 5.65 (s, 1H), 4.57-4.45 (m, 1H), 4.31-4.15 (m, 1H), 4.10-3.97 (m, 1H), 3.69-3.52 (m, 1H), 2.98-2.85 (m, 1H), 2.83-2.65 (m, 2H), 2.33 (s, 3H), 2.32 (s, 3H), 2.10-1.60 (m, 6H).

| | |
|---|---|
| 66 | 4-(1-methylpiperidin-4-yloxy)-2-thiazol-2-yl-9,10-dihydro-4H-3,10a-diaza-benzo[f]azulene oxalate |

$[M + H]^+ = 381.2; [M + Na]^+ = 403.1$

Example 34

4-(1-methylpiperidin-4-yloxy)-2-phenylethynyl-9,10-dihydro-4H-3,10a-diaza-benzo[f]azulene To a solution of compound 2-iodo-4-(1-methylpiperidin-4-yloxy)-9,10-dihydro-4H-3,10a-diaza-benzo[f]azulene (example 2A) (100 mg, 0.24 mmoles) in ACN (600 μL) in a screw-capped vial under argon are added CuI (9 mg, 0.048 mmole), Pd(PPh$_3$)$_4$ (28 mg, 24 μmoles), phenylacetylene (109 μL, 0.96 mmole) and NEt$_3$ (600 μL). The reaction mixture is heated at 80° C. overnight. Water is added and pH adjusted to 9-10 with concentrated aqueous ammonia solution. The aqueous phase is extracted three times with CH$_2$Cl$_2$. The organic phase is dried over magnesium sulphate, filtered and the solvent is removed under reduced pressure. The residue is pre-purified by silica gel chromatography using (CH$_2$Cl$_2$:MeOH:NH$_4$OH) as eluent with a gradient from (98:2:0.2) to (95:5:0.5) and the residue is submitted to a preparative thin-layer chromatography eluting with (CH$_2$Cl$_2$:MeOH:NH$_4$OH) (9:1:1) to afford 4-(1-methylpiperidin-4-yloxy)-2-phenylethynyl-9,10-dihydro-4H-3,10a-diaza-benzo[f] azulene.

$^1$H NMR: 7.57-7.45 (m, 2H), 7.35-7.18 (m, 7H), 7.12 (s, 1H), 5.60 (s, 1H), 4.56-4.45 (m, 1H), 4.35-4.18 (m, 1H), 4.10-3.96 (m, 1H), 3.60-3.45 (m, 1H), 2.98-2.88 (m, 1H), 2.75-2.60 (m, 2H), 2.24 (s, 3H), 2.20-2.02 (m, 2H), 2.00-1.60 (m, 4H).

The following compound is prepared using the same method.

| example | product |
|---|---|
| 63 | 4-(1-methylpiperidin-4-yloxy)-2-pyridin-3-ylethynyl-9,10-dihydro-4H-3,10a-diaza-benzo[f]azulene |
| | $[M + H]^+ = 399.2; [M + Na]^+ = 421.2$ |

Example 38

4-(1-methylpiperidin-4-yloxy)-2-phenethyl-9,10-dihydro-4H-3,10a-diaza-benzo[f]azulene oxalate To a solution of 4-(1-methylpiperidin-4-yloxy)-2-phenylethynyl-9,10-dihydro-4H-3,10a-diaza-benzo[f]azulene (example 34) (50 mg, 0.126 mmole) in MeOH (1.3 mL) is added PtO$_2$ (1.4 mg). The flask is evacuated and filled with hydrogen (balloon). The reaction mixture is stirred at room temperature overnight, then filtered on celite and cake washed with MeOH. Solvent is removed under reduced pressure. The residue is pre-purified by silica gel chromatography using (CH$_2$Cl$_2$:MeOH:NH$_4$OH) as eluent with a gradient from (98:2:0.2) to (95:5:0.5) and the residue is submitted to a preparative thin-layer chromatography eluting with (CH$_2$Cl$_2$:MeOH:NH$_4$OH) (9:1:1) to afford 4-(1-methylpiperidin-4-yloxy)-2-phenethyl-9,10-dihydro-4H-3,10a-diaza-benzo[f]azulene.

¹H NMR (base): 7.33-7.15 (m, 9H), 6.53 (s, 1H), 5.59 (s, 1H), 4.47-4.35 (m, 1H), 4.33-4.15 (m, 1H), 4.00-3.87 (m, 1H), 3.56-3.40 (m, 1H), 3.00-2.78 (m, 5H), 2.73-2.60 (m, 2H), 2.22 (s, 3H), 2.15-1.97 (m, 2H), 1.95-1.55 (m, 4H).

4-(1-methylpiperidin-4-yloxy)-2-phenethyl-9,10-dihydro-4H-3,10a-diaza-benzo[f]azulene is dissolved in acetone (0.85 mL) and oxalic acid (1 equivalent) is added. Acetone is removed under reduced pressure to afford the product as an oxalate.

The following compounds are prepared using the same method.

| example | product |
|---|---|
| 87 | 4-(1-methylpiperidin-4-yloxy)-2-(3-phenylpropyl)-9,10-dihydro-4H-3,10a-diaza-benzo[f]azulene oxalate<br>$[M + H]^+ = 416.2$ |
| 90 | 4-(1-methylpiperidin-4-yloxy)-2-(5-phenylpentyl)-9,10-dihydro-4H-3,10a-diaza-benzo[f]azulene oxalate<br>mp = 128° C. |
| 94 | 2-(3,3-dimethylbutyl)-4-(1-methylpiperidin-4-yloxy)-9,10-dihydro-4H-3,10a-diaza-benzo[f]azulene<br>mp = 65° C. |
| 95 | 2-(2-cyclohexylethyl)-4-(1-methylpiperidin-4-yloxy)-9,10-dihydro-4H-3,10a-diaza-benzo[f]azulene oxalate<br>mp = 90° C. |
| 105 | 2-(3-cyclopentylpropyl)-4-(1-methylpiperidin-4-yloxy)-9,10-dihydro-4H-3,10a-diaza-benzo[f]azulene<br>mp = 85° C. |
| 109 | 2-isobutyl-4-(1-methylpiperidin-4-yloxy)-9,10-dihydro-4H-3,10a-diaza-benzo[f]azulene oxalate<br>¹H NMR (base): 7.35-7.18 (m, 4H), 6.56 (s, 1H), 5.57 (s, 1H), 4.48-4.37 (m, 1H), 4.35-4.18 (m, 1H), 4.03-3.90 (m, 1H), 3.55-3.40 (m, 1H), 2.94-2.80 (m, 1H), 2.72-2.58 (m, 2H), 2.37 (d, J = 7.9 Hz, 2H), 2.21 (s, 3H), 2.10-1.81 (m, 4H), 1.70-1.50 (m, 3H), 0.96-0.85 (m, 6H). |
| 128 | 2-(3-benzyloxypropyl)-4-(1-methylpiperidin-4-yloxy)-9,10-dihydro-4H-3,10a-diaza-benzo[f]azulene oxalate<br>¹H NMR (base): 7.35-7.18 (m, 9H), 6.53 (s, 1H), 5.49 (s, 1H), 4.48 (s, 2H), 4.35-4.26 (m, 1H), 4.20-3.87 (m, 2H), 3.80-3.70 (m, 1H), 3.50 (t, J = 7.7 Hz, 2H), 3.13-2.80 (m, 3H), 2.68-2.53 (m, 5H), 2.30-2.06 (m, 3H), 2.05-1.80 (m, 5H). |
| 129 | 4-(1-methylpiperidin-4-yloxy)-2-(4-phenylbutyl)-9,10-dihydro-4H-3,10a-diaza-benzo[f]azulene oxalate<br>¹H NMR (base): 7.35-7.10 (m, 9H), 6.54 (s, 1H), 5.50 (s, 1H), 4.40-4.28 (m, 1H), 4.20-4.02 (m, 1H), 4.00-3.85 (m, 1H), 3.75-3.62 (m, 1H), 3.05-2.70 (m, 5H), 2.68-2.58 (m, 2H), 2.58-2.45 (m, 5H), 2.25-1.75 (m, 4H), 1.72-1.55 (m, 4H). |
| 159 | 2-[4-(2-methanesulfonylethyl)-phenyl]-1-methyl-4-(1-methylpiperidin-4-yloxy)-9,10-dihydro-4H-3,10a-diaza-benzo[f]azulene<br>mp = 80° C. |
| 177 | 4-{4-[1-methyl-4-(1-methylpiperidin-4-yloxy)-9,10-dihydro-4H-3,10a-diaza-benzo[f]azulen-2-yl]-phenyl}-piperidine-1-carboxylic acid tert-butyl ester<br>$[M + H]^+ = 571.48$ |
| 229 | 2-(3,3-dimethyl-butyl)-1-methyl-4-(1-methylpiperidin-4-yloxy)-9,10-dihydro-4H-3,10a-diaza-benzo[f]azulene<br>$[M + H]^+ = 396.38$ |

Example 53

3-[4-(1-methylpiperidin-4-yloxy)-9,10-dihydro-4H-3,10a-diaza-benzo[f]azulen-2-yl]-acrylic acid tert-butyl ester oxalate To a solution of compound 2-iodo-4-(1-methylpiperidin-4-yloxy)-9,10-dihydro-4H-3,10a-diaza-benzo[f]azulene (example 2A) (100 mg, 0.24 mmoles) in DMF (2.5 mL) in a screw-capped vial under argon are added Pd(OAc)$_2$ (5.4 mg, 24 μmole), PPh$_3$ (16 mg, 60 μmole), tert-butylacrylate (175 μL, 0.96 mmole) and NEt$_3$ (140 μL, 0.88 mmole). The reaction mixture is heated at 100° C. overnight. Water is added to the reaction mixture and pH adjusted to 9-10 by adding concentrated ammonia solution. The aqueous phase is extracted three times with CH$_2$Cl$_2$. The organic phase is dried over magnesium sulphate, filtered and the solvent is removed under reduced pressure. The residue is pre-purified by silica gel chromatography using (CH$_2$Cl$_2$:MeOH:NH$_4$OH) as eluent with a gradient from (98:2:0.1) to (96.5:3.5:0.35) and the residue is submitted to a preparative thin-layer chromatography eluting with (CH$_2$Cl$_2$:MeOH:NH$_4$OH) (9:1:1) to afford 3-[4-(1-methylpiperidin-4-yloxy)-9,10-dihydro-4H-3,10a-diaza-benzo[f]azulen-2-yl]-acrylic acid tert-butyl ester.

$[M+H]^+=424.1$; $[M+Na]^+=446.1$.

3-[4-(1-methyl piperidin-4-yloxy)-9,10-dihydro-4H-3,10a-diaza-benzo[f]azulen-2-yl]-acrylic acid tert-butyl ester is dissolved in acetone (1.7 mL) and oxalic acid (1 equivalent) is added. Acetone is removed under reduced pressure to afford the compound as an oxalate.

Example 54

Mixture of enantiomers of 2-(2-chlorophenyl)-4-(1-methylpiperidin-4-yloxy)-9,10-dihydro-4H-3,10a-diaza-benzo[f]azulene (example 26)

A mixture of both enantiomers of 2-(2-chlorophenyl)-4-(1-methylpiperidin-4-yloxy)-9,10-dihydro-4H-3,10a-diaza-benzo[f]azulene (example 26) is separated using a preparative HPLC on a Chiralpak AD-H column eluting with (heptane-diethylamine 0.1%:iPrOH-diethylamine 0.1%) (90:10) with a flow-rate of 1 mL·min$^{-1}$. Products are detected at 220 nm.

54A enantiomer A, retention time=8.22 minutes (enantiomeric purity=100%).

54B enantiomer B, retention time=10.16 minutes (enantiomeric purity=100%).

Example 58

2,2-dimethyl-N-{4-[4-(1-methylpiperidin-4-yloxy)-9,10-dihydro-4H-3,10a-diaza-benzo[f]azulen-2-yl]-phenyl}-propionamide To a solution of 4-[4-(1-methylpiperidin-4-yloxy)-9,10-dihydro-4H-3,10a-diaza-benzo[f]azulen-2-yl]-phenylamine (example 16A) (100 mg, 0.258 mmole) in $CH_2Cl_2$ (2 mL) is added $NEt_3$ (72 µL, 0.515 mmole) and pivaloylchloride (48 µL, 0.387 mmole). The reaction mixture is stirred at room temperature overnight. Solvent is removed under reduced pressure. AcOEt is added to the residue and the organic phase is washed with water and dried over magnesium sulphate, filtered and the solvent is removed under reduced pressure. The residue is purified by silica gel chromatography using ($CH_2Cl_2$:MeOH) as eluent with a gradient from (100:0) to (90:10) to afford 2,2-dimethyl-N-{4-[4-(1-methylpiperidin-4-yloxy)-9,10-dihydro-4H-3,10a-diaza-benzo[f]azulen-2-yl]-phenyl}-propionamide melting at 120° C.

The following compounds are prepared using the same method and different kinds of acylating agents.

| example | product |
|---|---|
| 101 | 2,2,N-trimethyl-N-{4-[4-(1-methylpiperidin-4-yloxy)-9,10-dihydro-4H-3,10a-diaza-benzo[f]azulen-2-yl]-phenyl}-propionamide oxalate<br>$^1$H NMR (base): 7.78-7.70 (m, 2H), 7.40-7.15 (m, 7H), 5.66 (s, 1H), 4.59-4.48 (m, 1H), 4.29-4.01 (m, 2H), 3.82-3.70 (m, 1H), 3.22 (s, 3H), 3.02-2.82 (m, 3H), 2.46 (s, 3H), 2.30-1.80 (m, 6H), 1.05 (s, 9H). |
| 136 | 2,2-dimethyl-N-{4-[4-(1-methylpiperidin-4-yloxy)-9,10-dihydro-4H-3,10a-diaza-benzo[f]azulen-2-yl]-benzyl}-propionamide<br>mp = 160° C. |
| 138 | 3-methoxy-N-{4-[4-(1-methylpiperidin-4-yloxy)-9,10-dihydro-4H-3,10a-diaza-benzo[f]azulen-2-yl]-benzyl}-propionamide<br>mp = 80° C. |

Example 60

1-{4-[4-(1-methylpiperidin-4-yloxy)-9,10-dihydro-4H-3,10a-diaza-benzo[f]azulen-2-yl]-phenyl}-3-propyl-urea To a solution of 4-[4-(1-methylpiperidin-4-yloxy)-9,10-dihydro-4H-3,10a-diaza-benzo[f]azulen-2-yl]-phenylamine (example 16) (100 mg, 0.258 mmole) in $CH_2Cl_2$ (2 mL) is added $NEt_3$ (72 µL, 0.515 mmole) and propylisocyanate (36 µL, 0.387 mmole). The reaction mixture is stirred at room temperature for 24 hours. Solvent is removed under reduced pressure. AcOEt is added to the residue and the organic phase is washed with water and dried over magnesium sulphate, filtered and the solvent is removed under reduced pressure. The residue is purified by silica gel chromatography using ($CH_2Cl_2$:MeOH) as eluent with a gradient from (100:0) to (90:10) to afford 1-{4-[4-(1-methylpiperidin-4-yloxy)-9,10-dihydro-4H-3,10a-diaza-benzo[f]azulen-2-yl]-phenyl}-3-propyl-urea melting at 130° C.

Example 67

2-benzylsulfanyl-4-(1-methylpiperidin-4-yloxy)-9,10-dihydro-4H-3,10a-diaza-benzo[f]azulene oxalate To a solution of compound 2-iodo-4-(1-methyl piperidin-4-yloxy)-9,10-dihydro-4H-3,10a-diaza-benzo[f]azulene (example 2A) (50 mg, 0.12 mmoles) in 1,4-dioxane (0.5 mL) in a screw-capped vial under argon are added DIEA (31 µL, 0.18 mmole), benzylmercaptan (21 µL, 0.18 mmole), bis (dibenzilideneacetone)Palladium(0) (3.5 mg, 6 µmole), Xantphos (3.5 mg, 6 µmole). The reaction mixture is heated at 120° C. overnight. As the reaction is not complete, bis(dibenzilideneacetone)Palladium(0) (3.5 mg, 6 µmole), Xantphos (3.5 mg, 6 µmole) are added to the reaction mixture. After one overnight at 120° C., water is added to the reaction mixture and pH adjusted to 9-10 by adding concentrated ammonia solution. The aqueous phase is extracted three times with $CH_2Cl_2$. The organic phase is dried over magnesium sulphate, filtered and the solvent is removed under reduced pressure. The residue is purified by silica gel chromatography using ($CH_2Cl_2$:MeOH:$NH_4OH$) as eluent with a gradient from (98:2:0.1) to (96.5:3.5:0.35) to afford 2-benzylsulfanyl-4-(1-methylpiperidin-4-yloxy)-9,10-dihydro-4H-3,10a-diaza-benzo[f]azulene.

$[M+H]^+$=420.2.

2-benzylsulfanyl-4-(1-methylpiperidin-4-yloxy)-9,10-dihydro-4H-3,10a-diaza-benzo[f]azulene is dissolved in acetone (0.7 mL) and oxalic acid (1 equivalent) is added. Acetone is removed under reduced pressure to afford the product as an oxalate.

The following compounds are prepared using the same method and different kinds of sulfides.

| example | product |
|---|---|
| 73 | 4-(1-methylpiperidin-4-yloxy)-2-phenylsulfanyl-9,10-dihydro-4H-3,10a-diaza-benzo[f]azulene oxalate<br>$[M + H]^+ = 406.2; [M + Na]^+ = 428.2$ |
| 84 | {2-[4-(1-methylpiperidin-4-yloxy)-9,10-dihydro-4H-3,10a-diaza-benzo[f]azulen-2-ylsulfanyl]-ethyl}-carbamic acid tert-butyl ester oxalate<br>mp = 100° C. |
| 85 | 2-(furan-2-ylmethylsulfanyl)-4-(1-methylpiperidin-4-yloxy)-9,10-dihydro-4H-3,10a-diaza-benzo[f]azulene oxalate<br>$[M + H]^+ = 410.2; [M + Na]^+ = 432.1$ |

-continued

| example | product |
|---|---|
| 86 | 2-cyclopentylsulfanyl-4-(1-methylpiperidin-4-yloxy)-9,10-dihydro-4H-3,10a-diaza-benzo[f]azulene oxalate<br>$[M + H]^+ = 398.2$ |
| 88 | 4-(1-methylpiperidin-4-yloxy)-2-(thiophen-2-ylmethylsulfanyl)-9,10-dihydro-4H-3,10a-diaza-benzo[f]azulene oxalate<br>$[M + H]^+ = 426.1$ |
| 98 | 2-cyclohexylsulfanyl-4-(1-methylpiperidin-4-yloxy)-9,10-dihydro-4H-3,10a-diaza-benzo[f]azulene oxalate<br>$^1$H NMR (base): 7.35-7.18 (m, 4H), 6.93 (s, 1H), 5.60 (s, 1H), 4.62-4.50 (m, 1H),<br>4.31-4.15 (m, 1H), 4.07-3.92 (m, 1H), 3.59-3.45 (m, 1H), 3.02-2.82 (m, 2H), 2.78-2.60 (m, 2H),<br>2.25 (s, 3H), 2.15-1.98 (m, 6H), 1.88-1.48 (m, 6H), 1.45-1.10 (m, 4H). |
| 114 | 4-[4-(1-methylpiperidin-4-yloxy)-9,10-dihydro-4H-3,10a-diaza-benzo[f]azulen-2-ylsulfanyl]-piperidine-1-carboxylic acid tert-butyl ester<br>mp = 151° C. |
| 119 | 4-(1-methylpiperidin-4-yloxy)-2-phenethylsulfanyl-9,10-dihydro-4H-3,10a-diaza-benzo[f]azulene<br>$[M + H]^+ = 434.1$ |

Example 70

2-(2-methyl-allyl)-4-(1-methylpiperidin-4-yloxy)-9,10-dihydro-4H-3,10a-diaza-benzo[f]azulene oxalate To a solution of 2-iodo-4-(1-methylpiperidin-4-yloxy)-9,10-dihydro-4H-3,10a-diaza-benzo[f]azulene (example 2A) (100 mg, 0.24 mmoles) in DMF (4 mL) in a screw-capped vial under argon are added methallyltributyltin (331 mg, 0.96 mmole), Pd(PPh$_3$)$_4$ (28 mg, 24 μmole), LiCl (51 mg, 1.2 mmoles). The reaction mixture is heated at 80° C. for 5 hours. A solution of 10% KF in water is added, and the aqueous phase is extracted three times with CH$_2$Cl$_2$. The organic phase is washed with a solution of 10% KF in water, brine, dried over magnesium sulphate, filtered and the solvent is removed under reduced pressure. The residue is purified by silica gel chromatography using (CH$_2$Cl$_2$:MeOH:NH$_4$OH) as eluent with a gradient from (98:2:0.2) to (96.5:3.5:0.35). As the residue is contaminated with tin salts, 1N aqueous HCl is added, and the aqueous phase is extracted three times with Et$_2$O. The aqueous phase is basified to pH 10 with 12N NaOH and the aqueous phase is extracted three times with AcOEt. The organic phase is dried over magnesium sulphate, filtered and the solvent is removed under reduced pressure to afford 2-(2-methyl-allyl)-4-(1-methylpiperidin-4-yloxy)-9,10-dihydro-4H-3,10a-diaza-benzo[f]azulene.

$[M+H]^+$=352.2; $[M+Na]^+$=374.2.

2-(2-methyl-allyl)-4-(1-methylpiperidin-4-yloxy)-9,10-dihydro-4H-3,10a-diaza-benzo[f]azulene is dissolved in acetone (0.7 mL) and oxalic acid (1 equivalent) is added. Acetone is removed under reduced pressure to afford the product as an oxalate.

The following compound is prepared using the same method and different kind of tributylstannyl reagent.

| example | product |
|---|---|
| 83 | 4-(1-methylpiperidin-4-yloxy)-2-(1-methyl-1H-pyrrol-2-yl)-9,10-dihydro-4H-3,10a-diaza-benzo[f]azulene<br>$^1$H NMR: 7.40-7.20 (m, 4H), 6.90 (s, 1H), 6.68-6.62 (m, 1H),<br>6.31-6.25 (m, 1H), 6.17-6.10 (m, 1H), 5.62 (s, 1H), 4.55-4.42 (m, 1H),<br>4.28-3.99 (m, 2H), 3.73 (s, 3H), 3.80-3.65 (m, 1H), 3.00-2.82 (m, 2H),<br>2.47 (s, 3H), 2.28-1.60 (m, 6H). |

Example 72

{3-[4-(1-methylpiperidin-4-yloxy)-9,10-dihydro-4H-3,10a-diaza-benzo[f]azulen-2-yl]-prop-2-ynyl}-carbamic acid tert-butyl ester To a solution of compound 2-iodo-4-(1-methyl piperidin-4-yloxy)-9,10-dihydro-4H-3,10a-diaza-benzo[f]azulene (example 2A) (80 mg, 0.19 mmoles) in DMF (0.5 mL) in a screw-capped vial under argon are added CuI (7.2 mg, 0.038 mmole), (PPh$_3$)$_2$PdCl$_2$ (13.3 mg, 19 μmole), N-Boc-propargylamine (91 mg, 0.57 mmole) and Et$_2$NH (58 μL, 0.57 mmole). The reaction mixture is heated at 50° C. overnight. Water is added and pH adjusted to 9-10 with concentrated aqueous ammonia solution. The aqueous phase is extracted three times with AcOEt. The organic phase is dried over magnesium sulphate, filtered and the solvent is removed under reduced pressure. The residue is pre-purified by silica gel chromatography using (CH$_2$Cl$_2$:MeOH) as eluent with a gradient from (95:5) to (90:10) and the residue is submitted to a preparative thin-layer chromatography eluting with (CH$_2$Cl$_2$:MeOH:NH$_4$OH) (9:1:1) to afford {3-[4-(1-methylpiperidin-4-yloxy)-9,10-dihydro-4H-3,10a-diaza-benzo[f]azulen-2-yl]-prop-2-ynyl}-carbamic acid tert-butyl ester.

$^1$H NMR: 7.38-7.20 (m, 4H), 7.00 (s, 1H), 5.51 (s, 1H), 4.75 (sl, 1H), 4.50-4.38 (m, 1H), 4.25-4.09 (m, 3H), 4.07-3.92 (m, 1H), 3.71-3.61 (m, 1H), 2.98-2.75 (m, 3H), 2.46 (s, 3H), 2.25-1.55 (m, 6H), 1.26 (s, 9H).

Example 78

78A 8-chloro-2-iodo-4-(1-methylpiperidin-4-yloxy)-9,10-dihydro-4H-3,10a-diaza-benzo[f]azulene To 1-[2-(2-chlorophenyl)ethyl]-4-iodoimidazole-2-carbaldehyde (example 78B) (200 mg, 0.55 mmole) is added trifluoromethanesulfonic acid (2 mL). The purple solution is stirred at room temperature overnight, 4-hydroxy-N-methylpiperidine (190 mg, 1.65 mmole) is added and solution is stirred at room temperature for 2 hours. Water is added and the solution is made alkaline by adding 5N NaOH to pH 10. The aqueous phase is extracted with AcOEt. The organic phase is washed with water, brine, dried over MgSO$_4$, filtered and the solvent removed under reduced pressure. The residue is purified by silica gel chromatography eluting with (CH$_2$Cl$_2$:MeOH) (100:0) to (90:10) then (CH$_2$Cl$_2$:MeOH:NH$_4$OH)

(9:1:0.1) to give 8-chloro-2-iodo-4-(1-methyl piperidin-4-yloxy)-9,10-dihydro-4H-3,10a-diaza-benzo[f]azulene.

$^1$H NMR: 7.43-7.33 (m, 1H), 7.20-7.10 (m, 2H), 6.96 (s, 1H), 5.59 (s, 1H), 4.54-4.41 (m, 1H), 4.25-3.93 (m, 2H), 3.59-3.42 (m, 2H), 2.75-2.60 (m, 2H), 2.26 (s, 3H), 2.20-2.02 (m, 2H), 1.99-1.55 (m, 4H).

78B 1-[2-(2-chlorophenyl)ethyl]-4-iodoimidazole-2-carbaldehyde

The compound is synthesized using the method described in example 2B starting from 1-[2-(2-chlorophenyl)ethyl]-4-iodoimidazole-2-carbaldehyde (example 78C).

$^1$H NMR $^1$H: 9.76 (s, 1H), 7.43-7.35 (m, 1H), 7.29-7.13 (m, 2H), 7.08-7.00 (m, 1H), 6.96 (s, 1H), 4.61 (t, J=8.6 Hz, 2H), 3.19 (m, J=8.6 Hz, 2H).

78C 1-[2-(2-chlorophenyl)ethyl]-4-iodoimidazole

The compound is synthesized using the method described in example 4C starting from 4-iodo-1H-imidazole and methanesulfonic acid 2-(2-chlorophenyl)-ethyl ester (example 78D).

NMR $^1$H, 7.42-7.37 (m, 1H), 7.30-7.10 (m, 3H), 7.02-6.91 (m, 2H), 4.19 (t, J=8.6 Hz, 2H), 3.17 (m, J=8.6 Hz, 2H).

78D methanesulfonic acid 2-(2-chlorophenyl)-ethyl ester

The compound is synthesized using the method described in example 4D starting from 2-(2-chlorophenyl)-ethanol.

Example 79

79A 8-bromo-2-iodo-4-(1-methylpiperidin-4-yloxy)-9,10-dihydro-4H-3,10a-diaza-benzo[f]azulene The compound is synthesized using the method described in example 78A-C starting from 4-iodo-1H-imidazole and 8-bromo-2-iodo-4-(1-methylpiperidin-4-yloxy)-9,10-dihydro-4H-3,10a-diaza-benzo[f]azulene (example 79B).

$^1$H NMR: 7.62-7.55 (m, 1H), 7.25-7.18 (m, 1H), 7.15-7.05 (m, 1H), 6.96 (s, 1H), 5.58 (s, 1H), 4.50-4.39 (m, 1H), 4.35-4.19 (m, 1H), 4.08-3.92 (m, 1H), 3.60-3.42 (m, 2H), 2.80-2.65 (m, 2H), 2.32 (s, 3H), 2.25-2.15 (m, 2H), 1.99-1.60 (m, 4H).

79B methanesulfonic acid 2-(2-bromophenyl)-ethyl ester

The compound is synthesized using the method described in example 4D starting from 2-(2-bromophenyl)-ethanol.

Example 81

2-(4-bromophenyl)-4-(1-methylpiperidin-4-yloxy)-9,10-dihydro-4H-3,10a-diaza-benzo[f]azulene The compound is synthesized according to the procedure already described in examples 2A, 2B and 103C starting from 4-(4-bromophenyl)-1H-imidazole to give 2-(4-bromophenyl)-4-(1-methylpiperidin-4-yloxy)-9,10-dihydro-4H-3,10a-diaza-benzo[f]azulene melting at 142° C.

Example 91

8-chloro-4-(1-methylpiperidin-4-yloxy)-2-phenyl-9,10-dihydro-4H-3,10a-diaza-benzo[f]azulene To a solution of 8-chloro-2-iodo-4-(1-methylpiperidin-4-yloxy)-9,10-dihydro-4H-3,10a-diaza-benzo[f]azulene (example 78A) (35 mg, 0.08 mmole) in THF (1 mL) in a screw-capped vial under argon are added 1M solution of $K_2CO_3$ (0.4 ml, 0.4 mmole), $PdCl_2(dppf)_2$ (3.5 mg) and benzeneboronic acid (13 mg, 0.104 mmole). The reaction mixture is heated at 100° C. overnight. Water is added to the reaction mixture and pH adjusted to 9-10 by adding concentrated ammonia solution. The aqueous phase is extracted three times with $CH_2Cl_2$. The organic phase is dried over magnesium sulphate, filtered and the solvent is removed under reduced pressure. The residue is pre-purified by silica gel chromatography using ($CH_2Cl_2$:MeOH) (100:0) to (90:10) then ($CH_2Cl_2$:MeOH:$NH_4OH$) (9:1:0.1) to give 8-chloro-4-(1-methylpiperidin-4-yloxy)-2-phenyl-9,10-dihydro-4H-3,10a-diaza-benzo[f]azulene. [M+H]$^+$=408.2 and 410.0 $^{35}$Cl/$^{37}$Cl.

Example 92

4-(1-methylpiperidin-4-yloxy)-2,8-diphenyl-9,10-dihydro-4H-3,10a-diaza-benzo[f]azulene To a solution of 8-bromo-2-iodo-4-(1-methylpiperidin-4-yloxy)-9,10-dihydro-4H-3,10a-diaza-benzo[f]azulene (example 79A) (82 mg, 0.163 mmole) in THF (2 mL) in a screw-capped vial under argon are added 1M solution of $K_2CO_3$ (0.8 ml, 0.4 mmole), $PdCl_2(dppf)_2$ (8.2 mg) and benzeneboronic acid (26 mg, 0.21 mmole). The reaction mixture is heated at 100° C. overnight. Water is added to the reaction mixture and pH adjusted to 9-10 by adding concentrated ammonia solution. The aqueous phase is extracted three times with $CH_2Cl_2$. The organic phase is dried over magnesium sulphate, filtered and the solvent is removed under reduced pressure. The residue is pre-purified by silica gel chromatography using ($CH_2Cl_2$:MeOH) (100:0) to (90:10) then ($CH_2Cl_2$:MeOH:$NH_4OH$) (9:1:0.1) to give 4-(1-methylpiperidin-4-yloxy)-2,8-diphenyl-9,10-dihydro-4H-3,10a-diaza-benzo[f]azulene.
[M+H]$^+$=450.2.

Example 96

4-(1-methylpiperidin-4-yloxy)-2-(5-methylthiophen-2-yl)-9,10-dihydro-4H-3,10a-diaza-benzo[f]azulene To a solution of 2-iodo-4-(1-methylpiperidin-4-yloxy)-9,10-dihydro-4H-3,10a-diaza-benzo[f]azulene (example 2A) (50 mg, 0.12 mmoles) in 1,4-dioxane (2.5 mL) in a screw-capped vial under argon are added 4-methylthiophene-2-boronic acid pinacol ester (40 mg, 0.18 mmole), $PdCl_2(dppf)_2$ (6.7 mg, 12 μmole), CsF (36 mg, 0.24 mmoles). The reaction mixture is heated at 100° C. overnight. As the reaction is not completed, CsF (18 mg, 0.12 mmole) and $PdCl_2(dppf)_2$ (6.7 mg, 12 μmole) are added and the reaction mixture is heated at 100° C. overnight. Water is added, pH is made alkaline by adding concentrated ammonia solution and the aqueous phase is extracted three times with $CH_2Cl_2$. The organic phase is dried over magnesium sulphate, filtered and the solvent is removed under reduced pressure. The residue is purified by silica gel chromatography using (CH$_2$Cl$_2$:MeOH: NH$_4$OH) as eluent with a gradient from (98:2:0.2) to (96.5: 3.5:0.35) followed by a purification on a preparative TLC over silica gel eluting with (9:1:0.1) to give 4-(1-methylpiperidin-4-yloxy)-2-(5-methylthiophen-2-yl)-9,10-dihydro-4H-3,10a-diaza-benzo[f]azulene.

$^1$H NMR: 7.38-7.20 (m, 5H), 7.09-7.05 (m, 1H), 7.04-6.99 (m, 1H), 6.74 (s, 1H), 5.66 (s, 1H), 4.57-4.45 (m, 1H), 4.32-4.18 (m, 1H), 4.10-3.95 (m, 1H), 3.62-3.48 (m, 1H), 2.98-2.85 (m, 1H), 2.75-2.58 (m, 2H), 2.30-2.20 (m, 6H), 2.20-1.95 (m, 3H), 1.95-1.55 (m, 3H).

4-(1-methylpiperidin-4-yloxy)-2-(5-methylthiophen-2-yl)-9,10-dihydro-4H-3,10a-diaza-benzo[f]azulene is dissolved in acetone (0.7 mL) and oxalic acid (1 equivalent) is added. Acetone is removed under reduced pressure to afford the compound as an oxalate.

Example 102

{4-[4-(1-methylpiperidin-4-yloxy)-9,10-dihydro-4H-3,10a-diaza-benzo[f]azulen-2-yl]-phenyl}-phenyl-methanone oxalate To a solution of 2-iodo-4-(1-methylpiperidin-4-yloxy)-9,10-dihydro-4H-3,10a-diaza-benzo[f]azulene (example 2A) (200 mg, 0.47 mmoles) in THF (2.6 mL) in a screw-capped vial under argon at −78° C. is added 2.3M nBuLi (0.44 mL, 0.94 mmole). The reaction mixture is stirred at −78° C. for 30 min. Benzaldehyde (96 µL, 1.03 mmole) is added. The reaction mixture is allowed to reach room temperature. Water and a NaHCO$_3$ saturated solution are added, and the aqueous phase is extracted three times with AcOEt. The organic phase is washed with water, brine, dried over magnesium sulphate, filtered and the solvent is removed under reduced pressure. The residue is purified by silica gel chromatography using (CH$_2$Cl$_2$:MeOH:NH$_4$OH) as eluent with a gradient from (98:2:0.2) to (95:5:0.5). The residue (130 mg, 0.285 mmole) is dissolved in 1,4-dioxane (1.4 mL) and barium manganate (73 mg, 0.285 mmole) as well as MnO$_2$ (100 mg, 1.14 mmole) are added. The reaction mixture is heated at 80° C. for 24 h. The reaction mixture is filtered over celite, cake washed with MeOH. The solvents are removed under reduced pressure. The residue is purified by silica gel chromatography using (CH$_2$Cl$_2$:MeOH:NH$_4$OH) as eluent with a gradient from (98: 2:0.2) to (96.5:3.5:0.35) to give {4-[4-(1-methylpiperidin-4-yloxy)-9,10-dihydro-4H-3,10a-diaza-benzo[f]azulen-2-yl]-phenyl}-phenyl-methanone.

$^1$H NMR: 8.20-8.10 (m, 2H), 7.60 (s, 1H), 7.58-7.42 (m, 3H), 7.40-7.20 (m, 4H), 5.72 (s, 1H), 4.69-4.58 (m, 1H), 4.35-4.05 (m, 2H), 3.60-3.48 (m, 1H), 3.05-2.90 (m, 1H), 2.75-2.60 (m, 2H), 2.24 (s, 3H), 2.18-2.00 (m, 2H), 1.98-1.55 (m, 4H).

The compound is dissolved in acetone (1 mL) and oxalic acid (1 equivalent) is added. Acetone is removed under reduced pressure to afford the compound as an oxalate.

Example 103

103A 1-Methyl-4-(1-methyl-piperidin-4-yloxy)-2-phenyl-9,10-dihydro-4H-3,10a-diaza-benzo[f]azulene To a solution of 5-methyl-1-phenethyl-4-phenyl-imidazole-2-carbaldehyde (example 103B) (50 mg, 0.172 mmole) in CHCl$_3$ (1 mL) is added 4-hydroxy-N-methylpiperidine (198 mg, 1.72 mmoles). Methanesulfonic acid is added dropwise until a purple colour developed. The reaction is completed (TLC control). A saturated solution of Na$_2$CO$_3$ is added to reach pH 10. The aqueous phase is extracted three times with CH$_2$Cl$_2$. The organic phase is dried over magnesium sulphate, filtered and the solvent is removed under reduced pressure. The residue is purified by preparative TLC over silica gel using (CH$_2$Cl$_2$:MeOH:NH$_4$OH) (92.5:7.5:0.75) to give 1-methyl-4-(1-methyl-piperidin-4-yloxy)-2-phenyl-9,10-dihydro-4H-3,10a-diaza-benzo[f]azulene.

$^1$H NMR: 7.61-7.53 (m, 2H), 7.41-7.18 (m, 7H), 5.69 (s, 1H), 4.43-4.28 (m, 2H), 3.90-3.75 (m, 1H), 3.60-3.46 (m, 1H), 3.00-2.88 (m, 1H), 2.75-2.60 (m, 2H), 2.33 (s, 3H), 2.24 (s, 3H), 2.18-2.00 (m, 2H), 1.99-1.78 (m, 2H) 1.77-1.60 (m, 2H).

103B 5-methyl-1-phenethyl-4-phenyl-imidazole-2-carbaldehyde

The compound is prepared according to the procedure described in example 2B.

$^1$H NMR: 9.84 (s, 1H), 7.62-7.55 (m, 2H), 7.49-7.40 (m, 2H), 7.39-7.22 (m, 4H), 7.18-7.08 (m, 2H), 4.57 (t, J=8.4 Hz, 2H), 3.06 (t, J=8.4 Hz, 2H), 2.09 (s, 3H).

103C 5-methyl-1-phenethyl-4-phenyl-imidazole and 4-methyl-1-phenethyl-5-phenyl-imidazole To a solution of 5-methyl-4-phenyl-1H-imidazole (example 103D) (1.02 g, 6.44 mmoles) in ACN (20 mL) are added K$_2$CO$_3$ (1.07 g, 7.72 mmoles) and methanesulfonic acid phenethyl ester (example 4D). The reaction mixture is heated at reflux overnight, then cooled to room temperature, filtered, cake washed with ACN and solvent is removed under reduced pressure. The residue is purified by silica gel chromatography using (toluene:acetone) (90:10) as eluent to give 5-methyl-1-phenethyl-4-phenyl-imidazole and 4-methyl-1-phenethyl-5-phenyl-imidazole.

$^1$H NMR: 7.68-7.60 (m, 2H), 7.45-7.35 (m, 2H), 7.32-7.22 (m, 5H), 7.12-7.05 (m, 2H), 4.13 (t, J=8.6 Hz, 2H), 3.05 (t, J=8.6 Hz, 2H), 2.27 (s, 3H).

4-methyl-1-phenethyl-5-phenyl-imidazole $^1$H NMR: 7.50-7.38 (m, 3H), 7.33 (s, 1H), 7.30-7.18 (m, 5H), 6.97-6.88 (m, 2H), 4.06 (t, J=8.9 Hz, 2H), 2.78 (t, J=8.9 Hz, 2H), 2.19 (s, 3H).

103D 5-methyl-4-phenyl-1H-imidazole

In a three-neck round bottom flask equipped with a thermometer and a condenser is added formamide (180 mL). The solvent is heated to 180° C., the 2-bromopropiophenone (21.3 g, 100 mmoles) is added portionwise over 45 minutes. The reaction mixture is heated at 180° C. for a further hour, then cooled to room temperature. The mixture is poured into water (0.7 L) and saturated NaHCO$_3$ solution (150 mL) is added. The suspension is stirred at room temperature for 15 minutes, then filtered. The cake is rinsed with water and filter-dried. The residual solid is re-crystallized from hot ACN to give 5-methyl-4-phenyl-1H-imidazole.

$^1$H NMR (DMSO-d$^6$): 12.20 and 11.94 (NH), 7.70-7.48 (m, 3H), 7.45-7.28 (m, 2H), 7.25-7.10 (m, 1H), 2.04 (s, 3H).

Example 107

107A 8-fluoro-4-(1-methylpiperidin-4-yloxy)-2-phenyl-9,10-dihydro-4H-3,10a-diaza-benzo[f]azulene The compound is synthesized using the same method described in example 91 starting from 8-fluoro-2-iodo-4-(1- methylpiperidin-4-yloxy)-9,10-dihydro-4H-3,10a-diaza-benzo[f]azulene (example 107B).

¹H NMR: ¹H NMR: 7.35-7.15 (m, 6H), 7.14-7.00 (m, 4H), 5.60 (s, 1H), 4.59-4.47 (m, 1H), 4.10-3.97 (m, 1H), 3.90-3.75 (m, 1H), 3.70-3.57 (m, 1H), 3.39-3.29 (m, 1H), 2.95-2.75 (m, 2H), 2.35 (s, 3H), 2.25-1.68 (m, 6H).

107B 8-fluoro-2-iodo-4-(1-methylpiperidin-4-yloxy)-9,10-dihydro-4H-3,10a-diaza-benzo[f]azulene The compound is synthesized using the method described in example 78A-C starting from 4-iodo-1H-imidazole and methanesulfonic acid 2-(2-fluorophenyl)-ethyl ester (example 107C).

¹H NMR: 7.27-7.15 (m, 2H), 7.14-7.02 (m, 2H), 6.99 (s, 1H), 5.59 (s, 1H), 4.58-4.47 (m, 1H), 4.10-3.98 (m, 1H), 3.90-3.75 (m, 1H), 3.70-3.57 (m, 1H), 3.39-3.29 (m, 1H), 2.95-2.75 (m, 2H), 2.35 (s, 3H), 2.25-1.68 (m, 6H).

107C methanesulfonic acid 2-(2-fluorophenyl)-ethyl ester

The compound is synthesized using the method described in example 4D starting from 2-(2-fluorophenyl)-ethanol.

Example 110

110A 2-benzyl-4-(1-methyl-piperidin-4-yloxy)-9,10-dihydro-4H-3,10a-diaza-benzo[f]azulene oxalate The compound is synthesized using the methods described in examples 2A and 2B starting from 4-benzyl-1-phenethyl-imidazole (example 110B).

¹H NMR (base): 7.48-7.18 (m, 9H), 6.42 (s, 1H), 5.57 (s, 1H), 4.40-4.30 (m, 1H), 4.29-4.15 (m, 1H), 3.98-3.82 (m, 3H), 3.58-3.42 (m, 1H), 2.95-2.80 (m, 1H), 2.78-2.62 (m, 2H), 2.28 (s, 3H), 2.25-2.08 (m, 2H), 2.00-1.85 (m, 1H), 1.85-1.55 (m, 3H).

110B 4-benzyl-1-phenethyl-imidazole

To a solution of 4-benzyl-1H-imidazole (example 110C) (1.23 g, 7.78 mmoles) in ACN (20 mL) are added $K_2CO_3$ (1.29 g, 9.34 mmoles), $Cs_2CO_3$ (253 mg, 0.778 mmole) and methanesulfonic acid phenethyl ester (example 4D) (1.86 g, 9.34 mmole). The reaction mixture is heated at reflux overnight, then cooled to room temperature, filtered, cake washed with ACN and filtrate concentrated under reduced pressure. The residue is purified by silica gel chromatography using (toluene:acetone) (90:10) to give 4-benzyl-1-phenethyl-imidazole.

¹H NMR: 7.35-7.15 (m, 9H), 7.08-7.00 (m, 2H), 6.44 (s, 1H), 4.07 (t, J=8.6 Hz, 2H), 3.91 (s, 2H), 3.00 (t, J=8.6 Hz, 2H).

110C 4-benzyl-1H-imidazole

To a solution of 1-trityl-imidazole-4-carboxaldehyde (5 g, 14.8 mmoles) in THF (40 mL) is added dropwise a solution of 1M phenylmagnesium bromide in THF (17.7 mL, 17.7 mmoles). The reaction mixture is stirred at room temperature for 3 h, then it is poured into a saturated solution of $NH_4Cl$. The aqueous phase is extracted three times with $CH_2Cl_2$. The organic phase is dried over magnesium sulphate, filtered and the solvent is removed under reduced pressure. The residue is dissolved in concentrated HI solution (75 mL) and the reaction mixture is heated at reflux overnight. After cooling at room temperature, the reaction mixture is extracted three times with $Et_2O$. The aqueous phase is basified by adding solid $Na_2CO_3$ to pH 7, solid $NaHSO_3$ is added until the red colour disappeared and the aqueous phase is extracted three times with $Et_2O$. The organic phase is dried over magnesium sulphate, filtered and the solvent is removed under reduced pressure to give 4-benzyl-1H-imidazole.

Example 116

116A 2-methyl-4-(1-methylpiperidin-4-yloxy)-9,10-dihydro-4H-3,10a-diazabenzo[f]azulene-1-carboxylic acid ethyl ester The compound is synthesized using the method described in example 2A-B starting from 5-methyl-3-phenethyl-3H-imidazole-4-carboxylic acid ethyl ester (example 116B) to afford 2-methyl-4-(1-methylpiperidin-4-yloxy)-9,10-dihydro-4H-3,10a-diazabenzo[f]azulene-1-carboxylic acid ethyl ester.

HPLC-MS analysis using method A: rt=3.81 min; [M+H]⁺=384.27; [M+Na]⁺=406.25.

116B 5-methyl-3-phenethyl-imidazole-4-carboxylic acid ethyl ester and 5-methyl-1-phenethyl-imidazole-4-carboxylic acid ethyl ester The compounds are synthesized using the method described in example 103C starting from 5-methyl-3H-imidazole-4-carboxylic acid ethyl ester and methanesulfonic acid phenethyl ester (example 4D).

5-methyl-3-phenethyl-3H-imidazole-4-carboxylic acid ethyl ester

¹H NMR: 7.30-7.17 (m, 3H), 7.12 (s, 1H), 7.10-7.02 (m, 2H), 4.42 (t, J=7.2 Hz, 2H), 4.34 (q, J=7.0 Hz, 2H), 2.99 (t, J=7.2 Hz), 2.47 (s, 3H), 1.38 (t, J=7.0 Hz, 3H).

5-methyl-1-phenethyl-imidazole-4-carboxylic acid ethyl ester

¹H NMR: 7.30-7.21 (m, 3H), 7.20 (s, 1H), 7.05-6.95 (m, 2H), 4.33 (q, J=7.2 Hz, 2H), 4.08 (t, J=7.0 Hz, 2H), 2.97 (t, J=7.0 Hz), 2.37 (s, 3H), 1.37 (t, J=7.2 Hz, 3H).

Example 117

117A 2-[1-(4-chlorophenyl)-1-methyl-ethyl]-4-(1-methylpiperidin-4-yloxy)-9,10-dihydro-4H-3,10a-diaza-benzo[f]azulene oxalate The compound is synthesized using the methods described in example 110A-B starting from 4-[1-(4-chlorophenyl)-1-methyl-ethyl]-1H-imidazole (example 117B).

¹H NMR (base): 7.35-7.15 (m, 8H), 6.54 (s, 1H), 5.58 (s, 1H), 4.48-4.37 (m, 1H), 4.29-4.15 (m, 1H), 4.04-3.90 (m, 1H), 3.50-3.35 (m, 1H), 2.95-2.82 (m, 1H), 2.70-2.58 (m, 2H), 2.36 (s, 3H), 2.05-1.80 (m, 4H), 1.62 (s, 6H), 1.60-1.50 (m, 2H).

117B 4-[1-(4-chlorophenyl)-1-methyl-ethyl]-1H-imidazole

The compound is synthesized using the methods described in example 103D starting from toluene-4-sulfonic acid 3-(4-chlorophenyl)-3-methyl-2-oxo-butyl ester (example 117C).

¹H NMR: 7.50 (s, 1H), 7.27-7.18 (m, 4H), 6.79 (s, 1H), 6.42 (sl, NH), 1.66 (s, 6H).

117C toluene-4-sulfonic acid 3-(4-chlorophenyl)-3-methyl-2-oxo-butyl ester

The compound is synthesized using the methods described in examples 269C-E starting from 2-(4-chlorophenyl)-2-methyl-propionic acid.

Example 118

1-methyl-4-(1-methylpiperidin-4-yloxy)-9,10-dihydro-4H-3,10a-diaza-benzo[f]azulene-2-carboxylic acid ethyl ester The compound is synthesized using the method described in example 2A-B starting from 5-methyl-1-phenethyl-imidazole-4-carboxylic acid ethyl ester (example 116B) to afford 1-methyl-4-(1-methylpiperidin-4-yloxy)-9,10-dihydro-4H-3,10a-diaza-benzo[f]azulene-2-carboxylic acid ethyl ester.

HPLC-MS analysis using method A: rt=3.76 min; $[M+H]^+=384.27$; $[M+Na]^+=406.25$.

Example 120

120A 1-ethyl-4-(1-methylpiperidin-4-yloxy)-2-phenyl-9,10-dihydro-4H-3,10a-diaza-benzo[f]azulene oxalate The compound is synthesized using the methods described in example 110A-B starting from 5-ethyl-4-phenyl-1H-imidazole (example 120B).

$^1$H NMR (base): 7.62-7.65 (m, 2H), 7.45-7.20 (m, 7H), 5.68 (s, 1H), 4.52-4.40 (m, 1H), 4.30-4.15 (m, 1H), 3.98-3.83 (m, 1H), 3.63-3.50 (m, 1H), 3.07-2.92 (m, 1H), 2.82-2.65 (m, 4H), 2.29 (s, 3H), 2.28-2.10 (m, 2H), 2.05-1.62 (m, 4H), 1.30-1.20 (m, 3H).

120B 5-ethyl-4-phenyl-1H-imidazole

The compound is synthesized using the methods described in examples 269C and 103D starting from 1-phenylbutan-1-one.

$^1$H NMR: 7.60-7.50 (m, 3H), 7.45-7.33 (m, 2H), 7.30-7.20 (m, 1H), 2.85 (q, J=9.1 Hz, 2H), 1.30 (t, J=9.1 Hz, 3H).

Example 122

122A 2-(4-bromophenyl)-1-methyl-4-(1-methylpiperidin-4-yloxy)-9,10-dihydro-4H-3,10a-diaza-benzo[f]azulene The compound is synthesized using the methods described in example 110A-B starting from 4-(4-bromophenyl)-5-methyl-imidazole (example 122B). The compound is melting at 160° C.

122B 4-(4-bromophenyl)-5-methyl-imidazole

The compound is synthesized using the methods described in example 103D starting from 2-bromo-1-(4-bromophenyl)-propan-1-one.

$^1$H NMR (DMSO-d$^6$): 7.60-7.45 (m, 5H), 2.20 (s, 3H).

Example 123

123A 2-methyl-4-(1-methylpiperidin-4-yloxy)-1-phenyl-9,10-dihydro-4H-3,10a-diaza-benzo[f]azulene oxalate To a solution of methanesulfonic acid (1.5 mL) and 4-hydroxy-N-methylpiperidine (658 mg, 5.72 mmoles) in CHCl$_3$ (1 mL) cooled at 0° C. is added a solution of 2-methyl-1-phenyl-9,10-dihydro-4H-3,10a-diaza-benzo[f]azulen-4-ol (example 123B) (166.1 mg, 0.573 mmole) in CHCl$_3$ (2 mL) dropwise. The reaction mixture is allowed to slowly reach room temperature and is stirred at room temperature for 2 hours. The reaction mixture is poured into a solution of saturated Na$_2$CO$_3$ (final pH 9-10). The aqueous phase is extracted three times with CH$_2$Cl$_2$. The organic phase is dried over magnesium sulphate, filtered and the solvent is removed under reduced pressure. The residue is purified by silica gel chromatography using (CH$_2$Cl$_2$:MeOH:NH$_4$OH) with a gradient from (100:0:0) to (95:5:0.5) to give 2-methyl-4-(1-methylpiperidin-4-yloxy)-1-phenyl-9,10-dihydro-4H-3,10a-diaza-benzo[f]azulene.

$^1$H NMR: 7.48-7.13 (m, 9H), 5.63 (s, 1H), 4.35-4.21 (m, 1H), 4.18-4.00 (m, 1H), 3.84-3.70 (m, 1H), 3.55-3.41 (m, 1H), 2.93-2.79 (m, 1H), 2.77-2.60 (m, 2H), 2.27 (s, 3H), 2.22 (s, 3H), 2.11-1.94 (m, 2H), 1.94-1.76 m, 2H), 1.76-1.55 m, 2H).

The compound is dissolved in acetone (2 mL) and oxalic acid (1 equivalent) is added. The acetone is removed under reduced pressure to give 2-methyl-4-(1-methylpiperidin-4-yloxy)-1-phenyl-9,10-dihydro-4H-3,10a-diaza-benzo[f]azulene as an oxalate.

123B 2-methyl-1-phenyl-9,10-dihydro-4H-3,10a-diaza-benzo[f]azulen-4-ol

To a solution of methanesulfonic acid (10 mL) in CHCl$_3$ cooled at 0° C. is added a solution of 4-methyl-1-phenethyl-5-phenyl-imidazole-2-carbaldehyde (example 123C) (290 mg, 1 mmole) in CHCl$_3$ (2 mL) dropwise. The reaction mixture is allowed to slowly reach room temperature and is stirred at room temperature for 1 h. The reaction mixture is poured into a solution of saturated Na$_2$CO$_3$ (final pH 9-10). The precipitate is filtered, washed with water and filter-dried. The residual solid is re-crystallized from hot ACN to give 2-methyl-1-phenyl-9,10-dihydro-4H-3,10a-diaza-benzo[f]azulen-4-ol.

$^1$H NMR: 7.68-7.60 (m, 1H), 7.50-7.15 (m, 8H), 6.08 (s, 1H), 5.75 (sl, OH), 4.00-3.90 (m, 2H), 3.62-3.48 (m, 1H), 3.29-3.15 (m, 1H), 2.11 (s, 3H).

123C 4-methyl-1-phenethyl-5-phenyl-imidazole-2-carbaldehyde

The compound is prepared according to the procedure described in example 2B starting from 4-methyl-1-phenethyl-5-phenyl-imidazole (example 103C).

$^1$H NMR: 9.81 (s, 1H), 7.50-7.40 (m, 3H), 7.25-7.09 (m, 5H), 6.98-6.88 (m, 2H), 4.50-4.40 (m, 2H), 2.95-2.85 (m, 2H), 2021 (s, 3H).

Example 126

4-(1-methylpiperidin-4-yloxy)-2-(2-thiophen-2-yl-ethyl)-9,10-dihydro-4H-3,10a-diaza-benzo[f]azulene oxalate To a solution of 4-(1-methylpiperidin-4-yloxy)-2-(2-thiophen-2-ylvinyl)-9,10-dihydro-4H-3,10a-diaza-benzo[f]azulene (example 111) (100 mg, 0.247 mmole) in MeOH (10 mL) is added Pd—BaSO$_4$ (100 mg). The flask is evacuated and filled with hydrogen (balloon). The reaction mixture is stirred overnight at room temperature. The mixture is filtered over celite, the cake is washed with MeOH and the filtrate is concentrated under reduced pressure. The residue is dissolved in acetone (1 mL) and oxalic acid (1 equivalent) is added. Acetone is removed under reduced pressure to afford 4-(1-methylpiperidin-4-yloxy)-2-(2-thiophen-2-ylethyl)-9,10-dihydro-4H-3,10a-diaza-benzo[f]azulene as an oxalate.

Example 127

2-(4-bromophenyl)-1-chloro-4-(1-methylpiperidin-4-yloxy)-9,10-dihydro-4H-3,10a-diaza-benzo[f]azulene To a solution of 2-(4-bromophenyl)-4-(1-methylpiperidin-4-yloxy)-9,10-dihydro-4H-3,10a-diaza-benzo[f]azulene (example 81A) (140 mg, 0.31 mmole) in $CH_2Cl_2$ (7 mL) cooled at 0° C. is added N-chlorosuccinimide (41 mg, 0.31 mmole). The reaction mixture is stirred at 0° C. for 1 h then is allowed to reach room temperature. Another portion of N-chlorosuccinimide (60 mg) is added. After 1 hour at room temperature, AcOEt is added and the reaction mixture is basified to pH 10 with 1N NaOH solution. The organic phase is washed with water, dried over magnesium sulphate, filtered and the solvent is removed under reduced pressure. The residue is purified by silica gel chromatography using ($CH_2Cl_2$:MeOH) with a gradient from (100:0) to (90:10) to give 2-(4-bromophenyl)-1-chloro-4-(1-methylpiperidin-4-yloxy)-9,10-dihydro-4H-3,10a-diaza-benzo[f]azulene melting at 169° C.

The following compounds are prepared using the same method.

| example | product |
|---|---|
| 134 | 1-chloro-4-(1-methylpiperidin-4-yloxy)-2-phenyl-9,10-dihydro-4H-3,10a-diaza-benzo[f]azulene<br>mp = 65° C. |
| 139 | 1-chloro-4-(1-methylpiperidin-4-yloxy)-2-(5-phenylpentyl)-9,10-dihydro-4H-3,10a-diaza-benzo[f]azulene oxalate |
| 141 | {4-[1-chloro-4-(1-methylpiperidin-4-yloxy)-9,10-dihydro-4H-3,10a-diaza-benzo[f]azulen-2-yl]-phenyl}-carbamic acid tert-butyl ester<br>mp = 202° C. |

Example 130

{4-[1-methyl-4-(1-methylpiperidin-4-yloxy)-9,10-dihydro-4H-3,10a-diaza-benzo[f]azulen-2-yl]-phenyl}-carbamic acid tert-butyl ester In a screw-capped vial are added 2-(4-bromophenyl)-1-methyl-4-(1-methylpiperidin-4-yloxy)-9,10-dihydro-4H-3,10a-diaza-benzo[f]azulene (example 122A) (250 mg, 0.54 mmole), $Pd(dba)_2$ (25 mg, 27 µmole), Xantphos (31 mg, 54 µmole), $Cs_2CO_3$ (704 mg, 2.16 mmoles), 1,4-dioxane (3.4 mL) and tert-butyl carbamate (316 mg, 2.7 mmoles). The flask is evacuated and filled with argon. The reaction mixture is heated at 110° C. for 4 hours. Water is added and pH adjusted to 10 with a few drops of 1N NaOH. The aqueous phase is extracted three times with $CH_2Cl_2$. The organic phase is dried over magnesium sulphate, filtered and the solvent is removed under reduced pressure. The residue is purified by silica gel chromatography using ($CH_2Cl_2$:MeOH:$NH_4OH$) with a gradient from (100:0:0) to (95:5:0.5) to give {4-[1-methyl-4-(1-methylpiperidin-4-yloxy)-9,10-dihydro-4H-3,10a-diaza-benzo[f]azulen-2-yl]-phenyl}-carbamic acid tert-butyl ester melting at 194° C.

The following compounds are prepared using the same method and different kind of nitrogen nucleophiles.

| example | product |
|---|---|
| 125 | methyl-{4-[1-methyl-4-(1-methylpiperidin-4-yloxy)-9,10-dihydro-4H-3,10a-diaza-benzo[f]azulen-2-yl]-phenyl}carbamic acid tert-butyl ester<br>$^1$H NMR: 7.75-7.65 (m, 2H), 7.40-7.18 (m, 6H), 7.12 (s, 1H), 5.69 (s, 1H), 4.60-4.48 (m, 1H), 4.35-4.18 (m, 1H), 4.14-4.00 (m, 1H), 3.60-3.48 (m, 1H), 3.26 (s, 3H), 3.00-2.88 (m, 1H), 2.75-2.60 (m, 1H), 2.23 (s, 3H), 2.18-1.85 (m, 3H), 1.85-1.55 (m, 6H), 1.45 (s, 9H). |
| 132 | 1-methyl-3-{4-[1-methyl-4-(1-methylpiperidin-4-yloxy)-9,10-dihydro-4H-3,10a-diaza-benzo[f]azulen-2-yl]-phenyl}-imidazolidin-2-one<br>mp = 142° C. |
| 140 | 1-tert-butyl-3-{4-[1-methyl-4-(1-methylpiperidin-4-yloxy)-9,10-dihydro-4H-3,10a-diaza-benzo[f]azulen-2-yl]-phenyl}-imidazolidin-2-one<br>mp = 138° C. |
| 172 | {4-[1-methyl-4-(1-methylpiperidin-4-yloxy)-9,10-dihydro-4H-3,10a-diaza-benzo[f]azulen-2-yl]-phenyl}-carbamic acid cyclopentyl ester<br>mp = 131° C. |
| 176 | 4-benzyl-3-{4-[1-methyl-4-(1-methylpiperidin-4-yloxy)-9,10-dihydro-4H-3,10a-diaza-benzo[f]azulen-2-yl]-phenyl}-oxazolidin-2-one<br>mp = 125° C. |
| 178 | 1-isopropyl-3-{4-[1-methyl-4-(1-methylpiperidin-4-yloxy)-9,10-dihydro-4H-3,10a-diaza-benzo[f]azulen-2-yl]-phenyl}-imidazolidin-2-one<br>mp = 131° C. |
| 213 | 1-adamantan-1-yl-3-{4-[1-methyl-4-(1-methylpiperidin-4-yloxy)-9,10-dihydro-4H-3,10a-diaza-benzo[f]azulen-2-yl]-phenyl}-urea<br>$[M + H]^+ = 580.54$ |
| 214 | N-{4-[1-methyl-4-(1-methylpiperidin-4-yloxy)-9,10-dihydro-4H-3,10a-diaza-benzo[f]azulen-2-yl]-phenyl}-hydrazinecarboxylic acid tert-butyl ester<br>mp = 122° C. |

Example 131

3-{4-[1-methyl-4-(1-methylpiperidin-4-yloxy)-9,10-dihydro-4H-3,10a-diaza-benzo[f]azulen-2-yl]-phenyl}-oxazolidin-2-one In a screw-capped vial are added 2-(4-bromophenyl)-1-methyl-4-(1-methylpiperidin-4-yloxy)-9,10-dihydro-4H-3,10a-diaza-benzo[f]azulene (example 122A) (50 mg, 0.107 mmole), $Pd(dba)_2$ (4.9 mg, 5.3 µmole), Xantphos (6.2 mg, 10.6 µmole), 1,4-dioxane (0.7 mL) and N-trimethylsilyloxazolidonone (25 µL, 0.16 mmoles). The flask is evacuated and filled with argon. $Bu_4NF$ 1M in THF (160 µL, 0.16 mmole) is added and the reaction mixture is heated at 110° C. overnight. Water is added and pH adjusted to 10 with a few drops of 1N NaOH. The aqueous phase is extracted three times with $CH_2Cl_2$. The organic phase is dried over magnesium sulphate, filtered and the solvent is removed under reduced pressure. The residue is pre-purified by silica gel chromatography using ($CH_2Cl_2$:MeOH:$NH_4OH$) with a gradient from (100:0:0) to (95:5:0.5). The residue is submitted to a preparative TLC eluting with ($CH_2Cl_2$:MeOH:$NH_4OH$) (92.5:7.5:0.75) to give 3-{4-[1-methyl-4-(1-methylpiperidin-4-yloxy)-9,10-dihydro-4H-3,10a-diaza-benzo[f]azulen-2-yl]-phenyl}-oxazolidin-2-one melting at 214° C.

Example 133

2-iodo-1-methyl-4-(1-methylpiperidin-4-yloxy)-9,10-dihydro-4H-3,10a-diaza-benzo[f]azulene The compound is synthesized using the same method described in example 2 starting from 4-iodo-5-methyl-1H- imidazole to give 2-iodo-1-methyl-4-(1-methylpiperidin-4-yloxy)-9,10-dihydro-4H-3,10a-diaza-benzo[f]azulene melting at 59° C.

Example 135

Mixture of enantiomers of 1-methyl-4-(1-methylpiperidin-4-yloxy)-2-phenyl-9,10-dihydro-4H-3,10a-diaza-benzo[f]azulene (example 103)

A mixture of both enantiomers of 1-methyl-4-(1-methylpiperidin-4-yloxy)-2-phenyl-9,10-dihydro-4H-3,10a-diaza-benzo[f]azulene (example 103) are separated using a preparative HPLC. The preparative separation of the racemate was performed on a 25.4×4.8 cm column, which was packed with 290 g of a pre-used Chiralpak AD, 20 Cm stationary phase. The racemate was dissolved in 2 mL of EtOH resulting in a clear solution. Two runs were made with a loading of 1 mL of feed solution. The separations were performed at room temperature using a flow rate of 100 mL/min. The eluent n-heptane:EtOH:DEA=95:5:0.1 (v:v:v) was used. Compounds were detected at 254 nm.

Separated compounds were submitted to HPLC analysis on a Chiralpak AD column eluting with n-heptane:EtOH:DEA=95:5:0.1 (v:v:v) using a flow rate of 1 mL/min.

135A Enantiomer A; retention time=10.30 min; enantiomeric purity=100%

135B Enantiomer B; retention time=24.10 min; enantiomeric purity=99.45%

Example 143

2-(3-fluorophenyl)-1-methyl-4-(1-methylpiperidin-4-yloxy)-9,10-dihydro-4H-3,10a-diaza-benzo[f]azulene To a solution of 2-iodo-1-methyl-4-(1-methylpiperidin-4-yloxy)-9,10-dihydro-4H-3,10a-diaza-benzo[f]azulene (example 133) (100 mg, 0.23 mmole) in toluene (2 mL) and ethanol (1 mL) in a screw-capped vial are added 3-fluorobenzeneboronic acid (64 mg, 0.46 mmole), [1,1'-bis(diphenylphosphino)ferrocene]dichloropalladium (10 mg) and an 1M aqueous solution of potassium carbonate (0.8 mL). The vial is evacuated and filled with argon. The reaction mixture is stirred at 95° C. for 20 hours. Water is added to the reaction mixture, and the pH is adjusted to 9-10 with 1N aqueous sodium hydroxide. The aqueous phase is extracted three times with ethyl acetate. The pooled organic extracts are dried over magnesium sulphate, filtered and the solvent is removed under reduced pressure. The residue is purified by silica gel chromatography using (CH$_2$Cl$_2$:MeOH:NH$_4$OH) as eluent with a gradient from (95:5:0.1) to (92:8:0.5) to give 2-(3-fluorophenyl)-1-methyl-4-(1-methylpiperidin-4-yloxy)-9,10-dihydro-4H-3,10a-diaza-benzo[f]azulene melting at 132° C.

The following compounds are prepared using the same method and different kinds of boronic acids or boronic acids pinacol esters.

| example | product | mp ° C. |
|---|---|---|
| 142 | 2-(2-fluorophenyl)-1-methyl-4-(1-methylpiperidin-4-yloxy)-9,10-dihydro-4H-3,10a-diaza-benzo[f]azulene | 68 |
| 144 | 1-methyl-4-(1-methylpiperidin-4-yloxy)-2-m-tolyl-9,10-dihydro-4H-3,10a-diaza-benzo[f]azulene | 66 |

-continued

| example | product | mp ° C. |
|---|---|---|
| 145 | 2-(3-chlorophenyl)-1-methyl-4-(1-methylpiperidin-4-yloxy)-9,10-dihydro-4H-3,10a-diaza-benzo[f]azulene | 72 |
| 146 | 2-(2-chlorophenyl)-1-methyl-4-(1-methylpiperidin-4-yloxy)-9,10-dihydro-4H-3,10a-diaza-benzo[f]azulene | 78 |
| 147 | 1-methyl-4-(1-methylpiperidin-4-yloxy)-2-o-tolyl-9,10-dihydro-4H-3,10a-diaza-benzo[f]azulene | 74 |
| 148 | 1-methyl-4-(1-methylpiperidin-4-yloxy)-2-thiophen-3-yl-9,10-dihydro-4H-3,10a-diaza-benzo[f]azulene | 74 |
| 149 | 2-(2-methoxyphenyl)-1-methyl-4-(1-methylpiperidin-4-yloxy)-9,10-dihydro-4H-3,10a-diaza-benzo[f]azulene | 139 |
| 150 | 2-(3-methoxyphenyl)-1-methyl-4-(1-methypiperidin-4-yloxy)-9,10-dihydro-4H-3,10a-diaza-benzo[f]azulene | 138 |
| 153 | 1-methyl-4-(1-methylpiperidin-4-yloxy)-2-p-tolyl-9,10-dihydro-4H-3,10a-diaza-benzo[f]azulene | 181 |
| 154 | 2-(4-fluorophenyl)-1-methyl-4-(1-methylpiperidin-4-yloxy)-9,10-dihydro-4H-3,10a-diaza-benzo[f]azulene | 168 |
| 155 | 2-(4-chlorophenyl)-1-methyl-4-(1-methylpiperidin-4-yloxy)-9,10-dihydro-4H-3,10a-diaza-benzo[f]azulene | 158 |
| 156 | 2-(4-methoxyphenyl)-1-methyl-4-(1-methylpiperidin-4-yloxy)-9,10-dihydro-4H-3,10a-diaza-benzo[f]azulene | 164 |
| 157 | 2-(2-chloro-4-methylphenyl)-1-methyl-4-(1-methylpiperidin-4-yloxy)-9,10-dihydro-4H-3,10a-diaza-benzo[f]azulene | 133 |

Example 151

3-{4-[1-methyl-4-(1-methylpiperidin-4-yloxy)-9,10-dihydro-4H-3,10a-diaza-benzo[f]azulen-2-yl]-phenyl}-acrylic acid tert-butyl ester To a solution of 2-(4-bromophenyl)-1-methyl-4-(1-methylpiperidin-4-yloxy)-9,10-dihydro-4H-3,10a-diaza-benzo[f]azulene (example 122A) (100 mg, 0.214 mmoles) in DMF (2.5 mL) in a screw-capped vial under argon are added Pd(OAc)$_2$ (5 mg, 10.7 µmole), PPh$_3$ (14 mg, 53.5 µmole), tert-butylacrylate (196 µL, 1.07 mmole) and triethylamine (115 µL, 0.856 mmole). The reaction mixture is heated at 100° C. overnight. Water is added to the reaction mixture and pH adjusted to 9-10 by adding concentrated ammonia solution. The aqueous phase is extracted three times with CH$_2$Cl$_2$. The organic phase is dried over magnesium sulphate, filtered and the solvent is removed under reduced pressure. The residue is pre-purified by silica gel chromatography using (CH$_2$Cl$_2$:MeOH:NH$_4$OH) as eluent with a gradient from (98:2:0.1) to (96.5:3.5:0.35) and the residue is submitted to a preparative thin-layer chromatography eluting with (CH$_2$Cl$_2$:MeOH:NH$_4$OH) (9:1:1) to afford 3-{4-[1-methyl-4-(1-methylpiperidin-4-yloxy)-9,10-dihydro-4H-3,10a-diaza-benzo[f]azulen-2-yl]-phenyl}-acrylic acid tert-butyl ester melting at 185° C.

The following compound is prepared using the same method using another kind of activated double-bond.

| example | product |
|---|---|
| 158 | 2-[4-(2-methanesulfonyl-vinyl)-phenyl]-1-methyl-4-(1-methylpiperidin-4-yloxy)-9,10-dihydro-4H-3,10a-diaza-benzo[f]azulene<br>mp = 152° C. |

Example 152

3-methyl-3-{4-[1-methyl-4-(1-methylpiperidin-4-yloxy)-9,10-dihydro-4H-3,10a-diaza-benzo[f]azulen-2-yl]-phenylsulfanyl}-butan-1-ol To a solution of compound 2-(4-bromophenyl)-1-methyl-4-(1-methylpiperidin-4-yloxy)-9,10-dihydro-4H-3,10a-diaza-benzo[f]azulene (example 122A) (60 mg, 0.129 mmoles) in 1,4-dioxane (1.5 mL) in a screw-capped vial under argon are added diisopropylethylamine (33 µL, 0.142 mmole), 3-mercapto-3-methylbutan-1-ol (20 µL, 0.193 mmole), bis(dibenzilideneacetone)palladium(0) (4 mg, 6.4 µmole), Xantphos (4 mg, 6.4 µmole). The reaction mixture is heated at 110° C. overnight. As the reaction is not complete, bis(dibenzilideneacetone)Palladium(0) (4 mg, 6.4 µmole), Xantphos (4 mg, 6.4 µmole), diisopropylethylamine (33 µL, 0.142 mmole), 3-mercapto-3-methylbutan-1-ol (20 µL, 0.193 mmole) are added to the reaction mixture. After one overnight at 120° C., water is added to the reaction mixture and pH adjusted to 9-10 by adding concentrated ammonia solution. The aqueous phase is extracted three times with $CH_2Cl_2$. The organic phase is dried over magnesium sulphate, filtered and the solvent is removed under reduced pressure. The residue is purified by silica gel chromatography using ($CH_2Cl_2$:MeOH) as eluent with a gradient from (95:5) to (90:10) to afford 3-methyl-3-{4-[1-methyl-4-(1-methylpiperidin-4-yloxy)-9,10-dihydro-4H-3,10a-diaza-benzo[f]azulen-2-yl]-phenylsulfanyl}-butan-1-ol.

NMR1H, 7.65-7.50 (m, 4H), 7.38-7.20 (m, 5H), 5.67 (s, 1H), 4.45-4.25 (m, 2H), 3.98-3.70 (m, 4H), 3.75-3.52 (m, 1H), 3.05-2.90 (m, 1H), 2.82-2.67 (m, 2H), 2.36 (s, 3H), 2.23 (s, 3H), 2.10-1.55 (m, 8H), 1.29 (s, 6H).

The following compounds are prepared using the same method using different kinds of sulfides.

Example 162

1-{4-[1-methyl-4-(1-methylpiperidin-4-yloxy)-9,10-dihydro-4H-3,10a-diaza-benzo[f]azulen-2-yl]-phenyl}-piperidin-2-one oxalate In a screw-capped vial are added MeOH (3.5 mL) and sodium metal (2 mg). After 10 min, valerolactam (16 mg, 0.16 mmole) is added. The solvent is removed under reduced pressure. To the residual solid are added 2-(4-bromophenyl)-1-methyl-4-(1-methylpiperidin-4-yloxy)-9,10-dihydro-4H-3,10a-diaza-benzo[f]azulene (example 122A) (50 mg, 0.107 mmole), Pd(dba)$_2$ (4.9 mg, 5.3 µmole), Xantphos (6.2 mg, 10.6 µmole), toluene (0.7 mL). The flask is evacuated and filled with argon and the reaction mixture is heated at 110° C. overnight. Water is added and pH adjusted to 10 with a few drops of 1N NaOH. The aqueous phase is extracted three times with $CH_2Cl_2$. The organic phase is dried over magnesium sulphate, filtered and the solvent is removed under reduced pressure. The residue is purified by silica gel chromatography using ($CH_2Cl_2$:MeOH:$NH_4OH$) with a gradient from (100:0:0) to (96.5:3.5:0.35) to give 1-{4-[1-methyl-4-(1-methylpiperidin-4-yloxy)-9,10-dihydro-4H-3,10a-diaza-benzo[f]azulen-2-yl]-phenyl}-piperidin-2-one.

$[M+H]^+=485.4$.

The residual solid is dissolved in acetone (0.3 mL) and oxalic acid (1 equivalent) is added. Acetone is removed under reduced pressure to give 1-{4-[1-methyl-4-(1-methylpiperidin-4-yloxy)-9,10-dihydro-4H-3,10a-diaza-benzo[f]azulen-2-yl]-phenyl}-piperidin-2-one as an oxalate.

| example | product |
|---|---|
| 160 | (2-{4-[1-methyl-4-(1-methylpiperidin-4-yloxy)-9,10-dihydro-4H-3,10a-diaza-benzo[f]azulen-2-yl]-phenylsulfanyl}-ethyl)-carbamic acid tert-butyl ester oxalate $[M + H]^+ = 563.42$ |
| 163 | N-(2-{4-[1-methyl-4-(1-methylpiperidin-4-yloxy)-9,10-dihydro-4H-3,10a-diaza-benzo[f]azulen-2-yl]-phenylsulfanyl}-ethyl)-acetamide oxalate |
| | NMR $^1$H (base): 7.58-7.50 (m, 2H), 7.45-7.37 (m, 2H), 7.35-7.20 (m, 4H), 5.83 (sl, NH), 5.67 (s, 1H), 4.45-4.35 (m, 2H), 3.90-3.75 (m, 1H), 3.58-3.42 (m, 3H), 3.06 (t, J = 7.4 Hz, 2H), 3.00-2.89 (m, 1H), 2.75-2.60 (m, 2H), 2.32 (s, 3H), 2.23 (s, 3H), 2.15-1.98 (m, 2H), 1.95 (s, 3H), 1.93-1.75 (m, 2H), 1.75-1.55 (m, 2H). |
| 164 | 2-(4-benzylsulfanylphenyl)-1-methyl-4-(1-methylpiperidin-4-yloxy)-9,10-dihydro-4H-3,10a-diaza-benzo[f]azulene oxalate |
| | NMR $^1$H (base): 7.50-7.41 (m, 2H), 7.35-7.18 (m, 11H), 5.64 (s, 1H), 4.38-4.20 (m, 2H), 4.12 (, 2H), 3.88-4.75 (m, 1H), 3.74-3.60 (m, 1H), 3.05-2.75 (m, 3H), 2.41 (s, 3H), 2.31 (s, 3H), 2.15-1.70 (m, 6H). |
| 165 | {4-[1-methyl-4-(1-methylpiperidin-4-yloxy)-9,10-dihydro-4H-3,10a-diaza-benzo[f]azulen-2-yl]-phenylsulfanyl}-acetic acid methyl ester oxalate |
| | NMR $^1$H (base): 7.55-7.38 (m, 4H), 7.35-7.20 (m, 4H), 5.66 (s, 1H), 4.38-4.22 (m, 2H), 3.90-3.75 (m, 1H), 3.72 (s, 3H), 3.66 (s, 2H), 3.65-3.52 (m, 1H), 3.05-2.90 (m, 1H), 2.85-2.68 (m, 2H), 2.50-2.20 (m, 2H), 2.32 (s, 3H), 2.30 (s, 3H), 1.95-1.60 (m, 4H). |
| 166 | 2-(4-tert-butylsulfanylphenyl)-1-methyl-4-(1-methylpiperidin-4-yloxy)-9,10-dihydro-4H-3,10a-diaza-benzo[f]azulene oxalate |
| | NMR $^1$H (base): 7.58-7.50 (m, 4H), 7.35-7.18 (m, 4H), 5.68 (s, 1H), 4.42-4.25 (m, 2H), 3.90-3.75 (m, 1H), 3.62-3.48 (m, 1H), 3.03-2.90 (m, 1H), 2.79-2.62 (m, 2H), 2.34 (s, 3H), 2.26 (s, 3H), 2.22-2.05 (m, 2H), 1.95-1.60 (m, 4H), 1.30 (s, 9H). |
| 167 | 2-[4-(furan-2-ylmethylsulfanyl)-phenyl]-1-methyl-4-(1-methylpiperidin-4-yloxy)-9,10-dihydro-4H-3,10a-diaza-benzo[f]azulene oxalate |
| | NMR $^1$H (base): 7.55-7.42 (m, 2H), 7.40-7.18 (m, 7H), 6.30-3.23 (m, 1H), 6.12-6.05 (m, 1H), 5.66 (s, 1H), 4.40-4.20 (m, 2H), 4.10 (s, 2H), 3.92-3.75 (m, 1H), 3.72-3.60 (m, 1H), 3.03-2.70 (m, 3H), 2.60-2.40 (m, 2H), 2.38 (s, 3H), 2.32 (s, 3H), 2.08-1.70 (m, 4H). |
| 194 | 3-{4-[4-(1-methylpiperidin-4-yloxy)-9,10-dihydro-4H-3,10a-diaza-benzo[f]azulen-2-yl]-phenylsulfanyl}-propane-1,2-diol $[M + H]^+ = 494.33$ |
| 195 | 3-{4-[4-(1-methylpiperidin-4-yloxy)-9,10-dihydro-4H-3,10a-diaza-benzo[f]azulen-2-yl]-phenylsulfanyl}-propan-1-ol |
| | NMR $^1$H: 7.55-7.47 (m, 2H), 7.43-7.20 (m, 6H), 5.68 (s, 1H), 4.45-4.25 (m, 2H), 3.90-3.72 (m, 3H), 3.59-3.45 (m, 1H), 3.10-2.90 (m, 3H), 2.75-2.60 (m, 2H), 2.31 (s, 3H), 2.22 (s, 3H), 2.15-2.00 (m, 2H), 1.95-1.78 (m, 4H), 1.75-1.55 (m, 2H). |

Example 168

4-{4-[1-methyl-4-(1-methyl-piperidin-4-yloxy)-9,10-dihydro-4H-3,10a-diaza-benzo[f]azulen-2-yl]-phenyl}-3,6-dihydro-2H-pyridine-1-carboxylic acid tert-butyl ester To a solution of compound 2-(4-bromophenyl)-1-methyl-4-(1-methylpiperidin-4-yloxy)-9,10-dihydro-4H-3,10a-diaza-benzo[f]azulene (example 122A) (100 mg, 0.214 mmoles) in 1,4-dioxane (1 mL) in a screw-capped vial under argon are added $K_2CO_3$ (89 mg, 0.642 mmole), $PdCl_2(dppf)_2$ (6 mg, 10.7 µmole), water (0.2 mL) and 4-(4,4,5,5-tetramethyl[1,3,2]dioxaborolan-2-yl)-3,6-dihydro-2H-pyridine-1-carboxylic acid tert-butyl ester (99 mg, 0.321 mmole). The reaction mixture is heated at 100° C. overnight. Water is added to the reaction mixture and pH adjusted to 9-10 by adding concentrated ammonia solution. The aqueous phase is extracted three times with $CH_2Cl_2$. The organic phase is dried over magnesium sulphate, filtered and the solvent is removed under reduced pressure. The residue is pre-purified by silica gel chromatography using ($CH_2Cl_2$:MeOH:$NH_4OH$) with a gradient from (98:2:0.2) to (96.5:3.5:0.35). The residue is purified by preparative TLC over silica gel using ($CH_2Cl_2$:MeOH:$NH_4OH$) with a gradient from (9:1:1) to afford 4-{4-[1-methyl-4-(1-methyl-piperidin-4-yloxy)-9,10-dihydro-4H-3,10a-diaza-benzo[f]azulen-2-yl]-phenyl}-3,6-dihydro-2H-pyridine-1-carboxylic acid tert-butyl ester melting at 171° C.

The following compounds are prepared using the same method and different kinds of boronic acids or boronic acids pinacol esters.

| example | product |
|---|---|
| 169 | 2-(4-cyclopent-1-enylphenyl)-1-methyl-4-(1-methylpiperidin-4-yloxy)-9,10-dihydro-4H-3,10a-diaza-benzo[f]azulene<br>mp = 184° C. |
| 170 | 2-(4-cyclohex-1-enylphenyl)-1-methyl-4-(1-methylpiperidin-4-yloxy)-9,10-dihydro-4H-3,10a-diaza-benzo[f]azulene<br>mp = 173° C. |
| 171 | 2-(4-cyclohept-1-enylphenyl)-1-methyl-4-(1-methylpiperidin-4-yloxy)-9,10-dihydro-4H-3,10a-diaza-benzo[f]azulene<br>mp = 126° C. |

Example 174

{4-[1-Methyl-4-(1-methyl-piperidin-4-yloxy)-9,10-dihydro-4H-3,10a-diaza-benzo[f]azulen-2-yl]-phenyl}-carbamic acid isobutyl ester To a solution of 4-[1-methyl-4-(1-methylpiperidin-4-yloxy)-9,10-dihydro-4H-3,10a-diaza-benzo[f]azulen-2-yl]-phenylamine (example 173) (50 mg, 0.124 mmole) in $CH_2Cl_2$ (0.5 mL) is added 4-dimethylaminopyridine (17 mg, 0.136 mmole). The reaction mixture is cooled to 0° C. and isobutylchloroformate (18 µL, 0.136 mmole) is added dropwise. The reaction mixture is stirred at room temperature 2 h, diluted with water and made alkaline with 1N NaOH. The aqueous phase is extracted three times with $CH_2Cl_2$. The organic phase is dried over magnesium sulphate, filtered and the solvent is removed under reduced pressure. The residue is purified by preparative TLC over silica gel eluting with (acetone:$NEt_3$) to afford {4-[1-methyl-4-(1-methyl-piperidin-4-yloxy)-9,10-dihydro-4H-3,10a-diaza-benzo[f]azulen-2-yl]-phenyl}-carbamic acid isobutyl ester melting at 196° C.

The following compound is prepared using the same method and different kind of chloroformate.

| example | product |
|---|---|
| 175 | {4-[1-methyl-4-(1-methylpiperidin-4-yloxy)-9,10-dihydro-4H-3,10a-diaza-benzo[f]azulen-2-yl]-phenyl}-carbamic acid 2,2,2-trichloro-1,1-dimethyl-ethyl ester<br>mp = 179° C. |

Example 187

4-[1-methyl-4-(1-methylpiperidin-4-yloxy)-9,10-dihydro-4H-3,10a-diaza-benzo[f]azulen-2-yl]-phenyl-cyclopropanesulfonamide To a solution of 4-[1-methyl-4-(1-methyl piperidin-4-yloxy)-9,10-dihydro-4H-3,10a-diaza-benzo[f]azulen-2-yl]-phenylamine (example 173) (50 mg, 0.124 mmole) in $CH_2Cl_2$ (0.5 mL) is added 4-dimethylaminopyridine (17 mg, 0.136 mmole). The reaction mixture is cooled to 0° C. and cyclopropylsulfonyl chloride (24 µL, 0.136 mmole) is added dropwise. The reaction mixture is stirred at room temperature 2 hours. MeOH is added as well as solid $K_2CO_3$. After stirring at room temperature overnight, solvents are removed under reduced pressure. The residue is diluted with water and made alkaline with 1N NaOH. The aqueous phase is extracted three times with $CH_2Cl_2$. The organic phase is dried over magnesium sulphate, filtered and the solvent is removed under reduced pressure. The residue is purified by silica gel chromatography eluting with ($CH_2Cl_2$:MeOH:$NH_4OH$) from (98:2:02) to (96.5:3.5:0.35) to give 4-[1-methyl-4-(1-methylpiperidin-4-yloxy)-9,10-dihydro-4H-3,10a-diaza-benzo[f]azulen-2-yl]-phenyl-cyclopropanesulfonamide.

$[M+H]^+$=507.33.

Example 200 tert-butyl-carbamic acid 2-{4-[4-(1-methylpiperidin-4-yloxy)-9,10-dihydro-4H-3,10a-diaza-benzo[f]azulen-2-yl]-phenyl}-ethyl ester To a solution of 2-{4-[4-(1-methylpiperidin-4-yloxy)-9,10-dihydro-4H-3,10a-diaza-benzo[f]azulen-2-yl]-phenyl}-ethanol (example 192) (53 mg, 0.127 mmole) in DMF (1 mL) are added tertbutylisocyanate (16 mg, 0.26 mmole) and CuCl (13 mg, 0.13 mmole). The reaction mixture is heated at 50° C. for 24 hours. Water is added, and 1N NaOH to reach pH 9-10. The aqueous phase is extracted three times with AcOEt, and the organic phase is washed with water, brine, dried over $MgSO_4$, filtered and the solvent is removed under reduced pressure. The residue is purified by silica gel chromatography eluting with ($CH_2Cl_2$:MeOH) with a gradient from (98:2) to (9:1) then ($CH_2Cl_2$:MeOH:$NH_4OH$) (9:9:1) to give tert-butyl-carbamic acid 2-{4-[4-(1-methylpiperidin-4-yloxy)-9,10-dihydro-4H-3,10a-diaza-benzo[f]azulen-2-yl]-phenyl}-ethyl ester.

$[M+H]^+$=517.45

Example 201

[1-methyl-4-(1-methylpiperidin-4-yloxy)-9,10-dihydro-4H-3,10a-diaza-benzo[f]azulen-2-yl]phenyl-methanol, formic acid salt To a solution of 2-iodo-1-methyl-4-(1-methylpiperidin-4-yloxy)-9,10-dihydro-4H-3,10a-diaza-benzo[f]azulene (example 133) (80 mg, 0, 18 mmole) in dichloromethane (3 mL) is added a 3M solution of ethylmagnesium bromide in diethyl ether (300 µL, 0.30 mmole) at room temperature. After stirring for 15 minutes benzaldehyde (91 µL, 0.90 mmole) is then added. One hour later the reaction mixture is diluted with water and extracted with dichloromethane. Pooled extracts are dried over magnesium sulphate and concentrated under reduced pressure. The residue is purified by preparative HPLC-MS (Waters AutoPurification HPLC/MS System, Sunfire Prep C18 5 µm OBD 30×150 mm column, eluents: water/0.1% formic acid (A) and acetonitrile/0.1% formic acid (B), linear gradient from 5% (B) to 40% (B) in 10 minutes) to afford pure [1-methyl-4-(1-methylpiperidin-4-yloxy)-9,10-dihydro-4H-3,10a-diaza-benzo[f]azulen-2-yl]phenylmethanol, formic acid salt, melting at 85° C.

Example 202

[1-methyl-4-(1-methylpiperidin-4-yloxy)-9,10-dihydro-4H-3,10a-diaza-benzo[f]azulen-2-yl]phenyl-methanone, formic acid salt

[1-Methyl-4-(1-methyl piperidin-4-yloxy)-9,10-dihydro-4H-3,10a-diaza-benzo[f]azulen-2-yl]phenylmethanone, formic acid salt melting at 71° C. is isolated by preparative HPLC-MS as side-product in the synthesis of example 201.

Example 203

1-methyl-4-(1-methylpiperidin-4-yloxy)-9,10-dihydro-4H-3,10a-diaza-benzo[f]azulene-2-carboxylic acid benzylmethylamide A mixture of 2-iodo-1-methyl-4-(1-methylpiperidin-4-yloxy)-9,10-dihydro-4H-3,10a-diaza-benzo[f]azulene (example 133) (80 mg, 0.18 mmole), N-benzylmethylamine (42 µL, 0.32 mmole), 1,8-diazabicyclo(5.4.0)undec-7-ene (24 µL, 0.16 mmole), trans-di-µ-acetatobis[2-(di-o-tolyl-phosphino)-benzyl]dipalladium(II) (11.5 mg), tri-tertbutylphosphonium tetrafluoroborate (8.5 mg) and molybdenum hexacarbonyl (30 mg, 0, 11 mmole) in tetrahydrofuran (1.5 mL) are introduced in a screw-capped vial. The vial is stirred at 130° C. for 1.5 hours, then cooled to room temperature, diluted with ethyl acetate and 1N aqueous sodium hydroxide. The organic phase is dried over magnesium sulphate and concentrated under reduced pressure. The residue is purified by preparative HPLC-MS (Waters AutoPurification HPLC/MS System, Sunfire Prep C18 5 µm OBD 30×150 mm column, eluents: water/0.1% formic acid (A) and acetonitrile/0.1% formic acid (B), focus gradient from 21% (B) to 31% (B) in 10 minutes) to afford pure 1-methyl-4-(1-methylpiperidin-4-yloxy)-9,10-dihydro-4H-3,10a-diaza-benzo[f]azulene-2-carboxylic acid benzylmethylamide melting at 61° C.

Example 204

1-methyl-4-(1-methylpiperidin-4-yloxy)-9,10-dihydro-4H-3,10a-diaza-benzo[f]azulene-2-carboxylic acid methylphenylamide 1-Methyl-4-(1-methylpiperidin-4-yloxy)-9,10-dihydro-4H-3,10a-diaza-benzo[f]azulene-2-carboxylic acid methylphenylamide melting at 75° C. is prepared analogously to example 203.

Example 205

1-methyl-4-(1-methylpiperidin-4-yloxy)-9,10-dihydro-4H-3,10a-diaza-benzo[f]azulene-2-carboxylic acid propylamide 1-Methyl-4-(1-methylpiperidin-4-yloxy)-9,10-dihydro-4H-3,10a-diaza-benzo[f]azulene-2-carboxylic acid propylamide melting at 60° C. is prepared analogously to example 203.

Example 206

1-isopropyl-3-{4-[4-(1-methylpiperidin-4-yloxy)-9,10-dihydro-4H-3,10a-diaza-benzo[f]azulen-2-yl]-phenyl}-thiourea To a solution of 4-[1-methyl-4-(1-methyl piperidin-4-yloxy)-9,10-dihydro-4H-3,10a-diaza-benzo[f]azulen-2-yl]-phenylamine (example 173) (50 mg, 0.124 mmole) in ACN (1 mL) are added DIEA (65 µL, 0.372 mmole) and isopropyl-isothiocyanate (18.8 mg, 0.182 mmole). The reaction mixture is heated overnight at 80° C. Solvent is removed under reduced pressure. The residue is purified by silica gel chromatography eluting with ($CH_2Cl_2$:MeOH:$NH_4OH$) from (98:2:02) to (96.5:3.5:0.35) to give 1-isopropyl-3-{4-[1-methyl-4-(1-methylpiperidin-4-yloxy)-9,10-dihydro-4H-3,10a-diazabenzo[f]azulen-2-yl]-phenyl}-thiourea. $[M+H]^+$= 504.37.

The following compound is prepared using the same method.

| example | product |
|---------|---------|
| 208 | 1-cyclopropyl-3-{4-[1-methyl-4-(1-methylpiperidin-4-yloxy)-9,10-dihydro-4H-3,10a-diaza-benzo[f]azulen-2-yl]-phenyl}-thiourea<br>mp = 170° C. |

Example 207

207A 2-(1-methyl-1-phenyl-ethyl)-4-(1-methylpiperidin-4-yloxy)-9,10-dihydro-4H-3,10a-diaza-benzo [f]azulene The compound is synthesized using the method described in example 2A, 2B and 110B starting from 4-(1-methyl-1-phenylethyl) imidazole (example 207B).

HPLC-MS analysis using method C: rt=4.68 min; $[M+H]^+$=416.32.

207B 4-(1-methyl-1-phenylethyl)-1H-imidazole

The compound is synthesized using the method described in example 103D starting from toluene-4-sulfonic acid 3-methyl-2-oxo-3-phenyl-butyl ester (example 207C) to give 4-(1-Methyl-1-phenyl-ethyl)-1H-imidazole.

$NMR^1H$, 7.48 (s, 1H), 7.32-7.23 (m, 4H), 7.20-7.13 (m, 1H), 6.82 (s, 1H), 5.28 (sl, NH), 4.67 (s, 6H).

207C toluene-4-sulfonic acid 3-methyl-2-oxo-3-phenyl-butyl ester

To a solution of 3-methyl-3-phenyl-butan-2-one (example 207D) (8.7 g, 53.6 mmoles) in ACN (150 mL) is added hydroxy(tosyloxy)iodobenzene (22.1 g, 56.3 mmoles). The reaction mixture is heated at reflux for 5 hours. Solvent and volatiles are removed under reduced pressure. The residue is purified by silica gel chromatography eluting with (heptane: AcOEt) (90:1) to give toluene-4-sulfonic acid 3-methyl-2-oxo-3-phenyl-butyl ester.

NMR $^1$H, 7.69 (d, J=8.4 Hz, 2H), 7.35-7.20 (m, 5H), 7.16 (m, 2H), 4.53 (s, 2H), 2.42 (s, 3H), 1.47 (s, 6H).

207D 3-methyl-3-phenyl-butan-2-one

To a solution of N-methoxy-N-methyl-2-phenyl-isobutyramide (example 207E) (16 g, 77.2 mmoles) in THF (300 mL) cooled at −50° C. is added dropwise a 1.6M solution of MeLi in Et$_2$O (80 mL, 131.2 mmoles). The reaction mixture is allowed to reach 0° C. and 1N HCl (130 mL, 130 mmoles) is added. The aqueous phase is extracted with Et$_2$O. The organic phase is washed with brine, dried over MgSO$_4$, filtered and the solvent is removed under reduced pressure to give 3-methyl-3-phenyl-butan-2-one.

NMR $^1$H, 7.35-7.20 (m, 5H), 1.90 (s, 3H), 1.47 (s, 6H).

207E N-methoxy-N-methyl-2-phenyl-isobutyramide

To a solution of 2-methyl-2-phenyl-propionic acid (24.06 g, 150 mmoles) in CH$_2$Cl$_2$ (150 mL) is added oxalylchloride (21 g, 0.165 mmoles) and 5 drops of DMF. The reaction mixture is stirred overnight at room temperatures (reaction vessel connected to a bubbler to remove gases formed during the reaction). The solvent and volatiles are removed under reduced pressure to afford the acylchloride.

A part of the residual oil (16 g, 87.6 mmoles) is dissolved in CH$_2$Cl$_2$ (20 ml) and N,O-dimethylhydroxylamine.hydrochloride (9.0 g, 90 mmoles) and NEt$_3$ (22.7 g, 219 mmoles) are added. The reaction mixture is stirred overnight at room temperature. CH$_2$Cl$_2$ is added to dilute the mixture and the organic phase is washed with water, 0.1N HCl, brine, dried over MgSO$_4$, filtered and the solvent is removed under reduced pressure to give N-methoxy-N-methyl-2-phenyl-isobutyramide.

NMR $^1$H: 7.40-7.15 (m, 5H), 3.12 (s, 3H), 2.65 (s, 3H), 1.56 (s, 6H).

Example 209

1-tertbutyl-3-{4-[1-methyl-4-(1-methylpiperidin-4-yloxy)-9,10-dihydro-4H-3,10a-diaza-benzo[f]azulen-2-yl]-phenyl}-urea To a solution of 4-[1-methyl-4-(1-methyl piperidin-4-yloxy)-9,10-dihydro-4H-3,10a-diaza-benzo[f]azulen-2-yl]-phenylamine (example 173) (50 mg, 0.124 mmole) in ACN (1 mL) are added DIEA (65 µL, 0.372 mmole) and tertbutylisocyanate (21 µL, 0.182 mmole). The reaction mixture is heated overnight at 80° C. Water is added as well as 1N NaOH to pH 10. The aqueous phase is extracted three times with CH$_2$Cl$_2$. The organic phase is dried over MgSO$_4$, filtered, and the solvent is removed under reduced pressure. The residue is pre-purified by silica gel chromatography eluting with (CH$_2$Cl$_2$:MeOH:NH$_4$OH) from (98:2:0.2) to (95:5:0.5), and the residue is submitted to a preparative TLC on silica gel eluting with (CH$_2$Cl$_2$:MeOH:NH$_4$OH) from (9:1:1) to give 1-tert-butyl-3-{4-[1-methyl-4-(1-methylpiperidin-4-yloxy)-9,10-dihydro-4H-3,10a-diaza-benzo[f]azulen-2-yl]-phenyl}-urea melting at 173° C.

Example 210

2-methyl-1-[1-methyl-4-(1-methylpiperidin-4-yloxy)-9,10-dihydro-4H-3,10a-diaza-benzo[f]azulen-2-yl]-propan-1-ol, oxalate 2-Methyl-1-[1-methyl-4-(1-methylpiperidin-4-yloxy)-9,10-dihydro-4H-3,10a-diaza-benzo[f]azulen-2-yl]propan-1-ol, oxalate melting at 120° C. is prepared analogously to example 201.

Example 211

N-(2-{4-[1-methyl-4-(1-methylpiperidin-4-yloxy)-9,10-dihydro-4H-3,10a-diaza-benzo[f]azulen-2-yl]-phenylsulfanyl}-ethyl)-guanidine To a solution of 2-{4-[1-methyl-4-(1-methylpiperidin-4-yloxy)-9,10-dihydro-4H-3,10a-diaza-benzo[f]azulen-2-yl]-phenylsulfanyl}-ethylamine (example 161) (170 mg, 0.368 mmole) in ACN (5 mL) are added N,N'-bis(tert-butoxycarbonyl)-1H-pyrazole-1-carboxamidine) (125 mg, 0.405 mmole) and DIEA (80 µL, 0.423 mmole). The reaction mixture is heated at 50° C. for 24 hours, then it is diluted with water and AcOEt. The organic phase is dried over MgSO$_4$, filtered and the solvent is removed under reduced pressure. The residue is dissolved in CH$_2$Cl$_2$ (2 mL) and TFA is added (2 mL). The reaction mixture is stirred at room temperature for 3 hours. The reaction mixture is diluted with water, then 10N NaOH is added dropwise until pH 10 is reached. The aqueous phase is extracted three times with CH$_2$Cl$_2$. The organic phase dried over magnesium sulphate, filtered and the solvent is removed under reduced pressure. The residue is purified by silica gel chromatography using (CH$_2$Cl$_2$:MeOH: NH$_4$OH) (90:1:0.1) to (8:2:0.2) to give N-(2-{4-[1-methyl-4-(1-methylpiperidin-4-yloxy)-9,10-dihydro-4H-3,10a-diaza-benzo[f]azulen-2-yl]-phenylsulfanyl}-ethyl)-guanidine.

[M+H]$^+$=505.39.

Example 216

N-(4-hydroxycyclohexyl)-4-[1-methyl-4-(1-methylpiperidin-4-yloxy)-9,10-dihydro-4H-3,10a-diaza-benzo[f]azulen-2-yl]-benzamide To a solution of 2-iodo-1-methyl-4-(1-methylpiperidin-4-yloxy)-9,10-dihydro-4H-3,10a-diaza-benzo[f]azulene (example 133) (50 mg, 0.114 mmoles) in THF (0.7 mL) in a screw-capped vial under argon are added a 1M aqueous solution of K$_2$CO$_3$ (0.5 mL, 0.5 mmole), PdCl$_2$(dppf)$_2$ (4.5 mg, 6 µmole) and 4-(trans-4-hydroxycyclohexylcarbamoyl)phenylboronic acid (45 mg, 0.150 mmole). The reaction mixture is heated at 95° C. overnight. Water is added to the reaction mixture and the aqueous phase is extracted three times with CH$_2$Cl$_2$. The organic phase is dried over magnesium sulphate, filtered and the solvent is removed under reduced pressure. The residue is pre-purified by silica gel chromatography using (CH$_2$Cl$_2$:MeOH:NH$_4$OH) with a gradient from (98:2: 0.2) to (96.5:3.5:0.35). The residue is purified by preparative TLC over silica gel using (CH$_2$Cl$_2$:MeOH:NH$_4$OH) with a gradient from (9:1:1) to afford N-(4-hydroxycyclohexyl)-4-[1-methyl-4-(1-methylpiperidin-4-yloxy)-9,10-dihydro-4H-3,10a-diaza-benzo[f]azulen-2-yl]benzamide.

[M+H]$^+$=529.45.

The following compounds are prepared using the same method and different kinds of boronic acids or boronic acids pinacol esters.

| Example | product |
|---|---|
| 217 | N-(2-hydroxyethyl)-4-[1-methyl-4-(1-methylpiperidin-4-yloxy)-9,10-dihydro-4H-3,10a-diaza-benzo[f]azulen-2-yl]-benzamide<br>$[M+H]^+ = 475.39$ |
| 218 | 1-{4-[1-methyl-4-(1-methylpiperidin-4-yloxy)-9,10-dihydro-4H-3,10a-diaza-benzo[f]azulen-2-yl]-benzoyl}-piperidin-4-one<br>$[M+H]^+ = 513.42$ |
| 223 | (2-{4-[1-methyl-4-(1-methylpiperidin-4-yloxy)-9,10-dihydro-4H-3,10a-diaza-benzo[f]azulen-2-yl]-phenyl}-ethyl)-carbamic acid tert-butyl ester<br>$[M+H]^+ = 531.47$ |
| 225 | 2-(3,3-dimethyl-but-1-enyl)-1-methyl-4-(1-methylpiperidin-4-yloxy)-9,10-dihydro-4H-3,10a-diaza-benzo[f]azulene<br>$[M+H]^+ = 394.16$ |
| 226 | 2-cyclohex-1-enyl-1-methyl-4-(1-methylpiperidin-4-yloxy)-9,10-dihydro-4H-3,10a-diaza-benzo[f]azulene<br>$[M+H]^+ = 392.34$ |

Example 219

1,2-diiodo-4-(1-methylpiperidin-4-yloxy)-9,10-dihydro-4H-3,10a-diaza-benzo[f]azulene The compound is prepared according to the procedure described in examples 2A-B and 110B starting from 4,5-diiodo-1H-imidazole to give 1,2-diiodo-4-(1-methylpiperidin-4-yloxy)-9,10-dihydro-4H-3,10a-diazabenzo[f]azulene melting at 163° C.

The following examples are synthesized using the same method and different kinds of alcohols.

| example | product |
|---|---|
| 264 | [2-(1,2-diiodo-9,10-dihydro-4H-3,10a-diaza-benzo[f]azulen-4-yloxy)-ethyl]-dimethyl-amine<br>HPLC-MS analysis method A: rt = 4.0 min, $[M+H]^+ = 524.46$ |
| 265 | 1,2-diiodo-4-(2-piperidin-1-yl-ethoxy)-9,10-dihydro-4H-3,10a-diaza-benzo[f]azulene<br>HPLC-MS analysis method A: rt = 4.11 min, $[M+H]^+ = 564.35$ |
| 268 | 1,2-diiodo-4-(1-methylpyrrolidin-3-yloxy)-9,10-dihydro-4H-3,10a-diaza-benzo[f]azulene<br>HPLC-MS analysis method A: rt = 3.99 min, $[M+H]^+ = 536.91$ |
| 269 | 1,2-diiodo-4-(8-methyl-8-aza-bicyclo[3.2.1]oct-3-yloxy)-9,10-dihydro-4H-3,10a-diaza-benzo[f]azulene<br>HPLC-MS analysis method A: rt = 4.15 min, $[M+H]^+ = 576.30$ |
| 270 | [3-(1,2-diiodo-9,10-dihydro-4H-3,10a-diaza-benzo[f]azulen-4-yloxy)-propyl]-dimethyl-amine<br>HPLC-MS analysis method A: rt = 4.11 min, $[M+H]^+ = 538.50$ |
| 271 | 4-(1-azabicyclo[2.2.2]oct-3-yloxy)-1,2-diiodo-9,10-dihydro-4H-3,10a-diaza-benzo[f]azulene oxalate<br>HPLC-MS analysis method A: rt = 4.12 min, $[M+H]^+ = 561.72$ |

Example 220

(4-hydroxypiperidin-1-yl)-{4-[1-methyl-4-(1-methylpiperidin-4-yloxy)-9,10-dihydro-4H-3,10a-diaza-benzo[f]azulen-2-yl]-phenyl}-methanone To a solution of 1-{4-[1-methyl-4-(1-methylpiperidin-4-yloxy)-9,10-dihydro-4H-3,10a-diaza-benzo[f]azulen-2-yl]-benzoyl}-piperidin-4-one (example 218) (93.7 mg, 0.183 mmole) in MeOH (2 mL) is added portionwise $NaBH_4$ (10.5 mg, 0.275 mmole). After 2 hours at room temperature, water is added and the aqueous phase is extracted with AcOEt. AcOEt phase is dried over $MgSO_4$, filtered and the solvent is removed under reduced pressure. The residue is purified by silica gel chromatography eluting with ($CH_2Cl_2$:MeOH) (90:1) then ($CH_2Cl_2$:MeOH:$NH_4OH$) (9:1:0.1). The residual solid is triturated three times with $Et_2O$ to give (4-hydroxypiperidin-1-yl)-{4-[1-methyl-4-(1-methylpiperidin-4-yloxy)-9,10-dihydro-4H-3,10a-diaza-benzo[f]azulen-2-yl]-phenyl}-methanone.
$[M+H]^+=515.41$.

Example 221

2-iodo-4-(1-methylpiperidin-4-yloxy)-9,10-dihydro-4H-3,10a-diaza-benzo[f]azulene-1-carbonitrile To a solution of 1,2-diiodo-4-(1-methylpiperidin-4-yloxy)-9,10-dihydro-4H-3,10a-diaza-benzo[f]azulene (example 219) (212 mg, 0.47 mmole) in $CH_2Cl_2$ (2 mL) at 0° C. is added MeMgBr 3M solution in $Et_2O$ (172 µL, 0.52 mmole). The ice bath is removed and the reaction mixture is stirred at room temperature for 30 minutes. A solution of p-toluenesulfonylcyanide (89 mg) in $CH_2Cl_2$ (1 mL) is added to the above solution. The reaction mixture is stirred at room temperature for 150 minutes. A saturated aqueous $NH_4Cl$ solution is added and the aqueous phase is extracted three times with $CH_2Cl_2$. The organic phase is dried over $MgSO_4$, filtered and the solvent removed under reduced pressure. The residue is purified by silica gel chromatography eluting with ($CH_2Cl_2$:MeOH) (100:0) to (95:5) to give 2-iodo-4-(1-methylpiperidin-4-yloxy)-9,10-dihydro-4H-3,10a-diaza-benzo[f]azulene-1-carbonitrile melting at 195° C.

Example 222

1-methyl-4-(1-methylpiperidin-4-yloxy)-9,10-dihydro-4H-3,10a-diaza-benzo[f]azulene-2-carboxylic acid benzylamide To a solution of 1,2-diiodo-4-(1-methylpiperidin-4-yloxy)-9,10-dihydro-4H-3,10a-diaza-benzo[f]azulene (example 219) (437 mg, 1 mmole) in $CH_2Cl_2$ (4 mL) and THF (1 mL) at 0° C. is added EtMgBr 3M solution in $Et_2O$ (1 mL, 3 mmoles). The ice bath is removed and the reaction mixture is stirred at room temperature for 90 minutes. Tert-butylisocyanate (618 µL, 5 mmoles) is added to the above solution. The reaction mixture is stirred at room temperature for 3 hours. A (1:1) solution of saturated aqueous $NH_4Cl$ and concentrated $NH_4OH$ is added and the aqueous phase is extracted three times with $CH_2Cl_2$. The organic phase is dried over $MgSO_4$, filtered and the solvent removed under reduced pressure. The residue is purified by silica gel chromatography eluting with ($CH_2Cl_2$:MeOH:$NH_4OH$) (98:2:0.2) to (95:5:0.5). The residue is triturated in $iPr_2O$ to afford 1-methyl-4-(1-methylpiperidin-4-yloxy)-9,10-dihydro-4H-3,10a-diaza-benzo[f]azulene-2-carboxylic acid benzylamide melting at 161° C.

Example 224

4-[1-cyano-4-(1-methylpiperidin-4-yloxy)-9,10-dihydro-4H-3,10a-diaza-benzo[f]azulen-2-yl]-benzoic acid tert-butyl ester To a solution of 2-iodo-4-(1-methylpiperidin-4-yloxy)-9,10-dihydro-4H-3,10a-diaza-benzo[f]azulene-1-carbonitrile (example 221) (215 mg, 0.48 mmole) in THF (3 mL) are added 4-(4,4,5,5-tetramethyl-[1,3,2]dioxaborolan-2-yl)-benzoic acid tert-butyl ester (191 mg, 0.63 mmole), 1M aqueous K₂CO₃ (2 mL) and PdCl₂(dppf)₂ (20 mg). The flask is evacuated and filled with argon. The reaction mixture is heated at 85° C. for 24 hours. AcOEt is added and the organic phase is washed with water, dried over MgSO₄, filtered and the solvent removed under reduced pressure. The residue is purified by silica gel chromatography eluting with (CH₂Cl₂:MeOH) (100:0) to (95:5) to give 4-[1-cyano-4-(1-methylpiperidin-4-yloxy)-9,10-dihydro-4H-3,10a-diaza-benzo[f]azulen-2-yl]-benzoic acid tert-butyl ester melting at 95° C.

The following examples are synthesized using the same method.

| example | product |
|---|---|
| 235 | 4-(1-methylpiperidin-4-yloxy)-2-phenyl-9,10-dihydro-4H-3,10a-diaza-benzo[f]azulene-1-carbonitrile [M + H]⁺ = 399.29; [M + Na]⁺ = 421.30 |
| 272 | 2-(2-chlorophenyl)-4-(1-methyl-piperidin-4-yloxy)-9,10-dihydro-4H-3,10a-diaza-benzo[f]azulene-1-carbonitrile oxalate HPLC-MS analysis using method A: rt = 4.17 min; [M + H]⁺ = 433.25 and 435.25. |

Example 227

4-[1-methyl-4-(1-methylpiperidin-4-yloxy)-9,10-dihydro-4H-3,10a-diaza-benzo[f]azulen-2-yl]-but-3-yn-1-ol To a solution of 2-iodo-1-methyl-4-(1-methylpiperidin-4-yloxy)-9,10-dihydro-4H-3,10a-diaza-benzo[f]azulene (example 133) (50 mg, 0.114 mmole) in THF (1 mL) are added potassium 4-tert-butyldimethylsilyloxybut-1-ynyltrifluoroborate (50 mg, 0.171 mmole), PdCl₂(dppf)₂ (8 mg, 0.011 mmole), water and Cs₂CO₃ (120 mg, 0.342 mmole). The flask is evacuated and filled with argon. The reaction mixture is heated at 80° C. for 24 hours. AcOEt and water are added, and the organic phase is washed with water, dried over MgSO₄, filtered and the solvent removed under reduced pressure. The residue is purified by silica gel chromatography eluting with (CH₂Cl₂:MeOH) (98:2) to (90:10) then (CH₂Cl₂:MeOH:NH₄OH) (9:1:0.1). The residue is dissolved in nBu₄NF 1M in THF (0.5 mL) and the reaction mixture is stirred overnight at room temperature. Water is added and the aqueous phase is extracted with AcOEt. The organic phase is dried over magnesium sulphate, filtered and the solvent is removed under reduced pressure. The residue is pre-purified by silica gel chromatography using (CH₂Cl₂:MeOH:NH₄OH) as eluent with a gradient from (98:2:0.1) to (96.5:3.5:0.35) and the residue is submitted to a preparative thin-layer chromatography eluting with (CH₂Cl₂:MeOH:NH₄OH) (9:1:1) to afford 4-[1-methyl-4-(1-methylpiperidin-4-yloxy)-9,10-dihydro-4H-3,10a-diaza-benzo[f]azulen-2-yl]-but-3-yn-1-ol.

[M+H]⁺=380.24.

The following example is synthesized using the same method.

| example | product |
|---|---|
| 228 | 2-(5-chloropent-1-ynyl)-1-methyl-4-(1-methylpiperidin-4-yloxy)-9,10-dihydro-4H-3,10a-diaza-benzo[f]azulene [M + H]⁺ = 426.31 and 428.28 ³⁵Cl/³⁷Cl |

Example 230

230A 10,10-dimethyl-4-(1-methylpiperidin-4-yloxy)-2-phenyl-9,10-dihydro-4H-3,10a-diaza-benzo[f]azulene The compound is synthesized using the methods described in examples 2A-B starting from 1-(1,1-dimethyl-2-phenyl-ethyl)-4-phenyl-1H-imidazole (example 230B) to afford 10,10-dimethyl-4-(1-methylpiperidin-4-yloxy)-2-phenyl-9,10-dihydro-4H-3,10a-diaza-benzo[f]azulene melting at 85° C.

230B 1-(1,1-dimethyl-2-phenylethyl)-4-phenyl-1H-imidazole

To a freshly prepared MeONa solution in MeOH (10 mL MeOH and 0.23 g Na metal) are added NMP (10 mL), 4-phenyl-1H-imidazole (1.44 g, 10 mmoles) and 2-chloro-2-methylpropyl)-benzene (1.69 g, 10 mmoles). The reaction mixture is heated at 170° C. (MeOH distilled and evacuated) for 24 hours. NMP is removed under reduced pressure. AcOEt is added and the organic phase is washed with water, dried over magnesium sulphate, filtered and the solvent is removed under reduced pressure. The residue is pre-purified by silica gel chromatography using (CH₂Cl₂:MeOH) as eluent with a gradient from (100:0) to (98:2) to give 1-(1,1-dimethyl-2-phenylethyl)-4-phenyl-1H-imidazole.

¹H NMR: 7.70-7.60 (s, 2H), 7.43-7.18 (m, 8H), 7.12 (s, 1H), 6.65 (s, 1H), 4.05 (s, 2H), 1.42 (s, 6H).

Example 231

231A 8-Bromo-4-(1-methyl-piperidin-4-yloxy)-2-phenyl-9,10-dihydro-4H-3,10a-diaza-benzo[f]azulene 8-Bromo-4-(1-methyl-piperidin-4-yloxy)-2-phenyl-9,10-dihydro-4H-3,10a-diaza-benzo[f]azulene melting at 83° C. is prepared analogously to example 123 from 8-bromo-2-phenyl-9,10-dihydro-4H-3,10a-diaza-benzo[f]azulen-4-ol (example 231 B).

231B 8-Bromo-2-phenyl-9,10-dihydro-4H-3,10a-diaza-benzo[f]azulen-4-ol

8-Bromo-2-phenyl-9,10-dihydro-4H-3,10a-diaza-benzo[f]azulen-4-ol is prepared from 1-[2-(2-bromophenyl)ethyl]-4-phenyl-imidazole-2-carbaldehyde (example 231C) analogously to general procedure 123B with trifluoromethanesulfonic acid instead of methanesulfonic acid.

231C 1-[2-(2-bromophenyl)ethyl]-4-phenyl-imidazole-2-carbaldehyde

1-[2-(2-bromophenyl)ethyl]-4-phenyl-imidazole-2-carbaldehyde is obtained in three steps analogously to example 4 from 2-(2-bromophenyl)ethanol and 4-phenyl-1H-imidazole.

Example 232

1,10,10-Trimethyl-4-(1-methyl-piperidin-4-yloxy)-2-phenyl-9,10-dihydro-4H-3,10a-diaza-benzo[f]azulene The procedure is the same as the one described in example 230 starting with 4-phenyl-1H-imidazole in example 230B to give 1,10,10-trimethyl-4-(1-methyl-piperidin-4-yloxy)-2-phenyl-9,10-dihydro-4H-3,10a-diaza-benzo[f]azulene melting at 152° C.

Example 233

8-benzyl-4-(1-methylpiperidin-4-yloxy)-2-phenyl-9,10-dihydro-4H-3,10a-diaza-benzo[f]azulene To a solution of 8-bromo-4-(1-methyl-piperidin-4-yloxy)-2-phenyl-9,10-dihydro-4H-3,10a-diaza-benzo[f]azulene (example 231) (150 mg) in toluene/dioxane/water 10/1/1 (6 mL) in a screw-capped vial are added benzylboronic pinacol ester (151 mg), [1,1'-bis(diphenylphosphino)ferrocene] dichloropalladium (50 mg) and potassium carbonate (137 mg). The vial is evacuated and filled with argon. The reaction mixture is stirred at 95° C. for 20 hours. Water is added to the reaction mixture, and the aqueous phase is extracted three times with dichloromethane. Pooled organic extracts are dried over magnesium sulphate, filtered and the solvent is removed under reduced pressure. The residue is purified by preparative HPLC-MS (Waters AutoPurification HPLC/MS System, Sunfire Prep C18 5 μm OBD 30×150 mm column, eluents: water/0.1% formic acid (A) and acetonitrile/0.1% formic acid (B), focus gradient from 23% (B) to 33% (B) in 10 minutes) to afford 8-benzyl-4-(1-methylpiperidin-4-yloxy)-2-phenyl-9,10-dihydro-4H-3,10a-diaza-benzo[f]azulene melting at 66° C.

Example 234

4-(1-methylpiperidin-4-yloxy)-8-methylsulfanyl-2-phenyl-9,10-dihydro-4H-3,10a-diaza-benzo[f]azulene To a solution of compound 8-bromo-4-(1-methyl-piperidin-4-yloxy)-2-phenyl-9,10-dihydro-4H-3,10a-diaza-benzo[f]azulene (example 231) (150 mg) in toluene (2 mL) in a screw-capped vial under argon are added diisopropylethylamine (0.2 mL), sodium thiomethoxide (29 mg), bis(dibenzilideneacetone)palladium(0) (50 mg) and Xantphos (50 mg). The reaction mixture is heated at 95° C. for 19 hours. The mixture is then diluted with water and extracted with dichloromethane. Pooled organic extracts are dried over magnesium sulphate, filtered and the solvent is removed under reduced pressure. The residue is purified by preparative HPLC-MS (Waters AutoPurification HPLC/MS System, Sunfire Prep C18 5 μm OBD 30×150 mm column, eluents: water/0.1% formic acid (A) and acetonitrile/0.1% formic acid (B), focus gradient from 17% (B) to 27% (B) in 10 minutes) to afford 4-(1-methylpiperidin-4-yloxy)-8-methylsulfanyl-2-phenyl-9,10-dihydro-4H-3,10a-diaza-benzo[f]azulene melting at 134° C.

Example 236

8-methyl-4-(1-methylpiperidin-4-yloxy)-2-phenyl-9,10-dihydro-4H-3,10a-diaza-benzo[f]azulene 8-Methyl-4-(1-methylpiperidin-4-yloxy)-2-phenyl-9,10-dihydro-4H-3,10a-diaza-benzo[f]azulene melting at 71° C. is prepared analogously to example 233 with methyl boronic acid.

Example 237

8-but-3-enyl-4-(1-methylpiperidin-4-yloxy)-2-phenyl-9,10-dihydro-4H-3,10a-diaza-benzo[f]azulene, oxalate 8-But-3-enyl-4-(1-methylpiperidin-4-yloxy)-2-phenyl-9,10-dihydro-4H-3,10a-diaza-benzo[f]azulene, oxalate melting at 107° C. is prepared analogously to example 233 with potassium but-3-enyl trifluoroborate.

Example 239

4-(1-methylpiperidin-4-yloxy)-2-phenyl-8-o-tolyl-9,10-dihydro-4H-3,10a-diaza-benzo[f]azulene 4-(1-methylpiperidin-4-yloxy)-2-phenyl-8-o-tolyl-9,10-dihydro-4H-3,10a-diaza-benzo[f]azulene melting at 94° C. is prepared analogously to example 233 with o-tolylboronic acid.

Example 240

8-(4-fluorophenyl)-4-(1-methylpiperidin-4-yloxy)-2-phenyl-9,10-dihydro-4H-3,10a-diaza-benzo[f]azulene 8-(4-Fluorophenyl)-4-(1-methylpiperidin-4-yloxy)-2-phenyl-9,10-dihydro-4H-3,10a-diaza-benzo[f]azulene melting at 95° C. is prepared analogously to example 233 with 4-fluorobenzeneboronic acid.

Example 241

8-(3-methoxyphenyl)-4-(1-methylpiperidin-4-yloxy)-2-phenyl-9,10-dihydro-4H-3,10a-diaza-benzo[f]azulene 8-(3-Methoxyphenyl)-4-(1-methylpiperidin-4-yloxy)-2-phenyl-9,10-dihydro-4H-3,10a-diaza-benzo[f]azulene melting at 93° C. is prepared analogously to example 233 with 3-methoxybenzeneboronic acid.

Example 242

3-[4-(1-methylpiperidin-4-yloxy)-2-phenyl-9,10-dihydro-4H-3,10a-diaza-benzo[f]azulen-8-yl]-phenylamine 242A 3-[4-(1-methylpiperidin-4-yloxy)-2-phenyl-9,10-dihydro-4H-3,10a-diaza-benzo[f]azulen-8-yl]-phenylamine A mixture of 4-(1-methylpiperidin-4-yloxy)-8-(3-nitrophenyl)-2-phenyl-9,10-dihydro-4H-3,10a-diaza-benzo[f]azulene (example 242 B) (0.6 mmole), tin(II) chloride dihydrate (2.83 g) in ethanol (15 mL) is refluxed for 2 hours. The mixture is then cooled to room temperature and extracted twice with chloroform. Pooled organic extracts are dried over magnesium sulphate, filtered and the solvent is removed under reduced pressure. The residue is purified by preparative HPLC-MS (Waters AutoPurification HPLC/MS System, Sunfire Prep C18 5 μm OBD 30×150 mm column, eluents: water/0.1% formic acid (A) and acetonitrile/0.1% formic acid (B), focus gradient from 14% (B) to 24% (B) in 10 minutes)

to afford 3-[4-(1-methylpiperidin-4-yloxy)-2-phenyl-9,10-dihydro-4H-3,10a-diaza-benzo[f]azulen-8-yl]-phenylamine melting at 120° C.

242B 4-(1-Methylpiperidin-4-yloxy)-8-(3-nitrophenyl)-2-phenyl-9,10-dihydro-4H-3,10a-diaza-benzo[f]azulene 4-(1-Methylpiperidin-4-yloxy)-8-(3-nitrophenyl)-2-phenyl-9,10-dihydro-4H-3,10a-diaza-benzo[f]azulene is prepared analogously to example 233 with 3-nitrobenzeneboronic acid.

Example 244 methyl-[4-(1-methylpiperidin-4-yloxy)-2-phenyl-9,10-dihydro-4H-3,10a-diaza-benzo[f]azulen-8-yl]-amine To a solution of 8-bromo-4-(1-methyl-piperidin-4-yloxy)-2-phenyl-9,10-dihydro-4H-3,10a-diaza-benzo[f]azulene (example 231) (276 mg, 0, 55 mmole) in dimethylformamide (5 mL) in a screw-capped vial are added a 3M solution of methylamine in methanol (2.8 mL, 5.5 mmoles), copper(I) iodide (100 mg, 0, 52 mmole) and cesium carbonate (250 mg, 0.77 mmole). The vial is evacuated and filled with argon. The reaction mixture is stirred at 100° C. for 36 hours. Water and ammonia are added to the reaction mixture, and the aqueous phase is extracted three times with dichloromethane. Pooled organic extracts are dried over magnesium sulphate, filtered and the solvent is removed under reduced pressure. The residue is purified by preparative HPLC-MS (Waters AutoPurification HPLC/MS System, Sunfire Prep C18 5 μm OBD 30×150 mm column, eluents: water/0.1% formic acid (A) and acetonitrile/0.1% formic acid (B), focus gradient from 11% (B) to 21% (B) in 10 minutes) to afford methyl-[4-(1-methylpiperidin-4-yloxy)-2-phenyl-9,10-dihydro-4H-3,10a-diaza-benzo[f]azulen-8-yl]-amine melting at 189° C.

Example 245

8-methoxy-4-(1-methylpiperidin-4-yloxy)-2-phenyl-9,10-dihydro-4H-3,10a-diaza-benzo[f]azulene 8-Methoxy-4-(1-methylpiperidin-4-yloxy)-2-phenyl-9,10-dihydro-4H-3,10a-diaza-benzo[f]azulene melting at 73° C. is isolated by preparative HPLC-MS as side-product in the synthesis of example 244.

Example 248

8-benzyloxy-4-(1-methylpiperidin-4-yloxy)-2-phenyl-9,10-dihydro-4H-3,10a-diaza-benzo[f]azulene To a solution of 8-bromo-4-(1-methyl-piperidin-4-yloxy)-2-phenyl-9,10-dihydro-4H-3,10a-diaza-benzo[f]azulene (example 231) (276 mg, 0, 40 mmole) in anhydrous toluene (5 mL) in a screw-capped vial are added benzyl alcohol (87 mg, 0, 80 mmole), copper(I) iodide (15.3 mg, 0.080 mmole), ground 4A molecular sieves (133 mg), 3,4,7,8-tetramethyl-1,10-phenanthroline (38 mg, 0, 16 mmole) and cesium carbonate (261 mg, 0, 80 mmole). The vial is evacuated and filled with argon. The reaction mixture is stirred at 90° C. for 3 days. Water and ammonia are added to the reaction mixture, and the aqueous phase is extracted three times with dichloromethane. Pooled organic extracts are dried over magnesium sulphate, filtered and the solvent is removed under reduced pressure. The residue is purified by preparative HPLC-MS (Waters AutoPurification HPLC/MS System, Sunfire Prep C18 5 μm OBD 30×150 mm column, eluents: water/0.1% formic acid (A) and acetonitrile/0.1°)/0 formic acid (B), focus gradient from 23% (B) to 33% (B) in 10 minutes) to afford 8-benzyloxy-4-(1-methylpiperidin-4-yloxy)-2-phenyl-9,10-dihydro-4H-3,10a-diaza-benzo[f]azulene melting at 68° C.

Example 249

4-(1-methyl-piperidin-4-yloxy)-8-phenethyl-2-phenyl-9,10-dihydro-4H-3,10a-diaza-benzo[f]azulene To a solution of 8-bromo-4-(1-methyl-piperidin-4-yloxy)-2-phenyl-9,10-dihydro-4H-3,10a-diaza-benzo[f]azulene (example 231) (276 mg, 0, 61 mmole) in anhydrous dimethylformamide (5 mL) in a screw-capped vial are added n-tetrabutylammonium bromide (196 mg, 0, 61 mmole), lithium chloride (26 mg, 0, 61 mmole), palladium(II) acetate (27 mg, 0, 12 mmole), styrene (174 μL, 1, 5 mmole) and potassium carbonate (420 mg, 3, 0 mmoles). The vial is evacuated and filled with argon. The reaction mixture is stirred at 95° C. for 20 hours. Water and diethyl ether are added to the reaction mixture. The organic phase is washed with water, dried over magnesium sulphate, filtered and concentrated under reduced pressure. To the residue are added methanol (10 mL), 10% Pd/C (150 mg) and ammonium formate (3 g). After reflux for 1.5 hours the mixture is filtered on a celite pad, concentrated under reduced pressure, diluted with ethyl acetate, washed with water, dried over magnesium sulphate and the solvent was removed under reduced pressure. The residue is purified by preparative HPLC-MS (Waters AutoPurification HPLC/MS System, Sunfire Prep C18 5 μm OBD 30×150 mm column, eluents: water/0.1% formic acid (A) and acetonitrile/0.1% formic acid (B), focus gradient from 23% (B) to 33% (B) in 10 minutes) to afford 4-(1-methyl-piperidin-4-yloxy)-8-phenethyl-2-phenyl-9,10-dihydro-4H-3,10a-diaza-benzo[f]azulene melting at 67° C.

Example 238

238A 4-(1-methylpiperidin-4-yloxy)-2-phenyl-1-propyl-9,10-dihydro-4H-3,10a-diaza-benzo[f]azulene The compound is synthesized using the methods described in example 2A-B starting from 1-phenethyl-4-phenyl-5-propylimidazole (example 238B) to afford 4-(1-methylpiperidin-4-yloxy)-2-phenyl-1-propyl-9,10-dihydro-4H-3,10a-diaza-benzo[f]azulene melting at 144° C.

238B 1-phenethyl-4-phenyl-5-propylimidazole and 1-phenethyl-5-phenyl-4-propylimidazole The two compounds are synthesized using the methods described in example 103C starting from 4-phenyl-5-propyl-1H-imidazole (example 238C) to afford 1-phenethyl-4-phenyl-5-propylimidazole and 1-phenethyl-5-phenyl-4-propylimidazole.

1-phenethyl-4-phenyl-5-propylimidazole $^1$H NMR: 7.70-7.60 (m, 2H), 7.45-7.20 (m, 7H), 7.17-7.10 (m, 2H), 4.11 (t, J=8.9 Hz, 2H), 2.77 (t, J=8.9 Hz, 2H), 2.46 (t, J=9.1 Hz, 2H), 1.80-1.58 (m, 2H), 0.98 (t, J=8.8 Hz, 3H)

1-phenethyl-5-phenyl-4-propylimidazole $^1$H NMR: 7.50-7.38 (m, 3H), 7.36 (s, 1H), 7.29-7.18 (m, 5H), 6.95-6.85 (m, 2H), 4.03 (t, J=8.9 Hz, 2H), 3.07 (t, J=8.9 Hz, 2H), 2.67 (t, J=9.7 Hz, 2H), 1.70-1.50 (m, 2H), 0.88 (t, J=8.8 Hz, 3H).

238C 4-phenyl-5-propyl-1H-imidazole

To a solution of valerophenone (4.87 g, 30 mmoles) in AcOH (100 mL) is added first 33% HBr in AcOH (10 mL) then portionwise N-bromosuccinimide (5.6 g, 31.5 mmoles) at room temperature. After 1 hour stirring at room temperature, solvents and volatiles are removed under reduced pressure. To the residue are added water and a saturated aqueous solution of NaHCO$_3$ to neutral pH. The aqueous phase is extracted three times with CH$_2$Cl$_2$. The organic phase is washed with water, brine, dried over MgSO$_4$, filtered and the solvent is removed under reduced pressure. The residue is added dropwise over 30 minutes to formamide (150 mL) and heated at 180-190° C. (inner temperature). The reaction mixture is heated furthermore at 180° C. for 2 hours, then cooled to room temperature. The mixture is poured into water (1 L) and saturated NaHCO$_3$ solution (150 mL) is added. The suspension is stirred at room temperature for 15 min, then filtered. The cake is rinsed with water and filter-dried. The residual solid is re-crystallized from hot ACN to give 4-phenyl-5-propyl-1H-imidazole.
$^1$H NMR: 7.62-7.55 (m, 2H), 7.56 (s, 1H), 7.45-7.35 (m, 2H), 7.30-7.20 (m, 1H), 2.80-2.70 (m, 2H), 1.80-1.63 (m, 2H), 0.95 (t, J=8.8 Hz, 3H).

Example 246

4-(1-methyl-piperidin-4-yloxy)-1-phenyl-2-propyl-9,10-dihydro-4H-3,10a-diaza-benzo[f]azulene The compound is synthesized using the methods described in example 2A-B starting from 1-phenethyl-5-phenyl-4-propylimidazole (example 238C) to afford 4-(1-methyl-piperidin-4-yloxy)-1-phenyl-2-propyl-9,10-dihydro-4H-3,10a-diaza-benzo[f]azulene.
[M+H]$^+$=416.36.

Example 243

243A 1-isopropyl-4-(1-methylpiperidin-4-yloxy)-2-phenyl-9,10-dihydro-4H-3,10a-diaza-benzo[f]azulene dioxalate The compound is synthesized using the methods described in example 2A starting from 5-isopropyl-1-phenethyl-4-phenylimidazole-2-carbaldehyde (example 243B) to give 1-isopropyl-4-(1-methylpiperidin-4-yloxy)-2-phenyl-9,10-dihydro-4H-3,10a-diaza-benzo[f]azulene dioxalate melting at 90° C.

243B 5-isopropyl-1-phenethyl-4-phenylimidazole-2-carbaldehyde

A solution of the mixture of 4-isopropyl-3-phenethyl-5-phenylimidazole and 5-isopropyl-3-phenethyl-4-phenylimidazole (example 243C) (1.2 g, 4.14 mmoles) in THF (15 mL) under argon is cooled to −78° C. A 2.0M LDA solution (2.2 mL, 4.4 mmoles) is added dropwise. After 30 minutes at −78° C., DMF (1.83 g, 25 mmoles) is added dropwise. The reaction mixture is allowed to reach 0° C., then it is quenched by adding a half-saturated NaHCO$_3$ solution. The aqueous phase is extracted three times with AcOEt. The organic phase is washed with water, brine, dried over magnesium sulphate, filtered and the solvent is removed under reduced pressure. The residue is purified by silica gel chromatography using (heptane:AcOEt) as eluent with a gradient from (1:0) to (8:1) to give 5-isopropyl-1-phenethyl-4-phenylimidazole-2-carbaldehyde.
$^1$H NMR: 9.87 (s, 1H), 7.50-7.40 (m, 3H), 7.25-7.15 (m, 3H), 7.11-7.01 (m, 2H), 6.94-6.85 (m, 2H), 4.48-4.35 (m, 2H), 2.95-2.75 (m, 3H), 1.28-1.18 (m, 6H).

243C Mixture of 4-isopropyl-3-phenethyl-5-phenylimidazole and 5-isopropyl-3-phenethyl-4-phenylimidazole The mixture of compounds is synthesized using the methods described in example 238B starting from 4-isopropyl-5-phenyl-1H-imidazole (example 243D).

243D 4-isopropyl-5-phenyl-1H-imidazole

The compound is synthesized using the methods described in example 238C starting from 3-methyl-1-phenylbutan-1-one.
$^1$H NMR: 7.50-7.40 (m, 3H), 7.45-7.35 (m, 2H), 7.35-7.25 (m, 1H), 3.45-3.23 (m, 2H), 1.32 (d, J=8.0 Hz, 6H).

Example 247

247A 1-iodo-4-(1-methylpiperidin-4-yloxy)-2-phenyl-9,10-dihydro-4H-3,10a-diaza-benzo[f]azulene The compound is synthesized using the methods described in example 2A starting from 5-iodo-1-phenethyl-4-phenylimidazole-2-carbaldehyde (example 247B) to afford 1-iodo-4-(1-methylpiperidin-4-yloxy)-2-phenyl-9,10-dihydro-4H-3,10a-diaza-benzo[f]azulene melting at 153° C.

247B 5-iodo-1-phenethyl-4-phenylimidazole-2-carbaldehyde

A solution of the mixture of 5-iodo-1-phenethyl-4-phenylimidazole and 4-iodo-1-phenethyl-5-phenylimidazole (example 247C) (0.7 g, 1.87 mmoles) in THF (9 mL) under argon is cooled to −78° C. A 2.0M LDA solution (1.9 mL, 3.8 mmoles) is added dropwise. After 30 minutes at −78° C., DMF (0.9 mL, 3.8 mmoles) is added dropwise. The reaction mixture is allowed to reach 0° C., then it is quenched by adding a half-saturated NaHCO$_3$ solution. The aqueous phase is extracted three times with AcOEt. The organic phase is washed with water, brine, dried over magnesium sulphate, filtered and the solvent is removed under reduced pressure. The residue is re-crystallized from AcOEt to give 5-iodo-1-phenethyl-4-phenylimidazole-2-carbaldehyde.
[M+H]$^+$=500.22.

247C Mixture of 5-iodo-1-phenethyl-4-phenylimidazole and 4-iodo-1-phenethyl-5-phenylimidazole The mixture of compounds is synthesized using the methods described in example 238B starting from 5-iodo-4-phenyl-1H-imidazole (example 247D).

247D 5-iodo-4-phenyl-1H-imidazole

To a solution of 4-phenyl-1H-imidazole (4.75 g, 33 mmoles) in CH$_2$Cl$_2$ (250 mL) is added N-iodosuccinimide (6.75 g, 30 mmoles). After 2 hours at room temperature, CH$_2$Cl$_2$ is removed under reduced pressure. The residual solid is triturated in hot ACN (150 mL), cooled down to room temperature and filtered. The white-off solid is triturated in hot ACN (60 mL), cooled down to room temperature and stirred overnight at room temperature. After a filtration, 5-iodo-4-phenyl-1H-imidazole is obtained.

$^1$H NMR (dmso-d$^6$): 12.76 (sl, NH), 7.81-7.60 (m, 3H), 7.50-7.25 (m, 3H).

Example 250

1-methyl-4-(1-methylpiperidin-4-yloxy)-2-pyridin-4-yl-9,10-dihydro-4H-3,10a-diaza-benzo[f]azulene To a solution of 2-iodo-1-methyl-4-(1-methylpiperidin-4-yloxy)-9,10-dihydro-4H-3,10a-diaza-benzo[f]azulene (example 133) (110 mg, 0.251 mmole) in DMF (4 mL) are added potassium 4-tributylstannylpyridine (354 mg, 1 mmole), Pd(PPh$_3$)$_4$ (28 mg, 0.025 mmole), LiCl (50 mg, 1.25 mmole). The flask is evacuated and filled with argon. The reaction mixture is heated at 110° C. for 5 hours. AcOEt and water are added, as well as a 10% KF solution. The aqueous phase is extracted with AcOEt. The organic phase is washed with 0.5N HCl. The HCl phase is made alkaline with 1H NaOH and the aqueous phase is extracted with AcOEt. The organic phase is dried over MgSO$_4$, filtered and the solvent removed under reduced pressure. The residue is purified by silica gel chromatography eluting with (CH$_2$Cl$_2$:MeOH) (98:2) then (CH$_2$Cl$_2$:MeOH:NH$_4$OH) (95:5:0.5). The residue is re-purified to afford by silica gel chromatography eluting with (toluene:acetone:NEt$_3$) (10:90:2) to (5:95:5) to give 1-methyl-4-(1-methylpiperidin-4-yloxy)-2-pyridin-4-yl-9,10-dihydro-4H-3,10a-diaza-benzo[f]azulene.

[M+H]$^+$=389.34.

The following examples are synthesized using the same method.

| example | product |
|---|---|
| 251 | 1-methyl-4-(1-methylpiperidin-4-yloxy)-2-pyridin-2-yl-9,10-dihydro-4H-3,10a-diaza-benzo[f]azulene<br>[M + H]$^+$ = 389.35 |
| 260 | 1-methyl-2-(2-methylallyl)-4-(1-methylpiperidin-4-yloxy)-9,10-dihydro-4H-3,10a-diaza-benzo[f]azulene<br>mp = 132° C. |

Example 252

4-(1-methylpiperidin-4-yloxy)-1,2-diphenyl-9,10-dihydro-4H-3,10a-diaza-benzo[f]azulene To a solution of 1,2-diiodo-4-(1-methylpiperidin-4-yloxy)-9,10-dihydro-4H-3,10a-diaza-benzo[f]azulene (example 219A) (212 mg, 0.386 mmole) in THF (3 mL) are added benzeneboronic acid (120 mg, 1 mmole), water (3 mL), Ba(OH)$_2$ (460 mg, 2 mmoles) and PdCl$_2$(dppf)$_2$ (40 mg). The flask is evacuated and filled with argon. The reaction mixture is heated at 105° C. for 48 hours. AcOEt is added and the organic phase is washed with water, dried over MgSO$_4$, filtered and the solvent removed under reduced pressure. The residue is purified by silica gel chromatography eluting with (CH$_2$Cl$_2$:MeOH) (100:0) to (95:5) to give 4-(1-methylpiperidin-4-yloxy)-1,2-diphenyl-9,10-dihydro-4H-3,10a-diaza-benzo[f]azulene melting at 90° C.

Example 253

2-iodo-4-(1-methylpiperidin-4-yloxy)-9,10-dihydro-4H-3,10a-diaza-benzo[f]azulene-1-carboxylic acid amide To a solution of 2-iodo-4-(1-methylpiperidin-4-yloxy)-9,10-dihydro-4H-3,10a-diaza-benzo[f]azulene-1-carbonitrile (example 221A) (220 mg, 0.5 mmole) in MeOH (3 mL) cooled at 0° C. is added dropwise a solution of 1N NaOH (1 mL) and 30% H$_2$O$_2$ (0.1 mL). The reaction mixture is stirred at 0° C. for 1 hour, then aqueous 1N Na$_2$S$_2$O$_3$ is added. The aqueous phase is extracted with AcOEt. The organic phase is dried over MgSO$_4$, filtered and the solvent removed under reduced pressure. The residue is purified by silica gel chromatography eluting with (CH$_2$Cl$_2$:MeOH:NH$_4$OH) from (100:0:0) to (90:10:1) to give 2-iodo-4-(1-methylpiperidin-4-yloxy)-9,10-dihydro-4H-3,10a-diaza-benzo[f]azulene-1-carboxylic acid amide melting at 85° C.

The following examples are synthesized using the same method.

| example | product |
|---|---|
| 266 | 2-(2-methylallyl)-4-(1-methylpiperidin-4-yloxy)-9,10-dihydro-4H-3,10a-diaza-benzo[f]azulene-1-carboxylic acid amide<br>mp = 75° C. |
| 273 | 2-(2-chlorophenyl)-4-(1-methylpiperidin-4-yloxy)-9,10-dihydro-4H-3,10a-diaza-benzo[f]azulene-1-carboxylic acid amide<br>HPLC-MS analysis using method A: rt = 3.65 min; [M + H]$^+$ = 451.24 and 453.20 |

Example 254

4-(1-methylpiperidin-4-yloxy)-2-phenyl-9,10-dihydro-4H-3,10a-diaza-benzo[f]azulene-1-carboxylic acid amide The compound is synthesized using the method described in example 224 starting from 2-iodo-4-(1-methylpiperidin-4-yloxy)-9,10-dihydro-4H-3,10a-diaza-benzo[f]azulene-1-carboxylic acid amide (example 253). The compound is melting at 102° C.

Example 255

4-(1-methylpiperidin-4-yloxy)-2-phenyl-1-trifluoromethyl-9,10-dihydro-4H-3,10a-diaza-benzo[f]azulene To a solution of 1-iodo-4-(1-methylpiperidin-4-yloxy)-2-phenyl-9,10-dihydro-4H-3,10a-diaza-benzo[f]azulene (example 247) (100 mg, 0.2 mmole) in CH$_2$Cl$_2$ (1 mL) cooled at −20° C. is added a EtMgBr 3M solution in Et$_2$O (0.2 mL, 0.6 mmole). The cooling bath is removed and the reaction mixture is stirred at room temperature for 90 minutes. The reaction mixture is the re-cooled to −20° C. and a solution of 3,3-dimethyl-1-trifluoromethyl-1,2-benzodioxole (330 mg, 1 mmole) in CH$_2$Cl$_2$ (0.5 mL) is added dropwise. The reaction mixture is heated at 60° C. for 72 hours. A (1:1) solution of saturated aqueous NH$_4$Cl and concentrated NH$_4$OH is added and the aqueous phase is extracted three times with CH$_2$Cl$_2$. The organic phase is dried over MgSO$_4$, filtered and the solvent removed under reduced pressure. The residue is pre-purified by silica gel chromatography eluting with (CH$_2$Cl$_2$:MeOH:NH$_4$OH) (98:2:0.2) to (95:5:0.5). The residue is purified by preparative HPLC to give 4-(1-methylpiperidin-4-yloxy)-2-phenyl-1-trifluoromethyl-9,10-dihydro-4H-3,10a-diaza-benzo[f]azulene.

HPLC-MS analysis using method B: rt=7.25 min, [M+H]$^+$=442.24.

Example 256

256A 4-(1-methylpiperidin-4-yloxy)-2-phenyl-9,10-dihydro-4H-3,10a-diaza-benzo[f]azulene-1-carboxylic acid methyl ester To a solution of 4-(1-methylpiperidin-4-yloxy)-2-phenyl-9,10-dihydro-4H-3,10a-diaza-benzo[f]azulene-1-carboxylic acid (example 256B) (50 mg, 0.120 mmole) in MeOH (2 mL) is added a 2M solution of trimethylsilyldiazomethane in $CH_2Cl_2$ (0.2 mL). After 2 hours, as the reaction is only partial, a 2M solution of trimethylsilyldiazomethane in $CH_2Cl_2$ (0.2 mL) is added and the reaction mixture is heated at 45° C. overnight. Water is added and the aqueous phase is extracted with AcOEt. The organic phase is dried over $MgSO_4$, filtered and the solvent removed under reduced pressure. The residue is purified by silica gel chromatography eluting with ($CH_2Cl_2$:MeOH) from (100:0) to (95:5) to give 4-(1-methylpiperidin-4-yloxy)-2-phenyl-9,10-dihydro-4H-3,10a-diaza-benzo[f]azulene-1-carboxylic acid methyl ester.

HPLC-MS analysis using method A: rt=6.42 min, [M+H]$^+$=432.31; [M+Na]$^+$=454.31.

256B 4-(1-methylpiperidin-4-yloxy)-2-phenyl-9,10-dihydro-4H-3,10a-diaza-benzo[f]azulene-1-carboxylic acid To 4-(1-methyl piperidin-4-yloxy)-2-phenyl-9,10-dihydro-4H-3,10a-diaza-benzo[f]azulene-1-carboxylic acid amide (example 254) (250 mg, 0.6 mmole) is added 30% aqueous NaOH solution (2 mL). The reaction mixture is heated to 125° C. overnight. Water (2 mL) is added as well as 1N HCl to pH 6-7. The solvent is removed under reduced pressure. The residue is dissolved in absolute EtOH and filtered to remove inorganic salts. EtOH is removed under reduced pressure. The residue is triturated in $Et_2O$, filtered to afford 4-(1-methylpiperidin-4-yloxy)-2-phenyl-9,10-dihydro-4H-3,10a-diaza-benzo[f]azulene-1-carboxylic acid melting at 185° C.

Example 257

[4-(1-methylpiperidin-4-yloxy)-2-phenyl-9,10-dihydro-4H-3,10a-diaza-benzo[f]azulen-1-yl]-methanol To a solution of 4-(1-methylpiperidin-4-yloxy)-2-phenyl-9,10-dihydro-4H-3,10a-diaza-benzo[f]azulene-1-carboxylic acid (example 256B) (50 mg, 0.120 mmole) in THF (2 mL) is added dropwise $BH_3$-$Me_2S$ (46 µL, 0.48 mmole). The reaction mixture is heated at 50° C. overnight. Water is added and the aqueous phase is extracted with AcOEt. The organic phase is dried over $MgSO_4$, filtered and the solvent removed under reduced pressure. The residue is purified by silica gel chromatography eluting with ($CH_2Cl_2$:MeOH) from (100:0) to (90:10) to give [4-(1-methylpiperidin-4-yloxy)-2-phenyl-9,10-dihydro-4H-3,10a-diaza-benzo[f]azulen-1-yl]-methanol melting at 120° C.

Example 258

258A 6-iodo-1-methyl-4-(1-methylpiperidin-4-yloxy)-2-phenyl-9,10-dihydro-4H-3,10a-diaza-benzo[f]azulene The compound is synthesized using the methods described in examples 2A-B, 110B starting from 5-methyl-4-phenyl-1H-imidazole and methanesulfonic acid 2-(3-iodophenyl)-ethyl ester (example 258B) to afford 6-iodo-1-methyl-4-(1-methylpiperidin-4-yloxy)-2-phenyl-9,10-dihydro-4H-3,10a-diaza-benzo[f]azulene.

$^1$H NMR: 7.65 (s, 1H), 7.62-7.53 (m, 3H), 7.47-7.35 (m, 2H), 7.31-7.22 (m, 1H), 7.06 (d, J=5.3 Hz, 1H), 5.62 (s, 1H), 4.48-4.20 (m, 2H), 3.90-3.78 (m, 1H), 3.66-3.54 (m, 1H), 2.98-2.85 (m, 1H), 2.82-2.68 (m, 2H), 2.34 (s, 3H), 2.30 (s, 3H), 2.40-2.15 (m, 2H), 2.05-1.82 (m, 2H) 2.82-1.65 (m, 2H).

258B methanesulfonic acid 2-(3-iodophenyl)-ethyl ester

The compound is synthesized using the method described in example 4D starting from 2-(3-iodophenyl)-ethanol.

Example 259

2-(2-methylallyl)-4-(1-methylpiperidin-4-yloxy)-9,10-dihydro-4H-3,10a-diaza-benzo[f]azulene-1-carbonitrile To a solution of 2-iodo-4-(1-methylpiperidin-4-yloxy)-9,10-dihydro-4H-3,10a-diaza-benzo[f]azulene-1-carbonitrile (example 221) (107 mg, 0.239 mmole) in DMF (4 mL) are added potassium methallyltributyltin (331 mg, 0.95 mmole), Pd(PPh$_3$)$_4$ (28 mg, 0.025 mmole), LiCl (51 mg, 1.30 mmole). The flask is evacuated and filled with argon. The reaction mixture is heated at 110° C. for 5 hours. AcOEt and water are added, as well as a 10% KF solution. The aqueous phase is extracted with AcOEt. The organic phase is washed with 0.5N HCl. The HCl phase is made alkaline with 1H NaOH and the aqueous phase is extracted with AcOEt. The organic phase is dried over $MgSO_4$, filtered and the solvent removed under reduced pressure. The residue is purified by silica gel chromatography eluting with ($CH_2Cl_2$:MeOH) (100:0) to (95:5) to give 2-(2-methylallyl)-4-(1-methylpiperidin-4-yloxy)-9,10-dihydro-4H-3,10a-diaza-benzo[f]azulene-1-carbonitrile.

HPLC-MS analysis using method A: rt=3.88 min; [M+H]$^+$=377.27; [M+Na]$^+$=399.26.

The following example is synthesized using the same method.

| example | product |
|---|---|
| 263 | 2-benzyl-4-(1-methylpiperidin-4-yloxy)-9,10-dihydro-4H-3,10a-diaza-benzo[f]azulene-1-carbonitrile.<br>HPLC-MS analysis using method B: rt = 6.95 min; [M + H]$^+$ = 412.29 |

Example 261

7-bromo-4-(1-methylpiperidin-4-yloxy)-2-phenyl-9,10-dihydro-4H-3,10a-diaza-benzo[f]azulene

261A

7-Bromo-4-(1-methylpiperidin-4-yloxy)-2-phenyl-9,10-dihydro-4H-3,10a-diaza-benzo[f]azulene melting at 92° C. is prepared analogously to example 123 from 7-bromo-2-phenyl-9,10-dihydro-4H-3,10a-diaza-benzo[f]azulen-4-ol (example 261B). Chloroform is replaced by dichloromethane and time of reaction is 16 hours.

261B

7-Bromo-2-phenyl-9,10-dihydro-4H-3,10a-diaza-benzo[f]azulen-4-ol is prepared analogously to example 123 from 1-[2-(3-bromophenyl)ethyl]-4-phenyl-imidazole-2-carbaldehyde (example 261C). 1,2-Dichloroethane replaces chloroform and the mixture refluxed for 6 hours.

261C

1-[2-(3-Bromophenyl)ethyl]-4-phenyl-imidazole-2-carbaldehyde is obtained in three steps analogously to example 4 from 2-(3-bromophenyl)ethanol and 4-phenyl-1H-imidazole.

Example 262

4-(1-methylpiperidin-4-yloxy)-2-phenyl-9,10-dihydro-4H-3,10a-diaza-benzo[f]azulene-1-carbaldehyde To a solution of [4-(1-methylpiperidin-4-yloxy)-2-phenyl-9,10-dihydro-4H-3,10a-diaza-benzo[f]azulen-1-yl]-methanol (example 257A) (300 mg, 0.745 mmole) in 1,4-dioxane (4 mL) is added $MnO_2$ (320 mg, 3.72 mmole) and the reaction mixture is heated at 90° C. overnight. Another portion of $MnO_2$ (320 mg, 3.72 mmole) is added and the reaction mixture is heated at 90° C. overnight. The reaction mixture is filtered onto celite, cake washed with AcOEt and the solvent is removed under reduced pressure. The residue is purified by silica gel chromatography eluting with ($CH_2Cl_2$:MeOH) (100:0) to (95:5) to give 4-(1-methylpiperidin-4-yloxy)-2-phenyl-9,10-dihydro-4H-3,10a-diaza-benzo[f]azulene-1-carbaldehyde melting at 70° C.

Example 267

1,2-bis-(2-methylallyl)-4-(1-methylpiperidin-4-yloxy)-9,10-dihydro-4H-3,10a-diaza-benzo[f]azulene dioxalate To a solution of 1,2-diiodo-4-(1-methylpiperidin-4-yloxy)-9,10-dihydro-4H-3,10a-diaza-benzo[f]azulene (example 219) (270 mg, 0.49 mmole) in DMF (5 mL) are added potassium methallyltributyltin (679 mg, 1.96 mmole), $Pd(PPh_3)_4$ (56 mg, 0.05 mmole), LiCl (102 mg, 2.60 mmole). The flask is evacuated and filled with argon. The reaction mixture is heated at 90° C. overnight. DMF is removed under reduced pressure. Water is added and the aqueous phase is extracted with $Et_2O$. The organic phase is dried over $MgSO_4$, filtered and the solvent removed under reduced pressure. The residue is purified by silica gel chromatography eluting with ($CH_2Cl_2$:MeOH) (100:0) to (90:10). The residue is dissolved in acetone and oxalic acid (2 equivalents) is added. Acetone is removed under reduced pressure to give 1,2-bis-(2-methylallyl)-4-(1-methyl piperidin-4-yloxy)-9,10-dihydro-4H-3,10a-diaza-benzo[f]azulene dioxalate melting at 70° C.

Biological Data
In Vitro Evaluation of Compounds
Membrane Preparation
SH-SY5Y cells stably expressing human H4 receptor are grown until sub-confluence and centrifuged at 300 g during 15 minutes at 4° C. Pellets are resuspended in buffer I (Tris-HCl 50 mM, $MgCl_2$ 10 mM, NaCl 140 mM, pH=7.4) supplemented by Leupeptin 10 µg/mL, Phenyl Methyl Sulphonyl Fluoride (PMSF) 0.1 mM, Aprotinin 2 µg/mL and Pepstatin 2 µM (or a 1/50 dilution of a mix of protease inhibitors). The obtained suspension is stirred gently and submitted to a 25-26×g mechanic pressure exerted through a syringe. The cell lysate is then centrifuged at 300 g during 15 minutes at 4° C. in order to eliminate nucleus and cell scraps. The obtained supernatant is then centrifuged at 48000 g during 30 minutes at 4° C. The final pellet is resuspended in buffer I with a potter homogenizer. Aliquots are frozen in liquid nitrogen and stored until use at −80° C. Protein content is measured by the Bradford method.

GTPγ [$^{35}$S] Binding

Defreezed membranes are diluted at a final concentration of 5 µg/180 µL/well in buffer I supplemented by GDP 10 µM and distributed in 96 well polystyrene microplate. GTPγ [$^{35}$S] labelled ligand (0.2-0.3 nM) is added for additional 30 minutes. After transfer in a Millipore GF/C HTS® microplate, the filtration of the reactional mix is followed by a three times 250 µl wash to stop the reaction.

The filter-bound radioactivity is measured in a liquid scintillation counter Microbeta TRILUX® with 50 µl of scintillation fluid.

GTPγ [$^{35}$S] dependent binding activity is determined in vitro for Histamine, Imetit, R(−)-alpha-methyl-histamine and all our compounds.

Compounds can also be tested against Histamine or Imetit to evaluate their antagonist potential. Results are expressed with IC50 and Ki values.

Membrane Preparation
CHO cells stably expressing human H4 receptor were grown until sub-confluence and centrifuged at 300 g during 15 minutes at 4° C. Pellets were resuspended in buffer I (Tris-HCl 50 mM, $MgCl_2$ 10 mM, NaCl 140 mM, pH=7.4) supplemented by a 1/50 dilution of a mix of protease inhibitors. The obtained suspension is stirred gently and submitted to a 25-26×g mechanic pressure exerted through a syringe. The cell lysate is then centrifuged at 300 g during 15 minutes at 4° C. in order to eliminate nucleus and cell scraps. The obtained supernatant was then centrifuged at 48000 g during 30 minutes at 4° C. The final pellet is resuspended in buffer I with a potter homogenizer. Aliquots were frozen in liquid nitrogen and stored until use at −80° C. Protein content is measured by the Bradford method.

[$^3$H]Histamine Binding

Defreezed membranes were diluted at a final concentration of 20 µg/180 µL/well in a binding buffer containing 50 mM Tris/HCl, 0.5 mM EDTA, pH=7.4 and distributed in 96 well polystyrene microplate. [$^3$H] Histamine labelled ligand (10-15 nM) is added for 60 minutes with compounds at room temperature under continuous stirring. Non specific binding was estimated in the presence of 10 µM BP 1,2404 (JNJ 7777120). The reaction was terminated by filtration through GF/B filters pre-soaked 2 hours at 4° C. in 1% polyethyleneimine. Filters were rinsed 3 times with 250 µl of ice cold incubation binding buffer.

The filter-bound radioactivity was measured in a liquid scintillation counter Microbeta TRILUX® with 50 µl of scintillation fluid.

The hH4 binding investigated by use of [$^3$H] Histamine give a Bmax ~1 µmole/mg protein and a Kd ~9 nM.

Compounds described hereabove have been evaluated in the GTPγ [$^{35}$S] assay or in the [$^3$H] histamine binding assay and have been found active with a Ki or IC50 under 1000 nM.

| Ex | Ki | IC50 |
|---|---|---|
| 1 | B | A |
| 1 | A | |
| 2 | B | |
| 3 | B | |
| 4 | B | B |
| 5 | C | B |
| 6 | B | B |
| 7 | A | |
| 8 | B | |
| 9 | A | |
| 10 | B | A |
| 11 | C | B |
| 12 | B | B |
| 13 | B | |
| 14 | B | B |
| 15 | C | C |
| 16 | A | |
| 17 | B | |
| 18 | A | |
| 19 | B | |
| 20 | C | C |
| 21 | B | C |
| 22 | C | B |
| 23 | A | |
| 24 | B | |
| 25 | C | C |
| 26 | C | B |
| 27 | B | B |
| 28 | C | |
| 29 | B | B |
| 30 | B | B |
| 31 | B | C |
| 32 | B | B |
| 33 | B | B |
| 34 | B | B |
| 35 | A | |
| 36 | C | C |
| 37 | C | C |
| 38 | B | C |
| 39 | A | |
| 40 | A | |
| 41 | C | B |
| 42 | C | C |
| 43 | B | B |
| 44 | A | |
| 45 | A | |
| 46 | C | C |
| 47 | B | B |
| 48 | A | |
| 49 | C | B |
| 50 | C | A |
| 51 | B | |
| 52 | C | |
| 53 | A | |
| 54B | B | C |
| 55 | B | |
| 56 | C | C |
| 57 | B | |
| 58 | B | |
| 59 | B | |
| 60 | B | |
| 61 | B | |
| 62 | B | B |
| 63 | A | |
| 64 | B | C |
| 65 | B | A |
| 66 | B | |
| 67 | B | B |
| 68 | C | B |
| 69 | C | B |
| 70 | B | B |
| 71 | C | |
| 72 | C | C |
| 73 | B | |
| 74 | B | B |
| 75 | B | C |
| 76 | C | B |
| 77 | C | B |
| 78 | B | |
| 79 | B | A |
| 80 | C | B |
| 81 | C | C |
| 82 | B | C |
| 83 | A | |
| 84 | B | |
| 85 | B | |
| 86 | B | C |
| 87 | C | C |
| 88 | B | A |
| 89 | C | |
| 90 | C | C |
| 91 | B | |
| 92 | B | |
| 93 | C | C |
| 94 | C | C |
| 95 | C | |
| 96 | B | B |
| 97 | C | C |
| 98 | B | |
| 99 | B | B |
| 100 | A | |
| 101 | B | |
| 102 | A | |
| 103 | C | C |
| 104 | C | |
| 105 | C | C |
| 106 | A | |
| 107 | A | |
| 108 | A | |
| 109 | B | |
| 110 | B | |
| 111 | C | |
| 112 | C | C |
| 113 | B | |
| 114 | B | |
| 115 | B | |
| 116 | B | |
| 117 | B | |
| 118 | A | |
| 119 | C | C |
| 120 | C | C |
| 121 | C | C |
| 122 | C | C |
| 123 | B | |
| 124 | B | |
| 125 | C | C |
| 126 | B | |
| 127 | C | C |
| 128 | B | |
| 129 | C | C |
| 130 | C | C |
| 131 | B | |
| 132 | B | |
| 133 | B | |
| 134 | C | C |
| 135B | C | C |
| 136 | B | |
| 138 | A | |
| 139 | C | C |
| 140 | C | B |
| 141 | C | |
| 142 | B | C |
| 143 | C | C |
| 144 | C | C |
| 145 | C | C |
| 146 | C | C |
| 147 | C | C |
| 148 | C | |
| 149 | B | |
| 150 | C | C |
| 151 | C | C |
| 152 | C | C |
| 153 | C | C |
| 154 | C | |
| 155 | C | |
| 156 | C | C |

| Ex | Ki | IC50 |
|---|---|---|
| 157 | C | |
| 158 | C | C |
| 159 | C | |
| 160 | C | |
| 161 | C | C |
| 162 | B | |
| 163 | C | C |
| 164 | C | C |
| 165 | C | |
| 166 | C | |
| 167 | C | C |
| 168 | C | |
| 169 | C | |
| 170 | C | |
| 171 | C | |
| 172 | C | |
| 173 | B | |
| 174 | C | |
| 175 | C | |
| 176 | C | |
| 177 | C | |
| 178 | C | |
| 179 | B | |
| 180 | B | |
| 181 | B | |
| 182 | B | |
| 183 | C | |
| 184 | A | |
| 185 | B | |
| 186 | B | |
| 187 | B | B |
| 188 | B | B |
| 189 | B | |
| 190 | B | |
| 191 | B | |
| 192 | B | |
| 193 | B | |
| 194 | B | C |
| 195 | C | C |
| 196 | B | |
| 197 | C | |
| 198 | B | |
| 199 | B | |
| 200 | B | |
| 201 | A | |
| 202 | A | |
| 203 | A | |
| 204 | A | |
| 205 | A | |
| 206 | C | C |
| 207 | A | |
| 208 | B | |
| 209 | C | |
| 210 | A | |
| 211 | C | |
| 212 | A | |
| 213 | C | |
| 214 | C | |
| 215 | B | |
| 216 | B | |
| 217 | B | |
| 218 | B | |
| 219 | C | C |
| 220 | B | |
| 221 | A | |
| 222 | A | |
| 223 | C | |
| 224 | C | |
| 225 | C | C |
| 226 | C | C |
| 227 | B | |
| 228 | C | |
| 229 | C | |
| 230 | A | |
| 231 | B | |
| 232 | A | |
| 233 | A | |
| 234 | A | |
| 235 | C | |
| 236 | B | |
| 237 | A | |
| 238 | B | |
| 239 | A | |
| 240 | B | |
| 241 | B | |
| 242 | A | |
| 243 | B | |
| 244 | A | |
| 245 | A | |
| 246 | B | |
| 247 | C | |
| 248 | A | |
| 249 | A | |
| 250 | A | |
| 251 | B | |
| 252 | B | |
| 253 | A | |
| 254 | B | B |
| 255 | C | B |
| 256 | B | |
| 257 | B | B |
| 258 | A | |
| 259 | B | B |
| 260 | B | |
| 261 | B | |
| 262 | B | |
| 263 | B | |
| 264 | A | |
| 265 | A | |
| 266 | B | |
| 267 | B | |
| 268 | B | |
| 269 | A | |
| 270 | A | |
| 271 | A | |
| 272 | C | |
| 273 | B | |

A: Ki or IC50 <1000 nM
B: Ki or IC50 <300 nM
C: Ki or IC50 <30 nM

The invention claimed is:
1. A compound of formula (I):

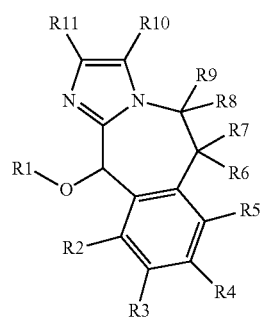

wherein
R1 is chosen from:
an alkyl optionally substituted by an amino, alkylamino, dialkylamino group or a monocyclic or bicyclic heterocycle possessing a nitrogen atom; and
a monocyclic or bicyclic heterocycle possessing a nitrogen atom, said heterocycle being optionally substituted by an alkyl group;

R2, R3, R4 and R5 identical or different are independently chosen from:
hydrogen-;
halogen-;
alkyl-;
alkenyl-;
optionally substituted aryl-;
aralkyl-;
alkylamino-;
dialkylamino-;
alkoxy-;
aralkoxy-;
alkylsulfanyl-;
R6, R7, R8 and R9 identical or different are independently chosen from:
hydrogen-;
alkyl-;
R10 and R11 identical or different are independently chosen from the following list L1:
hydrogen-;
halogen-;
alkyl-;
cycloalkyl-;
cycloalkylalkyl-;
cycloalkylalkenyl;
alkenyl-;
cycloalkenyl-;
alkynyl-;
aryl-;
aralkyl-;
aralkenyl-;
aralkynyl-;
aralkoxyalkyl-;
aryloxyalkyl-;
aralkoxyalkenyl-;
aryloxyalkenyl-;
arylcarbonyl-;
arylsulfanyl-;
aralkylsulfanyl-;
heteroaryl-;
heteroarylalkyl-;
heteroarylalkenyl-;
heteroarylalkynyl-;
heteroarylsulfanyl-;
heteroaralkylsulfanyl-;
heterocycle-;
heterocyclesulfanyl-;
alkoxy-;
alkylsulfanyl-;
cycloalkylsulfanyl-;
cyano-;
alkylcarbonyl-;
aminocarbonyl-;
alkylaminocarbonyl-;
dialkylaminocarbonyl-;
arylaminocarbonyl-;
aralkylaminocarbonyl-;
N-alkyl-arylaminocarbonyl-;
N-alkyl-aralkylaminocarbonyl-;
alkoxycarbonyl-;
alkoxycarbonylalkyl-;
alkoxycarbonylalkenyl-;
alkoxycarbonylalkynyl-;
alkoxycarbonylheterocycle-;
alkoxycarbonylheterocyclesulfanyl-;
the aryl and heteroaryl groups being optionally substituted with one or more:
halogen-;
hydroxyl-;
nitro-;
alkyl-;
(per)halogenoalkyl-;
alkenyl-;
alkynyl-;
cycloalkyl-;
cycloalkenyl-;
alkylcarbonyl-;
(per)halogenoalkylcarbonyl-;
cycloalkylalkyl-;
alkoxy-;
(per)halogenoalkoxy-;
alkoxyalkyl-;
alkenyloxy-;
akynyloxy-;
hydroxyalkyl-;
amino-;
alkylamino-;
dialkylamino-;
aminoalkyl-;
alkylaminoalkyl-;
dialkylaminoalkyl-;
aminoalkoxy-;
alkylaminoalkoxy-;
dialkylaminoalkoxy-;
alkylsulfonyl-;
alkylsulfanyl-;
alkylsulfonylalkyl-;
alkylsulfanylalkyl-;
alkylsulfonylalkenyl-;
alkylsulfanylalkenyl-;
alkylsulfonylalkynyl-;
alkylsulfanylalkynyl-;
hydroxyalkylsufanyl-;
aminoalkylsulfanyl-;
cycloalkylsulfonylamino-;
alkoxycarbonylaminoalkylsulfanyl-;
alkylcarbonylaminoalkylsulfanyl-;
guanidinoalkylsulfanyl-;
sulfamoyl-;
alkylsulfamoyl-;
dialkylsulfamoyl-;
cyano-;
cyanoalkyl-;
aryl-;
arylcarbonyl-;
aralkyl-;
aralkenyl-;
aralkynyl-;
arylsulfanyl-;
aralkylsulfanyl-;
heteroaryl-;
heteroarycarbonyl-;
heteroaralkyl-;
heteroaralkenyl-;
heteroaralkynyl-;
heteroarylsulfanyl-;
heteroaralkylsulfanyl-;
alkoxycarbonyl-;
alkoxycarbonylamino-;
(per)halogenoalkoxycarbonylamino-;
alkoxyalkylcarbonylaminoalkyl-;
cycloalkylalkoxy-;
cycloalkylalkoxycarbonylamino-;
N-alkyl-alkoxycarbonylamino-;

N-alkyl-aminocarbonyloxyalkyl-;
alkoxycarbonylhydrazinyl-;
alkylcarbonylamino-;
hydroxyalkylaminocarbonyl-;
alkoxyalkylcarbonylamino-;
N-alkyl-alkylcarbonylamino-;
2-oxopyrolidin-1-yl-;
2-oxopiperidin-1-yl-;
2-oxoperhydroazepin-1-yl-;
2-oxo-1,3-oxazolidin-3-yl-;
4-aralkyl-2-oxo-1,3-oxazolidin-3-yl-;
2-oxoimidazolidin-1-yl-;
3-alkyl-2-oxoimidazolidin-1-yl-;
2-oxopyrolidin-1-ylalkyl-;
2-oxopiperidin-1-ylalkyl-;
2-oxoperhydroazepin-1-ylalkyl-;
2-oxo-1,3-oxazolidin-3-ylalkyl-;
4-aralkyl-2-oxo-1,3-oxazolidin-3-ylalkyl-;
5,5-dialkyl-2,4-dioxo-1,3-oxazolidin-3-ylalkyl-;
2-oxoimidazolidin-1-ylalkyl-;
3-alkyl-2-oxoimidazolidin-1-ylalkyl-;
hydroxyheterocyclylcarbonyl-;
hydroxycycloalkylaminocarbonyl-;
hydroxyheterocyclylaminocarbonyl-;
alkoxycarbonylheterocyclyl-;
oxoheterocyclylcarbonyl-;
alkoxycarbonylalkyl-;
alkoxycarbonylalkenyl-;
alkoxycarbonylalkynyl-;
alkoxycarbonylalkylsulfanyl-;
alkoxycarbonylaminoalkyl-;
N-alkyl-alkoxycarbonylaminoalkyl-;
alkylcarbonylaminoalkyl-;
N-alkyl-acylaminoalkyl-;
ureido-;
alkylureido-;
cycloalkylureido-;
adamantylureido-;
thioureido-;
alkylthioureido-;
cycloalkylthioureido-;
oxo-;
the alkyl, alkenyl, alkynyl chains of L1 being optionally substituted with one or more:
halogen-;
hydroxyl-;
alkoxycarbonylamino-;
or {4-[1-methyl-4-(1-methylpiperidin-4-yloxy)-9,10-dihydro-4H-3,10a-diaza-benzo[f]azulen-2-yl]-phenyl}-carbamic acid cyclopentyl ester;
or 4-(1-methylpiperidin-4-yloxy)-2-phenyl-9,10-dihydro-4H-3,10a-diaza-benzo[f]azulene-1-carbaldehyde;
as well as its enantiomers, diastereomers, mixtures thereof and pharmaceutically acceptable salts, tautomers, and hydrates.

2. The compound according to claim 1, wherein:
R1 is chosen from:
an alkyl optionally substituted by an amino, alkylamino, dialkylamino group or a monocyclic or bicyclic heterocycle possessing a nitrogen atom; and
a monocyclic or bicyclic heterocycle possessing a nitrogen atom, said heterocycle being optionally substituted by an alkyl group;
R2, R3, R4 and R5 identical or different are independently chosen from:
hydrogen-;
halogen-;
alkyl-;
alkenyl-;
optionally substituted aryl-;
aralkyl-;
alkylamino-;
alkoxy-;
aralkoxy-;
alkylsulfanyl-;
R6, R7, R8 and R9 identical or different are independently chosen from:
hydrogen-;
alkyl-;
R10 and R11 identical or different are independently chosen from the following list L2:
hydrogen-;
halogen-;
alkyl-;
cycloalkyl-;
cycloalkylalkyl-;
cycloalkylalkenyl;
alkenyl-;
cycloalkenyl-;
alkynyl-;
aryl-;
aralkyl-;
aralkenyl-;
aralkynyl-;
aryloxyalkyl-;
aralkoxyalkenyl-;
aryloxyalkenyl-;
arylcarbonyl-;
arylsulfanyl-;
aralkylsulfanyl-;
heteroaryl-;
heteroarylalkyl-;
heteroarylalkenyl-;
heteroarylalkynyl-;
heteroarylsulfanyl-;
heteroaralkylsulfanyl-;
heterocycle-;
heterocyclesulfanyl-;
alkoxy-;
alkylsulfanyl-;
cycloalkylsulfanyl-;
cyano-;
alkylcarbonyl-;
aminocarbonyl-;
alkylaminocarbonyl-;
arylaminocarbonyl-;
aralkylaminocarbonyl-;
N-alkyl-arylaminocarbonyl-;
N-alkyl-aralkylaminocarbonyl-;
alkoxycarbonyl-;
alkoxycarbonylalkyl-;
alkoxycarbonylalkenyl-;
alkoxycarbonylalkynyl-;
alkoxycarbonylheterocycle-;
alkoxycarbonylheterocyclesulfanyl-;
the aryl and heteroaryl groups being optionally substituted with one or more:
halogen-;
hydroxyl-;
nitro-;
alkyl-;
(per)halogenoalkyl-;
cycloalkenyl-;
alkylcarbonyl-;

(per)halogenoalkylcarbonyl-;
cycloalkylalkyl-;
alkoxy-;
(per)halogenoalkoxy-;
alkoxyalkyl-;
alkenyloxy-;
hydroxyalkyl-;
amino-;
alkylamino-;
dialkylamino-;
aminoalkyl-;
dialkylaminoalkyl-;
dialkylaminoalkoxy-;
alkylsulfonyl-;
alkylsulfanyl-;
alkylsulfonylalkyl-;
alkylsulfanylalkyl-;
alkylsulfonylalkenyl-;
alkylsulfanylalkenyl-;
alkylsulfanylalkynyl-;
hydroxyalkylsufanyl-;
aminoalkylsulfanyl-;
cycloalkylsulfonylamino-;
alkoxycarbonylaminoalkylsulfanyl-;
alkylcarbonylaminoalkylsulfanyl-;
guanidinoalkylsulfanyl-;
sulfamoyl-;
alkylsulfamoyl-;
dialkylsulfamoyl-;
cyano-;
aralkylsulfanyl-;
heteroaryl-;
heteroaralkylsulfanyl-;
alkoxycarbonyl-;
alkoxycarbonylamino-;
(per)halogenoalkoxycarbonylamino-;
alkoxyalkylcarbonylaminoalkyl-;
cycloalkylalkoxy-;
cycloalkylalkoxycarbonylamino-;
N-alkyl-alkoxycarbonylamino-;
N-alkyl-aminocarbonyloxyalkyl-;
alkoxycarbonylhydrazinyl-;
alkylcarbonylamino-;
hydroxyalkylaminocarbonyl-;
N-alkyl-alkylcarbonylamino-;
2-oxopyrolidin-1-yl-;
2-oxopiperidin-1-yl-;
2-oxoperhydroazepin-1-yl-;
2-oxo-1,3-oxazolidin-3-yl-;
4-aralkyl-2-oxo-1,3-oxazolidin-3-yl-;
3-alkyl-2-oxoimidazolidin-1-yl-;
2-oxopyrolidin-1-ylalkyl-;
2-oxopiperidin-1-ylalkyl-;
2-oxoperhydroazepin-1-ylalkyl-;
2-oxo-1,3-oxazolidin-3-ylalkyl-;
5,5-dialkyl-2,4-dioxo-1,3-oxazolidin-3-ylalkyl-;
2-oxoimidazolidin-1-ylalkyl-;
3-alkyl-2-oxoimidazolidin-1-ylalkyl-;
hydroxyheterocyclylcarbonyl-;
hydroxycycloalkylaminocarbonyl-;
hydroxyheterocyclylaminocarbonyl-;
alkoxycarbonylheterocyclyl-;
oxoheterocyclylcarbonyl-;
alkoxycarbonylalkenyl-;
alkoxycarbonylalkylsulfanyl-;
alkoxycarbonylaminoalkyl-;
N-alkyl-alkoxycarbonylaminoalkyl-;
alkylcarbonylaminoalkyl-;
N-alkyl-acylaminoalkyl-;
alkylureido-;
cycloalkylureido-;
adamantylureido-;
alkylthioureido-;
cycloalkylthioureido-;
oxo-;
the alkyl, alkenyl, alkynyl chains of L2 being optionally substituted with one or more:
halogen-;
hydroxyl-;
alkoxycarbonylamino-;
as well as its enantiomers, diastereomers, mixtures thereof and pharmaceutically acceptable salts, tautomers, and hydrates.

3. A compound according to claim 1, wherein:
R1 is a monocyclic or bicyclic heterocycle possessing a nitrogen atom, said heterocycle being optionally substituted by an alkyl group;
R2, R3, R4, R5, R6, R7, R8 and R9 are hydrogen;
R10 represents:
hydrogen-;
halogen-;
alkyl-;
cyano-;
R11 is chosen from the following list L3:
halogen-;
alkyl-;
cycloalkyl-;
cycloalkylalkyl-;
cycloalkylalkenyl;
alkenyl-;
cycloalkenyl-;
alkynyl-;
aryl-;
aralkyl-;
aralkenyl-;
aralkylsulfanyl-;
aryloxyalkenyl-;
heteroaryl-;
heteroarylalkenyl-;
heteroarylsulfanyl-;
cycloalkylsulfanyl-;
the aryl and heteroaryl groups being optionally substituted with one or more:
halogen-;
alkyl-;
(per)halogenoalkyl-;
cycloalkyl-;
cycloalkenyl-;
alkylcarbonyl-;
(per)halogenoalkylcarbonyl-;
alkenyloxy-;
alkoxy-;
(per)halogenoalkoxy-;
alkoxyalkyl-;
alkylsulfanyl-;
alkylsulfonylalkyl-;
alkylsulfonylalkenyl-;
hydroxyalkylsufanyl-;
aminoalkylsulfanyl-;
alkoxycarbonylaminoalkylsulfanyl-;
alkylcarbonylaminoalkylsulfanyl-;
alkoxycarbonylalkylsulfanyl-;
guanidinoalkylsulfanyl-;
cyano-;

aralkylsulfanyl-;
heteroaralkylsulfanyl-;
alkoxycarbonyl-;
alkoxycarbonylamino-;
(per)halogenoalkoxycarbonylamino-;
cycloalkylalkoxycarbonylamino-;
alkoxycarbonylhydrazinyl-;
N-alkyl-alkoxycarbonylamino-;
N-alkyl-alkoxycarbonylaminoalkyl-;
3-alkyl-2-oxoimidazolidin-1-yl-;
4-aralkyl-2-oxo-1,3-oxazolidin-3-yl-;
alkoxycarbonylheterocyclyl-;
alkoxycarbonylalkyl-;
alkoxycarbonylaminoalkyl-;
alkylureido-;
cycloalkylureido-;
adamantylureido-;
alkylthioureido-;
the alkyl, alkenyl, alkynyl chains of L3 being optionally substituted with one or more:
halogen-;
hydroxyl-;
alkoxycarbonylamino-;
as well as its enantiomers, diastereomers, mixtures thereof and pharmaceutically acceptable salts, tautomers, and hydrates.

4. A compound according to claim 1, wherein:
R1 is chosen from:
8-Me-8-aza-bicyclo[3.2.1]oct-yl-;
Dimethylaminoethyl-;
Dimethylaminopropyl-;
N-Me-azetidin-3-ylmethyl-;
N-Me-piperidin-4-yl-;
N-Me-pyrrolidin-3-yl-;
Piperidinoethyl-;
Quinuclidin-3-yl-;
R2, R3, R4 and R5, R6, R7, R8 and R9 each represent hydrogen;
R10 represents:
hydrogen-;
halogen-;
alkyl-;
cyano-;
R11 is chosen from the following list L4:
halogen-;
alkyl-;
cycloalkyl-;
cycloalkylalky-;
cycloalkylalkenyl;
alkenyl-;
cycloalkenyl-;
alkynyl-;
aryl-;
aralkyl-;
aralkenyl-;
aralkylsulfanyl-;
aryloxyalkenyl-;
heteroaryl-;
heteroarylalkenyl-;
heteroarylsulfanyl-;
cycloalkylsulfanyl-;
the aryl and heteroaryl groups being optionally substituted with one or more:
halogen-;
alkyl-;
(per)halogenoalkyl-;
cycloalkyl-;
cycloalkenyl-;
alkylcarbonyl-;
(per)halogenoalkylcarbonyl-;
alkenyloxy-;
alkoxy-;
(per)halogenoalkoxy-;
alkoxyalkyl-;
alkylsulfanyl-;
alkylsulfonylalkyl-;
alkylsulfonylalkenyl-;
hydroxyalkylsufanyl-;
aminoalkylsulfanyl-;
alkoxycarbonylaminoalkylsulfanyl-;
alkylcarbonylaminoalkylsulfanyl-;
alkoxycarbonylalkylsulfanyl-;
guanidinoalkylsulfanyl-;
cyano-;
aralkylsulfanyl-;
heteroaralkylsulfanyl-;
alkoxycarbonyl-;
alkoxycarbonylamino-;
cycloalkylalkoxycarbonylamino-;
alkoxycarbonylhydrazinyl-;
N-alkyl-alkoxycarbonylamino-;
N-alkyl-alkoxycarbonylaminoalkyl-;
3-alkyl-2-oxoimidazolidin-1-yl-;
4-aralkyl-2-oxo-1,3-oxazolidin-3-yl-;
alkoxycarbonylheterocyclyl-;
alkoxycarbonylalkyl-;
alkoxycarbonylaminoalkyl-;
alkylureido-;
cycloalkylureido-;
adamantylureido-;
alkylthioureido-;
the alkyl, alkenyl, alkynyl chains of L4 being optionally substituted with one or more:
halogen-;
hydroxyl-;
alkoxycarbonylamino-;
as well as its enantiomers, diastereomers, mixtures thereof and pharmaceutically acceptable salts, tautomers, and hydrates.

5. A compound according to claim 1 where R1 is N-Me-piperidin-4-yl;
as well as its enantiomers, diastereomers, mixtures thereof and pharmaceutically acceptable salts, tautomers, and hydrates.

6. A compound according to claim 1 chosen from:
-4-(1-Methyl-piperidin-4-yloxy)-2-trifluoromethyl-9,10-dihydro-4H-3,10a-diaza-benzo[f]azulene
4-(1-Methyl-piperidin-4-yloxy)-1-trifluoromethyl-9,10-dihydro-4H-3,10a-diaza-benzo[f]azulene
2-Iodo-4-(1-methyl-piperidin-4-yloxy)-9,10-dihydro-4H-3,10a-diaza-benzo[f]azulene
1-Iodo-4-(1-methyl-piperidin-4-yloxy)-9,10-dihydro-4H-3,10a-diaza-benzo[f]azulene
4-(1-Methyl-piperidin-4-yloxy)-2-phenyl-9,10-dihydro-4H-3,10a-diaza-benzo[f]azulene
4-(1-Methyl-piperidin-4-yloxy)-2-p-tolyl-9,10-dihydro-4H-3,10a-diaza-benzo[f]azulene
4-(1-Methyl-piperidin-4-yloxy)-2-m-tolyl-9,10-dihydro-4H-3,10a-diaza-benzo[f]azulene
2-Iodo-4-(1-methyl-azetidin-3-ylmethoxy)-9,10-dihydro-4H-3,10a-diaza-benzo[f]azulene
4-(1-Methyl-piperidin-4-yloxy)-2-o-tolyl-9,10-dihydro-4H-3,10a-diaza-benzo[f]azulene 4-(1-Methyl-piperidin-4-yloxy)-2-vinyl-9,10-dihydro-4H-3,10a-diaza-benzo[f]azulene
2-(4-tert-Butyl-phenyl)-4-(1-methyl-piperidin-4-yloxy)-9,10-dihydro-4H-3,10a-diaza-benzo[f]azulene
1-{4-[4-(1-Methyl-piperidin-4-yloxy)-9,10-dihydro-4H-3,10a-diaza-benzo[f]azulen-2-yl]-phenyl}-ethanone
4-(1-Methyl-piperidin-4-yloxy)-2-thiophen-3-yl-9,10-dihydro-4H-3,10a-diaza-benzo[f]azulene
2-Ethyl-4-(1-methyl-piperidin-4-yloxy)-9,10-dihydro-4H-3,10a-diaza-benzo[f]azulene
2-(4-Methoxy-phenyl)-4-(1-methyl-piperidin-4-yloxy)-9,10-dihydro-4H-3,10a-diaza-benzo[f]azulene
4-(1-Methyl-piperidin-4-yloxy)-2-(4-trifluoromethoxy-phenyl)-9,10-dihydro-4H-3,10a-diaza-benzo[f]azulene
4-[4-(1-Methyl-piperidin-4-yloxy)-9,10-dihydro-4H-3,10a-diaza-benzo[f]azulen-2-yl]-phenylamine
2-(4-Methanesulfonyl-phenyl)-4-(1-methyl-piperidin-4-yloxy)-9,10-dihydro-4H-3,10a-diaza-benzo[f]azulene
{4-[4-(1-Methyl-piperidin-4-yloxy)-9,10-dihydro-4H-3,10a-diaza-benzo[f]azulen-2-yl]-phenyl}-methanol
2-(4-Methoxymethyl-phenyl)-4-(1-methyl-piperidin-4-yloxy)-9,10-dihydro-4H-3,10a-diaza-benzo[f]azulene
4-(1-Methyl-piperidin-4-yloxy)-2-(4-methylsulfanyl-phenyl)-9,10-dihydro-4H-3,10a-diaza-benzo[f]azulene
4-(1-Methyl-piperidin-4-yloxy)-2-(4-propyl-phenyl)-9,10-dihydro-4H-3,10a-diaza-benzo[f]azulene
4-(1-Methyl-piperidin-4-yloxy)-2-pyridin-2-yl-9,10-dihydro-4H-3,10a-diaza-benzo[f]azulene
2-Furan-2-yl-4-(1-methyl-piperidin-4-yloxy)-9,10-dihydro-4H-3,10a-diaza-benzo[f]azulene
4-(1-Methyl-piperidin-4-yloxy)-2-(4-trifluoromethyl-phenyl)-9,10-dihydro-4H-3,10a-diaza-benzo[f]azulene
2-(2-Chloro-phenyl)-4-(1-methyl-piperidin-4-yloxy)-9,10-dihydro-4H-3,10a-diaza-benzo[f]azulene
2-(2-Fluoro-phenyl)-4-(1-methyl-piperidin-4-yloxy)-9,10-dihydro-4H-3,10a-diaza-benzo[f]azulene
2-(4-Isobutyl-phenyl)-4-(1-methyl-piperidin-4-yloxy)-9,10-dihydro-4H-3,10a-diaza-benzo[f]azulene
N,N-Dimethyl-4-[4-(1-methyl-piperidin-4-yloxy)-9,10-dihydro-4H-3,10a-diaza-benzo[f]azulen-2-yl]-benzenesulfonamide
2-Allyl-4-(1-methyl-piperidin-4-yloxy)-9,10-dihydro-4H-3,10a-diaza-benzo[f]azulene
2,2,2-Trifluoro-1-{4-[4-(1-methyl-piperidin-4-yloxy)-9,10-dihydro-4H-3,10a-diaza-benzo[f]azulen-2-yl]-phenyl}-ethanone
2-(4-Isopropyl-phenyl)-4-(1-methyl-piperidin-4-yloxy)-9,10-dihydro-4H-3,10a-diaza-benzo[f]azulene
{4-[4-(1-Methyl-piperidin-4-yloxy)-9,10-dihydro-4H-3,10a-diaza-benzo[f]azulen-2-yl]-phenyl}-acetonitrile
4-(1-Methyl-piperidin-4-yloxy)-2-phenylethynyl-9,10-dihydro-4H-3,10a-diaza-benzo[f]azulene
Dimethyl-{4-[4-(1-methyl-piperidin-4-yloxy)-9,10-dihydro-4H-3,10a-diaza-benzo[f]azulen-2-yl]-phenyl}-amine
4-[4-(1-Methyl-piperidin-4-yloxy)-9,10-dihydro-4H-3,10a-diaza-benzo[f]azulen-2-yl]-benzoic acid tert-butyl ester
4-[4-(1-Methyl-piperidin-4-yloxy)-9,10-dihydro-4H-3,10a-diaza-benzo[f]azulen-2-yl]-benzonitrile
4-(1-Methyl-piperidin-4-yloxy)-2-phenethyl-9,10-dihydro-4H-3,10a-diaza-benzo[f]azulene
4-(1-Methyl-piperidin-4-yloxy)-2-(6-methyl-pyridin-3-yl)-9,10-dihydro-4H-3,10a-diaza-benzo[f]azulene
4-(1-Methyl-piperidin-4-yloxy)-2-oxazol-2-yl-9,10-dihydro-4H-3,10a-diaza-benzo[f]azulene
2-(4-Butyl-phenyl)-4-(1-methyl-piperidin-4-yloxy)-9,10-dihydro-4H-3,10a-diaza-benzo[f]azulene
4-(1-Methyl-piperidin-4-yloxy)-2-(4-pentyl-phenyl)-9,10-dihydro-4H-3,10a-diaza-benzo[f]azulene
2-(4-Hexyl-phenyl)-4-(1-methyl-piperidin-4-yloxy)-9,10-dihydro-4H-3,10a-diaza-benzo[f]azulene
4-(1-Methyl-piperidin-4-yloxy)-2-pyridin-4-yl-9,10-dihydro-4H-3,10a-diaza-benzo[f]azulene
4-(1-Methyl-piperidin-4-yloxy)-2-pyridin-3-yl-9,10-dihydro-4H-3,10a-diaza-benzo[f]azulene
2-(4-Ethylsulfanyl-phenyl)-4-(1-methyl-piperidin-4-yloxy)-9,10-dihydro-4H-3,10a-diaza-benzo[f]azulene
4-(1-Methyl-piperidin-4-yloxy)-2-thiophen-2-yl-9,10-dihydro-4H-3,10a-diaza-benzo[f]azulene
4-(1-Methyl-piperidin-4-yloxy)-2-thiazol-5-yl-9,10-dihydro-4H-3,10a-diaza-benzo[f]azulene
{4-[4-(1-Methyl-piperidin-4-yloxy)-9,10-dihydro-4H-3,10a-diaza-benzo[f]azulen-2-yl]-phenyl}-carbamic acid tert-butyl ester
2-Benzo[1,3]dioxol-5-yl-4-(1-methyl-piperidin-4-yloxy)-9,10-dihydro-4H-3,10a-diaza-benzo[f]azulene
2-(5-Methyl-furan-2-yl)-4-(1-methyl-piperidin-4-yloxy)-9,10-dihydro-4H-3,10a-diaza-benzo[f]azulene
2-(4-Chloro-phenyl)-4-(1-methyl-piperidin-4-yloxy)-9,10-dihydro-4H-3,10a-diaza-benzo[f]azulene
3-[4-(1-Methyl-piperidin-4-yloxy)-9,10-dihydro-4H-3,10a-diaza-benzo[f]azulen-2-yl]-acrylic acid tert-butyl ester
4-(1-Methyl-piperidin-4-yloxy)-2-(2-methyl-4-trifluoromethyl-phenyl)-9,10-dihydro-4H-3,10a-diaza-benzo[f]azulene
2-(4-Fluoro-phenyl)-4-(1-methyl-piperidin-4-yloxy)-9,10-dihydro-4H-3,10a-diaza-benzo[f]azulene
2-(3,6-Dihydro-2H-thiopyran-4-yl)-4-(1-methyl-piperidin-4-yloxy)-9,10-dihydro-4H-3,10a-diaza-benzo[f]azulene
2,2-Dimethyl-N-{4-[4-(1-methyl-piperidin-4-yloxy)-9,10-dihydro-4H-3,10a-diaza-benzo[f]azulen-2-yl]-phenyl}-propionamide
2-(2-Cyclohexyl-vinyl)-4-(1-methyl-piperidin-4-yloxy)-9,10-dihydro-4H-3,10a-diaza-benzo[f]azulene
1-{4-[4-(1-Methyl-piperidin-4-yloxy)-9,10-dihydro-4H-3,10a-diaza-benzo[f]azulen-2-yl]-phenyl}-3-propyl-urea
2-(2,4-Dimethyl-phenyl)-4-(1-methyl-piperidin-4-yloxy)-9,10-dihydro-4H-3,10a-diaza-benzo[f]azulene
2-Cyclohex-1-enyl-4-(1-methyl-piperidin-4-yloxy)-9,10-dihydro-4H-3,10a-diaza-benzo[f]azulene
4-(1-Methyl-piperidin-4-yloxy)-2-pyridin-3-ylethynyl-9,10-dihydro-4H-3,10a-diaza-benzo[f]azulene
2-[4-(1,1-Difluoro-ethyl)-phenyl]-4-(1-methyl-piperidin-4-yloxy)-9,10-dihydro-4H-3,10a-diaza-benzo[f]azulene
2-Cyclopent-1-enyl-4-(1-methyl-piperidin-4-yloxy)-9,10-dihydro-4H-3,10a-diaza-benzo[f]azulene
4-(1-Methyl-piperidin-4-yloxy)-2-thiazol-2-yl-9,10-dihydro-4H-3,10a-diaza-benzo[f]azulene
2-Benzylsulfanyl-4-(1-methyl-piperidin-4-yloxy)-9,10-dihydro-4H-3,10a-diaza-benzo[f]azulene
2-(3-Fluoro-phenyl)-4-(1-methyl-piperidin-4-yloxy)-9,10-dihydro-4H-3,10a-diaza-benzo[f]azulene
2-(4-Difluoromethyl-phenyl)-4-(1-methyl-piperidin-4-yloxy)-9,10-dihydro-4H-3,10a-diaza-benzo[f]azulene
2-(2-Methyl-allyl)-4-(1-methyl-piperidin-4-yloxy)-9,10-dihydro-4H-3,10a-diaza-benzo[f]azulene
2-(2,4-Dichloro-phenyl)-4-(1-methyl-piperidin-4-yloxy)-9,10-dihydro-4H-3,10a-diaza-benzo[f]azulene {3-[4-(1-Methyl-piperidin-4-yloxy)-9,10-dihydro-4H-3,10a-diaza-benzo[f]azulen-2-yl]-prop-2-ynyl}-carbamic acid tert-butyl ester
4-(1-Methyl-piperidin-4-yloxy)-2-phenylsulfanyl-9,10-dihydro-4H-3,10a-diaza-benzo[f]azulene
4-[4-(1-Methyl-piperidin-4-yloxy)-9,10-dihydro-4H-3,10a-diaza-benzo[f]azulen-2-yl]-3,6-dihydro-2H-pyridine-1-carboxylic acid tert-butyl ester
2-(2-Chloro-4-methyl-phenyl)-4-(1-methyl-piperidin-4-yloxy)-9,10-dihydro-4H-3,10a-diaza-benzo[f]azulene
4-(1-Methyl-piperidin-4-yloxy)-2-(3-phenyl-propenyl)-9,10-dihydro-4H-3,10a-diaza-benzo[f]azulene
2-(3-Chloro-phenyl)-4-(1-methyl-piperidin-4-yloxy)-9,10-dihydro-4H-3,10a-diaza-benzo[f]azulene
8-Chloro-2-iodo-4-(1-methyl-piperidin-4-yloxy)-9,10-dihydro-4H-3,10a-diaza-benzo[f]azulene
8-Bromo-2-iodo-4-(1-methyl-piperidin-4-yloxy)-9,10-dihydro-4H-3,10a-diaza-benzo[f]azulene
2-Cyclohept-1-enyl-4-(1-methyl-piperidin-4-yloxy)-9,10-dihydro-4H-3,10a-diaza-benzo[f]azulene
2-(4-Bromo-phenyl)-4-(1-methyl-piperidin-4-yloxy)-9,10-dihydro-4H-3,10a-diaza-benzo[f]azulene
2-(2-Fluoro-4-methyl-phenyl)-4-(1-methyl-piperidin-4-yloxy)-9,10-dihydro-4H-3,10a-diaza-benzo[f]azulene
4-(1-Methyl-piperidin-4-yloxy)-2-(1-methyl-1H-pyrrol-2-yl)-9,10-dihydro-4H-3,10a-diaza-benzo[f]azulene
{2-[4-(1-Methyl-piperidin-4-yloxy)-9,10-dihydro-4H-3,10a-diaza-benzo[f]azulen-2-ylsulfanyl]-ethyl}-carbamic acid tert-butyl ester
2-(Furan-2-ylmethylsulfanyl)-4-(1-methyl-piperidin-4-yloxy)-9,10-dihydro-4H-3,10a-diaza-benzo[f]azulene
2-Cyclopentylsulfanyl-4-(1-methyl-piperidin-4-yloxy)-9,10-dihydro-4H-3,10a-diaza-benzo[f]azulene
4-(1-Methyl-piperidin-4-yloxy)-2-(3-phenyl-propyl)-9,10-dihydro-4H-3,10a-diaza-benzo[f]azulene
4-(1-Methyl-piperidin-4-yloxy)-2-(thiophen-2-ylmethylsulfanyl)-9,10-dihydro-4H-3,10a-diaza-benzo[f]azulene
4-(1-Methyl-piperidin-4-yloxy)-2-(5-phenyl-pent-1-enyl)-9,10-dihydro-4H-3,10a-diaza-benzo[f]azulene
4-(1-Methyl-piperidin-4-yloxy)-2-(5-phenyl-pentyl)-9,10-dihydro-4H-3,10a-diaza-benzo[f]azulene
8-Chloro-4-(1-methyl-piperidin-4-yloxy)-2-phenyl-9,10-dihydro-4H-3,10a-diaza-benzo[f]azulene
4-(1-Methyl-piperidin-4-yloxy)-2,8-diphenyl-9,10-dihydro-4H-3,10a-diaza-benzo[f]azulene
2-(3,3-Dimethyl-but-1-enyl)-4-(1-methyl-piperidin-4-yloxy)-9,10-dihydro-4H-3,10a-diaza-benzo[f]azulene
2-(3,3-Dimethyl-butyl)-4-(1-methyl-piperidin-4-yloxy)-9,10-dihydro-4H-3,10a-diaza-benzo[f]azulene
2-(2-Cyclohexyl-ethyl)-4-(1-methyl-piperidin-4-yloxy)-9,10-dihydro-4H-3,10a-diaza-benzo[f]azulene
4-(1-Methyl-piperidin-4-yloxy)-2-(5-methyl-thiophen-2-yl)-9,10-dihydro-4H-3,10a-diaza-benzo[f]azulene
Methyl-{4-[4-(1-methyl-piperidin-4-yloxy)-9,10-dihydro-4H-3,10a-diaza-benzo[f]azulen-2-yl]-phenyl}-carbamic acid tert-butyl ester
2-Cyclohexylsulfanyl-4-(1-methyl-piperidin-4-yloxy)-9,10-dihydro-4H-3,10a-diaza-benzo[f]azulene
2-(2-Cyclopropyl-vinyl)-4-(1-methyl-piperidin-4-yloxy)-9,10-dihydro-4H-3,10a-diaza-benzo[f]azulene
Methyl-{4-[4-(1-methyl-piperidin-4-yloxy)-9,10-dihydro-4H-3,10a-diaza-benzo[f]azulen-2-yl]-phenyl}-amine
2,2,N-Trimethyl-N-{4-[4-(1-methyl-piperidin-4-yloxy)-9,10-dihydro-4H-3,10a-diaza-benzo[f]azulen-2-yl]-phenyl}-propionamide
[4-(1-Methyl-piperidin-4-yloxy)-9,10-dihydro-4H-3,10a-diaza-benzo[f]azulen-2-yl]-phenyl-methanone
1-Methyl-4-(1-methyl-piperidin-4-yloxy)-2-phenyl-9,10-dihydro-4H-3,10a-diaza-benzo[f]azulene
2-(3-Cyclopentyl-propenyl)-4-(1-methyl-piperidin-4-yloxy)-9,10-dihydro-4H-3,10a-diaza-benzo[f]azulene
2-(3-Cyclopentyl-propyl)-4-(1-methyl-piperidin-4-yloxy)-9,10-dihydro-4H-3,10a-diaza-benzo[f]azulene
2-(3,6-Dihydro-2H-pyran-4-yl)-4-(1-methyl-piperidin-4-yloxy)-9,10-dihydro-4H-3,10a-diaza-benzo[f]azulene
8-Fluoro-4-(1-methyl-piperidin-4-yloxy)-2-phenyl-9,10-dihydro-4H-3,10a-diaza-benzo[f]azulene
N-(4-Hydroxy-cyclohexyl)-4-[4-(1-methyl-piperidin-4-yloxy)-9,10-dihydro-4H-3,10a-diaza-benzo[f]azulen-2-yl]-benzamide
2-Isobutyl-4-(1-methyl-piperidin-4-yloxy)-9,10-dihydro-4H-3,10a-diaza-benzo[f]azulene
2-Benzyl-4-(1-methyl-piperidin-4-yloxy)-9,10-dihydro-4H-3,10a-diaza-benzo[f]azulene
4-(1-Methyl-piperidin-4-yloxy)-2-(2-thiophen-2-yl-vinyl)-9,10-dihydro-4H-3,10a-diaza-benzo[f]azulene
4-(1-Methyl-piperidin-4-yloxy)-2-(2-thiophen-3-yl-vinyl)-9,10-dihydro-4H-3,10a-diaza-benzo[f]azulene
Dimethyl-{4-[4-(1-methyl-piperidin-4-yloxy)-9,10-dihydro-4H-3,10a-diaza-benzo[f]azulen-2-yl]-benzyl}-amine
4-[4-(1-Methyl-piperidin-4-yloxy)-9,10-dihydro-4H-3,10a-diaza-benzo[f]azulen-2-ylsulfanyl]-piperidine-1-carboxylic acid tert-butyl ester
{4-[4-(1-Methyl-piperidin-4-yloxy)-9,10-dihydro-4H-3,10a-diaza-benzo[f]azulen-2-yl]-benzyl}-carbamic acid tert-butyl ester
2-Methyl-4-(1-methyl-piperidin-4-yloxy)-9,10-dihydro-4H-3,10a-diaza-benzo[f]azulene-1-carboxylic acid ethyl ester
2-[1-(4-Chloro-phenyl)-1-methyl-ethyl]-4-(1-methyl-piperidin-4-yloxy)-9,10-dihydro-4H-3,10a-diaza-benzo[f]azulene
1-Methyl-4-(1-methyl-piperidin-4-yloxy)-9,10-dihydro-4H-3,10a-diaza-benzo[f]azulene-2-carboxylic acid ethyl ester
4-(1-Methyl-piperidin-4-yloxy)-2-phenethylsulfanyl-9,10-dihydro-4H-3,10a-diaza-benzo[f]azulene
1-Ethyl-4-(1-methyl-piperidin-4-yloxy)-2-phenyl-9,10-dihydro-4H-3,10a-diaza-benzo[f]azulene
4-(1-Methyl-piperidin-4-yloxy)-2-(3-phenoxy-propenyl)-9,10-dihydro-4H-3,10a-diaza-benzo[f]azulene
2-(4-Bromo-phenyl)-1-methyl-4-(1-methyl-piperidin-4-yloxy)-9,10-dihydro-4H-3,10a-diaza-benzo[f]azulene
2-Methyl-4-(1-methyl-piperidin-4-yloxy)-1-phenyl-9,10-dihydro-4H-3,10a-diaza-benzo[f]azulene
2-(3-Benzyloxy-propenyl)-4-(1-methyl-piperidin-4-yloxy)-9,10-dihydro-4H-3,10a-diaza-benzo[f]azulene
Methyl-{4-[1-methyl-4-(1-methyl-piperidin-4-yloxy)-9,10-dihydro-4H-3,10a-diaza-benzo[f]azulen-2-yl]-phenyl}-carbamic acid tert-butyl ester
4-(1-Methyl-piperidin-4-yloxy)-2-(2-thiophen-2-yl-ethyl)-9,10-dihydro-4H-3,10a-diaza-benzo[f]azulene
2-(4-Bromo-phenyl)-1-chloro-4-(1-methyl-piperidin-4-yloxy)-9,10-dihydro-4H-3,10a-diaza-benzo[f]azulene
2-(3-Benzyloxy-propyl)-4-(1-methyl-piperidin-4-yloxy)-9,10-dihydro-4H-3,10a-diaza-benzo[f]azulene
4-(1-Methyl-piperidin-4-yloxy)-2-(4-phenyl-butyl)-9,10-dihydro-4H-3,10a-diaza-benzo[f]azulene
{4-[1-Methyl-4-(1-methyl-piperidin-4-yloxy)-9,10-dihydro-4H-3,10a-diaza-benzo[f]azulen-2-yl]-phenyl}-carbamic acid tert-butyl ester 3-{4-[1-Methyl-4-(1-methyl-piperidin-4-yloxy)-9,10-dihydro-4H-3,10a-diaza-benzo[f]azulen-2-yl]-phenyl}-oxazolidin-2-one 1-Methyl-3-{4-[1-methyl-4-(1-methyl-piperidin-4-yloxy)-9,10-dihydro-4H-3,10a-diaza-benzo[f]azulen-2-yl]-phenyl}-imidazolidin-2-one 2-Iodo-1-methyl-4-(1-methyl-piperidin-4-yloxy)-9,10-dihydro-4H-3,10a-diaza-benzo[f]azulene 1-Chloro-4-(1-methyl-piperidin-4-yloxy)-2-phenyl-9,10-dihydro-4H-3,10a-diaza-benzo[f]azulene 2,2-Dimethyl-N-{4-[4-(1-methyl-piperidin-4-yloxy)-9,10-dihydro-4H-3,10a-diaza-benzo[f]azulen-2-yl]-benzyl}-propionamide 1-Chloro-4-(1-methyl-piperidin-4-yloxy)-2-(5-phenyl-pentyl)-9,10-dihydro-4H-3,10a-diaza-benzo[f]azulene 1-tert-Butyl-3-{4-[1-methyl-4-(1-methyl-piperidin-4-yloxy)-9,10-dihydro-4H-3,10a-diaza-benzo[f]azulen-2-yl]-phenyl}-imidazolidin-2-one {4-[1-Chloro-4-(1-methyl-piperidin-4-yloxy)-9,10-dihydro-4H-3,10a-diaza-benzo[f]azulen-2-yl]-phenyl}-carbamic acid tert-butyl ester 2-(2-Fluoro-phenyl)-1-methyl-4-(1-methyl-piperidin-4-yloxy)-9,10-dihydro-4H-3,10a-diaza-benzo[f]azulene 2-(3-Fluoro-phenyl)-1-methyl-4-(1-methyl-piperidin-4-yloxy)-9,10-dihydro-4H-3,10a-diaza-benzo[f]azulene 1-Methyl-4-(1-methyl-piperidin-4-yloxy)-2-m-tolyl-9,10-dihydro-4H-3,10a-diaza-benzo[f]azulene 2-(3-Chloro-phenyl)-1-methyl-4-(1-methyl-piperidin-4-yloxy)-9,10-dihydro-4H-3,10a-diaza-benzo[f]azulene 2-(2-Chloro-phenyl)-1-methyl-4-(1-methyl-piperidin-4-yloxy)-9,10-dihydro-4H-3,10a-diaza-benzo[f]azulene 1-Methyl-4-(1-methyl-piperidin-4-yloxy)-2-o-tolyl-9,10-dihydro-4H-3,10a-diaza-benzo[f]azulene 1-Methyl-4-(1-methyl-piperidin-4-yloxy)-2-thiophen-3-yl-9,10-dihydro-4H-3,10a-diaza-benzo[f]azulene 2-(2-Methoxy-phenyl)-1-methyl-4-(1-methyl-piperidin-4-yloxy)-9,10-dihydro-4H-3,10a-diaza-benzo[f]azulene 2-(3-Methoxy-phenyl)-1-methyl-4-(1-methyl-piperidin-4-yloxy)-9,10-dihydro-4H-3,10a-diaza-benzo[f]azulene 3-{4-[1-Methyl-4-(1-methyl-piperidin-4-yloxy)-9,10-dihydro-4H-3,10a-diaza-benzo[f]azulen-2-yl]-phenyl}-acrylic acid tert-butyl ester 3-Methyl-3-{4-[1-methyl-4-(1-methyl-piperidin-4-yloxy)-9,10-dihydro-4H-3,10a-diaza-benzo[f]azulen-2-yl]-phenylsulfanyl}-butan-1-ol 1-Methyl-4-(1-methyl-piperidin-4-yloxy)-2-p-tolyl-9,10-dihydro-4H-3,10a-diaza-benzo[f]azulene 2-(4-Fluoro-phenyl)-1-methyl-4-(1-methyl-piperidin-4-yloxy)-9,10-dihydro-4H-3,10a-diaza-benzo[f]azulene 2-(4-Chloro-phenyl)-1-methyl-4-(1-methyl-piperidin-4-yloxy)-9,10-dihydro-4H-3,10a-diaza-benzo[f]azulene 2-(4-Methoxy-phenyl)-1-methyl-4-(1-methyl-piperidin-4-yloxy)-9,10-dihydro-4H-3,10a-diaza-benzo[f]azulene 2-(2-Chloro-4-methyl-phenyl)-1-methyl-4-(1-methyl-piperidin-4-yloxy)-9,10-dihydro-4H-3,10a-diaza-benzo[f]azulene 2-[4-(2-Methanesulfonyl-vinyl)-phenyl]-1-methyl-4-(1-methyl-piperidin-4-yloxy)-9,10-dihydro-4H-3,10a-diaza-benzo[f]azulene 2-[4-(2-Methanesulfonyl-ethyl)-phenyl]-1-methyl-4-(1-methyl-piperidin-4-yloxy)-9,10-dihydro-4H-3,10a-diaza-benzo[f]azulene (2-{4-[1-Methyl-4-(1-methyl-piperidin-4-yloxy)-9,10-dihydro-4H-3,10a-diaza-benzo[f]azulen-2-yl]-phenylsulfanyl}-ethyl)-carbamic acid tert-butyl ester 2-{4-[1-Methyl-4-(1-methyl-piperidin-4-yloxy)-9,10-dihydro-4H-3,10a-diaza-benzo[f]azulen-2-yl]-phenylsulfanyl}-ethylamine 1-{4-[1-Methyl-4-(1-methyl-piperidin-4-yloxy)-9,10-dihydro-4H-3,10a-diaza-benzo[f]azulen-2-yl]-phenyl}-piperidin-2-one N-(2-{4-[1-Methyl-4-(1-methyl-piperidin-4-yloxy)-9,10-dihydro-4H-3,10a-diaza-benzo[f]azulen-2-yl]-phenylsulfanyl}-ethyl)-acetamide 2-(4-Benzylsulfanyl-phenyl)-1-methyl-4-(1-methyl-piperidin-4-yloxy)-9,10-dihydro-4H-3,10a-diaza-benzo[f]azulene {4-[1-Methyl-4-(1-methyl-piperidin-4-yloxy)-9,10-dihydro-4H-3,10a-diaza-benzo[f]azulen-2-yl]-phenylsulfanyl}-acetic acid methyl ester 2-(4-tert-Butylsulfanyl-phenyl)-1-methyl-4-(1-methyl-piperidin-4-yloxy)-9,10-dihydro-4H-3,10a-diaza-benzo[f]azulene 2-[4-(Furan-2-ylmethylsulfanyl)-phenyl]-1-methyl-4-(1-methyl-piperidin-4-yloxy)-9,10-dihydro-4H-3,10a-diaza-benzo[f]azulene 4-{4-[1-Methyl-4-(1-methyl-piperidin-4-yloxy)-9,10-dihydro-4H-3,10a-diaza-benzo[f]azulen-2-yl]-phenyl}-3,6-dihydro-2H-pyridine-1-carboxylic acid tert-butyl ester 2-(4-Cyclopent-1-enyl-phenyl)-1-methyl-4-(1-methyl-piperidin-4-yloxy)-9,10-dihydro-4H-3,10a-diaza-benzo[f]azulene 2-(4-Cyclohex-1-enyl-phenyl)-1-methyl-4-(1-methyl-piperidin-4-yloxy)-9,10-dihydro-4H-3,10a-diaza-benzo[f]azulene 2-(4-Cyclohept-1-enyl-phenyl)-1-methyl-4-(1-methyl-piperidin-4-yloxy)-9,10-dihydro-4H-3,10a-diaza-benzo[f]azulene {4-[1-Methyl-4-(1-methyl-piperidin-4-yloxy)-9,10-dihydro-4H-3,10a-diaza-benzo[f]azulen-2-yl]-phenyl}-carbamic acid cyclopentyl ester 4-[1-Methyl-4-(1-methyl-piperidin-4-yloxy)-9,10-dihydro-4H-3,10a-diaza-benzo[f]azulen-2-yl]-phenylamine {4-[1-Methyl-4-(1-methyl-piperidin-4-yloxy)-9,10-dihydro-4H-3,10a-diaza-benzo[f]azulen-2-yl]-phenyl}-carbamic acid isobutyl ester {4-[1-Methyl-4-(1-methyl-piperidin-4-yloxy)-9,10-dihydro-4H-3,10a-diaza-benzo[f]azulen-2-yl]-phenyl}-carbamic acid 2,2,2-trichloro-1,1-dimethyl-ethyl ester 4-Benzyl-3-{4-[1-methyl-4-(1-methyl-piperidin-4-yloxy)-9,10-dihydro-4H-3,10a-diaza-benzo[f]azulen-2-yl]-phenyl}-oxazolidin-2-one 4-{4-[1-Methyl-4-(1-methyl-piperidin-4-yloxy)-9,10-dihydro-4H-3,10a-diaza-benzo[f]azulen-2-yl]-phenyl}-piperidine-1-carboxylic acid tert-butyl ester 1-Isopropyl-3-{4-[1-methyl-4-(1-methyl-piperidin-4-yloxy)-9,10-dihydro-4H-3,10a-diaza-benzo[f]azulen-2-yl]-phenyl}-imidazolidin-2-one {2-[4-(1-Methyl-piperidin-4-yloxy)-9,10-dihydro-4H-3,10a-diaza-benzo[f]azulen-2-yl]-phenyl}-methanol Dimethyl-(2-{4-[4-(1-methyl-piperidin-4-yloxy)-9,10-dihydro-4H-3,10a-diaza-benzo[f]azulen-2-yl]-phenoxy}-ethyl)-amine 3-{4-[4-(1-Methyl-piperidin-4-yloxy)-9,10-dihydro-4H-3,10a-diaza-benzo[f]azulen-2-yl]-benzyl}-oxazolidin-2-one Methyl-{4-[4-(1-methyl-piperidin-4-yloxy)-9,10-dihydro-4H-3,10a-diaza-benzo[f]azulen-2-yl]-benzyl}-carbamic acid tert-butyl ester
2-(4-Allyloxy-phenyl)-4-(1-methyl-piperidin-4-yloxy)-9,10-dihydro-4H-3,10a-diaza-benzo[f]azulene
1-{4-[4-(1-Methyl-piperidin-4-yloxy)-9,10-dihydro-4H-3,10a-diaza-benzo[f]azulen-2-yl]-benzyl}-pyrrolidin-2-one
1-{4-[4-(1-Methyl-piperidin-4-yloxy)-9,10-dihydro-4H-3,10a-diaza-benzo[f]azulen-2-yl]-benzyl}-piperidin-2-one
2-(4-Isopropylsulfanylmethyl-phenyl)-4-(1-methyl-piperidin-4-yloxy)-9,10-dihydro-4H-3,10a-diaza-benzo[f]azulene
Cyclopropanesulfonic acid {4-[1-methyl-4-(1-methyl-piperidin-4-yloxy)-9,10-dihydro-4H-3,10a-diaza-benzo[f]azulen-2-yl]-phenyl}-amide
1-{4-[4-(1-Methyl-piperidin-4-yloxy)-9,10-dihydro-4H-3,10a-diaza-benzo[f]azulen-2-yl]-benzyl}-azepan-2-one
2-[4-(2-tert-Butylsulfanyl-ethyl)-phenyl]-4-(1-methyl-piperidin-4-yloxy)-9,10-dihydro-4H-3,10a-diaza-benzo[f]azulene
4-(1-Methyl-piperidin-4-yloxy)-2-(2-nitro-phenyl)-9,10-dihydro-4H-3,10a-diaza-benzo[f]azulene
1-tert-Butyl-3-{4-[4-(1-methyl-piperidin-4-yloxy)-9,10-dihydro-4H-3,10a-diaza-benzo[f]azulen-2-yl]-benzyl}-imidazolidin-2-one
2-{4-[4-(1-Methyl-piperidin-4-yloxy)-9,10-dihydro-4H-3,10a-diaza-benzo[f]azulen-2-yl]-phenyl}-ethanol
2-(4-Cyclopropylmethoxy-phenyl)-4-(1-methyl-piperidin-4-yloxy)-9,10-dihydro-4H-3,10a-diaza-benzo[f]azulene
3-{4-[1-Methyl-4-(1-methyl-piperidin-4-yloxy)-9,10-dihydro-4H-3,10a-diaza-benzo[f]azulen-2-yl]-phenylsulfanyl}-propane-1,2-diol
3-{4-[1-Methyl-4-(1-methyl-piperidin-4-yloxy)-9,10-dihydro-4H-3,10a-diaza-benzo[f]azulen-2-yl]-phenylsulfanyl}-propan-1-ol
(2-{4-[4-(1-Methyl-piperidin-4-yloxy)-9,10-dihydro-4H-3,10a-diaza-benzo[f]azulen-2-yl]-phenyl}-ethyl)-carbamic acid tert-butyl ester
Methyl-(2-{4-[4-(1-methyl-piperidin-4-yloxy)-9,10-dihydro-4H-3,10a-diaza-benzo[f]azulen-2-yl]-phenyl}-ethyl)-carbamic acid tert-butyl ester
5,5-Dimethyl-3-{4-[4-(1-methyl-piperidin-4-yloxy)-9,10-dihydro-4H-3,10a-diaza-benzo[f]azulen-2-yl]-benzyl}-oxazolidine-2,4-dione
(2-{4-[4-(1-Methyl-piperidin-4-yloxy)-9,10-dihydro-4H-3,10a-diaza-benzo[f]azulen-2-yl]-benzylsulfanyl}-ethyl)-carbamic acid tert-butyl ester
tert-Butyl-carbamic acid 2-{4-[4-(1-methyl-piperidin-4-yloxy)-9,10-dihydro-4H-3,10a-diaza-benzo[f]azulen-2-yl]-phenyl}-ethyl ester
[1-Methyl-4-(1-methyl-piperidin-4-yloxy)-9,10-dihydro-4H-3,10a-diaza-benzo[f]azulen-2-yl]-phenyl-methanol
[1-Methyl-4-(1-methyl-piperidin-4-yloxy)-9,10-dihydro-4H-3,10a-diaza-benzo[f]azulen-2-yl]-phenyl-methanone
1-Methyl-4-(1-methyl-piperidin-4-yloxy)-9,10-dihydro-4H-3,10a-diaza-benzo[f]azulene-2-carboxylic acid benzyl-methyl-amide
1-Methyl-4-(1-methyl-piperidin-4-yloxy)-9,10-dihydro-4H-3,10a-diaza-benzo[f]azulene-2-carboxylic acid methyl-phenyl-amide
1-Methyl-4-(1-methyl-piperidin-4-yloxy)-9,10-dihydro-4H-3,10a-diaza-benzo[f]azulene-2-carboxylic acid propylamide
1-Isopropyl-3-{4-[1-methyl-4-(1-methyl-piperidin-4-yloxy)-9,10-dihydro-4H-3,10a-diaza-benzo[f]azulen-2-yl]-phenyl}-thiourea
2-(1-Methyl-1-phenyl-ethyl)-4-(1-methyl-piperidin-4-yloxy)-9,10-dihydro-4H-3,10a-diaza-benzo[f]azulene
1-Cyclopropyl-3-{4-[1-methyl-4-(1-methyl-piperidin-4-yloxy)-9,10-dihydro-4H-3,10a-diaza-benzo[f]azulen-2-yl]-phenyl}-thiourea
1-tert-Butyl-3-{4-[1-methyl-4-(1-methyl-piperidin-4-yloxy)-9,10-dihydro-4H-3,10a-diaza-benzo[f]azulen-2-yl]-phenyl}-urea
2-Methyl-1-[1-methyl-4-(1-methyl-piperidin-4-yloxy)-9,10-dihydro-4H-3,10a-diaza-benzo[f]azulen-2-yl]-propan-1-ol
N-(2-{4-[1-Methyl-4-(1-methyl-piperidin-4-yloxy)-9,10-dihydro-4H-3,10a-diaza-benzo[f]azulen-2-yl]-phenylsulfanyl}-ethyl)-guanidine
N-(2-Hydroxy-ethyl)-4-[4-(1-methyl-piperidin-4-yloxy)-9,10-dihydro-4H-3,10a-diaza-benzo[f]azulen-2-yl]-benzamide
1-Adamantan-1-yl-3-{4-[1-methyl-4-(1-methyl-piperidin-4-yloxy)-9,10-dihydro-4H-3,10a-diaza-benzo[f]azulen-2-yl]-phenyl}-urea
N-{4-[1-Methyl-4-(1-methyl-piperidin-4-yloxy)-9,10-dihydro-4H-3,10a-diaza-benzo[f]azulen-2-yl]-phenyl}-hydrazinecarboxylic acid tert-butyl ester
1-{4-[4-(1-Methyl-piperidin-4-yloxy)-9,10-dihydro-4H-3,10a-diaza-benzo[f]azulen-2-yl]-benzoyl}-piperidin-4-one
N-(4-Hydroxy-cyclohexyl)-4-[1-methyl-4-(1-methyl-piperidin-4-yloxy)-9,10-dihydro-4H-3,10a-diaza-benzo[f]azulen-2-yl]-benzamide
N-(2-Hydroxy-ethyl)-4-[1-methyl-4-(1-methyl-piperidin-4-yloxy)-9,10-dihydro-4H-3,10a-diaza-benzo[f]azulen-2-yl]-benzamide
1-{4-[1-Methyl-4-(1-methyl-piperidin-4-yloxy)-9,10-dihydro-4H-3,10a-diaza-benzo[f]azulen-2-yl]-benzoyl}-piperidin-4-one
1,2-Diiodo-4-(1-methyl-piperidin-4-yloxy)-9,10-dihydro-4H-3,10a-diaza-benzo[f]azulene
(4-Hydroxy-piperidin-1-yl)-{4-[1-methyl-4-(1-methyl-piperidin-4-yloxy)-9,10-dihydro-4H-3,10a-diaza-benzo[f]azulen-2-yl]-phenyl}-methanone
2-Iodo-4-(1-methyl-piperidin-4-yloxy)-9,10-dihydro-4H-3,10a-diaza-benzo[f]azulene-1-carbonitrile
1-Methyl-4-(1-methyl-piperidin-4-yloxy)-9,10-dihydro-4H-3,10a-diaza-benzo[f]azulene-2-carboxylic acid benzylamide
(2-{4-[1-Methyl-4-(1-methyl-piperidin-4-yloxy)-9,10-dihydro-4H-3,10a-diaza-benzo[f]azulen-2-yl]-phenyl}-ethyl)-carbamic acid tert-butyl ester
4-[1-Cyano-4-(1-methyl-piperidin-4-yloxy)-9,10-dihydro-4H-3,10a-diaza-benzo[f]azulen-2-yl]-benzoic acid tert-butyl ester
2-(3,3-Dimethyl-but-1-enyl)-1-methyl-4-(1-methyl-piperidin-4-yloxy)-9,10-dihydro-4H-3,10a-diaza-benzo[f]azulene
2-Cyclohex-1-enyl-1-methyl-4-(1-methyl-piperidin-4-yloxy)-9,10-dihydro-4H-3,10a-diaza-benzo[f]azulene
4-[1-Methyl-4-(1-methyl-piperidin-4-yloxy)-9,10-dihydro-4H-3,10a-diaza-benzo[f]azulen-2-yl]-but-3-yn-1-ol 2-(6-Chloro-hex-1-ynyl)-1-methyl-4-(1-methyl-piperidin-4-yloxy)-9,10-dihydro-4H-3,10a-diaza-benzo[f]azulene
2-(3,3-Dimethyl-butyl)-1-methyl-4-(1-methyl-piperidin-4-yloxy)-9,10-dihydro-4H-3,10a-diaza-benzo[f]azulene
9,9-Dimethyl-4-(1-methyl-piperidin-4-yloxy)-2-phenyl-9,10-dihydro-4H-3,10a-diaza-benzo[f]azulene
8-Bromo-4-(1-methyl-piperidin-4-yloxy)-2-phenyl-9,10-dihydro-4H-3,10a-diaza-benzo[f]azulene
1,9,9-Trimethyl-4-(1-methyl-piperidin-4-yloxy)-2-phenyl-9,10-dihydro-4H-3,10a-diaza-benzo[f]azulene
8-Benzyl-4-(1-methyl-piperidin-4-yloxy)-2-phenyl-9,10-dihydro-4H-3,10a-diaza-benzo[f]azulene
4-(1-Methyl-piperidin-4-yloxy)-8-methylsulfanyl-2-phenyl-9,10-dihydro-4H-3,10a-diaza-benzo[f]azulene
4-(1-Methyl-piperidin-4-yloxy)-2-phenyl-9,10-dihydro-4H-3,10a-diaza-benzo[f]azulene-1-carbonitrile
8-Methyl-4-(1-methyl-piperidin-4-yloxy)-2-phenyl-9,10-dihydro-4H-3,10a-diaza-benzo[f]azulene
8-But-3-enyl-4-(1-methyl-piperidin-4-yloxy)-2-phenyl-9,10-dihydro-4H-3,10a-diaza-benzo[f]azulene
4-(1-Methyl-piperidin-4-yloxy)-2-phenyl-1-propyl-9,10-dihydro-4H-3,10a-diaza-benzo[f]azulene
4-(1-Methyl-piperidin-4-yloxy)-2-phenyl-8-o-tolyl-9,10-dihydro-4H-3,10a-diaza-benzo[f]azulene
8-(4-Fluoro-phenyl)-4-(1-methyl-piperidin-4-yloxy)-2-phenyl-9,10-dihydro-4H-3,10a-diaza-benzo[f]azulene
8-(3-Methoxy-phenyl)-4-(1-methyl-piperidin-4-yloxy)-2-phenyl-9,10-dihydro-4H-3,10a-diaza-benzo[f]azulene
3-[4-(1-Methyl-piperidin-4-yloxy)-2-phenyl-9,10-dihydro-4H-3,10a-diaza-benzo[f]azulen-8-yl]-phenylamine
1-Isopropyl-4-(1-methyl-piperidin-4-yloxy)-2-phenyl-9,10-dihydro-4H-3,10a-diaza-benzo[f]azulene
Methyl-[4-(1-methyl-piperidin-4-yloxy)-2-phenyl-9,10-dihydro-4H-3,10a-diaza-benzo[f]azulen-8-yl]-amine
8-Methoxy-4-(1-methyl-piperidin-4-yloxy)-2-phenyl-9,10-dihydro-4H-3,10a-diaza-benzo[f]azulene
4-(1-Methyl-piperidin-4-yloxy)-1-phenyl-2-propyl-9,10-dihydro-4H-3,10a-diaza-benzo[f]azulene
1-Iodo-4-(1-methyl-piperidin-4-yloxy)-2-phenyl-9,10-dihydro-4H-3,10a-diaza-benzo[f]azulene
8-Benzyloxy-4-(1-methyl-piperidin-4-yloxy)-2-phenyl-9,10-dihydro-4H-3,10a-diaza-benzo[f]azulene
4-(1-Methyl-piperidin-4-yloxy)-8-phenethyl-2-phenyl-9,10-dihydro-4H-3,10a-diaza-benzo[f]azulene
1-Methyl-4-(1-methyl-piperidin-4-yloxy)-2-pyridin-4-yl-9,10-dihydro-4H-3,10a-diaza-benzo[f]azulene
1-Methyl-4-(1-methyl-piperidin-4-yloxy)-2-pyridin-2-yl-9,10-dihydro-4H-3,10a-diaza-benzo[f]azulene
4-(1-Methyl-piperidin-4-yloxy)-1,2-diphenyl-9,10-dihydro-4H-3,10a-diaza-benzo[f]azulene
2-Iodo-4-(1-methyl-piperidin-4-yloxy)-9,10-dihydro-4H-3,10a-diaza-benzo[f]azulene-1-carboxylic acid amide
4-(1-Methyl-piperidin-4-yloxy)-2-phenyl-9,10-dihydro-4H-3,10a-diaza-benzo[f]azulene-1-carboxylic acid amide
4-(1-Methyl-piperidin-4-yloxy)-2-phenyl-1-trifluoromethyl-9,10-dihydro-4H-3,10a-diaza-benzo[f]azulene
4-(1-Methyl-piperidin-4-yloxy)-2-phenyl-9,10-dihydro-4H-3,10a-diaza-benzo[f]azulene-1-carboxylic acid methyl ester
[4-(1-Methyl-piperidin-4-yloxy)-2-phenyl-9,10-dihydro-4H-3,10a-diaza-benzo[f]azulen-1-yl]-methanol
6-Iodo-1-methyl-4-(1-methyl-piperidin-4-yloxy)-2-phenyl-9,10-dihydro-4H-3,10a-diaza-benzo[f]azulene
2-(2-Methyl-allyl)-4-(1-methyl-piperidin-4-yloxy)-9,10-dihydro-4H-3,10a-diaza-benzo[f]azulene-1-carbonitrile
1-Methyl-2-(2-methyl-allyl)-4-(1-methyl-piperidin-4-yloxy)-9,10-dihydro-4H-3,10a-diaza-benzo[f]azulene
7-Bromo-4-(1-methyl-piperidin-4-yloxy)-2-phenyl-9,10-dihydro-4H-3,10a-diaza-benzo[f]azulene
4-(1-Methyl-piperidin-4-yloxy)-2-phenyl-9,10-dihydro-4H-3,10a-diaza-benzo[f]azulene-1-carbaldehyde
2-Benzyl-4-(1-methyl-piperidin-4-yloxy)-9,10-dihydro-4H-3,10a-diaza-benzo[f]azulene-1-carbonitrile
[2-(1,2-Diiodo-9,10-dihydro-4H-3,10a-diaza-benzo[f]azulen-4-yloxy)-ethyl]-dimethyl-amine
1,2-Diiodo-4-(2-piperidin-1-yl-ethoxy)-9,10-dihydro-4H-3,10a-diaza-benzo[f]azulene
2-(2-Methyl-allyl)-4-(1-methyl-piperidin-4-yloxy)-9,10-dihydro-4H-3,10a-diaza-benzo[f]azulene-1-carboxylic acid amide
1,2-Bis-(2-methyl-allyl)-4-(1-methyl-piperidin-4-yloxy)-9,10-dihydro-4H-3,10a-diaza-benzo[f]azulene
1,2-Diiodo-4-(1-methyl-pyrrolidin-3-yloxy)-9,10-dihydro-4H-3,10a-diaza-benzo[f]azulene
1,2-Diiodo-4-(8-methyl-8-aza-bicyclo[3.2.1]oct-3-yloxy)-9,10-dihydro-4H-3,10a-diaza-benzo[f]azulene
[3-(1,2-Diiodo-9,10-dihydro-4H-3,10a-diaza-benzo[f]azulen-4-yloxy)-propyl]-dimethyl-amine
4-(1-Aza-bicyclo[2.2.2]oct-3-yloxy)-1,2-diiodo-9,10-dihydro-4H-3,10a-diaza-benzo[f]azulene
2-(2-Chloro-phenyl)-4-(1-methyl-piperidin-4-yloxy)-9,10-dihydro-4H-3,10a-diaza-benzo[f]azulene-1-carbonitrile
2-(2-Chloro-phenyl)-4-(1-methyl-piperidin-4-yloxy)-9,10-dihydro-4H-3,10a-diaza-benzo[f]azulene-1-carboxylic acid amide as well as its enantiomers, diastereomers, mixtures thereof and pharmaceutically acceptable salts, tautomers, and hydrates.

7. A compound according to claim 1 chosen from:
4-(1-Methyl-piperidin-4-yloxy)-2-trifluoromethyl-9,10-dihydro-4H-3,10a-diaza-benzo[f]azulene, oxalate
4-(1-Methyl-piperidin-4-yloxy)-1-trifluoromethyl-9,10-dihydro-4H-3,10a-diaza-benzo[f]azulene, oxalate
2-Iodo-4-(1-methyl-piperidin-4-yloxy)-9,10-dihydro-4H-3,10a-diaza-benzo[f]azulene
1-Iodo-4-(1-methyl-piperidin-4-yloxy)-9,10-dihydro-4H-3,10a-diaza-benzo[f]azulene
4-(1-Methyl-piperidin-4-yloxy)-2-phenyl-9,10-dihydro-4H-3,10a-diaza-benzo[f]azulene
4-(1-Methyl-piperidin-4-yloxy)-2-p-tolyl-9,10-dihydro-4H-3,10a-diaza-benzo[f]azulene
4-(1-Methyl-piperidin-4-yloxy)-2-m-tolyl-9,10-dihydro-4H-3,10a-diaza-benzo[f]azulene, oxalate
2-Iodo-4-(1-methyl-azetidin-3-ylmethoxy)-9,10-dihydro-4H-3,10a-diaza-benzo[f]azulene
4-(1-Methyl-piperidin-4-yloxy)-2-o-tolyl-9,10-dihydro-4H-3,10a-diaza-benzo[f]azulene, oxalate
4-(1-Methyl-piperidin-4-yloxy)-2-vinyl-9,10-dihydro-4H-3,10a-diaza-benzo[f]azulene, oxalate
2-(4-tert-Butyl-phenyl)-4-(1-methyl-piperidin-4-yloxy)-9,10-dihydro-4H-3,10a-diaza-benzo[f]azulene, oxalate
1-{4-[4-(1-Methyl-piperidin-4-yloxy)-9,10-dihydro-4H-3,10a-diaza-benzo[f]azulen-2-yl]-phenyl}-ethanone, oxalate
4-(1-Methyl-piperidin-4-yloxy)-2-thiophen-3-yl-9,10-dihydro-4H-3,10a-diaza-benzo[f]azulene, oxalate
2-Ethyl-4-(1-methyl-piperidin-4-yloxy)-9,10-dihydro-4H-3,10a-diaza-benzo[f]azulene, oxalate 2-(4-Methoxy-phenyl)-4-(1-methyl-piperidin-4-yloxy)-9,10-dihydro-4H-3,10a-diaza-benzo[f]azulene, oxalate
4-(1-Methyl-piperidin-4-yloxy)-2-(4-trifluoromethoxy-phenyl)-9,10-dihydro-4H-3,10a-diaza-benzo[f]azulene, oxalate
4-[4-(1-Methyl-piperidin-4-yloxy)-9,10-dihydro-4H-3,10a-diaza-benzo[f]azulen-2-yl]-phenylamine
2-(4-Methanesulfonyl-phenyl)-4-(1-methyl-piperidin-4-yloxy)-9,10-dihydro-4H-3,10a-diaza-benzo[f]azulene
{4-[4-(1-Methyl-piperidin-4-yloxy)-9,10-dihydro-4H-3,10a-diaza-benzo[f]azulen-2-yl]-phenyl}-methanol
2-(4-Methoxymethyl-phenyl)-4-(1-methyl-piperidin-4-yloxy)-9,10-dihydro-4H-3,10a-diaza-benzo[f]azulene, oxalate
4-(1-Methyl-piperidin-4-yloxy)-2-(4-methylsulfanyl-phenyl)-9,10-dihydro-4H-3,10a-diaza-benzo[f]azulene
4-(1-Methyl-piperidin-4-yloxy)-2-(4-propyl-phenyl)-9,10-dihydro-4H-3,10a-diaza-benzo[f]azulene
4-(1-Methyl-piperidin-4-yloxy)-2-pyridin-2-yl-9,10-dihydro-4H-3,10a-diaza-benzo[f]azulene, oxalate
2-Furan-2-yl-4-(1-methyl-piperidin-4-yloxy)-9,10-dihydro-4H-3,10a-diaza-benzo[f]azulene, oxalate
4-(1-Methyl-piperidin-4-yloxy)-2-(4-trifluoromethyl-phenyl)-9,10-dihydro-4H-3,10a-diaza-benzo[f]azulene
2-(2-Chloro-phenyl)-4-(1-methyl-piperidin-4-yloxy)-9,10-dihydro-4H-3,10a-diaza-benzo[f]azulene, oxalate
2-(2-Fluoro-phenyl)-4-(1-methyl-piperidin-4-yloxy)-9,10-dihydro-4H-3,10a-diaza-benzo[f]azulene
2-(4-Isobutyl-phenyl)-4-(1-methyl-piperidin-4-yloxy)-9,10-dihydro-4H-3,10a-diaza-benzo[f]azulene
N,N-Dimethyl-4-[4-(1-methyl-piperidin-4-yloxy)-9,10-dihydro-4H-3,10a-diaza-benzo[f]azulen-2-yl]-benzenesulfonamide
2-Allyl-4-(1-methyl-piperidin-4-yloxy)-9,10-dihydro-4H-3,10a-diaza-benzo[f]azulene, oxalate
2,2,2-Trifluoro-1-{4-[4-(1-methyl-piperidin-4-yloxy)-9,10-dihydro-4H-3,10a-diaza-benzo[f]azulen-2-yl]-phenyl}-ethanone, oxalate
2-(4-Isopropyl-phenyl)-4-(1-methyl-piperidin-4-yloxy)-9,10-dihydro-4H-3,10a-diaza-benzo[f]azulene, oxalate
{4-[4-(1-Methyl-piperidin-4-yloxy)-9,10-dihydro-4H-3,10a-diaza-benzo[f]azulen-2-yl]-phenyl}-acetonitrile, oxalate
4-(1-Methyl-piperidin-4-yloxy)-2-phenylethynyl-9,10-dihydro-4H-3,10a-diaza-benzo[f]azulene, oxalate
Dimethyl-{4-[4-(1-methyl-piperidin-4-yloxy)-9,10-dihydro-4H-3,10a-diaza-benzo[f]azulen-2-yl]-phenyl}-amine, oxalate
4-[4-(1-Methyl-piperidin-4-yloxy)-9,10-dihydro-4H-3,10a-diaza-benzo[f]azulen-2-yl]-benzoic acid tert-butyl ester
4-[4-(1-Methyl-piperidin-4-yloxy)-9,10-dihydro-4H-3,10a-diaza-benzo[f]azulen-2-yl]-benzonitrile
4-(1-Methyl-piperidin-4-yloxy)-2-phenethyl-9,10-dihydro-4H-3,10a-diaza-benzo[f]azulene, oxalate
4-(1-Methyl-piperidin-4-yloxy)-2-(6-methyl-pyridin-3-yl)-9,10-dihydro-4H-3,10a-diaza-benzo[f]azulene, oxalate
4-(1-Methyl-piperidin-4-yloxy)-2-oxazol-2-yl-9,10-dihydro-4H-3,10a-diaza-benzo[f]azulene, oxalate
2-(4-Butyl-phenyl)-4-(1-methyl-piperidin-4-yloxy)-9,10-dihydro-4H-3,10a-diaza-benzo[f]azulene
2-(4-Butyl-phenyl)-4-(1-methyl-piperidin-4-yloxy)-9,10-dihydro-4H-3,10a-diaza-benzo[f]azulene, oxalate
4-(1-Methyl-piperidin-4-yloxy)-2-(4-pentyl-phenyl)-9,10-dihydro-4H-3,10a-diaza-benzo[f]azulene
2-(4-Hexyl-phenyl)-4-(1-methyl-piperidin-4-yloxy)-9,10-dihydro-4H-3,10a-diaza-benzo[f]azulene
4-(1-Methyl-piperidin-4-yloxy)-2-pyridin-4-yl-9,10-dihydro-4H-3,10a-diaza-benzo[f]azulene, oxalate
4-(1-Methyl-piperidin-4-yloxy)-2-pyridin-3-yl-9,10-dihydro-4H-3,10a-diaza-benzo[f]azulene, oxalate
2-(4-Ethylsulfanyl-phenyl)-4-(1-methyl-piperidin-4-yloxy)-9,10-dihydro-4H-3,10a-diaza-benzo[f]azulene, oxalate
4-(1-Methyl-piperidin-4-yloxy)-2-thiophen-2-yl-9,10-dihydro-4H-3,10a-diaza-benzo[f]azulene, oxalate
4-(1-Methyl-piperidin-4-yloxy)-2-thiazol-5-yl-9,10-dihydro-4H-3,10a-diaza-benzo[f]azulene, oxalate
{4-[4-(1-Methyl-piperidin-4-yloxy)-9,10-dihydro-4H-3,10a-diaza-benzo[f]azulen-2-yl]-phenyl}-carbamic acid tert-butyl ester
2-Benzo[1,3]dioxol-5-yl-4-(1-methyl-piperidin-4-yloxy)-9,10-dihydro-4H-3,10a-diaza-benzo[f]azulene
2-(5-Methyl-furan-2-yl)-4-(1-methyl-piperidin-4-yloxy)-9,10-dihydro-4H-3,10a-diaza-benzo[f]azulene, oxalate
2-(4-Chloro-phenyl)-4-(1-methyl-piperidin-4-yloxy)-9,10-dihydro-4H-3,10a-diaza-benzo[f]azulene, oxalate
3-[4-(1-Methyl-piperidin-4-yloxy)-9,10-dihydro-4H-3,10a-diaza-benzo[f]azulen-2-yl]-acrylic acid tert-butyl ester, oxalate
4-(1-Methyl-piperidin-4-yloxy)-2-(2-methyl-4-trifluoromethyl-phenyl)-9,10-dihydro-4H-3,10a-diaza-benzo[f]azulene
2-(4-Fluoro-phenyl)-4-(1-methyl-piperidin-4-yloxy)-9,10-dihydro-4H-3,10a-diaza-benzo[f]azulene
2-(3,6-Dihydro-2H-thiopyran-4-yl)-4-(1-methyl-piperidin-4-yloxy)-9,10-dihydro-4H-3,10a-diaza-benzo[f]azulene
2,2-Dimethyl-N-{4-[4-(1-methyl-piperidin-4-yloxy)-9,10-dihydro-4H-3,10a-diaza-benzo[f]azulen-2-yl]-phenyl}-propionamide
2-(2-Cyclohexyl-vinyl)-4-(1-methyl-piperidin-4-yloxy)-9,10-dihydro-4H-3,10a-diaza-benzo[f]azulene
1-{4-[4-(1-Methyl-piperidin-4-yloxy)-9,10-dihydro-4H-3,10a-diaza-benzo[f]azulen-2-yl]-phenyl}-3-propyl-urea
2-(2,4-Dimethyl-phenyl)-4-(1-methyl-piperidin-4-yloxy)-9,10-dihydro-4H-3,10a-diaza-benzo[f]azulene
2-Cyclohex-1-enyl-4-(1-methyl-piperidin-4-yloxy)-9,10-dihydro-4H-3,10a-diaza-benzo[f]azulene, oxalate
4-(1-Methyl-piperidin-4-yloxy)-2-pyridin-3-ylethynyl-9,10-dihydro-4H-3,10a-diaza-benzo[f]azulene, oxalate
2-[4-(1,1-Difluoro-ethyl)-phenyl]-4-(1-methyl-piperidin-4-yloxy)-9,10-dihydro-4H-3,10a-diaza-benzo[f]azulene, oxalate
2-Cyclopent-1-enyl-4-(1-methyl-piperidin-4-yloxy)-9,10-dihydro-4H-3,10a-diaza-benzo[f]azulene
4-(1-Methyl-piperidin-4-yloxy)-2-thiazol-2-yl-9,10-dihydro-4H-3,10a-diaza-benzo[f]azulene, oxalate
2-Benzylsulfanyl-4-(1-methyl-piperidin-4-yloxy)-9,10-dihydro-4H-3,10a-diaza-benzo[f]azulene, oxalate
2-(3-Fluoro-phenyl)-4-(1-methyl-piperidin-4-yloxy)-9,10-dihydro-4H-3,10a-diaza-benzo[f]azulene, oxalate
2-(4-Difluoromethyl-phenyl)-4-(1-methyl-piperidin-4-yloxy)-9,10-dihydro-4H-3,10a-diaza-benzo[f]azulene, oxalate
2-(2-Methyl-allyl)-4-(1-methyl-piperidin-4-yloxy)-9,10-dihydro-4H-3,10a-diaza-benzo[f]azulene, oxalate
2-(2,4-Dichloro-phenyl)-4-(1-methyl-piperidin-4-yloxy)-9,10-dihydro-4H-3,10a-diaza-benzo[f]azulene, oxalate {3-[4-(1-Methyl-piperidin-4-yloxy)-9,10-dihydro-4H-3,10a-diaza-benzo[f]azulen-2-yl]-prop-2-ynyl}-carbamic acid tert-butyl ester 4-(1-Methyl-piperidin-4-yloxy)-2-phenylsulfanyl-9,10-dihydro-4H-3,10a-diaza-benzo[f]azulene, oxalate 4-[4-(1-Methyl-piperidin-4-yloxy)-9,10-dihydro-4H-3,10a-diaza-benzo[f]azulen-2-yl]-3,6-dihydro-2H-pyridine-1-carboxylic acid tert-butyl ester, oxalate 2-(2-Chloro-4-methyl-phenyl)-4-(1-methyl-piperidin-4-yloxy)-9,10-dihydro-4H-3,10a-diaza-benzo[f]azulene, oxalate 4-(1-Methyl-piperidin-4-yloxy)-2-(3-phenyl-propenyl)-9,10-dihydro-4H-3,10a-diaza-benzo[f]azulene, oxalate 2-(3-Chloro-phenyl)-4-(1-methyl-piperidin-4-yloxy)-9,10-dihydro-4H-3,10a-diaza-benzo[f]azulene, oxalate 8-Chloro-2-iodo-4-(1-methyl-piperidin-4-yloxy)-9,10-dihydro-4H-3,10a-diaza-benzo[f]azulene 8-Bromo-2-iodo-4-(1-methyl-piperidin-4-yloxy)-9,10-dihydro-4H-3,10a-diaza-benzo[f]azulene 2-Cyclohept-1-enyl-4-(1-methyl-piperidin-4-yloxy)-9,10-dihydro-4H-3,10a-diaza-benzo[f]azulene 2-(4-Bromo-phenyl)-4-(1-methyl-piperidin-4-yloxy)-9,10-dihydro-4H-3,10a-diaza-benzo[f]azulene 2-(2-Fluoro-4-methyl-phenyl)-4-(1-methyl-piperidin-4-yloxy)-9,10-dihydro-4H-3,10a-diaza-benzo[f]azulene 4-(1-Methyl-piperidin-4-yloxy)-2-(1-methyl-1H-pyrrol-2-yl)-9,10-dihydro-4H-3,10a-diaza-benzo[f]azulene {2-[4-(1-Methyl-piperidin-4-yloxy)-9,10-dihydro-4H-3,10a-diaza-benzo[f]azulen-2-ylsulfanyl]-ethyl}-carbamic acid tert-butyl ester, oxalate 2-(Furan-2-ylmethylsulfanyl)-4-(1-methyl-piperidin-4-yloxy)-9,10-dihydro-4H-3,10a-diaza-benzo[f]azulene, oxalate 2-Cyclopentylsulfanyl-4-(1-methyl-piperidin-4-yloxy)-9,10-dihydro-4H-3,10a-diaza-benzo[f]azulene, oxalate 4-(1-Methyl-piperidin-4-yloxy)-2-(3-phenyl-propyl)-9,10-dihydro-4H-3,10a-diaza-benzo[f]azulene, oxalate 4-(1-Methyl-piperidin-4-yloxy)-2-(thiophen-2-ylmethylsulfanyl)-9,10-dihydro-4H-3,10a-diaza-benzo[f]azulene, oxalate 4-(1-Methyl-piperidin-4-yloxy)-2-(5-phenyl-pent-1-enyl)-9,10-dihydro-4H-3,10a-diaza-benzo[f]azulene 4-(1-Methyl-piperidin-4-yloxy)-2-(5-phenyl-pentyl)-9,10-dihydro-4H-3,10a-diaza-benzo[f]azulene, oxalate 8-Chloro-4-(1-methyl-piperidin-4-yloxy)-2-phenyl-9,10-dihydro-4H-3,10a-diaza-benzo[f]azulene 4-(1-Methyl-piperidin-4-yloxy)-2,8-diphenyl-9,10-dihydro-4H-3,10a-diaza-benzo[f]azulene 2-(3,3-Dimethyl-but-1-enyl)-4-(1-methyl-piperidin-4-yloxy)-9,10-dihydro-4H-3,10a-diaza-benzo[f]azulene 2-(3,3-Dimethyl-butyl)-4-(1-methyl-piperidin-4-yloxy)-9,10-dihydro-4H-3,10a-diaza-benzo[f]azulene 2-(2-Cyclohexyl-ethyl)-4-(1-methyl-piperidin-4-yloxy)-9,10-dihydro-4H-3,10a-diaza-benzo[f]azulene, oxalate 4-(1-Methyl-piperidin-4-yloxy)-2-(5-methyl-thiophen-2-yl)-9,10-dihydro-4H-3,10a-diaza-benzo[f]azulene, oxalate Methyl-{4-[4-(1-methyl-piperidin-4-yloxy)-9,10-dihydro-4H-3,10a-diaza-benzo[f]azulen-2-yl]-phenyl}-carbamic acid tert-butyl ester, oxalate 2-Cyclohexylsulfanyl-4-(1-methyl-piperidin-4-yloxy)-9,10-dihydro-4H-3,10a-diaza-benzo[f]azulene, oxalate 2-(2-Cyclopropyl-vinyl)-4-(1-methyl-piperidin-4-yloxy)-9,10-dihydro-4H-3,10a-diaza-benzo[f]azulene, oxalate Methyl-{4-[4-(1-methyl-piperidin-4-yloxy)-9,10-dihydro-4H-3,10a-diaza-benzo[f]azulen-2-yl]-phenyl}-amine, oxalate 2,2,N-Trimethyl-N-{4-[4-(1-methyl-piperidin-4-yloxy)-9,10-dihydro-4H-3,10a-diaza-benzo[f]azulen-2-yl]-phenyl}-propionamide, oxalate

[4-(1-Methyl-piperidin-4-yloxy)-9,10-dihydro-4H-3,10a-diaza-benzo[f]azulen-2-yl]-phenyl-methanone, oxalate 1-Methyl-4-(1-methyl-piperidin-4-yloxy)-2-phenyl-9,10-dihydro-4H-3,10a-diaza-benzo[f]azulene 2-(3-Cyclopentyl-propenyl)-4-(1-methyl-piperidin-4-yloxy)-9,10-dihydro-4H-3,10a-diaza-benzo[f]azulene 2-(3-Cyclopentyl-propyl)-4-(1-methyl-piperidin-4-yloxy)-9,10-dihydro-4H-3,10a-diaza-benzo[f]azulene 2-(3,6-Dihydro-2H-pyran-4-yl)-4-(1-methyl-piperidin-4-yloxy)-9,10-dihydro-4H-3,10a-diaza-benzo[f]azulene 8-Fluoro-4-(1-methyl-piperidin-4-yloxy)-2-phenyl-9,10-dihydro-4H-3,10a-diaza-benzo[f]azulene N-(4-Hydroxy-cyclohexyl)-4-[4-(1-methyl-piperidin-4-yloxy)-9,10-dihydro-4H-3,10a-diaza-benzo[f]azulen-2-yl]-benzamide 2-Isobutyl-4-(1-methyl-piperidin-4-yloxy)-9,10-dihydro-4H-3,10a-diaza-benzo[f]azulene, oxalate 2-Benzyl-4-(1-methyl-piperidin-4-yloxy)-9,10-dihydro-4H-3,10a-diaza-benzo[f]azulene, oxalate 4-(1-Methyl-piperidin-4-yloxy)-2-(2-thiophen-2-yl-vinyl)-9,10-dihydro-4H-3,10a-diaza-benzo[f]azulene 4-(1-Methyl-piperidin-4-yloxy)-2-(2-thiophen-3-yl-vinyl)-9,10-dihydro-4H-3,10a-diaza-benzo[f]azulene Dimethyl-{4-[4-(1-methyl-piperidin-4-yloxy)-9,10-dihydro-4H-3,10a-diaza-benzo[f]azulen-2-yl]-benzyl}-amine 4-[4-(1-Methyl-piperidin-4-yloxy)-9,10-dihydro-4H-3,10a-diaza-benzo[f]azulen-2-ylsulfanyl]-piperidine-1-carboxylic acid tert-butyl ester {4-[4-(1-Methyl-piperidin-4-yloxy)-9,10-dihydro-4H-3,10a-diaza-benzo[f]azulen-2-yl]-benzyl}-carbamic acid tert-butyl ester 2-Methyl-4-(1-methyl-piperidin-4-yloxy)-9,10-dihydro-4H-3,10a-diaza-benzo[f]azulene-1-carboxylic acid ethyl ester 2-[1-(4-Chloro-phenyl)-1-methyl-ethyl]-4-(1-methyl-piperidin-4-yloxy)-9,10-dihydro-4H-3,10a-diaza-benzo[f]azulene, oxalate 1-Methyl-4-(1-methyl-piperidin-4-yloxy)-9,10-dihydro-4H-3,10a-diaza-benzo[f]azulene-2-carboxylic acid ethyl ester 4-(1-Methyl-piperidin-4-yloxy)-2-phenethylsulfanyl-9,10-dihydro-4H-3,10a-diaza-benzo[f]azulene, oxalate 1-Ethyl-4-(1-methyl-piperidin-4-yloxy)-2-phenyl-9,10-dihydro-4H-3,10a-diaza-benzo[f]azulene, oxalate 4-(1-Methyl-piperidin-4-yloxy)-2-(3-phenoxy-propenyl)-9,10-dihydro-4H-3,10a-diaza-benzo[f]azulene, oxalate 2-(4-Bromo-phenyl)-1-methyl-4-(1-methyl-piperidin-4-yloxy)-9,10-dihydro-4H-3,10a-diaza-benzo[f]azulene 2-Methyl-4-(1-methyl-piperidin-4-yloxy)-1-phenyl-9,10-dihydro-4H-3,10a-diaza-benzo[f]azulene, oxalate 2-(3-Benzyloxy-propenyl)-4-(1-methyl-piperidin-4-yloxy)-9,10-dihydro-4H-3,10a-diaza-benzo[f]azulene, oxalate Methyl-{4-[1-methyl-4-(1-methyl-piperidin-4-yloxy)-9,10-dihydro-4H-3,10a-diaza-benzo[f]azulen-2-yl]-phenyl}-carbamic acid tert-butyl ester, oxalate 4-(1-Methyl-piperidin-4-yloxy)-2-(2-thiophen-2-yl-ethyl)-9,10-dihydro-4H-3,10a-diaza-benzo[f]azulene, oxalate 2-(4-Bromo-phenyl)-1-chloro-4-(1-methyl-piperidin-4-yloxy)-9,10-dihydro-4H-3,10a-diaza-benzo[f]azulene 2-(3-Benzyloxy-propyl)-4-(1-methyl-piperidin-4-yloxy)-9,10-dihydro-4H-3,10a-diaza-benzo[f]azulene, oxalate 4-(1-Methyl-piperidin-4-yloxy)-2-(4-phenyl-butyl)-9,10-dihydro-4H-3,10a-diaza-benzo[f]azulene, oxalate {4-[1-Methyl-4-(1-methyl-piperidin-4-yloxy)-9,10-dihydro-4H-3,10a-diaza-benzo[f]azulen-2-yl]-phenyl}-carbamic acid tert-butyl ester 3-{4-[1-Methyl-4-(1-methyl-piperidin-4-yloxy)-9,10-dihydro-4H-3,10a-diaza-benzo[f]azulen-2-yl]-phenyl}-oxazolidin-2-one 1-Methyl-3-{4-[1-methyl-4-(1-methyl-piperidin-4-yloxy)-9,10-dihydro-4H-3,10a-diaza-benzo[f]azulen-2-yl]-phenyl}-imidazolidin-2-one 2-Iodo-1-methyl-4-(1-methyl-piperidin-4-yloxy)-9,10-dihydro-4H-3,10a-diaza-benzo[f]azulene 1-Chloro-4-(1-methyl-piperidin-4-yloxy)-2-phenyl-9,10-dihydro-4H-3,10a-diaza-benzo[f]azulene 2,2-Dimethyl-N-{4-[4-(1-methyl-piperidin-4-yloxy)-9,10-dihydro-4H-3,10a-diaza-benzo[f]azulen-2-yl]-benzyl}-propionamide 1-Chloro-4-(1-methyl-piperidin-4-yloxy)-2-(5-phenyl-pentyl)-9,10-dihydro-4H-3,10a-diaza-benzo[f]azulene, oxalate 1-tert-Butyl-3-{4-[1-methyl-4-(1-methyl-piperidin-4-yloxy)-9,10-dihydro-4H-3,10a-diaza-benzo[f]azulen-2-yl]-phenyl}-imidazolidin-2-one {4-[1-Chloro-4-(1-methyl-piperidin-4-yloxy)-9,10-dihydro-4H-3,10a-diaza-benzo[f]azulen-2-yl]-phenyl}-carbamic acid tert-butyl ester 2-(2-Fluoro-phenyl)-1-methyl-4-(1-methyl-piperidin-4-yloxy)-9,10-dihydro-4H-3,10a-diaza-benzo[f]azulene 2-(3-Fluoro-phenyl)-1-methyl-4-(1-methyl-piperidin-4-yloxy)-9,10-dihydro-4H-3,10a-diaza-benzo[f]azulene 1-Methyl-4-(1-methyl-piperidin-4-yloxy)-2-m-tolyl-9,10-dihydro-4H-3,10a-diaza-benzo[f]azulene 2-(3-Chloro-phenyl)-1-methyl-4-(1-methyl-piperidin-4-yloxy)-9,10-dihydro-4H-3,10a-diaza-benzo[f]azulene 2-(2-Chloro-phenyl)-1-methyl-4-(1-methyl-piperidin-4-yloxy)-9,10-dihydro-4H-3,10a-diaza-benzo[f]azulene 1-Methyl-4-(1-methyl-piperidin-4-yloxy)-2-o-tolyl-9,10-dihydro-4H-3,10a-diaza-benzo[f]azulene 1-Methyl-4-(1-methyl-piperidin-4-yloxy)-2-thiophen-3-yl-9,10-dihydro-4H-3,10a-diaza-benzo[f]azulene 2-(2-Methoxy-phenyl)-1-methyl-4-(1-methyl-piperidin-4-yloxy)-9,10-dihydro-4H-3,10a-diaza-benzo[f]azulene 2-(3-Methoxy-phenyl)-1-methyl-4-(1-methyl-piperidin-4-yloxy)-9,10-dihydro-4H-3,10a-diaza-benzo[f]azulene 3-{4-[1-Methyl-4-(1-methyl-piperidin-4-yloxy)-9,10-dihydro-4H-3,10a-diaza-benzo[f]azulen-2-yl]-phenyl}-acrylic acid tert-butyl ester 3-Methyl-3-{4-[1-methyl-4-(1-methyl-piperidin-4-yloxy)-9,10-dihydro-4H-3,10a-diaza-benzo[f]azulen-2-yl]-phenylsulfanyl}-butan-1-ol, oxalate 1-Methyl-4-(1-methyl-piperidin-4-yloxy)-2-p-tolyl-9,10-dihydro-4H-3,10a-diaza-benzo[f]azulene 2-(4-Fluoro-phenyl)-1-methyl-4-(1-methyl-piperidin-4-yloxy)-9,10-dihydro-4H-3,10a-diaza-benzo[f]azulene 2-(4-Chloro-phenyl)-1-methyl-4-(1-methyl-piperidin-4-yloxy)-9,10-dihydro-4H-3,10a-diaza-benzo[f]azulene 2-(4-Methoxy-phenyl)-1-methyl-4-(1-methyl-piperidin-4-yloxy)-9,10-dihydro-4H-3,10a-diaza-benzo[f]azulene 2-(2-Chloro-4-methyl-phenyl)-1-methyl-4-(1-methyl-piperidin-4-yloxy)-9,10-dihydro-4H-3,10a-diaza-benzo[f]azulene, oxalate 2-[4-(2-Methanesulfonyl-vinyl)-phenyl]-1-methyl-4-(1-methyl-piperidin-4-yloxy)-9,10-dihydro-4H-3,10a-diaza-benzo[f]azulene 2-[4-(2-Methanesulfonyl-ethyl)-phenyl]-1-methyl-4-(1-methyl-piperidin-4-yloxy)-9,10-dihydro-4H-3,10a-diaza-benzo[f]azulene (2-{4-[1-Methyl-4-(1-methyl-piperidin-4-yloxy)-9,10-dihydro-4H-3,10a-diaza-benzo[f]azulen-2-yl]-phenylsulfanyl}-ethyl)-carbamic acid tert-butyl ester, oxalate 2-{4-[1-Methyl-4-(1-methyl-piperidin-4-yloxy)-9,10-dihydro-4H-3,10a-diaza-benzo[f]azulen-2-yl]-phenylsulfanyl}-ethylamine, oxalate 1-{4-[1-Methyl-4-(1-methyl-piperidin-4-yloxy)-9,10-dihydro-4H-3,10a-diaza-benzo[f]azulen-2-yl]-phenyl}-piperidin-2-one, oxalate N-(2-{4-[1-Methyl-4-(1-methyl-piperidin-4-yloxy)-9,10-dihydro-4H-3,10a-diaza-benzo[f]azulen-2-yl]-phenylsulfanyl}-ethyl)-acetamide, oxalate 2-(4-Benzylsulfanyl-phenyl)-1-methyl-4-(1-methyl-piperidin-4-yloxy)-9,10-dihydro-4H-3,10a-diaza-benzo[f]azulene, oxalate {4-[1-Methyl-4-(1-methyl-piperidin-4-yloxy)-9,10-dihydro-4H-3,10a-diaza-benzo[f]azulen-2-yl]-phenylsulfanyl}-acetic acid methyl ester, oxalate 2-(4-tert-Butylsulfanyl-phenyl)-1-methyl-4-(1-methyl-piperidin-4-yloxy)-9,10-dihydro-4H-3,10a-diaza-benzo[f]azulene, oxalate 2-[4-(Furan-2-ylmethylsulfanyl)-phenyl]-1-methyl-4-(1-methyl-piperidin-4-yloxy)-9,10-dihydro-4H-3,10a-diaza-benzo[f]azulene, oxalate 4-{4-[1-Methyl-4-(1-methyl-piperidin-4-yloxy)-9,10-dihydro-4H-3,10a-diaza-benzo[f]azulen-2-yl]-phenyl}-3,6-dihydro-2H-pyridine-1-carboxylic acid tert-butyl ester 2-(4-Cyclopent-1-enyl-phenyl)-1-methyl-4-(1-methyl-piperidin-4-yloxy)-9,10-dihydro-4H-3,10a-diaza-benzo[f]azulene 2-(4-Cyclohex-1-enyl-phenyl)-1-methyl-4-(1-methyl-piperidin-4-yloxy)-9,10-dihydro-4H-3,10a-diaza-benzo[f]azulene 2-(4-Cyclohept-1-enyl-phenyl)-1-methyl-4-(1-methyl-piperidin-4-yloxy)-9,10-dihydro-4H-3,10a-diaza-benzo[f]azulene {4-[1-Methyl-4-(1-methyl-piperidin-4-yloxy)-9,10-dihydro-4H-3,10a-diaza-benzo[f]azulen-2-yl]-phenyl}-carbamic acid cyclopentyl ester 4-[1-Methyl-4-(1-methyl-piperidin-4-yloxy)-9,10-dihydro-4H-3,10a-diaza-benzo[f]azulen-2-yl]-phenylamine {4-[1-Methyl-4-(1-methyl-piperidin-4-yloxy)-9,10-dihydro-4H-3,10a-diaza-benzo[f]azulen-2-yl]-phenyl}-carbamic acid isobutyl ester {4-[1-Methyl-4-(1-methyl-piperidin-4-yloxy)-9,10-dihydro-4H-3,10a-diaza-benzo[f]azulen-2-yl]-phenyl}-carbamic acid 2,2,2-trichloro-1,1-dimethyl-ethyl ester 4-Benzyl-3-{4-[1-methyl-4-(1-methyl-piperidin-4-yloxy)-9,10-dihydro-4H-3,10a-diaza-benzo[f]azulen-2-yl]-phenyl}-oxazolidin-2-one 4-{4-[1-Methyl-4-(1-methyl-piperidin-4-yloxy)-9,10-dihydro-4H-3,10a-diaza-benzo[f]azulen-2-yl]-phenyl}-piperidine-1-carboxylic acid tert-butyl ester 1-Isopropyl-3-{4-[1-methyl-4-(1-methyl-piperidin-4-yloxy)-9,10-dihydro-4H-3,10a-diaza-benzo[f]azulen-2-yl]-phenyl}-imidazolidin-2-one {2-[4-(1-Methyl-piperidin-4-yloxy)-9,10-dihydro-4H-3,10a-diaza-benzo[f]azulen-2-yl]-phenyl}-methanol, oxalate Dimethyl-(2-{4-[4-(1-methyl-piperidin-4-yloxy)-9,10-dihydro-4H-3,10a-diaza-benzo[f]azulen-2-yl]-phenoxy}-ethyl)-amine, dioxalate
3-{4-[4-(1-Methyl-piperidin-4-yloxy)-9,10-dihydro-4H-3,10a-diaza-benzo[f]azulen-2-yl]-benzyl}-oxazolidin-2-one
Methyl-{4-[4-(1-methyl-piperidin-4-yloxy)-9,10-dihydro-4H-3,10a-diaza-benzo[f]azulen-2-yl]-benzyl}-carbamic acid tert-butyl ester
2-(4-Allyloxy-phenyl)-4-(1-methyl-piperidin-4-yloxy)-9,10-dihydro-4H-3,10a-diaza-benzo[f]azulene
1-{4-[4-(1-Methyl-piperidin-4-yloxy)-9,10-dihydro-4H-3,10a-diaza-benzo[f]azulen-2-yl]-benzyl}-pyrrolidin-2-one
1-{4-[4-(1-Methyl-piperidin-4-yloxy)-9,10-dihydro-4H-3,10a-diaza-benzo[f]azulen-2-yl]-benzyl}-piperidin-2-one
2-(4-Isopropylsulfanylmethyl-phenyl)-4-(1-methyl-piperidin-4-yloxy)-9,10-dihydro-4H-3,10a-diaza-benzo[f]azulene
Cyclopropanesulfonic acid {4-[1-methyl-4-(1-methyl-piperidin-4-yloxy)-9,10-dihydro-4H-3,10a-diaza-benzo[f]azulen-2-yl]-phenyl}-amide
1-{4-[4-(1-Methyl-piperidin-4-yloxy)-9,10-dihydro-4H-3,10a-diaza-benzo[f]azulen-2-yl]-benzyl}-azepan-2-one
2-[4-(2-tert-Butylsulfanyl-ethyl)-phenyl]-4-(1-methyl-piperidin-4-yloxy)-9,10-dihydro-4H-3,10a-diaza-benzo[f]azulene
4-(1-Methyl-piperidin-4-yloxy)-2-(2-nitro-phenyl)-9,10-dihydro-4H-3,10a-diaza-benzo[f]azulene
1-tert-Butyl-3-{4-[4-(1-methyl-piperidin-4-yloxy)-9,10-dihydro-4H-3,10a-diaza-benzo[f]azulen-2-yl]-benzyl}-imidazolidin-2-one
2-{4-[4-(1-Methyl-piperidin-4-yloxy)-9,10-dihydro-4H-3,10a-diaza-benzo[f]azulen-2-yl]-phenyl}-ethanol
2-(4-Cyclopropylmethoxy-phenyl)-4-(1-methyl-piperidin-4-yloxy)-9,10-dihydro-4H-3,10a-diaza-benzo[f]azulene
3-{4-[1-Methyl-4-(1-methyl-piperidin-4-yloxy)-9,10-dihydro-4H-3,10a-diaza-benzo[f]azulen-2-yl]-phenylsulfanyl}-propane-1,2-diol
3-{4-[1-Methyl-4-(1-methyl-piperidin-4-yloxy)-9,10-dihydro-4H-3,10a-diaza-benzo[f]azulen-2-yl]-phenylsulfanyl}-propan-1-ol
(2-{4-[4-(1-Methyl-piperidin-4-yloxy)-9,10-dihydro-4H-3,10a-diaza-benzo[f]azulen-2-yl]-phenyl}-ethyl)-carbamic acid tert-butyl ester
Methyl-(2-{4-[4-(1-methyl-piperidin-4-yloxy)-9,10-dihydro-4H-3,10a-diaza-benzo[f]azulen-2-yl]-phenyl}-ethyl)-carbamic acid tert-butyl ester
5,5-Dimethyl-3-{ 4-[4-(1-methyl-piperidin-4-yloxy)-9,10-dihydro-4H-3,10a-diaza-benzo[f]azulen-2-yl]-benzyl}-oxazolidine-2,4-dione
(2-{4-[4-(1-Methyl-piperidin-4-yloxy)-9,10-dihydro-4H-3,10a-diaza-benzo[f]azulen-2-yl]-benzylsulfanyl}-ethyl)-carbamic acid tert-butyl ester
tert-Butyl-carbamic acid 2-{4-[4-(1-methyl-piperidin-4-yloxy)-9,10-dihydro-4H-3,10a-diaza-benzo[f]azulen-2-yl]-phenyl}-ethyl ester
[1-Methyl-4-(1-methyl-piperidin-4-yloxy)-9,10-dihydro-4H-3,10a-diaza-benzo[f]azulen-2-yl]-phenyl-methanol, formate
[1-Methyl-4-(1-methyl-piperidin-4-yloxy)-9,10-dihydro-4H-3,10a-diaza-benzo[f]azulen-2-yl]-phenyl-methanone, formate
1-Methyl-4-(1-methyl-piperidin-4-yloxy)-9,10-dihydro-4H-3,10a-diaza-benzo[f]azulene-2-carboxylic acid benzyl-methyl-amide
1-Methyl-4-(1-methyl-piperidin-4-yloxy)-9,10-dihydro-4H-3,10a-diaza-benzo[f]azulene-2-carboxylic acid methyl-phenyl-amide
1-Methyl-4-(1-methyl-piperidin-4-yloxy)-9,10-dihydro-4H-3,10a-diaza-benzo[f]azulene-2-carboxylic acid propylamide
1-Isopropyl-3-{4-[1-methyl-4-(1-methyl-piperidin-4-yloxy)-9,10-dihydro-4H-3,10a-diaza-benzo[f]azulen-2-yl]-phenyl}-thiourea
2-(1-Methyl-1-phenyl-ethyl)-4-(1-methyl-piperidin-4-yloxy)-9,10-dihydro-4H-3,10a-diaza-benzo[f]azulene
1-Cyclopropyl-3-{4-[1-methyl-4-(1-methyl-piperidin-4-yloxy)-9,10-dihydro-4H-3,10a-diaza-benzo[f]azulen-2-yl]-phenyl}-thiourea
1-tert-Butyl-3-{4-[1-methyl-4-(1-methyl-piperidin-4-yloxy)-9,10-dihydro-4H-3,10a-diaza-benzo[f]azulen-2-yl]-phenyl}-urea
2-Methyl-1-[1-methyl-4-(1-methyl-piperidin-4-yloxy)-9,10-dihydro-4H-3,10a-diaza-benzo[f]azulen-2-yl]-propan-1-ol, oxalate
N-(2-{4-[1-Methyl-4-(1-methyl-piperidin-4-yloxy)-9,10-dihydro-4H-3,10a-diaza-benzo[f]azulen-2-yl]-phenylsulfanyl}-ethyl)-guanidine
N-(2-Hydroxy-ethyl)-4-[4-(1-methyl-piperidin-4-yloxy)-9,10-dihydro-4H-3,10a-diaza-benzo[f]azulen-2-yl]-benzamide
1-Adamantan-1-yl-3-{4-[1-methyl-4-(1-methyl-piperidin-4-yloxy)-9,10-dihydro-4H-3,10a-diaza-benzo[f]azulen-2-yl]-phenyl}-urea
N-{4-[1-Methyl-4-(1-methyl-piperidin-4-yloxy)-9,10-dihydro-4H-3,10a-diaza-benzo[f]azulen-2-yl]-phenyl}-hydrazinecarboxylic acid tert-butyl ester
1-{4-[4-(1-Methyl-piperidin-4-yloxy)-9,10-dihydro-4H-3,10a-diaza-benzo[f]azulen-2-yl]-benzoyl}-piperidin-4-one
N-(4-Hydroxy-cyclohexyl)-4-[1-methyl-4-(1-methyl-piperidin-4-yloxy)-9,10-dihydro-4H-3,10a-diaza-benzo[f]azulen-2-yl]-benzamide
N-(2-Hydroxy-ethyl)-4-[1-methyl-4-(1-methyl-piperidin-4-yloxy)-9,10-dihydro-4H-3,10a-diaza-benzo[f]azulen-2-yl]-benzamide
1-{4-[1-Methyl-4-(1-methyl-piperidin-4-yloxy)-9,10-dihydro-4H-3,10a-diaza-benzo[f]azulen-2-yl]-benzoyl}-piperidin-4-one
1,2-Diiodo-4-(1-methyl-piperidin-4-yloxy)-9,10-dihydro-4H-3,10a-diaza-benzo[f]azulene
(4-Hydroxy-piperidin-1-yl)-{4-[1-methyl-4-(1-methyl-piperidin-4-yloxy)-9,10-dihydro-4H-3,10a-diaza-benzo[f]azulen-2-yl]-phenyl}-methanone
2-Iodo-4-(1-methyl-piperidin-4-yloxy)-9,10-dihydro-4H-3,10a-diaza-benzo[f]azulene-1-carbonitrile
1-Methyl-4-(1-methyl-piperidin-4-yloxy)-9,10-dihydro-4H-3,10a-diaza-benzo[f]azulene-2-carboxylic acid benzylamide
(2-{4-[1-Methyl-4-(1-methyl-piperidin-4-yloxy)-9,10-dihydro-4H-3,10a-diaza-benzo[f]azulen-2-yl]-phenyl}-ethyl)-carbamic acid tert-butyl ester
4-[1-Cyano-4-(1-methyl-piperidin-4-yloxy)-9,10-dihydro-4H-3,10a-diaza-benzo[f]azulen-2-yl]-benzoic acid tert-butyl ester
2-(3,3-Dimethyl-but-1-enyl)-1-methyl-4-(1-methyl-piperidin-4-yloxy)-9,10-dihydro-4H-3,10a-diaza-benzo[f]azulene 2-Cyclohex-1-enyl-1-methyl-4-(1-methyl-piperidin-4-yloxy)-9,10-dihydro-4H-3,10a-diaza-benzo[f]azulene 4-[1-Methyl-4-(1-methyl-piperidin-4-yloxy)-9,10-dihydro-4H-3,10a-diaza-benzo[f]azulen-2-yl]-but-3-yn-1-ol 2-(6-Chloro-hex-1-ynyl)-1-methyl-4-(1-methyl-piperidin-4-yloxy)-9,10-dihydro-4H-3,10a-diaza-benzo[f]azulene 2-(3,3-Dimethyl-butyl)-1-methyl-4-(1-methyl-piperidin-4-yloxy)-9,10-dihydro-4H-3,10a-diaza-benzo[f]azulene 9,9-Dimethyl-4-(1-methyl-piperidin-4-yloxy)-2-phenyl-9,10-dihydro-4H-3,10a-diaza-benzo[f]azulene 8-Bromo-4-(1-methyl-piperidin-4-yloxy)-2-phenyl-9,10-dihydro-4H-3,10a-diaza-benzo[f]azulene 1,9,9-Trimethyl-4-(1-methyl-piperidin-4-yloxy)-2-phenyl-9,10-dihydro-4H-3,10a-diaza-benzo[f]azulene 8-Benzyl-4-(1-methyl-piperidin-4-yloxy)-2-phenyl-9,10-dihydro-4H-3,10a-diaza-benzo[f]azulene 4-(1-Methyl-piperidin-4-yloxy)-8-methylsulfanyl-2-phenyl-9,10-dihydro-4H-3,10a-diaza-benzo[f]azulene, oxalate 4-(1-Methyl-piperidin-4-yloxy)-2-phenyl-9,10-dihydro-4H-3,10a-diaza-benzo[f]azulene-1-carbonitrile 8-Methyl-4-(1-methyl-piperidin-4-yloxy)-2-phenyl-9,10-dihydro-4H-3,10a-diaza-benzo[f]azulene 8-But-3-enyl-4-(1-methyl-piperidin-4-yloxy)-2-phenyl-9,10-dihydro-4H-3,10a-diaza-benzo[f]azulene, oxalate 4-(1-Methyl-piperidin-4-yloxy)-2-phenyl-1-propyl-9,10-dihydro-4H-3,10a-diaza-benzo[f]azulene 4-(1-Methyl-piperidin-4-yloxy)-2-phenyl-8-o-tolyl-9,10-dihydro-4H-3,10a-diaza-benzo[f]azulene 8-(4-Fluoro-phenyl)-4-(1-methyl-piperidin-4-yloxy)-2-phenyl-9,10-dihydro-4H-3,10a-diaza-benzo[f]azulene 8-(3-Methoxy-phenyl)-4-(1-methyl-piperidin-4-yloxy)-2-phenyl-9,10-dihydro-4H-3,10a-diaza-benzo[f]azulene 3-[4-(1-Methyl-piperidin-4-yloxy)-2-phenyl-9,10-dihydro-4H-3,10a-diaza-benzo[f]azulen-8-yl]-phenylamine 1-Isopropyl-4-(1-methyl-piperidin-4-yloxy)-2-phenyl-9,10-dihydro-4H-3,10a-diaza-benzo[f]azulene, dioxalate Methyl-[4-(1-methyl-piperidin-4-yloxy)-2-phenyl-9,10-dihydro-4H-3,10a-diaza-benzo[f]azulen-8-yl]-amine 8-Methoxy-4-(1-methyl-piperidin-4-yloxy)-2-phenyl-9,10-dihydro-4H-3,10a-diaza-benzo[f]azulene 4-(1-Methyl-piperidin-4-yloxy)-1-phenyl-2-propyl-9,10-dihydro-4H-3,10a-diaza-benzo[f]azulene 1-Iodo-4-(1-methyl-piperidin-4-yloxy)-2-phenyl-9,10-dihydro-4H-3,10a-diaza-benzo[f]azulene 8-Benzyloxy-4-(1-methyl-piperidin-4-yloxy)-2-phenyl-9,10-dihydro-4H-3,10a-diaza-benzo[f]azulene 4-(1-Methyl-piperidin-4-yloxy)-8-phenethyl-2-phenyl-9,10-dihydro-4H-3,10a-diaza-benzo[f]azulene 1-Methyl-4-(1-methyl-piperidin-4-yloxy)-2-pyridin-4-yl-9,10-dihydro-4H-3,10a-diaza-benzo[f]azulene 1-Methyl-4-(1-methyl-piperidin-4-yloxy)-2-pyridin-2-yl-9,10-dihydro-4H-3,10a-diaza-benzo[f]azulene 4-(1-Methyl-piperidin-4-yloxy)-1,2-diphenyl-9,10-dihydro-4H-3,10a-diaza-benzo[f]azulene 2-Iodo-4-(1-methyl-piperidin-4-yloxy)-9,10-dihydro-4H-3,10a-diaza-benzo[f]azulene-1-carboxylic acid amide 4-(1-Methyl-piperidin-4-yloxy)-2-phenyl-9,10-dihydro-4H-3,10a-diaza-benzo[f]azulene-1-carboxylic acid amide 4-(1-Methyl-piperidin-4-yloxy)-2-phenyl-1-trifluoromethyl-9,10-dihydro-4H-3,10a-diaza-benzo[f]azulene, oxalate 4-(1-Methyl-piperidin-4-yloxy)-2-phenyl-9,10-dihydro-4H-3,10a-diaza-benzo[f]azulene-1-carboxylic acid methyl ester

[4-(1-Methyl-piperidin-4-yloxy)-2-phenyl-9,10-dihydro-4H-3,10a-diaza-benzo[f]azulen-1-yl]-methanol 6-Iodo-1-methyl-4-(1-methyl-piperidin-4-yloxy)-2-phenyl-9,10-dihydro-4H-3,10a-diaza-benzo[f]azulene 2-(2-Methyl-allyl)-4-(1-methyl-piperidin-4-yloxy)-9,10-dihydro-4H-3,10a-diaza-benzo[f]azulene-1-carbonitrile 1-Methyl-2-(2-methyl-allyl)-4-(1-methyl-piperidin-4-yloxy)-9,10-dihydro-4H-3,10a-diaza-benzo[f]azulene 7-Bromo-4-(1-methyl-piperidin-4-yloxy)-2-phenyl-9,10-dihydro-4H-3,10a-diaza-benzo[f]azulene 4-(1-Methyl-piperidin-4-yloxy)-2-phenyl-9,10-dihydro-4H-3,10a-diaza-benzo[f]azulene-1-carbaldehyde 2-Benzyl-4-(1-methyl-piperidin-4-yloxy)-9,10-dihydro-4H-3,10a-diaza-benzo[f]azulene-1-carbonitrile

[2-(1,2-Diiodo-9,10-dihydro-4H-3,10a-diaza-benzo[f]azulen-4-yloxy)-ethyl]-dimethyl-amine 1,2-Diiodo-4-(2-piperidin-1-yl-ethoxy)-9,10-dihydro-4H-3,10a-diaza-benzo[f]azulene 2-(2-Methyl-allyl)-4-(1-methyl-piperidin-4-yloxy)-9,10-dihydro-4H-3,10a-diaza-benzo[f]azulene-1-carboxylic acid amide 1,2-Bis-(2-methyl-allyl)-4-(1-methyl-piperidin-4-yloxy)-9,10-dihydro-4H-3,10a-diaza-benzo[f]azulene, dioxalate 1,2-Diiodo-4-(1-methyl-pyrrolidin-3-yloxy)-9,10-dihydro-4H-3,10a-diaza-benzo[f]azulene 1,2-Diiodo-4-(8-methyl-8-aza-bicyclo[3.2.1]oct-3-yloxy)-9,10-dihydro-4H-3,10a-diaza-benzo[f]azulene

[3-(1,2-Diiodo-9,10-dihydro-4H-3,10a-diaza-benzo[f]azulen-4-yloxy)-propyl]-dimethyl-amine 4-(1-Aza-bicyclo[2.2.2]oct-3-yloxy)-1,2-diiodo-9,10-dihydro-4H-3,10a-diaza-benzo[f]azulene, oxalate 2-(2-Chloro-phenyl)-4-(1-methyl-piperidin-4-yloxy)-9,10-dihydro-4H-3,10a-diaza-benzo[f]azulene-1-carbonitrile, oxalate 2-(2-Chloro-phenyl)-4-(1-methyl-piperidin-4-yloxy)-9,10-dihydro-4H-3,10a-diaza-benzo[f]azulene-1-carboxylic acid amide, oxalate as well as its enantiomers, diastereomers, mixtures thereof and tautomers, and hydrates.

8. Process of preparation of a compound of formula (I) according to claim 1 comprising the step of condensing an alcohol of formula (II)

in which R1 is as defined in formula (I) in claim 1

141 with an alcohol of formula (III)

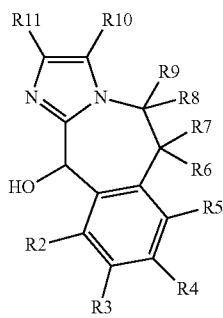

in which R2, R3, R4, R5, R6, R7, R8, R9, R10 and R11 are as defined in formula (I) in claim 1.

9. Process of preparation of a compound of formula (I) according to claim 1 comprising the step of by condensing an alcohol of formula (II)

in which R1 is as defined in formula (I) in claim 1 with an aldehyde of formula (IV)

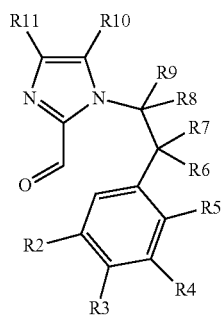

142 in which R2, R3, R4, R5, R6, R7, R8, R9, R10 and R11 are as defined in formula (I) in claim 1.

10. The process according to claim 8, further comprising the additional step of isolating the desired compound.

11. A compound of formula (III):

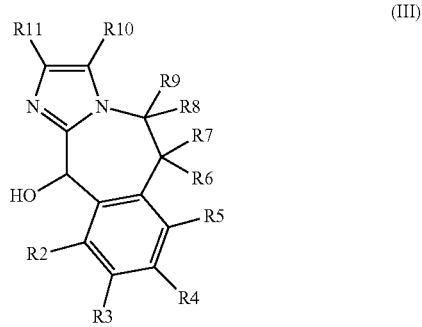

in which R2, R3, R4, R5, R6, R7, R8, R9, R10 and R11 are as defined in formula (I) in claim 1.

12. A pharmaceutical composition comprising a compound according to claim 1 with a pharmaceutically acceptable excipient.

13. A method of treatment comprising administering an effective amount of a compound according to claim 1 for treating a disease associated with $H_4$ dysfunction selected from the group consisting of adult respiratory distress syndrome, acute respiratory distress syndrome, bronchitis, chronic bronchitis, chronic obstructive pulmonary disease, cystic fibrosis, asthma, emphysema, rhinitis, chronic sinusitis, allergy, allergy induced airway responses, allergic rhinitis, viral rhinitis, non-allergic rhinitis, perennial and seasonal rhinitis, conjunctivitis, nasal congestion, allergic congestion; dermatitis and psoriasis and treatment of itchy skin; inflammatory bowel disease, Crohn's disease, ulcerative colitis, food allergy; rheumatoid arthritis, multiple sclerosis; pain; chronic hypereosinophilias; and chronic diseases associated with mast-cell multiplication.

* * * * *